US012599070B2

(12) United States Patent
Liu et al.

(10) Patent No.: US 12,599,070 B2
(45) Date of Patent: Apr. 14, 2026

(54) GENETIC LOCI ASSOCIATED WITH DISEASE RESISTANCE IN SOYBEANS

(71) Applicant: Syngenta Crop Protection AG, Basel (CH)

(72) Inventors: Qingli Liu, Durham, NC (US); Robert Arthur Dietrich, Durham, NC (US); Thomas Joseph Curley, Jr., Durham, NC (US); John Daniel Hipskind, Durham, NC (US); Becky Welsh Breitinger, Durham, NC (US); John Luther Dawson, Durham, NC (US)

(73) Assignee: SYNGENTA CROP PROTECTION AG, Basel (CH)

( * ) Notice: Subject to any disclaimer, the term of this patent is extended or adjusted under 35 U.S.C. 154(b) by 664 days.

(21) Appl. No.: 17/631,324

(22) PCT Filed: Jul. 31, 2020

(86) PCT No.: PCT/US2020/044367
§ 371 (c)(1),
(2) Date: Jan. 28, 2022

(87) PCT Pub. No.: WO2021/022101
PCT Pub. Date: Feb. 4, 2021

(65) Prior Publication Data
US 2022/0338433 A1     Oct. 27, 2022

Related U.S. Application Data

(60) Provisional application No. 62/881,035, filed on Jul. 31, 2019.

(51) Int. Cl.
*A01H 1/04* (2006.01)
*A01H 1/00* (2006.01)
(Continued)

(52) U.S. Cl.
CPC .......... *A01H 1/045* (2021.01); *A01H 1/1255* (2021.01); *A01H 6/542* (2018.05); *C12Q 1/6895* (2013.01);
(Continued)

(58) Field of Classification Search
None
See application file for complete search history.

(56) References Cited

U.S. PATENT DOCUMENTS 7,842,850 B2     11/2010  Singh
2004/0031072 A1   2/2004  La Rosa et al.
(Continued)

FOREIGN PATENT DOCUMENTS

WO      WO-2008153804 A2 *  12/2008  ............... A01H 1/02
WO      2017/222827      12/2017
WO      2019/103918      5/2019

OTHER PUBLICATIONS

Burdon & Speer ("A set of Differential Glycine Hosts for the Identification of Races of Phakopsora Pachyrhizi Syd." 1984 Euphytica 33:891-896). (Year: 1984).*
(Continued)

*Primary Examiner* — Matthew R Keogh
*Assistant Examiner* — Rebecca Stephens
(74) *Attorney, Agent, or Firm* — Suparna Kanjilal

(57) ABSTRACT

The present invention relates to methods and compositions for identifying, selecting and/or producing a Disease resistant soybean plant or germplasm using markers, genes and chromosomal intervals derived from *Glycine clandestina*, e.g. PI339656, or a progeny thereof. A soybean plant or germplasm that has been identified, selected and/or produced by any of the methods of the present invention is also
(Continued)

PI 339656 Chromosomal Mapping for SNPS Associated with ASR Resistance
Significantly Linked SNPs in Private Genome Mapped to Public Genome (Gmax_275_v2.0)[N=552 Markers]

Chr01  Chr03  Chr05  Chr07  Chr09  Chr11  Chr13  Chr15  Chr17  Chr19
Chr02  Chr04  Chr06  Chr08  Chr10  Chr12  Chr14  Chr16  Chr18  Chr20

[Broken line shows private SNPs b not scaffold 9588 mapped to single location; Solid line shows private SNPs from scaffold 14882 mapped to single location]

provided. Disease resistant soybean seeds, plants and germplasms are also provided.

3 Claims, 5 Drawing Sheets

Specification includes a Sequence Listing.

(51) Int. Cl.
*A01H 6/54* (2018.01)
*C12Q 1/6895* (2018.01)

(52) U.S. Cl.
CPC ... *C12Q 2600/13* (2013.01); *C12Q 2600/156* (2013.01)

(56) References Cited

U.S. PATENT DOCUMENTS

| | | | |
|---|---|---|---|
| 2013/0333061 A1 | 12/2013 | Wu et al. | |
| 2014/0255922 A1* | 9/2014 | Wu | C12Q 1/6895 |
| | | | 536/24.3 |
| 2015/0135359 A1* | 5/2015 | Baley | A01H 5/10 |
| | | | 800/267 |
| 2016/0272997 A1* | 9/2016 | Da Rosa | C12N 15/8271 |
| 2018/0103600 A1 | 4/2018 | Rairdan et al. | |
| 2022/0256795 A1* | 8/2022 | Liu | C12Q 1/6895 |
| 2022/0267789 A1* | 8/2022 | Liu | A01H 6/542 |

OTHER PUBLICATIONS

Hartman et al. ("Sources of Resistance to Soybean Rust in Perennial Glycine Species" 1992 Plant Disease 76(4): 396-399). (Year: 1992).*
Collard & Mackill ("Marker-assisted selection: an approach for precision plant breeding in the twenty-first century" Aug. 22, 2007 Phil. Trans. R. Soc. B 363:557-572 doi:10.1098/rstb.2007.2170; 16 total pages). (Year: 2007).*
Extended European Search Report for European U.S. Appl. No. 20/847,482 mailed Sep. 11, 2023, 9 total pages. (Year: 2023).*
International Preliminary Report on Patentability for International Application No. PCT/US2020/044367, mailed Feb. 10, 2022, 12 total pages. (Year: 2022).*
Written Opinion for International Application No. PCT/US2020/044367, mailed Feb. 15, 2021, 11 total pages. (Year: 2021).*
ISR for PCT/US2020/044367. Search dated Dec. 14, 2020.
Extended European Search Report for European Application No. 20847482.5, mailed Sep. 11, 2023, 9 Pages.
International Preliminary Report on Patentability for International Application No. PCT/US2020/044367, mailed Feb. 10, 2022, 13 Pages.
Written Opinion for International Application No. PCT/US2020/044367, mailed Jan. 22, 2021, 11 Pages.

* cited by examiner

FIG. 1: Screening of Wild Glycine Lines for Rust Resistance

FIG. 2: Rust Rating Scale

| | |
|---|---|
| RB0-NSP | No reaction to infection, or extremely small flecks/lesions |
| RB1-2-NSP | Necrotic or chlorotic flecks only, no sporulation |
| | Large or dense necrotic or chlorotic flecks only, no sporulation |
| RB3-NSP | minute uredia, large necrotic or chlorotic zones, few spores |
| RB4-SP | Small uredia with some associated necrotic or chlorotic tissues |
| TAN1-5-SP | large profusely sporelating uredia, little/no necrosis or chlorosis, 1-5 is the level of sporulations, density and severity |

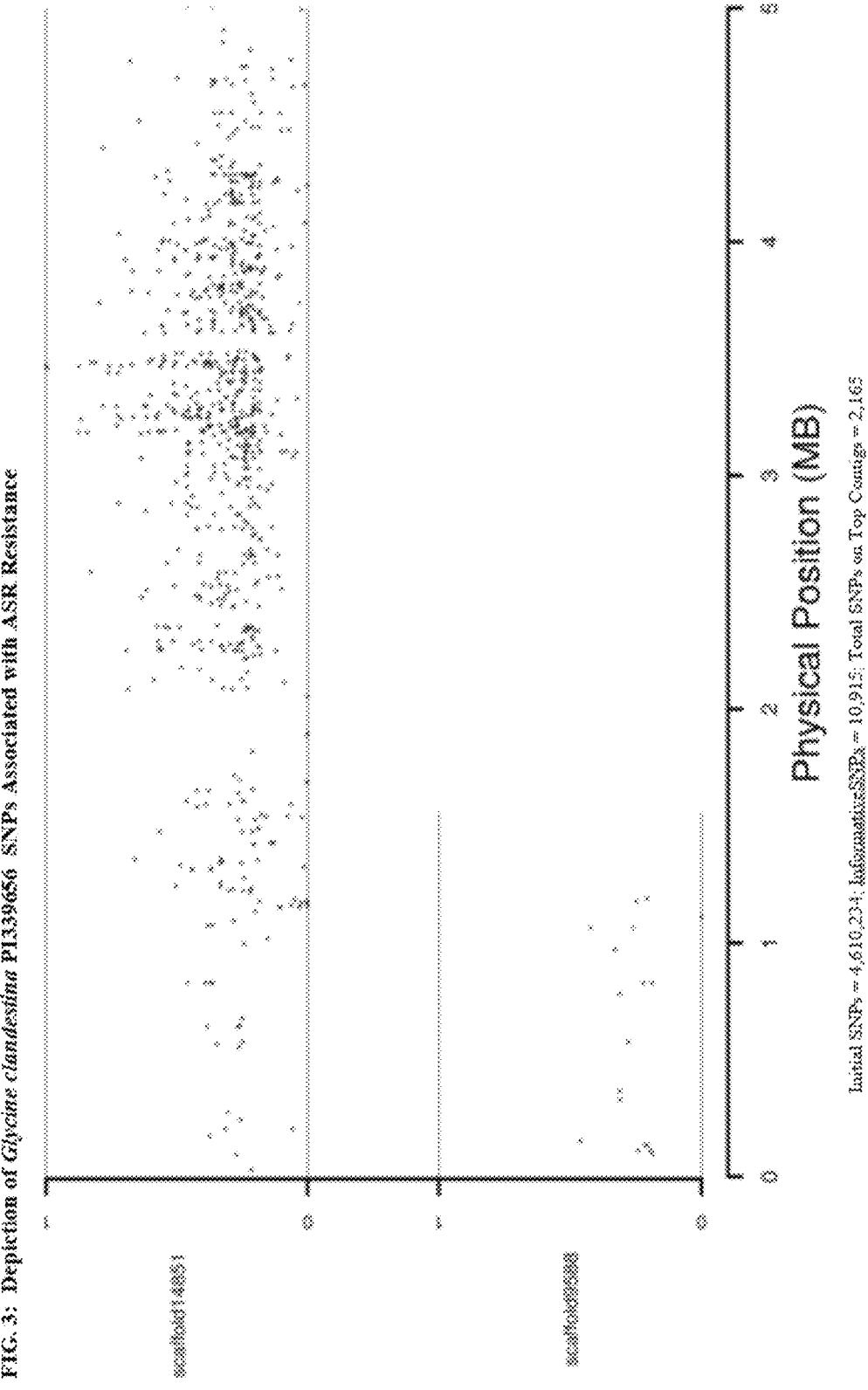
FIG. 3: Depiction of *Glycine clandestina* PI339656 SNPs Associated with ASR Resistance

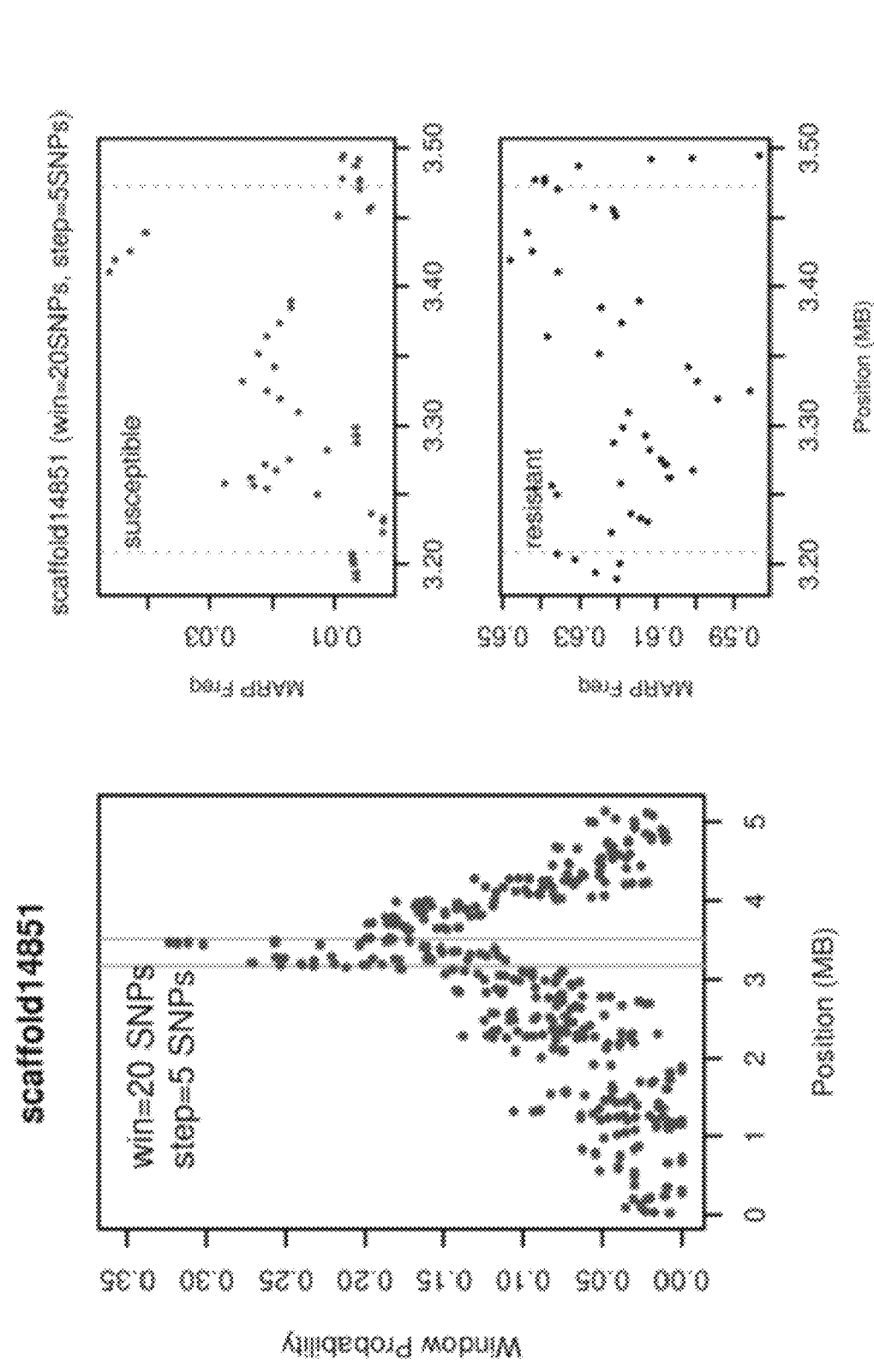
FIG. 4: Mapping Interval Discovery for Scaffold 14851 (Suggested Interval Chromosome 14: 3.18-3.5Mb)

Figure 5:
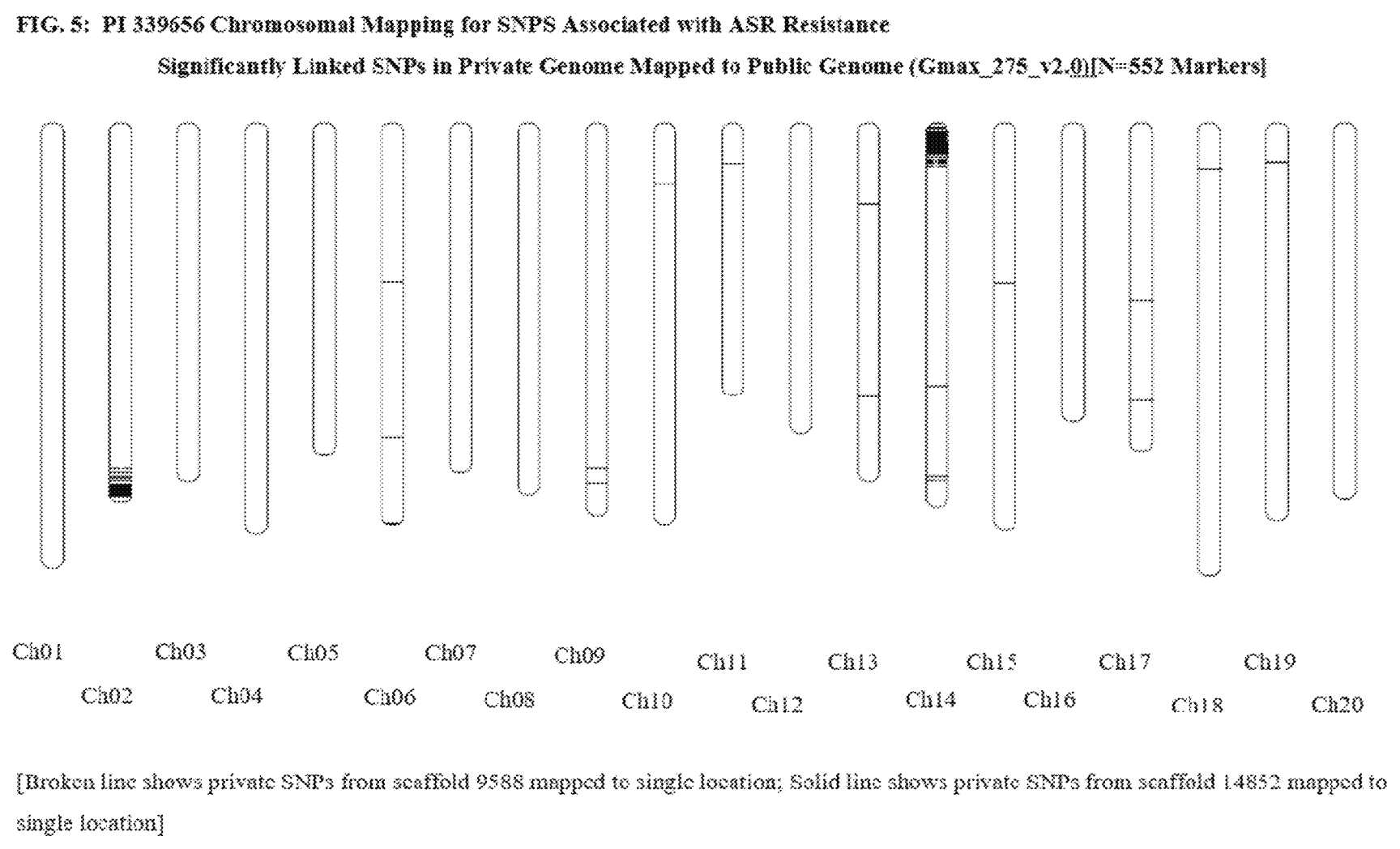

FIG. 5: PI 339656 Chromosomal Mapping for SNPS Associated with ASR Resistance

Significantly Linked SNPs in Private Genome Mapped to Public Genome (Gmax_275_v2.0)[N=552 Markers]

Ch01  Ch02  Ch03  Ch04  Ch05  Ch06  Ch07  Ch08  Ch09  Ch10  Ch11  Ch12  Ch13  Ch14  Ch15  Ch16  Ch17  Ch18  Ch19  Ch20

[Broken line shows private SNPs from scaffold 9588 mapped to single location; Solid line shows private SNPs from scaffold 14852 mapped to single location]

GENETIC LOCI ASSOCIATED WITH DISEASE RESISTANCE IN SOYBEANS

RELATED APPLICATION INFORMATION

This application is a 371 of International Application No. PCT/US2020/044367, filed 31 Jul. 2020, which claims priority to 62/881,035 filed 31 Jul. 2019, the contents of which are incorporated herein by reference herein.

FIELD OF THE INVENTION

The present invention relates to compositions and methods for identifying, selecting and producing enhanced disease and/or pathogen resistant soybean plants.

STATEMENT REGARDING ELECTRONIC SUBMISSION OF A SEQUENCE LISTING

A Sequence Listing in ASCII text format, submitted under 37 C.F.R. § 1.821, entitled "81923-US-REG-ORG-NAT-1_SeqList_ST25.txt", 6.44 MB (6,760,290 bytes) in size, generated on Jul. 31, 2019 and filed via EFS-Web is provided in lieu of a paper copy. This Sequence Listing is hereby incorporated by reference into the specification for its disclosures.

BACKGROUND

Plant pathogens are known to cause considerable damage to important crops, resulting in significant agricultural losses with widespread consequences for both the food supply and other industries that rely on plant materials. As such, there is a long felt need to reduce the incidence and/or impact of agricultural pathogens on crop production.

Several pathogens have been associated with damage to soybeans, which individually and collectively have the potential to cause significant yield losses in the United States and throughout the world. Exemplary pathogens include, but are not limited to fungi (e.g., genus *Phytophthora* and Asian Soybean rust *Phakopsora pahyrhizi*), nematodes (e.g., genus *Meloidogyne*, particularly, *Meloidogyne javanica*), and soybean stem canker. Given the significant threat to global food supplies that these pathogens present and the time and expense associated with treating soybean crops to prevent loss, new methods for producing pathogen resistant soybean cultivars are needed. What is needed is novel resistance genes (herein, "R-Genes") that can be introduced into commercial soybean plants to control soybean pathogens

SUMMARY OF THE INVENTION

This summary lists several embodiments of the presently disclosed subject matter, and in many cases lists variations of these embodiments.

Thus, it is an object of the presently disclosed subject matter to provide methods for conveying pathogen resistance into non-resistant soybean germplasm, which object is achieved in whole or in part by the presently disclosed subject matter.

BRIEF DESCRIPTION OF THE SEQUENCE LISTING

SEQ ID NO: 1 is a chromosomal intervals derived from *Glycine clandestina* line accession PI339656 referred to herein as "Scaffold 14851". Scaffold 14851 has been mapped to *G. clandestina* chromosome 14 at an approximate interval of 3.18 to 3.50 MB on Scaffold 14851. This chromosomal intervals or portions thereof may be introduced (i.e. introgressed through use of embryo rescue and/or marker assisted breeding (MAB) or transgenically into *Glycine max* lines to create *Glycine max* lines resistant to disease (e.g. Asian Soybean Rust (ASR)). In some embodiments, genes from this interval is expected to encode polypeptide(s) that may be transgenically expressed or genetically modified (i.e. gene edited via TALEN or CRISPR) in plants to confer disease resistance (e.g. Asian Soy Rust (ASR) resistance) Table 1 indicates single nucleotide polymorphisms (SNP) within SEQ ID NO: 1 that associate with ASR resistance. All alleles for the SNPs identified in Table 1 were determined to be significantly linked with resistance or susceptibility (p<0.05).

TABLE 1

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9101548 \| \| scaffold14851_3660_SNP | 3660 | T | C |
| S_9101624 \| \| scaffold14851_4916_SNP | 4916 | T | G |
| S_9101695 \| \| scaffold14851_5591_SNP | 5591 | T | A |
| S_9101714 \| \| scaffold14851_5936_SNP | 5936 | G | A |
| S_9101723 \| \| scaffold14851_5964_SNP | 5964 | C | T |
| S_9101793 \| \| scaffold14851_6357_SNP | 6357 | A | G |
| S_9101908 \| \| scaffold14851_8045_SNP | 8045 | C | T |
| S_9101915 \| \| scaffold14851_8146_SNP | 8146 | A | C |
| S_9101958 \| \| scaffold14851_8638_SNP | 8638 | A | G |
| S_9101965 \| \| scaffold14851_8849_SNP | 8849 | G | A |
| S_9101966 \| \| scaffold14851_8850_SNP | 8850 | A | T |
| S_9102048 \| \| scaffold14851_10133_SNP | 10133 | G | A |
| S_9102152 \| \| scaffold14851_10847_SNP | 10847 | G | A |
| S_9102195 \| \| scaffold14851_11463_SNP | 11463 | A | C |
| S_9102196 \| \| scaffold14851_11485_SNP | 11485 | G | C |
| S_9102198 \| \| scaffold14851_11518_SNP | 11518 | G | A |
| S_9102224 \| \| scaffold14851_11846_SNP | 11846 | A | T |
| S_9102229 \| \| scaffold14851_11956_SNP | 11956 | T | G |
| S_9102236 \| \| scaffold14851_12051_SNP | 12051 | T | A |
| S_9102250 \| \| scaffold14851_12194_SNP | 12194 | C | T |
| S_9102253 \| \| scaffold14851_12263_SNP | 12263 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9102254 \| \| scaffold14851_12273_SNP | 12273 | A | T |
| S_9102255 \| \| scaffold14851_12290_SNP | 12290 | T | A |
| S_9102478 \| \| scaffold14851_15258_SNP | 15258 | A | T |
| S_9102479 \| \| scaffold14851_15272_SNP | 15272 | C | T |
| S_9102492 \| \| scaffold14851_15462_SNP | 15462 | C | T |
| S_9102493 \| \| scaffold14851_15467_SNP | 15467 | C | T |
| S_9102497 \| \| scaffold14851_15499_SNP | 15499 | T | C |
| S_9102501 \| \| scaffold14851_15528_SNP | 15528 | C | T |
| S_9102596 \| \| scaffold14851_17027_SNP | 17027 | C | T |
| S_9102609 \| \| scaffold14851_17236_SNP | 17236 | T | A |
| S_9102700 \| \| scaffold14851_18500_SNP | 18500 | G | A |
| S_9102816 \| \| scaffold14851_19612_SNP | 19612 | G | C |
| S_9102831 \| \| scaffold14851_19897_SNP | 19897 | A | G |
| S_9102834 \| \| scaffold14851_19955_SNP | 19955 | T | C |
| S_9102835 \| \| scaffold14851_19973_SNP | 19973 | G | A |
| S_9102997 \| \| scaffold14851_21795_SNP | 21795 | A | G |
| S_9103003 \| \| scaffold14851_21853_SNP | 21853 | T | G |
| S_9103029 \| \| scaffold14851_22141_SNP | 22141 | T | C |
| S_9103088 \| \| scaffold14851_22602_SNP | 22602 | A | G |
| S_9103094 \| \| scaffold14851_22690_SNP | 22690 | A | G |
| S_9103098 \| \| scaffold14851_22765_SNP | 22765 | C | T |
| S_9103101 \| \| scaffold14851_22792_SNP | 22792 | T | A |
| S_9103103 \| \| scaffold14851_22802_SNP | 22802 | T | C |
| S_9103106 \| \| scaffold14851_22856_SNP | 22856 | G | A |
| S_9103125 \| \| scaffold14851_23000_SNP | 23000 | T | G |
| S_9103131 \| \| scaffold14851_23028_SNP | 23028 | C | A |
| S_9103132 \| \| scaffold14851_23034_SNP | 23034 | C | T |
| S_9103183 \| \| scaffold14851_23790_SNP | 23790 | A | T |
| S_9103185 \| \| scaffold14851_23822_SNP | 23822 | A | G |
| S_9103311 \| \| scaffold14851_25521_SNP | 25521 | G | T |
| S_9103336 \| \| scaffold14851_26070_SNP | 26070 | A | C |
| S_9103360 \| \| scaffold14851_26409_SNP | 26409 | T | C |
| S_9103394 \| \| scaffold14851_26715_SNP | 26715 | T | C |
| S_9103395 \| \| scaffold14851_26722_SNP | 26722 | G | T |
| S_9103405 \| \| scaffold14851_26886_SNP | 26886 | G | T |
| S_9103428 \| \| scaffold14851_27158_SNP | 27158 | T | A |
| S_9103449 \| \| scaffold14851_27369_SNP | 27369 | C | T |
| S_9103545 \| \| scaffold14851_28688_SNP | 28688 | T | C |
| S_9103547 \| \| scaffold14851_28693_SNP | 28693 | C | G |
| S_9103572 \| \| scaffold14851_29075_SNP | 29075 | T | G |
| S_9103573 \| \| scaffold14851_29095_SNP | 29095 | G | A |
| S_9103711 \| \| scaffold14851_31375_SNP | 31375 | T | C |
| S_9103717 \| \| scaffold14851_31522_SNP | 31522 | C | T |
| S_9103727 \| \| scaffold14851_31712_SNP | 31712 | C | G |
| S_9103910 \| \| scaffold14851_33901_SNP | 33901 | T | C |
| S_9103930 \| \| scaffold14851_34159_SNP | 34159 | G | A |
| S_9103975 \| \| scaffold14851_34788_SNP | 34788 | G | A |
| S_9104008 \| \| scaffold14851_35433_SNP | 35433 | G | T |
| S_9104009 \| \| scaffold14851_35447_SNP | 35447 | G | C |
| S_9104027 \| \| scaffold14851_35728_SNP | 35728 | A | G |
| S_9104028 \| \| scaffold14851_35732_SNP | 35732 | A | G |
| S_9104054 \| \| scaffold14851_36288_SNP | 36288 | T | A |
| S_9104093 \| \| scaffold14851_36783_SNP | 36783 | G | T |
| S_9104106 \| \| scaffold14851_37111_SNP | 37111 | A | G |
| S_9104487 \| \| scaffold14851_41584_SNP | 41584 | T | C |
| S_9104715 \| \| scaffold14851_44891_SNP | 44891 | A | T |
| S_9104748 \| \| scaffold14851_45503_SNP | 45503 | T | G |
| S_9104975 \| \| scaffold14851_48280_SNP | 48280 | A | C |
| S_9104996 \| \| scaffold14851_48646_SNP | 48646 | T | G |
| S_9105000 \| \| scaffold14851_48759_SNP | 48759 | C | A |
| S_9105220 \| \| scaffold14851_51087_SNP | 51087 | C | T |
| S_9105230 \| \| scaffold14851_51159_SNP | 51159 | T | G |
| scaffold14851_51786_SNP | 51786 | A | G |
| S_9105282 \| \| scaffold14851_51816_SNP | 51816 | A | G |
| S_9105380 \| \| scaffold14851_53311_SNP | 53311 | C | G |
| S_9105385 \| \| scaffold14851_53387_SNP | 53387 | G | C |
| S_9105393 \| \| scaffold14851_53494_SNP | 53494 | G | T |
| S_9105420 \| \| scaffold14851_53829_SNP | 53829 | T | C |
| S_9105818 \| \| scaffold14851_59533_SNP | 59533 | A | C |
| S_9105830 \| \| scaffold14851_59807_SNP | 59807 | T | C |
| S_9105831 \| \| scaffold14851_59808_SNP | 59808 | G | A |
| S_9105866 \| \| scaffold14851_60355_SNP | 60355 | G | A |
| S_9105886 \| \| scaffold14851_60673_SNP | 60673 | T | C |
| S_9105999 \| \| scaffold14851_61299_SNP | 61299 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9106000 \| \| scaffold14851_61300_SNP | 61300 | C | G |
| S_9106002 \| \| scaffold14851_61341_SNP | 61341 | T | C |
| S_9106010 \| \| scaffold14851_61461_SNP | 61461 | G | T |
| S_9106105 \| \| scaffold14851_62776_SNP | 62776 | T | G |
| S_9106128 \| \| scaffold14851_62877_SNP | 62877 | G | A |
| S_9106131 \| \| scaffold14851_62911_SNP | 62911 | T | G |
| S_9106136 \| \| scaffold14851_62934_SNP | 62934 | G | T |
| S_9106220 \| \| scaffold14851_64304_SNP | 64304 | A | G |
| S_9106235 \| \| scaffold14851_64510_SNP | 64510 | C | G |
| S_9106340 \| \| scaffold14851_65613_SNP | 65613 | C | T |
| S_9106377 \| \| scaffold14851_66281_SNP | 66281 | C | A |
| S_9106383 \| \| scaffold14851_66359_SNP | 66359 | A | C |
| S_9106409 \| \| scaffold14851_66622_SNP | 66622 | T | G |
| S_9106418 \| \| scaffold14851_66702_SNP | 66702 | A | G |
| S_9106471 \| \| scaffold14851_67357_SNP | 67357 | T | G |
| S_9106646 \| \| scaffold14851_69492_SNP | 69492 | A | G |
| S_9106654 \| \| scaffold14851_69598_SNP | 69598 | A | G |
| S_9106684 \| \| scaffold14851_70118_SNP | 70118 | T | A |
| S_9106693 \| \| scaffold14851_70213_SNP | 70213 | G | C |
| S_9106740 \| \| scaffold14851_70796_SNP | 70796 | A | G |
| S_9106938 \| \| scaffold14851_73249_SNP | 73249 | T | C |
| S_9106979 \| \| scaffold14851_73945_SNP | 73945 | A | T |
| S_9106983 \| \| scaffold14851_73975_SNP | 73975 | T | A |
| S_9106995 \| \| scaffold14851_74161_SNP | 74161 | T | A |
| S_9107002 \| \| scaffold14851_74325_SNP | 74325 | G | A |
| S_9107050 \| \| scaffold14851_75069_SNP | 75069 | G | A |
| S_9107106 \| \| scaffold14851_75877_SNP | 75877 | A | C |
| S_9107243 \| \| scaffold14851_77407_SNP | 77407 | A | T |
| S_9107277 \| \| scaffold14851_77779_SNP | 77779 | G | T |
| S_9107288 \| \| scaffold14851_77993_SNP | 77993 | G | A |
| S_9107312 \| \| scaffold14851_78103_SNP | 78103 | T | A |
| S_9107339 \| \| scaffold14851_78607_SNP | 78607 | T | A |
| S_9107372 \| \| scaffold14851_79277_SNP | 79277 | C | T |
| S_9107374 \| \| scaffold14851_79283_SNP | 79283 | G | A |
| S_9107382 \| \| scaffold14851_79421_SNP | 79421 | A | T |
| S_9107383 \| \| scaffold14851_79429_SNP | 79429 | A | G |
| S_9107421 \| \| scaffold14851_79800_SNP | 79800 | A | G |
| S_9107437 \| \| scaffold14851_80132_SNP | 80132 | C | T |
| S_9107453 \| \| scaffold14851_80396_SNP | 80396 | T | C |
| S_9107472 \| \| scaffold14851_80592_SNP | 80592 | A | G |
| S_9107521 \| \| scaffold14851_81046_SNP | 81046 | A | C |
| S_9107838 \| \| scaffold14851_84321_SNP | 84321 | C | T |
| S_9107840 \| \| scaffold14851_84337_SNP | 84337 | A | G |
| S_9107853 \| \| scaffold14851_84464_SNP | 84464 | A | G |
| S_9107856 \| \| scaffold14851_84480_SNP | 84480 | C | T |
| S_9107869 \| \| scaffold14851_84637_SNP | 84637 | G | A |
| S_9107870 \| \| scaffold14851_84640_SNP | 84640 | C | T |
| S_9107871 \| \| scaffold14851_84643_SNP | 84643 | C | T |
| S_9108036 \| \| scaffold14851_85719_SNP | 85719 | G | A |
| S_9108093 \| \| scaffold14851_86230_SNP | 86230 | T | C |
| S_9108129 \| \| scaffold14851_86746_SNP | 86746 | G | A |
| S_9108147 \| \| scaffold14851_87098_SNP | 87098 | G | A |
| S_9108210 \| \| scaffold14851_88001_SNP | 88001 | C | G |
| S_9108215 \| \| scaffold14851_88078_SNP | 88078 | C | A |
| S_9108254 \| \| scaffold14851_88580_SNP | 88580 | G | A |
| S_9108258 \| \| scaffold14851_88616_SNP | 88616 | A | T |
| S_9108374 \| \| scaffold14851_89544_SNP | 89544 | G | A |
| S_9108379 \| \| scaffold14851_89630_SNP | 89630 | T | G |
| S_9108393 \| \| scaffold14851_89771_SNP | 89771 | A | T |
| S_9108397 \| \| scaffold14851_89805_SNP | 89805 | A | T |
| S_9108489 \| \| scaffold14851_90808_SNP | 90808 | C | A |
| S_9108510 \| \| scaffold14851_91042_SNP | 91042 | C | A |
| S_9108552 \| \| scaffold14851_91634_SNP | 91634 | C | T |
| S_9108553 \| \| scaffold14851_91635_SNP | 91635 | C | T |
| S_9108561 \| \| scaffold14851_91811_SNP | 91811 | A | G |
| S_9108599 \| \| scaffold14851_92509_SNP | 92509 | A | G |
| S_9108600 \| \| scaffold14851_92510_SNP | 92510 | T | A |
| S_9108639 \| \| scaffold14851_92972_SNP | 92972 | C | G |
| S_9108663 \| \| scaffold14851_93254_SNP | 93254 | A | C |
| S_9108665 \| \| scaffold14851_93287_SNP | 93287 | T | A |
| S_9108667 \| \| scaffold14851_93302_SNP | 93302 | G | A |
| S_9108672 \| \| scaffold14851_93347_SNP | 93347 | G | A |
| S_9108840 \| \| scaffold14851_95114_SNP | 95114 | C | A |
| S_9108843 \| \| scaffold14851_95144_SNP | 95144 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9108844 \| \| scaffold14851_95167_SNP | 95167 | A | G |
| S_9108962 \| \| scaffold14851_96063_SNP | 96063 | G | A |
| S_9108965 \| \| scaffold14851_96162_SNP | 96162 | G | T |
| S_9108967 \| \| scaffold14851_96254_SNP | 96254 | A | T |
| S_9109058 \| \| scaffold14851_97640_SNP | 97640 | G | A |
| S_9109076 \| \| scaffold14851_97887_SNP | 97887 | C | T |
| S_9109093 \| \| scaffold14851_98078_SNP | 98078 | T | G |
| S_9109224 \| \| scaffold14851_101273_SNP | 101273 | G | T |
| S_9109387 \| \| scaffold14851_105359_SNP | 105359 | C | T |
| S_9109457 \| \| scaffold14851_106071_SNP | 106071 | A | G |
| S_9109822 \| \| scaffold14851_109392_SNP | 109392 | A | G |
| S_9109994 \| \| scaffold14851_111503_SNP | 111503 | G | A |
| S_9110003 \| \| scaffold14851_111729_SNP | 111729 | T | C |
| S_9110021 \| \| scaffold14851_112028_SNP | 112028 | T | A |
| S_9110123 \| \| scaffold14851_113183_SNP | 113183 | C | T |
| S_9110124 \| \| scaffold14851_113185_SNP | 113185 | A | T |
| S_9110154 \| \| scaffold14851_113720_SNP | 113720 | T | C |
| S_9110202 \| \| scaffold14851_114457_SNP | 114457 | G | A |
| S_9110226 \| \| scaffold14851_115063_SNP | 115063 | A | G |
| S_9110231 \| \| scaffold14851_115097_SNP | 115097 | G | A |
| S_9110234 \| \| scaffold14851_115132_SNP | 115132 | T | A |
| S_9110261 \| \| scaffold14851_115414_SNP | 115414 | G | T |
| S_9110267 \| \| scaffold14851_115440_SNP | 115440 | G | T |
| S_9110329 \| \| scaffold14851_115865_SNP | 115865 | T | C |
| S_9110330 \| \| scaffold14851_115907_SNP | 115907 | A | C |
| S_9110331 \| \| scaffold14851_115910_SNP | 115910 | T | A |
| S_9110348 \| \| scaffold14851_116144_SNP | 116144 | C | A |
| S_9110359 \| \| scaffold14851_116271_SNP | 116271 | G | C |
| S_9110398 \| \| scaffold14851_116676_SNP | 116676 | G | T |
| S_9110550 \| \| scaffold14851_118844_SNP | 118844 | G | A |
| S_9110593 \| \| scaffold14851_119667_SNP | 119667 | A | G |
| S_9110619 \| \| scaffold14851_119964_SNP | 119964 | C | A |
| S_9110671 \| \| scaffold14851_120680_SNP | 120680 | C | G |
| S_9110682 \| \| scaffold14851_120850_SNP | 120850 | T | C |
| S_9110695 \| \| scaffold14851_121031_SNP | 121031 | A | C |
| S_9110703 \| \| scaffold14851_121204_SNP | 121204 | T | C |
| S_9110720 \| \| scaffold14851_121633_SNP | 121633 | C | A |
| S_9110724 \| \| scaffold14851_121650_SNP | 121650 | G | A |
| S_9110929 \| \| scaffold14851_123608_SNP | 123608 | A | T |
| S_9110958 \| \| scaffold14851_123851_SNP | 123851 | A | G |
| scaffold14851_124068_SNP | 124068 | A | G |
| S_9111236 \| \| scaffold14851_124759_SNP | 124759 | C | T |
| S_9111609 \| \| scaffold14851_128383_SNP | 128383 | A | T |
| S_9111617 \| \| scaffold14851_128692_SNP | 128692 | G | A |
| S_9111641 \| \| scaffold14851_128920_SNP | 128920 | C | T |
| S_9111643 \| \| scaffold14851_128926_SNP | 128926 | G | A |
| S_9111658 \| \| scaffold14851_128969_SNP | 128969 | G | A |
| S_9111727 \| \| scaffold14851_129913_SNP | 129913 | T | A |
| S_9111856 \| \| scaffold14851_132830_SNP | 132830 | A | G |
| S_9111889 \| \| scaffold14851_133233_SNP | 133233 | A | G |
| S_9111890 \| \| scaffold14851_133248_SNP | 133248 | C | T |
| S_9111892 \| \| scaffold14851_133284_SNP | 133284 | T | A |
| S_9111933 \| \| scaffold14851_133957_SNP | 133957 | T | C |
| S_9111936 \| \| scaffold14851_133986_SNP | 133986 | T | C |
| S_9111987 \| \| scaffold14851_134471_SNP | 134471 | A | G |
| scaffold14851_136653_SNP | 136653 | T | C |
| scaffold14851_136700_SNP | 136700 | A | G |
| S_9112204 \| \| scaffold14851_136749_SNP | 136749 | G | A |
| S_9112206 \| \| scaffold14851_136762_SNP | 136762 | A | C |
| S_9112208 \| \| scaffold14851_136776_SNP | 136776 | T | C |
| S_9112210 \| \| scaffold14851_136792_SNP | 136792 | T | C |
| S_9112240 \| \| scaffold14851_137009_SNP | 137009 | A | C |
| S_9112270 \| \| scaffold14851_137334_SNP | 137334 | G | T |
| S_9112277 \| \| scaffold14851_137454_SNP | 137454 | T | C |
| S_9112278 \| \| scaffold14851_137458_SNP | 137458 | G | A |
| scaffold14851_137644_SNP | 137644 | T | C |
| scaffold14851_138141_SNP | 138141 | A | C |
| scaffold14851_138144_SNP | 138144 | C | T |
| S_9112986 \| \| scaffold14851_141031_SNP | 141031 | A | G |
| S_9112996 \| \| scaffold14851_141167_SNP | 141167 | T | A |
| S_9113228 \| \| scaffold14851_143952_SNP | 143952 | G | A |
| S_9113290 \| \| scaffold14851_144707_SNP | 144707 | T | G |
| S_9113405 \| \| scaffold14851_146060_SNP | 146060 | G | A |
| S_9113412 \| \| scaffold14851_146167_SNP | 146167 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9113570 \| \| scaffold14851_148538_SNP | 148538 | T | G |
| S_9113582 \| \| scaffold14851_148731_SNP | 148731 | C | T |
| S_9113728 \| \| scaffold14851_150853_SNP | 150853 | G | A |
| S_9113949 \| \| scaffold14851_154714_SNP | 154714 | A | G |
| scaffold14851_158439_SNP | 158439 | A | G |
| S_9114145 \| \| scaffold14851_158445_SNP | 158445 | A | T |
| S_9114151 \| \| scaffold14851_158710_SNP | 158710 | A | T |
| S_9114154 \| \| scaffold14851_158743_SNP | 158743 | A | G |
| S_9114159 \| \| scaffold14851_158830_SNP | 158830 | G | A |
| S_9114165 \| \| scaffold14851_158944_SNP | 158944 | T | G |
| S_9114167 \| \| scaffold14851_158957_SNP | 158957 | C | G |
| S_9114260 \| \| scaffold14851_159409_SNP | 159409 | C | T |
| S_9114432 \| \| scaffold14851_161394_SNP | 161394 | G | A |
| S_9114588 \| \| scaffold14851_163173_SNP | 163173 | G | A |
| S_9114613 \| \| scaffold14851_163471_SNP | 163471 | G | A |
| S_9114916 \| \| scaffold14851_167422_SNP | 167422 | G | A |
| S_9114929 \| \| scaffold14851_167617_SNP | 167617 | A | G |
| S_9115007 \| \| scaffold14851_167860_SNP | 167860 | G | A |
| S_9115010 \| \| scaffold14851_167877_SNP | 167877 | T | A |
| S_9115084 \| \| scaffold14851_168709_SNP | 168709 | C | T |
| S_9115172 \| \| scaffold14851_169754_SNP | 169754 | T | G |
| S_9115202 \| \| scaffold14851_170006_SNP | 170006 | C | T |
| S_9115210 \| \| scaffold14851_170164_SNP | 170164 | A | C |
| S_9115227 \| \| scaffold14851_170478_SNP | 170478 | T | A |
| S_9115235 \| \| scaffold14851_170618_SNP | 170618 | T | G |
| S_9115236 \| \| scaffold14851_170654_SNP | 170654 | C | T |
| S_9115241 \| \| scaffold14851_170752_SNP | 170752 | T | C |
| S_9115243 \| \| scaffold14851_170793_SNP | 170793 | A | G |
| S_9115246 \| \| scaffold14851_170846_SNP | 170846 | G | A |
| S_9115250 \| \| scaffold14851_170931_SNP | 170931 | T | C |
| S_9115252 \| \| scaffold14851_170977_SNP | 170977 | T | C |
| S_9115472 \| \| scaffold14851_171642_SNP | 171642 | G | A |
| S_9115490 \| \| scaffold14851_171927_SNP | 171927 | C | T |
| S_9115491 \| \| scaffold14851_171933_SNP | 171933 | G | A |
| S_9115571 \| \| scaffold14851_173349_SNP | 173349 | T | A |
| S_9115626 \| \| scaffold14851_174121_SNP | 174121 | T | A |
| S_9115732 \| \| scaffold14851_175869_SNP | 175869 | C | A |
| S_9115749 \| \| scaffold14851_176118_SNP | 176118 | A | G |
| S_9115750 \| \| scaffold14851_176133_SNP | 176133 | C | G |
| S_9115760 \| \| scaffold14851_176229_SNP | 176229 | T | A |
| S_9115826 \| \| scaffold14851_177472_SNP | 177472 | C | A |
| S_9115832 \| \| scaffold14851_177537_SNP | 177537 | T | C |
| S_9115855 \| \| scaffold14851_177941_SNP | 177941 | C | T |
| S_9115863 \| \| scaffold14851_178119_SNP | 178119 | A | G |
| S_9115868 \| \| scaffold14851_178207_SNP | 178207 | A | T |
| S_9115885 \| \| scaffold14851_178522_SNP | 178522 | A | G |
| S_9115887 \| \| scaffold14851_178551_SNP | 178551 | C | T |
| S_9115938 \| \| scaffold14851_179498_SNP | 179498 | C | T |
| S_9115941 \| \| scaffold14851_179552_SNP | 179552 | T | G |
| S_9116111 \| \| scaffold14851_181340_SNP | 181340 | A | G |
| S_9116126 \| \| scaffold14851_181587_SNP | 181587 | T | C |
| S_9116245 \| \| scaffold14851_182434_SNP | 182434 | A | C |
| S_9116252 \| \| scaffold14851_182461_SNP | 182461 | T | G |
| S_9116260 \| \| scaffold14851_182599_SNP | 182599 | G | C |
| S_9116278 \| \| scaffold14851_182916_SNP | 182916 | G | A |
| S_9116299 \| \| scaffold14851_183113_SNP | 183113 | G | A |
| S_9116326 \| \| scaffold14851_183533_SNP | 183533 | T | C |
| S_9116330 \| \| scaffold14851_183590_SNP | 183590 | T | A |
| S_9116464 \| \| scaffold14851_185878_SNP | 185878 | C | A |
| S_9116468 \| \| scaffold14851_185938_SNP | 185938 | G | A |
| S_9116476 \| \| scaffold14851_186146_SNP | 186146 | C | T |
| S_9116477 \| \| scaffold14851_186158_SNP | 186158 | T | G |
| S_9116666 \| \| scaffold14851_188346_SNP | 188346 | A | G |
| S_9116711 \| \| scaffold14851_189085_SNP | 189085 | A | T |
| S_9116939 \| \| scaffold14851_192255_SNP | 192255 | G | A |
| S_9117225 \| \| scaffold14851_195663_SNP | 195663 | A | C |
| S_9117227 \| \| scaffold14851_195715_SNP | 195715 | G | C |
| S_9117256 \| \| scaffold14851_196171_SNP | 196171 | G | A |
| S_9117271 \| \| scaffold14851_196318_SNP | 196318 | A | C |
| S_9117357 \| \| scaffold14851_197099_SNP | 197099 | A | T |
| S_9117358 \| \| scaffold14851_197112_SNP | 197112 | G | T |
| S_9117373 \| \| scaffold14851_197370_SNP | 197370 | A | C |
| S_9117377 \| \| scaffold14851_197427_SNP | 197427 | T | G |
| S_9117397 \| \| scaffold14851_197799_SNP | 197799 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9117423 \| \| scaffold14851_198177_SNP | 198177 | A | T |
| S_9117437 \| \| scaffold14851_198536_SNP | 198536 | G | A |
| S_9117483 \| \| scaffold14851_199218_SNP | 199218 | A | G |
| S_9117499 \| \| scaffold14851_199524_SNP | 199524 | T | C |
| S_9117501 \| \| scaffold14851_199549_SNP | 199549 | A | G |
| S_9117509 \| \| scaffold14851_199777_SNP | 199777 | A | G |
| S_9117599 \| \| scaffold14851_201986_SNP | 201986 | G | T |
| S_9117601 \| \| scaffold14851_201993_SNP | 201993 | A | T |
| S_9117603 \| \| scaffold14851_202011_SNP | 202011 | A | T |
| S_9117605 \| \| scaffold14851_202042_SNP | 202042 | T | A |
| S_9117606 \| \| scaffold14851_202059_SNP | 202059 | C | A |
| S_9117655 \| \| scaffold14851_202742_SNP | 202742 | A | C |
| S_9117725 \| \| scaffold14851_203819_SNP | 203819 | T | C |
| S_9117789 \| \| scaffold14851_204813_SNP | 204813 | T | C |
| S_9118058 \| \| scaffold14851_207263_SNP | 207263 | C | A |
| S_9118065 \| \| scaffold14851_207405_SNP | 207405 | C | G |
| S_9118100 \| \| scaffold14851_207828_SNP | 207828 | A | T |
| S_9118120 \| \| scaffold14851_208111_SNP | 208111 | C | T |
| S_9118139 \| \| scaffold14851_208348_SNP | 208348 | T | A |
| S_9118141 \| \| scaffold14851_208380_SNP | 208380 | T | A |
| S_9118165 \| \| scaffold14851_208619_SNP | 208619 | C | T |
| S_9118248 \| \| scaffold14851_209819_SNP | 209819 | A | G |
| S_9118251 \| \| scaffold14851_209847_SNP | 209847 | C | T |
| S_9118403 \| \| scaffold14851_211195_SNP | 211195 | G | A |
| S_9118452 \| \| scaffold14851_212035_SNP | 212035 | G | A |
| S_9118453 \| \| scaffold14851_212042_SNP | 212042 | G | C |
| S_9118465 \| \| scaffold14851_212161_SNP | 212161 | A | T |
| S_9118497 \| \| scaffold14851_212821_SNP | 212821 | A | C |
| S_9118506 \| \| scaffold14851_212911_SNP | 212911 | A | T |
| S_9118514 \| \| scaffold14851_213081_SNP | 213081 | A | C |
| S_9118515 \| \| scaffold14851_213130_SNP | 213130 | A | G |
| S_9118525 \| \| scaffold14851_213266_SNP | 213266 | C | A |
| S_9118620 \| \| scaffold14851_214897_SNP | 214897 | T | C |
| S_9118624 \| \| scaffold14851_214943_SNP | 214943 | C | T |
| S_9118672 \| \| scaffold14851_215692_SNP | 215692 | C | T |
| S_9118674 \| \| scaffold14851_215698_SNP | 215698 | C | A |
| S_9118700 \| \| scaffold14851_216037_SNP | 216037 | C | T |
| S_9118707 \| \| scaffold14851_216120_SNP | 216120 | T | C |
| S_9118768 \| \| scaffold14851_217077_SNP | 217077 | C | T |
| S_9118769 \| \| scaffold14851_217089_SNP | 217089 | G | C |
| S_9118780 \| \| scaffold14851_217300_SNP | 217300 | A | G |
| S_9118782 \| \| scaffold14851_217314_SNP | 217314 | G | C |
| S_9118784 \| \| scaffold14851_217347_SNP | 217347 | A | G |
| S_9118814 \| \| scaffold14851_217789_SNP | 217789 | T | A |
| S_9118861 \| \| scaffold14851_218824_SNP | 218824 | T | A |
| S_9118902 \| \| scaffold14851_219798_SNP | 219798 | G | T |
| S_9118903 \| \| scaffold14851_219807_SNP | 219807 | G | T |
| S_9119052 \| \| scaffold14851_220953_SNP | 220953 | T | C |
| S_9119065 \| \| scaffold14851_221188_SNP | 221188 | C | T |
| S_9119098 \| \| scaffold14851_221607_SNP | 221607 | A | T |
| S_9119196 \| \| scaffold14851_222838_SNP | 222838 | A | C |
| S_9119229 \| \| scaffold14851_223550_SNP | 223550 | T | C |
| S_9119231 \| \| scaffold14851_223561_SNP | 223561 | A | G |
| S_9119232 \| \| scaffold14851_223576_SNP | 223576 | G | A |
| S_9119293 \| \| scaffold14851_224502_SNP | 224502 | T | G |
| S_9119312 \| \| scaffold14851_224873_SNP | 224873 | C | T |
| S_9119345 \| \| scaffold14851_225572_SNP | 225572 | T | C |
| S_9119484 \| \| scaffold14851_227137_SNP | 227137 | G | A |
| S_9119664 \| \| scaffold14851_229315_SNP | 229315 | T | C |
| S_9119679 \| \| scaffold14851_229491_SNP | 229491 | G | A |
| S_9119680 \| \| scaffold14851_229592_SNP | 229592 | G | A |
| S_9120065 \| \| scaffold14851_234463_SNP | 234463 | C | A |
| S_9120075 \| \| scaffold14851_234596_SNP | 234596 | A | G |
| S_9120129 \| \| scaffold14851_235664_SNP | 235664 | A | C |
| S_9120130 \| \| scaffold14851_235682_SNP | 235682 | A | T |
| S_9120134 \| \| scaffold14851_235800_SNP | 235800 | T | A |
| S_9120135 \| \| scaffold14851_235802_SNP | 235802 | G | A |
| S_9120138 \| \| scaffold14851_235947_SNP | 235947 | C | T |
| S_9120145 \| \| scaffold14851_236009_SNP | 236009 | C | T |
| S_9120273 \| \| scaffold14851_237748_SNP | 237748 | C | T |
| S_9120276 \| \| scaffold14851_237771_SNP | 237771 | C | G |
| S_9120359 \| \| scaffold14851_239260_SNP | 239260 | A | G |
| S_9120374 \| \| scaffold14851_239503_SNP | 239503 | C | G |
| S_9120376 \| \| scaffold14851_239529_SNP | 239529 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9120377 \| \| scaffold14851_239552_SNP | 239552 | G | A |
| S_9120455 \| \| scaffold14851_240480_SNP | 240480 | G | T |
| S_9120459 \| \| scaffold14851_240526_SNP | 240526 | C | T |
| S_9120464 \| \| scaffold14851_240574_SNP | 240574 | A | G |
| S_9120466 \| \| scaffold14851_240582_SNP | 240582 | C | A |
| S_9120468 \| \| scaffold14851_240600_SNP | 240600 | G | A |
| S_9120495 \| \| scaffold14851_240827_SNP | 240827 | A | G |
| S_9120497 \| \| scaffold14851_240855_SNP | 240855 | C | G |
| S_9120501 \| \| scaffold14851_240906_SNP | 240906 | C | G |
| S_9120514 \| \| scaffold14851_241083_SNP | 241083 | A | T |
| S_9120850 \| \| scaffold14851_244081_SNP | 244081 | T | C |
| S_9120870 \| \| scaffold14851_244274_SNP | 244274 | T | A |
| S_9120887 \| \| scaffold14851_244510_SNP | 244510 | C | G |
| S_9120938 \| \| scaffold14851_245488_SNP | 245488 | A | G |
| S_9121354 \| \| scaffold14851_250765_SNP | 250765 | A | G |
| $_9121381 \| \| scaffold14851_251251_SNP | 251251 | A | T |
| S_9121382 \| \| scaffold14851_251252_SNP | 251252 | G | A |
| S_9121432 \| \| scaffold14851_251890_SNP | 251890 | T | C |
| S_9121459 \| \| scaffold14851_252248_SNP | 252248 | C | T |
| S_9121462 \| \| scaffold14851_252338_SNP | 252338 | G | T |
| S_9121463 \| \| scaffold14851_252354_SNP | 252354 | C | T |
| S_9121468 \| \| scaffold14851_252427_SNP | 252427 | T | A |
| S_9121470 \| \| scaffold14851_252445_SNP | 252445 | T | C |
| S_9121471 \| \| scaffold14851_252506_SNP | 252506 | T | G |
| S_9121489 \| \| scaffold14851_252827_SNP | 252827 | A | C |
| S_9121490 \| \| scaffold14851_252853_SNP | 252853 | C | G |
| S_9121521 \| \| scaffold14851_253221_SNP | 253221 | A | C |
| S_9121571 \| \| scaffold14851_253738_SNP | 253738 | T | A |
| S_9121630 \| \| scaffold14851_254897_SNP | 254897 | A | T |
| S_9121631 \| \| scaffold14851_254907_SNP | 254907 | A | G |
| S_9121633 \| \| scaffold14851_254944_SNP | 254944 | C | T |
| S_9121637 \| \| scaffold14851_254993_SNP | 254993 | A | G |
| S_9121638 \| \| scaffold14851_255054_SNP | 255054 | G | T |
| S_9121692 \| \| scaffold14851_255319_SNP | 255319 | G | A |
| S_9121693 \| \| scaffold14851_255320_SNP | 255320 | A | T |
| S_9121694 \| \| scaffold14851_255321_SNP | 255321 | T | G |
| S_9121695 \| \| scaffold14851_255323_SNP | 255323 | C | A |
| S_9121716 \| \| scaffold14851_255610_SNP | 255610 | A | G |
| S_9121748 \| \| scaffold14851_256108_SNP | 256108 | C | T |
| S_9121764 \| \| scaffold14851_256230_SNP | 256230 | G | T |
| S_9121866 \| \| scaffold14851_257222_SNP | 257222 | T | C |
| S_9121871 \| \| scaffold14851_257470_SNP | 257470 | G | A |
| S_9121934 \| \| scaffold14851_258042_SNP | 258042 | C | T |
| S_9121941 \| \| scaffold14851_258178_SNP | 258178 | G | A |
| S_9121963 \| \| scaffold14851_258431_SNP | 258431 | C | G |
| S_9121964 \| \| scaffold14851_258434_SNP | 258434 | G | A |
| S_9121965 \| \| scaffold14851_258438_SNP | 258438 | C | T |
| S_9121969 \| \| scaffold14851_258473_SNP | 258473 | C | T |
| S_9121971 \| \| scaffold14851_258488_SNP | 258488 | C | T |
| S_9121973 \| \| scaffold14851_258512_SNP | 258512 | C | A |
| S_9121974 \| \| scaffold14851_258535_SNP | 258535 | A | G |
| S_9122017 \| \| scaffold14851_259210_SNP | 259210 | A | G |
| S_9122051 \| \| scaffold14851_259421_SNP | 259421 | G | C |
| S_9122055 \| \| scaffold14851_259443_SNP | 259443 | A | G |
| scaffold14851_259510_SNP | 259510 | T | C |
| scaffold14851_259524_SNP | 259524 | A | G |
| scaffold14851_259531_SNP | 259531 | C | A |
| S_9122245 \| \| scaffold14851_260142_SNP | 260142 | C | G |
| S_9122458 \| \| scaffold14851_261948_SNP | 261948 | C | T |
| S_9122573 \| \| scaffold14851_263314_SNP | 263314 | G | T |
| S_9122586 \| \| scaffold14851_263464_SNP | 263464 | G | A |
| S_9122638 \| \| scaffold14851_263973_SNP | 263973 | T | G |
| S_9123163 \| \| scaffold14851_270089_SNP | 270089 | C | G |
| S_9123176 \| \| scaffold14851_270422_SNP | 270422 | T | A |
| S_9123217 \| \| scaffold14851_270617_SNP | 270617 | C | A |
| S_9123222 \| \| scaffold14851_270631_SNP | 270631 | G | T |
| S_9123275 \| \| scaffold14851_271320_SNP | 271320 | T | G |
| S_9123597 \| \| scaffold14851_275511_SNP | 275511 | C | G |
| S_9123601 \| \| scaffold14851_275550_SNP | 275550 | G | A |
| S_9123604 \| \| scaffold14851_275589_SNP | 275589 | G | T |
| S_9123631 \| \| scaffold14851_275813_SNP | 275813 | A | G |
| S_9123928 \| \| scaffold14851_278435_SNP | 278435 | G | C |
| S_9123933 \| \| scaffold14851_278540_SNP | 278540 | A | T |
| S_9123934 \| \| scaffold14851_278541_SNP | 278541 | C | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9124383 \| \| scaffold14851_283692_SNP | 283692 | A | C |
| S_9124519 \| \| scaffold14851_285638_SNP | 285638 | T | C |
| S_9124611 \| \| scaffold14851_286914_SNP | 286914 | C | T |
| S_9124636 \| \| scaffold14851_287373_SNP | 287373 | C | T |
| S_9125010 \| \| scaffold14851_293572_SNP | 293572 | T | G |
| S_9125011 \| \| scaffold14851_293583_SNP | 293583 | T | A |
| S_9125012 \| \| scaffold14851_293584_SNP | 293584 | T | A |
| S_9125013 \| \| scaffold14851_293585_SNP | 293585 | T | A |
| S_9125014 \| \| scaffold14851_293635_SNP | 293635 | A | T |
| S_9125015 \| \| scaffold14851_293658_SNP | 293658 | T | A |
| S_9125016 \| \| scaffold14851_293680_SNP | 293680 | A | C |
| S_9125021 \| \| scaffold14851_293782_SNP | 293782 | G | A |
| S_9125023 \| \| scaffold14851_293809_SNP | 293809 | G | A |
| S_9125029 \| \| scaffold14851_294067_SNP | 294067 | C | T |
| S_9125046 \| \| scaffold14851_294360_SNP | 294360 | A | C |
| S_9125048 \| \| scaffold14851_294364_SNP | 294364 | A | C |
| S_9125117 \| \| scaffold14851_295200_SNP | 295200 | G | A |
| S_9125384 \| \| scaffold14851_298137_SNP | 298137 | A | C |
| S_9125385 \| \| scaffold14851_298154_SNP | 298154 | A | T |
| S_9125402 \| \| scaffold14851_298422_SNP | 298422 | G | A |
| S_9125403 \| \| scaffold14851_298424_SNP | 298424 | T | C |
| S_9125405 \| \| scaffold14851_298445_SNP | 298445 | T | C |
| S_9125605 \| \| scaffold14851_300654_SNP | 300654 | G | A |
| S_9125656 \| \| scaffold14851_301057_SNP | 301057 | G | A |
| S_9125764 \| \| scaffold14851_302481_SNP | 302481 | T | G |
| S_9125788 \| \| scaffold14851_303123_SNP | 303123 | A | C |
| S_9125790 \| \| scaffold14851_303158_SNP | 303158 | A | G |
| S_9125791 \| \| scaffold14851_303192_SNP | 303192 | T | A |
| S_9125833 \| \| scaffold14851_303918_SNP | 303918 | T | G |
| S_9125892 \| \| scaffold14851_304503_SNP | 304503 | A | G |
| S_9125909 \| \| scaffold14851_304940_SNP | 304940 | C | G |
| S_9125948 \| \| scaffold14851_305619_SNP | 305619 | T | C |
| S_9125953 \| \| scaffold14851_305733_SNP | 305733 | A | T |
| S_9125989 \| \| scaffold14851_306216_SNP | 306216 | A | G |
| S_9125990 \| \| scaffold14851_306224_SNP | 306224 | A | T |
| S_9126022 \| \| scaffold14851_306716_SNP | 306716 | G | C |
| S_9126023 \| \| scaffold14851_306719_SNP | 306719 | A | G |
| S_9126078 \| \| scaffold14851_307299_SNP | 307299 | A | G |
| S_9126096 \| \| scaffold14851_307471_SNP | 307471 | A | C |
| scaffold14851_307718_SNP | 307718 | T | A |
| S_9126133 \| \| scaffold14851_307720_SNP | 307720 | A | T |
| S_9126148 \| \| scaffold14851_308112_SNP | 308112 | C | T |
| S_9126154 \| \| scaffold14851_308296_SNP | 308296 | G | C |
| S_9126156 \| \| scaffold14851_308311_SNP | 308311 | T | G |
| S_9126169 \| \| scaffold14851_308587_SNP | 308587 | G | A |
| S_9126171 \| \| scaffold14851_308621_SNP | 308621 | A | C |
| S_9126293 \| \| scaffold14851_309819_SNP | 309819 | G | T |
| S_9126294 \| \| scaffold14851_309821_SNP | 309821 | T | A |
| S_9126303 \| \| scaffold14851_309904_SNP | 309904 | T | C |
| S_9126305 \| \| scaffold14851_309915_SNP | 309915 | A | T |
| S_9126311 \| \| scaffold14851_309952_SNP | 309952 | A | C |
| S_9126419 \| \| scaffold14851_311144_SNP | 311144 | G | A |
| S_9126447 \| \| scaffold14851_311545_SNP | 311545 | C | T |
| S_9126630 \| \| scaffold14851_313785_SNP | 313785 | T | A |
| S_9126677 \| \| scaffold14851_314297_SNP | 314297 | T | A |
| S_9126696 \| \| scaffold14851_314686_SNP | 314686 | C | T |
| S_9126731 \| \| scaffold14851_315242_SNP | 315242 | T | C |
| S_9126827 \| \| scaffold14851_316238_SNP | 316238 | C | A |
| S_9126856 \| \| scaffold14851_316723_SNP | 316723 | C | G |
| S_9126858 \| \| scaffold14851_316765_SNP | 316765 | G | A |
| S_9126878 \| \| scaffold14851_316999_SNP | 316999 | C | T |
| S_9126895 \| \| scaffold14851_317387_SNP | 317387 | T | C |
| S_9126896 \| \| scaffold14851_317391_SNP | 317391 | G | A |
| S_9126897 \| \| scaffold14851_317406_SNP | 317406 | A | G |
| S_9126925 \| \| scaffold14851_317646_SNP | 317646 | C | T |
| S_9126963 \| \| scaffold14851_317895_SNP | 317895 | C | T |
| S_9126965 \| \| scaffold14851_317917_SNP | 317917 | G | C |
| S_9127237 \| \| scaffold14851_319711_SNP | 319711 | C | T |
| S_9127249 \| \| scaffold14851_319965_SNP | 319965 | A | G |
| S_9127256 \| \| scaffold14851_320041_SNP | 320041 | C | G |
| S_9127272 \| \| scaffold14851_320460_SNP | 320460 | C | T |
| S_9127345 \| \| scaffold14851_321471_SNP | 321471 | C | T |
| S_9127406 \| \| scaffold14851_322384_SNP | 322384 | T | A |
| S_9127409 \| \| scaffold14851_322417_SNP | 322417 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9127417 \| \| scaffold14851_322529_SNP | 322529 | G | T |
| S_9127421 \| \| scaffold14851_322641_SNP | 322641 | C | T |
| S_9127496 \| \| scaffold14851_324200_SNP | 324200 | G | A |
| S_9127583 \| \| scaffold14851_325327_SNP | 325327 | C | T |
| S_9127627 \| \| scaffold14851_325652_SNP | 325652 | C | G |
| S_9127628 \| \| scaffold14851_325687_SNP | 325687 | G | A |
| S_9127701 \| \| scaffold14851_326315_SNP | 326315 | C | G |
| S_9127768 \| \| scaffold14851_327593_SNP | 327593 | C | A |
| S_9127811 \| \| scaffold14851_328579_SNP | 328579 | A | C |
| S_9127855 \| \| scaffold14851_329178_SNP | 329178 | G | A |
| S_9127900 \| \| scaffold14851_329741_SNP | 329741 | T | G |
| S_9127902 \| \| scaffold14851_329786_SNP | 329786 | T | C |
| S_9127960 \| \| scaffold14851_330871_SNP | 330871 | A | G |
| S_9127990 \| \| scaffold14851_331080_SNP | 331080 | C | T |
| S_9128002 \| \| scaffold14851_331296_SNP | 331296 | C | G |
| S_9128016 \| \| scaffold14851_331631_SNP | 331631 | C | T |
| S_9128058 \| \| scaffold14851_332334_SNP | 332334 | A | T |
| S_9128065 \| \| scaffold14851_332655_SNP | 332655 | C | A |
| S_9128122 \| \| scaffold14851_333609_SNP | 333609 | T | C |
| S_9128124 \| \| scaffold14851_333633_SNP | 333633 | G | T |
| S_9128225 \| \| scaffold14851_334966_SNP | 334966 | A | G |
| scaffold14851_335766_SNP | 335766 | T | A |
| S_9128337 \| \| scaffold14851_335772_SNP | 335772 | A | G |
| S_9128453 \| \| scaffold14851_337629_SNP | 337629 | T | C |
| S_9128468 \| \| scaffold14851_337894_SNP | 337894 | A | C |
| S_9128480 \| \| scaffold14851_338049_SNP | 338049 | A | C |
| S_9128522 \| \| scaffold14851_338775_SNP | 338775 | G | C |
| S_9128523 \| \| scaffold14851_338782_SNP | 338782 | C | T |
| S_9128553 \| \| scaffold14851_339279_SNP | 339279 | A | C |
| S_9128559 \| \| scaffold14851_339365_SNP | 339365 | G | T |
| S_9128620 \| \| scaffold14851_340019_SNP | 340019 | G | T |
| S_9128621 \| \| scaffold14851_340032_SNP | 340032 | G | A |
| S_9128622 \| \| scaffold14851_340044_SNP | 340044 | C | T |
| S_9128681 \| \| scaffold14851_341082_SNP | 341082 | T | C |
| S_9128702 \| \| scaffold14851_341315_SNP | 341315 | C | G |
| S_9128721 \| \| scaffold14851_341492_SNP | 341492 | C | T |
| S_9128724 \| \| scaffold14851_341519_SNP | 341519 | G | T |
| S_9128837 \| \| scaffold14851_344827_SNP | 344827 | G | A |
| S_9128845 \| \| scaffold14851_344939_SNP | 344939 | A | T |
| S_9128984 \| \| scaffold14851_346562_SNP | 346562 | T | C |
| S_9129080 \| \| scaffold14851_348070_SNP | 348070 | A | G |
| S_9129092 \| \| scaffold14851_348215_SNP | 348215 | C | G |
| S_9129132 \| \| scaffold14851_348427_SNP | 348427 | C | G |
| S_9129152 \| \| scaffold14851_348577_SNP | 348577 | C | G |
| S_9129169 \| \| scaffold14851_348894_SNP | 348894 | T | A |
| S_9129216 \| \| scaffold14851_349681_SNP | 349681 | C | T |
| S_9129265 \| \| scaffold14851_350118_SNP | 350118 | A | C |
| S_9129287 \| \| scaffold14851_350475_SNP | 350475 | G | A |
| S_9129289 \| \| scaffold14851_350547_SNP | 350547 | G | T |
| scaffold14851_352387_SNP | 352387 | T | C |
| S_9129547 \| \| scaffold14851_353239_SNP | 353239 | A | G |
| S_9129549 \| \| scaffold14851_353312_SNP | 353312 | A | T |
| S_9129566 \| \| scaffold14851_353623_SNP | 353623 | C | T |
| S_9129567 \| \| scaffold14851_353646_SNP | 353646 | C | T |
| S_9129580 \| \| scaffold14851_353855_SNP | 353855 | T | C |
| S_9129583 \| \| scaffold14851_353909_SNP | 353909 | G | A |
| S_9129595 \| \| scaffold14851_354051_SNP | 354051 | A | G |
| S_9129599 \| \| scaffold14851_354129_SNP | 354129 | C | G |
| S_9129601 \| \| scaffold14851_354181_SNP | 354181 | G | T |
| S_9129603 \| \| scaffold14851_354291_SNP | 354291 | A | T |
| S_9129607 \| \| scaffold14851_354334_SNP | 354334 | T | G |
| S_9129609 \| \| scaffold14851_354357_SNP | 354357 | G | A |
| S_9129612 \| \| scaffold14851_354410_SNP | 354410 | T | C |
| S_9129624 \| \| scaffold14851_354564_SNP | 354564 | T | G |
| S_9129627 \| \| scaffold14851_354600_SNP | 354600 | C | T |
| S_9129629 \| \| scaffold14851_354618_SNP | 354618 | T | C |
| S_9129641 \| \| scaffold14851_354784_SNP | 354784 | C | A |
| S_9129830 \| \| scaffold14851_357327_SNP | 357327 | T | C |
| S_9129838 \| \| scaffold14851_357473_SNP | 357473 | T | C |
| S_9129915 \| \| scaffold14851_358503_SNP | 358503 | T | A |
| S_9129983 \| \| scaffold14851_358811_SNP | 358811 | A | C |
| S_9130001 \| \| scaffold14851_359023_SNP | 359023 | G | A |
| S_9130004 \| \| scaffold14851_359052_SNP | 359052 | T | G |
| S_9130014 \| \| scaffold14851_359123_SNP | 359123 | T | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9130022 \|\| scaffold14851_359290_SNP | 359290 | T | G |
| S_9130026 \|\| scaffold14851_359392_SNP | 359392 | C | T |
| S_9130040 \|\| scaffold14851_359589_SNP | 359589 | A | G |
| S_9130099 \|\| scaffold14851_360141_SNP | 360141 | C | T |
| S_9130105 \|\| scaffold14851_360168_SNP | 360168 | T | A |
| S_9130131 \|\| scaffold14851_360487_SNP | 360487 | A | G |
| S_9130133 \|\| scaffold14851_360515_SNP | 360515 | A | T |
| S_9130196 \|\| scaffold14851_360985_SNP | 360985 | T | C |
| S_9130198 \|\| scaffold14851_360990_SNP | 360990 | C | T |
| S_9130206 \|\| scaffold14851_361029_SNP | 361029 | T | C |
| S_9130345 \|\| scaffold14851_363475_SNP | 363475 | A | G |
| S_9130504 \|\| scaffold14851_366163_SNP | 366163 | A | G |
| S_9130538 \|\| scaffold14851_366349_SNP | 366349 | T | A |
| S_9130578 \|\| scaffold14851_367031_SNP | 367031 | G | A |
| S_9130626 \|\| scaffold14851_367825_SNP | 367825 | A | C |
| S_9130657 \|\| scaffold14851_368398_SNP | 368398 | T | G |
| S_9130819 \|\| scaffold14851_370159_SNP | 370159 | G | T |
| S_9130820 \|\| scaffold14851_370161_SNP | 370161 | G | A |
| S_9130821 \|\| scaffold14851_370162_SNP | 370162 | A | T |
| S_9130822 \|\| scaffold14851_370204_SNP | 370204 | T | C |
| S_9131320 \|\| scaffold14851_376732_SNP | 376732 | G | A |
| S_9131323 \|\| scaffold14851_376793_SNP | 376793 | G | A |
| S_9131330 \|\| scaffold14851_376983_SNP | 376983 | A | T |
| S_9131452 \|\| scaffold14851_378373_SNP | 378373 | G | C |
| S_9131453 \|\| scaffold14851_378388_SNP | 378388 | G | T |
| S_9131458 \|\| scaffold14851_378473_SNP | 378473 | G | C |
| S_9131461 \|\| scaffold14851_378567_SNP | 378567 | C | T |
| S_9131464 \|\| scaffold14851_378677_SNP | 378677 | C | A |
| S_9131478 \|\| scaffold14851_379027_SNP | 379027 | C | T |
| S_9131479 \|\| scaffold14851_379033_SNP | 379033 | G | T |
| S_9131480 \|\| scaffold14851_379047_SNP | 379047 | T | G |
| S_9131498 \|\| scaffold14851_379225_SNP | 379225 | A | C |
| S_9131523 \|\| scaffold14851_379740_SNP | 379740 | G | A |
| S_9131526 \|\| scaffold14851_379775_SNP | 379775 | C | A |
| S_9131530 \|\| scaffold14851_379819_SNP | 379819 | A | C |
| S_9131532 \|\| scaffold14851_379846_SNP | 379846 | C | A |
| S_9131540 \|\| scaffold14851_379957_SNP | 379957 | T | G |
| S_9131543 \|\| scaffold14851_379995_SNP | 379995 | C | T |
| S_9131558 \|\| scaffold14851_380158_SNP | 380158 | G | A |
| S_9131565 \|\| scaffold14851_380224_SNP | 380224 | G | A |
| S_9131569 \|\| scaffold14851_380250_SNP | 380250 | T | G |
| S_9131570 \|\| scaffold14851_380253_SNP | 380253 | C | G |
| S_9131575 \|\| scaffold14851_380340_SNP | 380340 | C | G |
| S_9131576 \|\| scaffold14851_380350_SNP | 380350 | A | G |
| S_9131690 \|\| scaffold14851_381535_SNP | 381535 | T | C |
| S_9131779 \|\| scaffold14851_382884_SNP | 382884 | G | A |
| S_9131813 \|\| scaffold14851_383229_SNP | 383229 | G | A |
| S_9131815 \|\| scaffold14851_383235_SNP | 383235 | C | T |
| S_9131816 \|\| scaffold14851_383245_SNP | 383245 | A | G |
| S_9131856 \|\| scaffold14851_383717_SNP | 383717 | G | T |
| S_9131857 \|\| scaffold14851_383725_SNP | 383725 | G | T |
| S_9131864 \|\| scaffold14851_383871_SNP | 383871 | C | T |
| S_9131867 \|\| scaffold14851_383941_SNP | 383941 | A | G |
| S_9131930 \|\| scaffold14851_384333_SNP | 384333 | C | G |
| S_9131934 \|\| scaffold14851_384371_SNP | 384371 | C | T |
| S_9132030 \|\| scaffold14851_384823_SNP | 384823 | T | C |
| S_9132316 \|\| scaffold14851_386965_SNP | 386965 | C | A |
| S_9132372 \|\| scaffold14851_387063_SNP | 387063 | C | A |
| S_9132448 \|\| scaffold14851_388712_SNP | 388712 | C | G |
| S_9132457 \|\| scaffold14851_388855_SNP | 388855 | C | T |
| S_9132644 \|\| scaffold14851_390666_SNP | 390666 | T | G |
| S_9132654 \|\| scaffold14851_390898_SNP | 390898 | T | A |
| S_9132868 \|\| scaffold14851_392337_SNP | 392337 | T | C |
| S_9132869 \|\| scaffold14851_392344_SNP | 392344 | C | T |
| S_9132896 \|\| scaffold14851_392570_SNP | 392570 | C | T |
| S_9133259 \|\| scaffold14851_397585_SNP | 397585 | C | T |
| S_9133332 \|\| scaffold14851_398649_SNP | 398649 | G | A |
| S_9133372 \|\| scaffold14851_398787_SNP | 398787 | A | C |
| S_9133446 \|\| scaffold14851_399332_SNP | 399332 | T | C |
| S_9133487 \|\| scaffold14851_400234_SNP | 400234 | C | T |
| S_9133567 \|\| scaffold14851_401670_SNP | 401670 | T | A |
| S_9133593 \|\| scaffold14851_402006_SNP | 402006 | T | C |
| S_9133597 \|\| scaffold14851_402083_SNP | 402083 | G | A |
| S_9133619 \|\| scaffold14851_402280_SNP | 402280 | G | A |

TABLE 1-continued

<u>SNP Positions within SEQ ID NO: 1 that are associated with increased resistance to ASR</u>

| Name | Position SEQ ID NO: 1 | Favorabale Allele (Rust Resistant) | Unfavorable Allele (Rust Susceptible) |
|---|---|---|---|
| S_9133641 \| \| scaffold14851_402563_SNP | 402563 | T | C |
| S_9133655 \| \| scaffold14851_402783_SNP | 402783 | A | C |
| S_9133657 \| \| scaffold14851_402796_SNP | 402796 | A | G |
| S_9133658 \| \| scaffold14851_402811_SNP | 402811 | A | T |
| S_9133663 \| \| scaffold14851_402990_SNP | 402990 | C | A |
| S_9133685 \| \| scaffold14851_403275_SNP | 403275 | C | G |
| S_9133771 \| \| scaffold14851_404072_SNP | 404072 | A | C |
| S_9133797 \| \| scaffold14851_404532_SNP | 404532 | A | C |
| S_9133813 \| \| scaffold14851_404831_SNP | 404831 | A | G |
| S_9133825 \| \| scaffold14851_405067_SNP | 405067 | A | G |
| S_9133870 \| \| scaffold14851_406067_SNP | 406067 | C | A |
| S_9133976 \| \| scaffold14851_407021_SNP | 407021 | T | C |
| S_9134081 \| \| scaffold14851_407836_SNP | 407836 | A | T |
| S_9134097 \| \| scaffold14851_408109_SNP | 408109 | C | A |
| S_9134101 \| \| scaffold14851_408234_SNP | 408234 | T | C |
| S_9134158 \| \| scaffold14851_409032_SNP | 409032 | T | G |
| S_9134159 \| \| scaffold14851_409033_SNP | 409033 | G | A |
| S_9134160 \| \| scaffold14851_409074_SNP | 409074 | A | G |
| S_9134170 \| \| scaffold14851_409200_SNP | 409200 | C | T |
| S_9134181 \| \| scaffold14851_409543_SNP | 409543 | C | G |
| S_9134324 \| \| scaffold14851_411458_SNP | 411458 | A | G |
| S_9134330 \| \| scaffold14851_411513_SNP | 411513 | C | G |
| S_9134566 \| \| scaffold14851_414575_SNP | 414575 | C | G |
| S_9134571 \| \| scaffold14851_414691_SNP | 414691 | A | T |
| S_9134573 \| \| scaffold14851_414694_SNP | 414694 | T | C |
| S_9134699 \| \| scaffold14851_415390_SNP | 415390 | G | A |
| S_9134716 \| \| scaffold14851_415736_SNP | 415736 | C | T |
| S_9134726 \| \| scaffold14851_415840_SNP | 415840 | T | A |
| S_9134768 \| \| scaffold14851_416353_SNP | 416353 | A | G |
| S_9134770 \| \| scaffold14851_416368_SNP | 416368 | T | C |
| S_9134827 \| \| scaffold14851_417270_SNP | 417270 | C | A |
| S_9134866 \| \| scaffold14851_417954_SNP | 417954 | T | G |
| S_9134867 \| \| scaffold14851_418028_SNP | 418028 | G | A |
| S_9134886 \| \| scaffold14851_418346_SNP | 418346 | C | G |
| S_9134966 \| \| scaffold14851_419287_SNP | 419287 | C | T |
| S_9135002 \| \| scaffold14851_419772_SNP | 419772 | T | C |
| S_9135003 \| \| scaffold14851_419774_SNP | 419774 | G | T |
| S_9135081 \| \| scaffold14851_420685_SNP | 420685 | G | A |
| S_9135159 \| \| scaffold14851_421251_SNP | 421251 | G | C |
| S_9135160 \| \| scaffold14851_421256_SNP | 421256 | A | T |
| S_9135161 \| \| scaffold14851_421266_SNP | 421266 | A | G |
| S_9135164 \| \| scaffold14851_421354_SNP | 421354 | G | T |
| S_9135191 \| \| scaffold14851_421765_SNP | 421765 | A | C |
| S_9135194 \| \| scaffold14851_421936_SNP | 421936 | G | A |
| S_9135219 \| \| scaffold14851_422243_SNP | 422243 | T | C |
| S_9135231 \| \| scaffold14851_422373_SNP | 422373 | G | T |
| S_9135250 \| \| scaffold14851_422609_SNP | 422609 | T | C |
| S_9135255 \| \| scaffold14851_422657_SNP | 422657 | A | C |
| S_9135264 \| \| scaffold14851_422785_SNP | 422785 | T | G |
| S_9135270 \| \| scaffold14851_422816_SNP | 422816 | A | T |
| S_9135280 \| \| scaffold14851_422955_SNP | 422955 | G | A |
| S_9135313 \| \| scaffold14851_423379_SNP | 423379 | G | C |
| S_9135337 \| \| scaffold14851_423825_SNP | 423825 | A | T |
| S_9135341 \| \| scaffold14851_423915_SNP | 423915 | G | A |
| S_9135343 \| \| scaffold14851_423950_SNP | 423950 | G | T |
| S_9135440 \| \| scaffold14851_425232_SNP | 425232 | T | C |
| S_9135441 \| \| scaffold14851_425243_SNP | 425243 | T | C |
| S_9135511 \| \| scaffold14851_426398_SNP | 426398 | C | A |
| S_9135513 \| \| scaffold14851_426451_SNP | 426451 | C | A |
| S_9135559 \| \| scaffold14851_426771_SNP | 426771 | C | A |
| S_9135775 \| \| scaffold14851_429398_SNP | 429398 | T | A |
| S_9136669 \| \| scaffold14851_434789_SNP | 434789 | G | A |
| S_9136676 \| \| scaffold14851_434936_SNP | 434936 | T | A |
| S_9136723 \| \| scaffold14851_435711_SNP | 435711 | A | C |
| S_9136753 \| \| scaffold14851_436210_SNP | 436210 | T | C |
| S_9136802 \| \| scaffold14851_436880_SNP | 436880 | A | G |
| S_9136803 \| \| scaffold14851_436889_SNP | 436889 | A | T |
| S_9136804 \| \| scaffold14851_436898_SNP | 436898 | A | T |
| S_9136842 \| \| scaffold14851_437421_SNP | 437421 | T | C |
| S_9136994 \| \| scaffold14851_439598_SNP | 439598 | C | G |
| S_9137172 \| \| scaffold14851_441483_SNP | 441483 | G | T |
| S_9137238 \| \| scaffold14851_442480_SNP | 442480 | G | T |
| S_9137239 \| \| scaffold14851_442511_SNP | 442511 | C | A |
| S_9137338 \| \| scaffold14851_444846_SNP | 444846 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9137349 \| \| scaffold14851_444963_SNP | 444963 | A | G |
| S_9137486 \| \| scaffold14851_445405_SNP | 445405 | A | G |
| S_9137691 \| \| scaffold14851_448365_SNP | 448365 | C | A |
| S_9137750 \| \| scaffold14851_449044_SNP | 449044 | T | G |
| S_9137853 \| \| scaffold14851_450011_SNP | 450011 | G | A |
| S_9137899 \| \| scaffold14851_451355_SNP | 451355 | A | G |
| S_9137917 \| \| scaffold14851_451435_SNP | 451435 | C | T |
| S_9137930 \| \| scaffold14851_451716_SNP | 451716 | A | T |
| S_9138057 \| \| scaffold14851_453195_SNP | 453195 | A | G |
| S_9138063 \| \| scaffold14851_453344_SNP | 453344 | G | C |
| S_9138128 \| \| scaffold14851_454472_SNP | 454472 | C | T |
| S_9138129 \| \| scaffold14851_454523_SNP | 454523 | G | A |
| S_9138250 \| \| scaffold14851_455419_SNP | 455419 | T | G |
| S_9138265 \| \| scaffold14851_455693_SNP | 455693 | G | A |
| S_9138266 \| \| scaffold14851_455697_SNP | 455697 | A | T |
| S_9138267 \| \| scaffold14851_455716_SNP | 455716 | C | T |
| S_9138270 \| \| scaffold14851_455865_SNP | 455865 | A | G |
| S_9138335 \| \| scaffold14851_457015_SNP | 457015 | G | A |
| S_9138425 \| \| scaffold14851_458213_SNP | 458213 | A | T |
| S_9138548 \| \| scaffold14851_461812_SNP | 461812 | G | T |
| S_9138586 \| \| scaffold14851_462643_SNP | 462643 | T | C |
| S_9138589 \| \| scaffold14851_462656_SNP | 462656 | A | G |
| S_9138603 \| \| scaffold14851_462790_SNP | 462790 | A | T |
| S_9138614 \| \| scaffold14851_462929_SNP | 462929 | A | G |
| S_9138616 \| \| scaffold14851_462954_SNP | 462954 | A | G |
| S_9138618 \| \| scaffold14851_462964_SNP | 462964 | G | T |
| S_9138659 \| \| scaffold14851_463818_SNP | 463818 | A | G |
| S_9138660 \| \| scaffold14851_463868_SNP | 463868 | A | C |
| S_9138661 \| \| scaffold14851_463958_SNP | 463958 | C | T |
| S_9138667 \| \| scaffold14851_464097_SNP | 464097 | G | A |
| S_9138756 \| \| scaffold14851_465482_SNP | 465482 | G | A |
| S_9138785 \| \| scaffold14851_465766_SNP | 465766 | C | G |
| S_9138816 \| \| scaffold14851_466171_SNP | 466171 | C | T |
| S_9138841 \| \| scaffold14851_466314_SNP | 466314 | A | C |
| S_9138855 \| \| scaffold14851_466332_SNP | 466332 | G | C |
| S_9138895 \| \| scaffold14851_466584_SNP | 466584 | T | A |
| S_9138975 \| \| scaffold14851_467592_SNP | 467592 | T | A |
| S_9138976 \| \| scaffold14851_467599_SNP | 467599 | C | G |
| S_9138992 \| \| scaffold14851_468024_SNP | 468024 | A | G |
| S_9139023 \| \| scaffold14851_468486_SNP | 468486 | A | G |
| S_9139044 \| \| scaffold14851_468833_SNP | 468833 | C | T |
| scaffold14851_468849_SNP | 468849 | G | A |
| S_9139166 \| \| scaffold14851_469888_SNP | 469888 | C | T |
| S_9139181 \| \| scaffold14851_470094_SNP | 470094 | G | A |
| S_9139193 \| \| scaffold14851_470362_SNP | 470362 | T | C |
| S_9139223 \| \| scaffold14851_470789_SNP | 470789 | T | C |
| S_9139306 \| \| scaffold14851_471802_SNP | 471802 | T | G |
| S_9139370 \| \| scaffold14851_472687_SNP | 472687 | C | A |
| S_9139384 \| \| scaffold14851_473007_SNP | 473007 | G | A |
| S_9139448 \| \| scaffold14851_474062_SNP | 474062 | A | G |
| S_9139918 \| \| scaffold14851_478547_SNP | 478547 | G | T |
| S_9139922 \| \| scaffold14851_478574_SNP | 478574 | T | A |
| S_9139930 \| \| scaffold14851_478637_SNP | 478637 | G | C |
| S_9140027 \| \| scaffold14851_480027_SNP | 480027 | A | T |
| S_9140034 \| \| scaffold14851_480252_SNP | 480252 | A | G |
| S_9140036 \| \| scaffold14851_480267_SNP | 480267 | A | G |
| S_9140323 \| \| scaffold14851_483448_SNP | 483448 | G | T |
| S_9140361 \| \| scaffold14851_483777_SNP | 483777 | C | T |
| S_9140531 \| \| scaffold14851_486307_SNP | 486307 | G | T |
| S_9140535 \| \| scaffold14851_486339_SNP | 486339 | C | G |
| S_9140599 \| \| scaffold14851_487142_SNP | 487142 | T | C |
| S_9140620 \| \| scaffold14851_487342_SNP | 487342 | G | A |
| S_9140624 \| \| scaffold14851_487403_SNP | 487403 | C | G |
| S_9140642 \| \| scaffold14851_487577_SNP | 487577 | G | A |
| S_9140896 \| \| scaffold14851_489873_SNP | 489873 | C | T |
| S_9140974 \| \| scaffold14851_490904_SNP | 490904 | G | T |
| S_9141070 \| \| scaffold14851_492200_SNP | 492200 | G | A |
| S_9141072 \| \| scaffold14851_492333_SNP | 492333 | T | A |
| scaffold14851_493327_SNP | 493327 | A | T |
| scaffold14851_493363_SNP | 493363 | G | A |
| S_9141226 \| \| scaffold14851_493493_SNP | 493493 | T | C |
| S_9141231 \| \| scaffold14851_493580_SNP | 493580 | C | T |
| S_9141320 \| \| scaffold14851_494959_SNP | 494959 | T | A |
| S_9141363 \| \| scaffold14851_495531_SNP | 495531 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9141457 \|\| scaffold14851_496773_SNP | 496773 | T | G |
| S_9141461 \|\| scaffold14851_496814_SNP | 496814 | C | T |
| S_9141473 \|\| scaffold14851_496946_SNP | 496946 | A | T |
| S_9141474 \|\| scaffold14851_496956_SNP | 496956 | C | G |
| S_9141497 \|\| scaffold14851_497211_SNP | 497211 | A | T |
| S_9141539 \|\| scaffold14851_497852_SNP | 497852 | A | T |
| S_9141680 \|\| scaffold14851_498944_SNP | 498944 | T | C |
| S_9141681 \|\| scaffold14851_498959_SNP | 498959 | G | C |
| S_9141684 \|\| scaffold14851_499060_SNP | 499060 | G | T |
| S_9141688 \|\| scaffold14851_499101_SNP | 499101 | T | G |
| S_9141689 \|\| scaffold14851_499160_SNP | 499160 | C | T |
| S_9142540 \|\| scaffold14851_509524_SNP | 509524 | T | C |
| S_9142541 \|\| scaffold14851_509525_SNP | 509525 | T | C |
| S_9142626 \|\| scaffold14851_510516_SNP | 510516 | A | C |
| S_9142627 \|\| scaffold14851_510517_SNP | 510517 | C | T |
| S_9142820 \|\| scaffold14851_514279_SNP | 514279 | A | G |
| S_9142837 \|\| scaffold14851_514501_SNP | 514501 | G | A |
| S_9142849 \|\| scaffold14851_514663_SNP | 514663 | A | T |
| S_9142859 \|\| scaffold14851_514853_SNP | 514853 | T | G |
| S_9142963 \|\| scaffold14851_517185_SNP | 517185 | A | T |
| S_9142974 \|\| scaffold14851_517392_SNP | 517392 | A | G |
| S_9142991 \|\| scaffold14851_517641_SNP | 517641 | T | A |
| S_9143000 \|\| scaffold14851_517805_SNP | 517805 | T | C |
| S_9143048 \|\| scaffold14851_518193_SNP | 518193 | C | T |
| S_9143065 \|\| scaffold14851_518329_SNP | 518329 | A | G |
| S_9143093 \|\| scaffold14851_518682_SNP | 518682 | C | T |
| S_9143095 \|\| scaffold14851_518702_SNP | 518702 | A | G |
| S_9143132 \|\| scaffold14851_519075_SNP | 519075 | C | T |
| S_9143133 \|\| scaffold14851_519087_SNP | 519087 | C | T |
| S_9143155 \|\| scaffold14851_519319_SNP | 519319 | C | G |
| S_9143157 \|\| scaffold14851_519326_SNP | 519326 | A | G |
| S_9143173 \|\| scaffold14851_519487_SNP | 519487 | T | C |
| S_9143184 \|\| scaffold14851_519544_SNP | 519544 | A | G |
| S_9143189 \|\| scaffold14851_519632_SNP | 519632 | A | G |
| S_9143235 \|\| scaffold14851_519902_SNP | 519902 | T | C |
| S_9143242 \|\| scaffold14851_520071_SNP | 520071 | C | T |
| S_9143249 \|\| scaffold14851_520176_SNP | 520176 | T | C |
| S_9143253 \|\| scaffold14851_520259_SNP | 520259 | C | T |
| S_9143259 \|\| scaffold14851_520350_SNP | 520350 | T | C |
| scaffold14851_521206_SNP | 521206 | G | A |
| S_9143572 \|\| scaffold14851_523585_SNP | 523585 | T | C |
| S_9143604 \|\| scaffold14851_524059_SNP | 524059 | T | C |
| S_9143631 \|\| scaffold14851_524288_SNP | 524288 | A | T |
| S_9143658 \|\| scaffold14851_524685_SNP | 524685 | G | A |
| S_9143674 \|\| scaffold14851_524990_SNP | 524990 | A | T |
| S_9143694 \|\| scaffold14851_525347_SNP | 525347 | T | A |
| S_9143704 \|\| scaffold14851_525434_SNP | 525434 | T | A |
| S_9143725 \|\| scaffold14851_525772_SNP | 525772 | T | G |
| S_9143732 \|\| scaffold14851_525864_SNP | 525864 | G | T |
| S_9143743 \|\| scaffold14851_526120_SNP | 526120 | G | A |
| S_9143749 \|\| scaffold14851_526169_SNP | 526169 | T | G |
| S_9143761 \|\| scaffold14851_526380_SNP | 526380 | T | G |
| S_9143795 \|\| scaffold14851_526942_SNP | 526942 | C | T |
| S_9143802 \|\| scaffold14851_527108_SNP | 527108 | A | G |
| S_9143816 \|\| scaffold14851_527194_SNP | 527194 | C | T |
| S_9143821 \|\| scaffold14851_527296_SNP | 527296 | A | G |
| S_9143864 \|\| scaffold14851_527999_SNP | 527999 | A | G |
| S_9143916 \|\| scaffold14851_528946_SNP | 528946 | A | G |
| S_9143951 \|\| scaffold14851_529353_SNP | 529353 | A | G |
| S_9144037 \|\| scaffold14851_530908_SNP | 530908 | G | A |
| S_9144167 \|\| scaffold14851_533059_SNP | 533059 | C | T |
| S_9144221 \|\| scaffold14851_533960_SNP | 533960 | A | C |
| S_9144265 \|\| scaffold14851_534923_SNP | 534923 | C | A |
| S_9144305 \|\| scaffold14851_535513_SNP | 535513 | G | T |
| S_9144366 \|\| scaffold14851_536471_SNP | 536471 | A | G |
| S_9144490 \|\| scaffold14851_538073_SNP | 538073 | C | T |
| S_9144492 \|\| scaffold14851_538086_SNP | 538086 | A | G |
| S_9144624 \|\| scaffold14851_540098_SNP | 540098 | T | C |
| S_9144820 \|\| scaffold14851_542578_SNP | 542578 | G | A |
| S_9144917 \|\| scaffold14851_543842_SNP | 543842 | A | C |
| S_9145082 \|\| scaffold14851_546673_SNP | 546673 | A | T |
| S_9145137 \|\| scaffold14851_548068_SNP | 548068 | G | T |
| S_9145138 \|\| scaffold14851_548075_SNP | 548075 | T | A |
| S_9145182 \|\| scaffold14851_548510_SNP | 548510 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9145194 \| \| scaffold14851_548733_SNP | 548733 | G | T |
| S_9145254 \| \| scaffold14851_549785_SNP | 549785 | C | T |
| S_9145466 \| \| scaffold14851_553451_SNP | 553451 | T | G |
| S_9145496 \| \| scaffold14851_553955_SNP | 553955 | A | G |
| S_9145540 \| \| scaffold14851_554598_SNP | 554598 | A | G |
| S_9145557 \| \| scaffold14851_554899_SNP | 554899 | G | A |
| S_9145600 \| \| scaffold14851_554995_SNP | 554995 | C | T |
| S_9145638 \| \| scaffold14851_555239_SNP | 555239 | C | T |
| S_9145680 \| \| scaffold14851_555302_SNP | 555302 | G | A |
| S_9145705 \| \| scaffold14851_555485_SNP | 555485 | A | C |
| S_9145719 \| \| scaffold14851_555679_SNP | 555679 | C | G |
| S_9145721 \| \| scaffold14851_555696_SNP | 555696 | A | T |
| S_9145744 \| \| scaffold14851_556074_SNP | 556074 | C | T |
| S_9145751 \| \| scaffold14851_556249_SNP | 556249 | G | T |
| S_9145767 \| \| scaffold14851_556512_SNP | 556512 | T | C |
| S_9145799 \| \| scaffold14851_556931_SNP | 556931 | G | A |
| S_9145816 \| \| scaffold14851_557139_SNP | 557139 | C | T |
| S_9145837 \| \| scaffold14851_557422_SNP | 557422 | T | C |
| S_9145844 \| \| scaffold14851_557501_SNP | 557501 | A | G |
| S_9145959 \| \| scaffold14851_559093_SNP | 559093 | C | A |
| S_9145960 \| \| scaffold14851_559105_SNP | 559105 | T | C |
| S_9145992 \| \| scaffold14851_559592_SNP | 559592 | A | G |
| S_9145993 \| \| scaffold14851_559595_SNP | 559595 | G | A |
| S_9146428 \| \| scaffold14851_562289_SNP | 562289 | C | T |
| S_9146684 \| \| scaffold14851_563985_SNP | 563985 | T | G |
| S_9146710 \| \| scaffold14851_564605_SNP | 564605 | G | T |
| S_9146794 \| \| scaffold14851_565859_SNP | 565859 | C | A |
| S_9146801 \| \| scaffold14851_565953_SNP | 565953 | T | C |
| S_9146822 \| \| scaffold14851_566106_SNP | 566106 | A | T |
| S_9146843 \| \| scaffold14851_566440_SNP | 566440 | A | T |
| S_9146845 \| \| scaffold14851_566456_SNP | 566456 | C | A |
| S_9146952 \| \| scaffold14851_572464_SNP | 572464 | G | A |
| S_9146954 \| \| scaffold14851_572537_SNP | 572537 | A | T |
| S_9146978 \| \| scaffold14851_572812_SNP | 572812 | C | T |
| S_9146986 \| \| scaffold14851_573027_SNP | 573027 | T | G |
| S_9146996 \| \| scaffold14851_573273_SNP | 573273 | T | C |
| S_9146997 \| \| scaffold14851_573291_SNP | 573291 | C | T |
| S_9147002 \| \| scaffold14851_573372_SNP | 573372 | C | T |
| S_9147003 \| \| scaffold14851_573382_SNP | 573382 | C | T |
| S_9147008 \| \| scaffold14851_573452_SNP | 573452 | G | A |
| S_9147009 \| \| scaffold14851_573467_SNP | 573467 | A | G |
| S_9147011 \| \| scaffold14851_573482_SNP | 573482 | G | A |
| S_9147044 \| \| scaffold14851_573857_SNP | 573857 | A | G |
| S_9147047 \| \| scaffold14851_573866_SNP | 573866 | C | T |
| S_9147048 \| \| scaffold14851_573884_SNP | 573884 | C | T |
| S_9147049 \| \| scaffold14851_573899_SNP | 573899 | C | T |
| S_9147085 \| \| scaffold14851_574311_SNP | 574311 | C | T |
| S_9147086 \| \| scaffold14851_574321_SNP | 574321 | G | A |
| S_9147094 \| \| scaffold14851_574404_SNP | 574404 | G | A |
| S_9147096 \| \| scaffold14851_574431_SNP | 574431 | C | A |
| S_9147097 \| \| scaffold14851_574434_SNP | 574434 | G | T |
| S_9147106 \| \| scaffold14851_574526_SNP | 574526 | G | A |
| S_9147107 \| \| scaffold14851_574542_SNP | 574542 | C | T |
| S_9147108 \| \| scaffold14851_574545_SNP | 574545 | A | G |
| S_9147115 \| \| scaffold14851_574650_SNP | 574650 | C | T |
| S_9147121 \| \| scaffold14851_574698_SNP | 574698 | T | C |
| S_9147123 \| \| scaffold14851_574715_SNP | 574715 | G | A |
| S_9147125 \| \| scaffold14851_574725_SNP | 574725 | C | T |
| S_9147202 \| \| scaffold14851_575320_SNP | 575320 | A | T |
| S_9147242 \| \| scaffold14851_575408_SNP | 575408 | A | G |
| S_9147250 \| \| scaffold14851_575514_SNP | 575514 | C | T |
| S_9147256 \| \| scaffold14851_575602_SNP | 575602 | G | A |
| S_9147303 \| \| scaffold14851_576182_SNP | 576182 | G | C |
| S_9147325 \| \| scaffold14851_576352_SNP | 576352 | C | G |
| S_9147437 \| \| scaffold14851_577536_SNP | 577536 | A | G |
| S_9147476 \| \| scaffold14851_577792_SNP | 577792 | G | T |
| S_9147479 \| \| scaffold14851_577803_SNP | 577803 | A | T |
| S_9147488 \| \| scaffold14851_577873_SNP | 577873 | A | G |
| S_9147826 \| \| scaffold14851_581189_SNP | 581189 | G | A |
| S_9147828 \| \| scaffold14851_581198_SNP | 581198 | T | C |
| S_9147970 \| \| scaffold14851_583090_SNP | 583090 | A | T |
| S_9147993 \| \| scaffold14851_583419_SNP | 583419 | T | C |
| S_9147997 \| \| scaffold14851_583692_SNP | 583692 | T | C |
| S_9148089 \| \| scaffold14851_584402_SNP | 584402 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9148120 \| \| scaffold14851_584958_SNP | 584958 | T | G |
| S_9148144 \| \| scaffold14851_585259_SNP | 585259 | C | T |
| S_9148148 \| \| scaffold14851_585277_SNP | 585277 | T | A |
| S_9148150 \| \| scaffold14851_585331_SNP | 585331 | C | T |
| S_9148242 \| \| scaffold14851_587210_SNP | 587210 | C | T |
| S_9148295 \| \| scaffold14851_587970_SNP | 587970 | A | T |
| S_9148310 \| \| scaffold14851_588322_SNP | 588322 | C | G |
| S_9148314 \| \| scaffold14851_588371_SNP | 588371 | G | T |
| S_9148316 \| \| scaffold14851_588426_SNP | 588426 | A | G |
| S_9148326 \| \| scaffold14851_588684_SNP | 588684 | A | C |
| S_9148441 \| \| scaffold14851_590098_SNP | 590098 | A | G |
| S_9148448 \| \| scaffold14851_590181_SNP | 590181 | C | T |
| S_9148459 \| \| scaffold14851_590332_SNP | 590332 | T | C |
| S_9148508 \| \| scaffold14851_591051_SNP | 591051 | C | G |
| S_9148549 \| \| scaffold14851_591772_SNP | 591772 | C | T |
| S_9148641 \| \| scaffold14851_592585_SNP | 592585 | T | C |
| S_9148643 \| \| scaffold14851_592626_SNP | 592626 | T | G |
| S_9148649 \| \| scaffold14851_592704_SNP | 592704 | C | T |
| S_9148656 \| \| scaffold14851_592785_SNP | 592785 | T | C |
| S_9148663 \| \| scaffold14851_592858_SNP | 592858 | T | C |
| S_9148665 \| \| scaffold14851_592910_SNP | 592910 | A | G |
| S_9148666 \| \| scaffold14851_592914_SNP | 592914 | C | T |
| S_9148668 \| \| scaffold14851_592971_SNP | 592971 | G | A |
| S_9148672 \| \| scaffold14851_593036_SNP | 593036 | G | C |
| S_9148685 \| \| scaffold14851_593405_SNP | 593405 | T | G |
| S_9148686 \| \| scaffold14851_593425_SNP | 593425 | A | T |
| S_9148689 \| \| scaffold14851_593454_SNP | 593454 | T | C |
| S_9148699 \| \| scaffold14851_593575_SNP | 593575 | C | T |
| S_9148702 \| \| scaffold14851_593597_SNP | 593597 | G | A |
| S_9148738 \| \| scaffold14851_593961_SNP | 593961 | A | C |
| S_9149037 \| \| scaffold14851_596493_SNP | 596493 | A | G |
| S_9149039 \| \| scaffold14851_596512_SNP | 596512 | T | G |
| S_9149040 \| \| scaffold14851_596518_SNP | 596518 | A | T |
| S_9149044 \| \| scaffold14851_596579_SNP | 596579 | G | A |
| S_9149047 \| \| scaffold14851_596601_SNP | 596601 | C | T |
| S_9149060 \| \| scaffold14851_596692_SNP | 596692 | A | G |
| S_9149177 \| \| scaffold14851_597865_SNP | 597865 | A | G |
| S_9149185 \| \| scaffold14851_598000_SNP | 598000 | A | G |
| S_9149194 \| \| scaffold14851_598142_SNP | 598142 | T | C |
| S_9149197 \| \| scaffold14851_598175_SNP | 598175 | G | A |
| S_9149215 \| \| scaffold14851_598523_SNP | 598523 | A | C |
| S_9149246 \| \| scaffold14851_598564_SNP | 598564 | T | G |
| S_9149294 \| \| scaffold14851_598958_SNP | 598958 | C | A |
| S_9149375 \| \| scaffold14851_600014_SNP | 600014 | T | A |
| S_9149393 \| \| scaffold14851_600427_SNP | 600427 | T | C |
| S_9149441 \| \| scaffold14851_601403_SNP | 601403 | T | A |
| S_9149465 \| \| scaffold14851_601769_SNP | 601769 | G | C |
| S_9149540 \| \| scaffold14851_602459_SNP | 602459 | T | C |
| S_9149642 \| \| scaffold14851_603900_SNP | 603900 | G | A |
| S_9149643 \| \| scaffold14851_603905_SNP | 603905 | A | C |
| S_9149647 \| \| scaffold14851_603956_SNP | 603956 | A | G |
| S_9149784 \| \| scaffold14851_605886_SNP | 605886 | C | T |
| S_9149785 \| \| scaffold14851_605905_SNP | 605905 | T | C |
| S_9149833 \| \| scaffold14851_606508_SNP | 606508 | G | A |
| S_9149835 \| \| scaffold14851_606534_SNP | 606534 | C | G |
| S_9149901 \| \| scaffold14851_607450_SNP | 607450 | C | A |
| S_9149931 \| \| scaffold14851_607780_SNP | 607780 | C | T |
| S_9149945 \| \| scaffold14851_607911_SNP | 607911 | A | T |
| S_9149953 \| \| scaffold14851_607977_SNP | 607977 | T | A |
| S_9149955 \| \| scaffold14851_607984_SNP | 607984 | G | C |
| S_9149962 \| \| scaffold14851_608067_SNP | 608067 | G | A |
| S_9149964 \| \| scaffold14851_608117_SNP | 608117 | A | G |
| S_9149969 \| \| scaffold14851_608236_SNP | 608236 | T | A |
| S_9149970 \| \| scaffold14851_608241_SNP | 608241 | T | G |
| S_9149988 \| \| scaffold14851_608363_SNP | 608363 | C | G |
| S_9150017 \| \| scaffold14851_608789_SNP | 608789 | G | A |
| S_9150043 \| \| scaffold14851_609309_SNP | 609309 | C | T |
| S_9150129 \| \| scaffold14851_610360_SNP | 610360 | C | A |
| S_9150393 \| \| scaffold14851_614436_SNP | 614436 | A | G |
| S_9150417 \| \| scaffold14851_614893_SNP | 614893 | T | C |
| S_9150493 \| \| scaffold14851_616402_SNP | 616402 | T | C |
| S_9150514 \| \| scaffold14851_616941_SNP | 616941 | G | A |
| S_9150523 \| \| scaffold14851_617133_SNP | 617133 | G | C |
| S_9150572 \| \| scaffold14851_617991_SNP | 617991 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9150590 \| \| scaffold14851_618117_SNP | 618117 | C | T |
| S_9150592 \| \| scaffold14851_618146_SNP | 618146 | G | A |
| S_9150598 \| \| scaffold14851_618198_SNP | 618198 | T | C |
| S_9150769 \| \| scaffold14851_619419_SNP | 619419 | C | A |
| S_9150778 \| \| scaffold14851_619628_SNP | 619628 | T | A |
| S_9150846 \| \| scaffold14851_620594_SNP | 620594 | G | A |
| S_9150913 \| \| scaffold14851_621669_SNP | 621669 | A | C |
| S_9150920 \| \| scaffold14851_621810_SNP | 621810 | G | A |
| S_9150985 \| \| scaffold14851_622670_SNP | 622670 | G | A |
| S_9150990 \| \| scaffold14851_622699_SNP | 622699 | T | C |
| S_9151065 \| \| scaffold14851_623597_SNP | 623597 | T | C |
| scaffold14851_623774_SNP | 623774 | A | G |
| S_9151203 \| \| scaffold14851_625969_SNP | 625969 | C | A |
| S_9151249 \| \| scaffold14851_626502_SNP | 626502 | G | T |
| S_9151250 \| \| scaffold14851_626506_SNP | 626506 | C | T |
| S_9151264 \| \| scaffold14851_626816_SNP | 626816 | T | C |
| S_9151268 \| \| scaffold14851_626876_SNP | 626876 | T | G |
| S_9151270 \| \| scaffold14851_626970_SNP | 626970 | G | T |
| S_9151273 \| \| scaffold14851_627005_SNP | 627005 | C | T |
| S_9151278 \| \| scaffold14851_627059_SNP | 627059 | G | A |
| S_9151288 \| \| scaffold14851_627230_SNP | 627230 | A | T |
| S_9151289 \| \| scaffold14851_627231_SNP | 627231 | G | A |
| S_9151400 \| \| scaffold14851_627867_SNP | 627867 | A | T |
| S_9151472 \| \| scaffold14851_628987_SNP | 628987 | G | A |
| S_9151499 \| \| scaffold14851_629472_SNP | 629472 | A | C |
| S_9151795 \| \| scaffold14851_633959_SNP | 633959 | A | G |
| S_9151813 \| \| scaffold14851_634102_SNP | 634102 | G | C |
| S_9151814 \| \| scaffold14851_634120_SNP | 634120 | C | G |
| S_9152023 \| \| scaffold14851_636210_SNP | 636210 | G | T |
| S_9152058 \| \| scaffold14851_636550_SNP | 636550 | T | C |
| S_9152171 \| \| scaffold14851_638222_SNP | 638222 | T | A |
| S_9152172 \| \| scaffold14851_638226_SNP | 638226 | A | T |
| S_9152174 \| \| scaffold14851_638255_SNP | 638255 | A | T |
| S_9152197 \| \| scaffold14851_638798_SNP | 638798 | G | A |
| scaffold14851_639157_SNP | 639157 | T | A |
| S_9152265 \| \| scaffold14851_639551_SNP | 639551 | T | G |
| S_9152271 \| \| scaffold14851_639728_SNP | 639728 | T | A |
| S_9152280 \| \| scaffold14851_639845_SNP | 639845 | A | T |
| S_9152281 \| \| scaffold14851_639855_SNP | 639855 | A | C |
| S_9152284 \| \| scaffold14851_639966_SNP | 639966 | A | C |
| S_9152286 \| \| scaffold14851_640056_SNP | 640056 | T | G |
| S_9152313 \| \| scaffold14851_640592_SNP | 640592 | T | G |
| S_9152319 \| \| scaffold14851_640667_SNP | 640667 | G | T |
| S_9152320 \| \| scaffold14851_640690_SNP | 640690 | T | A |
| S_9152333 \| \| scaffold14851_640986_SNP | 640986 | C | A |
| S_9152359 \| \| scaffold14851_641291_SNP | 641291 | A | C |
| S_9152364 \| \| scaffold14851_641352_SNP | 641352 | T | C |
| S_9152366 \| \| scaffold14851_641374_SNP | 641374 | G | A |
| S_9152379 \| \| scaffold14851_641556_SNP | 641556 | A | G |
| S_9152381 \| \| scaffold14851_641599_SNP | 641599 | G | T |
| S_9152382 \| \| scaffold14851_641625_SNP | 641625 | C | T |
| S_9152435 \| \| scaffold14851_642454_SNP | 642454 | T | A |
| S_9152465 \| \| scaffold14851_642949_SNP | 642949 | A | G |
| S_9152524 \| \| scaffold14851_643714_SNP | 643714 | G | C |
| S_9152632 \| \| scaffold14851_644716_SNP | 644716 | G | T |
| S_9152713 \| \| scaffold14851_646024_SNP | 646024 | T | A |
| S_9152817 \| \| scaffold14851_647568_SNP | 647568 | C | T |
| S_9152823 \| \| scaffold14851_647673_SNP | 647673 | T | G |
| S_9152889 \| \| scaffold14851_648602_SNP | 648602 | A | T |
| S_9153021 \| \| scaffold14851_649743_SNP | 649743 | T | C |
| S_9153080 \| \| scaffold14851_650540_SNP | 650540 | G | T |
| S_9153081 \| \| scaffold14851_650544_SNP | 650544 | G | T |
| S_9153113 \| \| scaffold14851_651090_SNP | 651090 | T | C |
| S_9153202 \| \| scaffold14851_652368_SNP | 652368 | T | A |
| S_9153256 \| \| scaffold14851_653571_SNP | 653571 | G | T |
| S_9153522 \| \| scaffold14851_657176_SNP | 657176 | T | C |
| S_9153525 \| \| scaffold14851_657239_SNP | 657239 | T | C |
| S_9153527 \| \| scaffold14851_657274_SNP | 657274 | T | G |
| S_9153531 \| \| scaffold14851_657391_SNP | 657391 | T | C |
| S_9153536 \| \| scaffold14851_657426_SNP | 657426 | T | C |
| S_9153538 \| \| scaffold14851_657441_SNP | 657441 | A | T |
| S_9153549 \| \| scaffold14851_657688_SNP | 657688 | C | T |
| S_9153777 \| \| scaffold14851_659622_SNP | 659622 | A | G |
| S_9153807 \| \| scaffold14851_660124_SNP | 660124 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9153842 \| \| scaffold14851_660565_SNP | 660565 | C | T |
| S_9153912 \| \| scaffold14851_660935_SNP | 660935 | A | C |
| S_9153926 \| \| scaffold14851_661173_SNP | 661173 | C | T |
| S_9154018 \| \| scaffold14851_662149_SNP | 662149 | T | C |
| S_9154020 \| \| scaffold14851_662171_SNP | 662171 | G | T |
| S_9154021 \| \| scaffold14851_662173_SNP | 662173 | A | T |
| S_9154046 \| \| scaffold14851_662498_SNP | 662498 | C | T |
| S_9154181 \| \| scaffold14851_663557_SNP | 663557 | A | G |
| S_9154203 \| \| scaffold14851_663867_SNP | 663867 | T | C |
| S_9154237 \| \| scaffold14851_664397_SNP | 664397 | A | T |
| S_9154290 \| \| scaffold14851_670122_SNP | 670122 | G | A |
| S_9154325 \| \| scaffold14851_670619_SNP | 670619 | C | T |
| S_9154359 \| \| scaffold14851_671095_SNP | 671095 | G | A |
| S_9154372 \| \| scaffold14851_671222_SNP | 671222 | G | T |
| S_9154401 \| \| scaffold14851_671638_SNP | 671638 | A | T |
| S_9154447 \| \| scaffold14851_672189_SNP | 672189 | A | G |
| S_9154484 \| \| scaffold14851_673159_SNP | 673159 | C | T |
| S_9154485 \| \| scaffold14851_673160_SNP | 673160 | A | G |
| S_9154488 \| \| scaffold14851_673176_SNP | 673176 | A | G |
| S_9154489 \| \| scaffold14851_673191_SNP | 673191 | C | T |
| S_9154493 \| \| scaffold14851_673251_SNP | 673251 | G | A |
| S_9154698 \| \| scaffold14851_675044_SNP | 675044 | A | C |
| S_9154731 \| \| scaffold14851_675543_SNP | 675543 | C | T |
| S_9154732 \| \| scaffold14851_675551_SNP | 675551 | A | G |
| S_9154748 \| \| scaffold14851_675826_SNP | 675826 | C | G |
| S_9154768 \| \| scaffold14851_676123_SNP | 676123 | A | T |
| S_9154772 \| \| scaffold14851_676232_SNP | 676232 | G | A |
| S_9154774 \| \| scaffold14851_676299_SNP | 676299 | A | G |
| S_9154802 \| \| scaffold14851_676473_SNP | 676473 | A | G |
| S_9154810 \| \| scaffold14851_676483_SNP | 676483 | T | A |
| S_9154814 \| \| scaffold14851_676486_SNP | 676486 | A | G |
| S_9154817 \| \| scaffold14851_676489_SNP | 676489 | A | G |
| S_9154899 \| \| scaffold14851_677667_SNP | 677667 | G | A |
| S_9154934 \| \| scaffold14851_678207_SNP | 678207 | C | T |
| S_9155052 \| \| scaffold14851_679917_SNP | 679917 | A | G |
| S_9155054 \| \| scaffold14851_679925_SNP | 679925 | G | A |
| S_9155055 \| \| scaffold14851_679929_SNP | 679929 | T | C |
| S_9155062 \| \| scaffold14851_679958_SNP | 679958 | A | G |
| S_9155066 \| \| scaffold14851_680039_SNP | 680039 | A | G |
| S_9155068 \| \| scaffold14851_680083_SNP | 680083 | G | A |
| S_9155069 \| \| scaffold14851_680109_SNP | 680109 | C | T |
| S_9155070 \| \| scaffold14851_680139_SNP | 680139 | C | T |
| S_9155071 \| \| scaffold14851_680144_SNP | 680144 | C | T |
| S_9155072 \| \| scaffold14851_680150_SNP | 680150 | A | G |
| S_9155079 \| \| scaffold14851_680352_SNP | 680352 | A | G |
| S_9155081 \| \| scaffold14851_680368_SNP | 680368 | T | G |
| S_9155082 \| \| scaffold14851_680369_SNP | 680369 | A | G |
| S_9155177 \| \| scaffold14851_680981_SNP | 680981 | T | A |
| S_9155179 \| \| scaffold14851_680993_SNP | 680993 | G | A |
| S_9155201 \| \| scaffold14851_681502_SNP | 681502 | C | G |
| S_9155279 \| \| scaffold14851_681925_SNP | 681925 | G | A |
| S_9155341 \| \| scaffold14851_683024_SNP | 683024 | T | G |
| S_9155361 \| \| scaffold14851_683499_SNP | 683499 | C | T |
| S_9155453 \| \| scaffold14851_684338_SNP | 684338 | T | C |
| S_9155603 \| \| scaffold14851_685190_SNP | 685190 | A | G |
| S_9155646 \| \| scaffold14851_685950_SNP | 685950 | C | A |
| S_9155805 \| \| scaffold14851_688163_SNP | 688163 | G | T |
| S_9156025 \| \| scaffold14851_690615_SNP | 690615 | T | A |
| S_9156026 \| \| scaffold14851_690616_SNP | 690616 | T | A |
| S_9156030 \| \| scaffold14851_690704_SNP | 690704 | C | A |
| S_9156052 \| \| scaffold14851_690902_SNP | 690902 | T | C |
| S_9156116 \| \| scaffold14851_691269_SNP | 691269 | G | T |
| S_9156119 \| \| scaffold14851_691446_SNP | 691446 | A | T |
| S_9156122 \| \| scaffold14851_691483_SNP | 691483 | G | T |
| S_9156123 \| \| scaffold14851_691502_SNP | 691502 | C | A |
| S_9156155 \| \| scaffold14851_692183_SNP | 692183 | A | G |
| S_9156253 \| \| scaffold14851_693641_SNP | 693641 | A | T |
| S_9156256 \| \| scaffold14851_693673_SNP | 693673 | A | G |
| S_9156262 \| \| scaffold14851_693792_SNP | 693792 | A | T |
| S_9156266 \| \| scaffold14851_693855_SNP | 693855 | C | T |
| S_9156269 \| \| scaffold14851_693894_SNP | 693894 | C | T |
| S_9156272 \| \| scaffold14851_693934_SNP | 693934 | C | A |
| S_9156351 \| \| scaffold14851_694968_SNP | 694968 | C | T |
| S_9156352 \| \| scaffold14851_694970_SNP | 694970 | G | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9156353 \| \| scaffold14851_695009_SNP | 695009 | A | G |
| S_9156369 \| \| scaffold14851_695232_SNP | 695232 | A | C |
| S_9156375 \| \| scaffold14851_695316_SNP | 695316 | A | C |
| S_9156376 \| \| scaffold14851_695317_SNP | 695317 | C | A |
| S_9156381 \| \| scaffold14851_695378_SNP | 695378 | T | G |
| S_9156392 \| \| scaffold14851_695562_SNP | 695562 | G | C |
| S_9156393 \| \| scaffold14851_695563_SNP | 695563 | T | C |
| S_9156442 \| \| scaffold14851_696228_SNP | 696228 | G | C |
| S_9156534 \| \| scaffold14851_696735_SNP | 696735 | A | G |
| S_9156645 \| \| scaffold14851_697754_SNP | 697754 | A | C |
| S_9156681 \| \| scaffold14851_698090_SNP | 698090 | C | A |
| S_9156682 \| \| scaffold14851_698101_SNP | 698101 | T | G |
| S_9156785 \| \| scaffold14851_699219_SNP | 699219 | G | C |
| S_9157027 \| \| scaffold14851_703488_SNP | 703488 | G | T |
| S_9157029 \| \| scaffold14851_703505_SNP | 703505 | A | T |
| S_9157044 \| \| scaffold14851_703719_SNP | 703719 | T | A |
| S_9157058 \| \| scaffold14851_704005_SNP | 704005 | C | T |
| S_9157101 \| \| scaffold14851_704275_SNP | 704275 | T | C |
| S_9157102 \| \| scaffold14851_704281_SNP | 704281 | G | A |
| scaffold14851_704418_SNP | 704418 | G | A |
| scaffold14851_704423_SNP | 704423 | T | C |
| scaffold14851_704434_SNP | 704434 | C | G |
| S_9157125 \| \| scaffold14851_704458_SNP | 704458 | T | C |
| S_9157147 \| \| scaffold14851_704545_SNP | 704545 | A | C |
| scaffold14851_704824_SNP | 704824 | G | C |
| scaffold14851_704897_SNP | 704897 | C | T |
| S_9157352 \| \| scaffold14851_706992_SNP | 706992 | A | C |
| S_9157359 \| \| scaffold14851_707069_SNP | 707069 | C | T |
| S_9157380 \| \| scaffold14851_707305_SNP | 707305 | A | G |
| S_9157809 \| \| scaffold14851_712878_SNP | 712878 | C | G |
| S_9157843 \| \| scaffold14851_713467_SNP | 713467 | C | A |
| S_9157844 \| \| scaffold14851_713468_SNP | 713468 | A | T |
| S_9158149 \| \| scaffold14851_718205_SNP | 718205 | A | C |
| S_9158165 \| \| scaffold14851_718449_SNP | 718449 | G | A |
| S_9158176 \| \| scaffold14851_718602_SNP | 718602 | C | T |
| S_9158206 \| \| scaffold14851_718982_SNP | 718982 | T | C |
| S_9158207 \| \| scaffold14851_719008_SNP | 719008 | C | A |
| S_9158269 \| \| scaffold14851_719846_SNP | 719846 | A | G |
| S_9158297 \| \| scaffold14851_720384_SNP | 720384 | C | A |
| S_9158312 \| \| scaffold14851_720573_SNP | 720573 | G | A |
| S_9158367 \| \| scaffold14851_721352_SNP | 721352 | T | C |
| S_9158419 \| \| scaffold14851_721949_SNP | 721949 | T | C |
| S_9158456 \| \| scaffold14851_722453_SNP | 722453 | A | G |
| S_9158474 \| \| scaffold14851_722807_SNP | 722807 | G | A |
| S_9158557 \| \| scaffold14851_723843_SNP | 723843 | T | G |
| S_9158745 \| \| scaffold14851_725802_SNP | 725802 | C | T |
| S_9158752 \| \| scaffold14851_725862_SNP | 725862 | A | T |
| S_9158754 \| \| scaffold14851_725927_SNP | 725927 | C | T |
| S_9158760 \| \| scaffold14851_726118_SNP | 726118 | C | A |
| S_9158773 \| \| scaffold14851_726342_SNP | 726342 | A | C |
| S_9158777 \| \| scaffold14851_726479_SNP | 726479 | G | A |
| S_9158809 \| \| scaffold14851_726593_SNP | 726593 | G | C |
| S_9158820 \| \| scaffold14851_726693_SNP | 726693 | G | C |
| S_9158836 \| \| scaffold14851_726842_SNP | 726842 | G | A |
| S_9158840 \| \| scaffold14851_726887_SNP | 726887 | T | C |
| S_9158845 \| \| scaffold14851_726985_SNP | 726985 | T | G |
| S_9158868 \| \| scaffold14851_727063_SNP | 727063 | T | C |
| S_9158900 \| \| scaffold14851_727410_SNP | 727410 | C | T |
| S_9158903 \| \| scaffold14851_727452_SNP | 727452 | A | G |
| S_9159024 \| \| scaffold14851_728794_SNP | 728794 | T | A |
| S_9159378 \| \| scaffold14851_735113_SNP | 735113 | T | C |
| S_9159379 \| \| scaffold14851_735125_SNP | 735125 | G | C |
| S_9159540 \| \| scaffold14851_737442_SNP | 737442 | G | T |
| S_9159771 \| \| scaffold14851_740739_SNP | 740739 | T | A |
| S_9160049 \| \| scaffold14851_743466_SNP | 743466 | C | T |
| S_9160060 \| \| scaffold14851_743629_SNP | 743629 | G | A |
| S_9160067 \| \| scaffold14851_743727_SNP | 743727 | C | G |
| S_9160074 \| \| scaffold14851_743860_SNP | 743860 | G | C |
| S_9160075 \| \| scaffold14851_743865_SNP | 743865 | A | C |
| S_9160080 \| \| scaffold14851_743936_SNP | 743936 | T | G |
| S_9160240 \| \| scaffold14851_746579_SNP | 746579 | T | C |
| S_9160273 \| \| scaffold14851_746880_SNP | 746880 | T | A |
| S_9160303 \| \| scaffold14851_747198_SNP | 747198 | G | A |
| S_9160343 \| \| scaffold14851_747785_SNP | 747785 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9160372 \| \| scaffold14851_748041_SNP | 748041 | C | A |
| S_9160381 \| \| scaffold14851_748137_SNP | 748137 | G | A |
| S_9160407 \| \| scaffold14851_748516_SNP | 748516 | C | T |
| S_9160435 \| \| scaffold14851_748896_SNP | 748896 | G | A |
| S_9160486 \| \| scaffold14851_749525_SNP | 749525 | T | G |
| S_9160498 \| \| scaffold14851_749798_SNP | 749798 | T | C |
| S_9160592 \| \| scaffold14851_750582_SNP | 750582 | T | A |
| S_9160809 \| \| scaffold14851_752508_SNP | 752508 | C | A |
| S_9160909 \| \| scaffold14851_754161_SNP | 754161 | C | T |
| S_9161035 \| \| scaffold14851_755405_SNP | 755405 | T | C |
| S_9161058 \| \| scaffold14851_755692_SNP | 755692 | T | G |
| S_9161210 \| \| scaffold14851_756642_SNP | 756642 | G | A |
| S_9161211 \| \| scaffold14851_756687_SNP | 756687 | T | A |
| S_9161212 \| \| scaffold14851_756755_SNP | 756755 | A | C |
| S_9161218 \| \| scaffold14851_756807_SNP | 756807 | T | C |
| S_9161236 \| \| scaffold14851_757115_SNP | 757115 | C | A |
| S_9161241 \| \| scaffold14851_757263_SNP | 757263 | A | G |
| S_9161243 \| \| scaffold14851_757387_SNP | 757387 | A | G |
| S_9161254 \| \| scaffold14851_757547_SNP | 757547 | G | T |
| S_9161290 \| \| scaffold14851_758245_SNP | 758245 | A | T |
| S_9161311 \| \| scaffold14851_758395_SNP | 758395 | G | A |
| S_9161325 \| \| scaffold14851_758737_SNP | 758737 | C | A |
| S_9161384 \| \| scaffold14851_759448_SNP | 759448 | C | A |
| S_9161505 \| \| scaffold14851_760681_SNP | 760681 | A | G |
| S_9161584 \| \| scaffold14851_761339_SNP | 761339 | T | C |
| S_9161864 \| \| scaffold14851_763327_SNP | 763327 | A | G |
| S_9162113 \| \| scaffold14851_767164_SNP | 767164 | A | G |
| S_9162212 \| \| scaffold14851_768078_SNP | 768078 | A | T |
| S_9162262 \| \| scaffold14851_768897_SNP | 768897 | A | G |
| S_9162270 \| \| scaffold14851_769004_SNP | 769004 | T | C |
| S_9162536 \| \| scaffold14851_771097_SNP | 771097 | G | A |
| S_9162652 \| \| scaffold14851_772833_SNP | 772833 | T | G |
| S_9162654 \| \| scaffold14851_772865_SNP | 772865 | C | T |
| S_9162655 \| \| scaffold14851_772875_SNP | 772875 | C | T |
| S_9162674 \| \| scaffold14851_773072_SNP | 773072 | T | A |
| S_9162675 \| \| scaffold14851_773073_SNP | 773073 | C | T |
| S_9162676 \| \| scaffold14851_773080_SNP | 773080 | A | G |
| S_9162805 \| \| scaffold14851_774271_SNP | 774271 | A | C |
| S_9162808 \| \| scaffold14851_774314_SNP | 774314 | G | A |
| S_9162809 \| \| scaffold14851_774315_SNP | 774315 | G | T |
| S_9162825 \| \| scaffold14851_774508_SNP | 774508 | C | A |
| S_9162827 \| \| scaffold14851_774542_SNP | 774542 | T | A |
| S_9162848 \| \| scaffold14851_774823_SNP | 774823 | A | C |
| S_9162855 \| \| scaffold14851_774966_SNP | 774966 | T | A |
| S_9162908 \| \| scaffold14851_775348_SNP | 775348 | T | C |
| S_9162920 \| \| scaffold14851_775607_SNP | 775607 | T | A |
| S_9162946 \| \| scaffold14851_775828_SNP | 775828 | T | G |
| S_9162964 \| \| scaffold14851_775904_SNP | 775904 | C | T |
| S_9162989 \| \| scaffold14851_776283_SNP | 776283 | G | A |
| S_9163008 \| \| scaffold14851_776562_SNP | 776562 | A | G |
| S_9163225 \| \| scaffold14851_780303_SNP | 780303 | C | G |
| S_9163290 \| \| scaffold14851_781242_SNP | 781242 | C | T |
| S_9163350 \| \| scaffold14851_782315_SNP | 782315 | A | C |
| S_9163361 \| \| scaffold14851_782437_SNP | 782437 | T | A |
| S_9163376 \| \| scaffold14851_782709_SNP | 782709 | G | A |
| S_9163435 \| \| scaffold14851_783249_SNP | 783249 | G | A |
| S_9163437 \| \| scaffold14851_783259_SNP | 783259 | A | G |
| S_9163442 \| \| scaffold14851_783327_SNP | 783327 | A | G |
| S_9163444 \| \| scaffold14851_783350_SNP | 783350 | G | A |
| S_9163524 \| \| scaffold14851_784518_SNP | 784518 | A | G |
| S_9163578 \| \| scaffold14851_785569_SNP | 785569 | C | A |
| S_9163579 \| \| scaffold14851_785605_SNP | 785605 | G | A |
| S_9163590 \| \| scaffold14851_785967_SNP | 785967 | G | A |
| S_9163591 \| \| scaffold14851_785991_SNP | 785991 | G | T |
| S_9163641 \| \| scaffold14851_786585_SNP | 786585 | A | T |
| S_9163664 \| \| scaffold14851_786915_SNP | 786915 | G | C |
| S_9163681 \| \| scaffold14851_787118_SNP | 787118 | C | A |
| S_9163691 \| \| scaffold14851_787258_SNP | 787258 | T | C |
| S_9163694 \| \| scaffold14851_787327_SNP | 787327 | T | G |
| S_9163770 \| \| scaffold14851_788160_SNP | 788160 | C | T |
| S_9163774 \| \| scaffold14851_788210_SNP | 788210 | C | T |
| S_9163782 \| \| scaffold14851_788301_SNP | 788301 | C | T |
| scaffold14851_788826_SNP | 788826 | A | G |
| scaffold14851_788838_SNP | 788838 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9163849 \| \| scaffold14851_788975_SNP | 788975 | G | C |
| S_9163888 \| \| scaffold14851_789482_SNP | 789482 | G | A |
| S_9163890 \| \| scaffold14851_789489_SNP | 789489 | A | T |
| S_9163896 \| \| scaffold14851_789782_SNP | 789782 | C | T |
| S_9163897 \| \| scaffold14851_789783_SNP | 789783 | C | A |
| S_9164021 \| \| scaffold14851_792053_SNP | 792053 | A | G |
| S_9164049 \| \| scaffold14851_792387_SNP | 792387 | T | C |
| S_9164057 \| \| scaffold14851_792505_SNP | 792505 | T | G |
| S_9164086 \| \| scaffold14851_793039_SNP | 793039 | A | G |
| S_9164096 \| \| scaffold14851_793274_SNP | 793274 | G | C |
| S_9164097 \| \| scaffold14851_793342_SNP | 793342 | G | T |
| S_9164148 \| \| scaffold14851_794049_SNP | 794049 | T | C |
| S_9164212 \| \| scaffold14851_794583_SNP | 794583 | G | T |
| S_9164235 \| \| scaffold14851_794903_SNP | 794903 | G | A |
| S_9164236 \| \| scaffold14851_794904_SNP | 794904 | A | T |
| S_9164239 \| \| scaffold14851_794925_SNP | 794925 | T | C |
| S_9164273 \| \| scaffold14851_795283_SNP | 795283 | G | A |
| S_9164299 \| \| scaffold14851_795948_SNP | 795948 | G | T |
| S_9164414 \| \| scaffold14851_797655_SNP | 797655 | G | C |
| S_9164427 \| \| scaffold14851_797824_SNP | 797824 | A | C |
| S_9164429 \| \| scaffold14851_797836_SNP | 797836 | C | G |
| S_9164430 \| \| scaffold14851_797868_SNP | 797868 | G | A |
| S_9164449 \| \| scaffold14851_798130_SNP | 798130 | C | T |
| scaffold14851_801198_SNP | 801198 | T | A |
| S_9164802 \| \| scaffold14851_801205_SNP | 801205 | G | A |
| S_9165057 \| \| scaffold14851_803670_SNP | 803670 | A | G |
| S_9165058 \| \| scaffold14851_803671_SNP | 803671 | A | C |
| S_9165059 \| \| scaffold14851_803672_SNP | 803672 | G | C |
| S_9165364 \| \| scaffold14851_806344_SNP | 806344 | T | C |
| S_9165365 \| \| scaffold14851_806356_SNP | 806356 | A | T |
| S_9165385 \| \| scaffold14851_806533_SNP | 806533 | G | A |
| S_9167225 \| \| scaffold14851_824740_SNP | 824740 | C | T |
| S_9167975 \| \| scaffold14851_830032_SNP | 830032 | A | G |
| S_9168018 \| \| scaffold14851_830741_SNP | 830741 | T | C |
| S_9168019 \| \| scaffold14851_830749_SNP | 830749 | A | G |
| S_9168023 \| \| scaffold14851_830781_SNP | 830781 | T | C |
| S_9168074 \| \| scaffold14851_831587_SNP | 831587 | C | A |
| S_9168079 \| \| scaffold14851_831638_SNP | 831638 | G | A |
| S_9168242 \| \| scaffold14851_834096_SNP | 834096 | C | T |
| S_9168677 \| \| scaffold14851_836479_SNP | 836479 | G | C |
| S_9169339 \| \| scaffold14851_842490_SNP | 842490 | C | T |
| S_9169340 \| \| scaffold14851_842577_SNP | 842577 | C | T |
| S_9169342 \| \| scaffold14851_842611_SNP | 842611 | T | A |
| S_9169367 \| \| scaffold14851_842861_SNP | 842861 | C | A |
| S_9169407 \| \| scaffold14851_843314_SNP | 843314 | T | A |
| S_9169411 \| \| scaffold14851_843390_SNP | 843390 | C | G |
| scaffold14851_843765_SNP | 843765 | C | G |
| S_9171625 \| \| scaffold14851_858825_SNP | 858825 | T | C |
| S_9171694 \| \| scaffold14851_859657_SNP | 859657 | G | A |
| S_9171716 \| \| scaffold14851_859847_SNP | 859847 | C | T |
| S_9171815 \| \| scaffold14851_860664_SNP | 860664 | T | G |
| S_9172261 \| \| scaffold14851_864073_SNP | 864073 | G | A |
| S_9175599 \| \| scaffold14851_892750_SNP | 892750 | C | T |
| S_9176716 \| \| scaffold14851_905079_SNP | 905079 | A | G |
| S_9177569 \| \| scaffold14851_915675_SNP | 915675 | A | T |
| scaffold14851_915679_SNP | 915679 | G | A |
| S_9179270 \| \| scaffold14851_931527_SNP | 931527 | C | A |
| S_9179493 \| \| scaffold14851_934643_SNP | 934643 | A | T |
| S_9179513 \| \| scaffold14851_934925_SNP | 934925 | C | T |
| S_9180028 \| \| scaffold14851_940662_SNP | 940662 | C | T |
| scaffold14851_954099_SNP | 954099 | G | A |
| S_9180584 \| \| scaffold14851_954424_SNP | 954424 | C | T |
| S_9181469 \| \| scaffold14851_965459_SNP | 965459 | A | G |
| scaffold14851_965621_SNP | 965621 | G | C |
| S_9181488 \| \| scaffold14851_965626_SNP | 965626 | G | T |
| S_9181737 \| \| scaffold14851_969364_SNP | 969364 | T | C |
| S_9185658 \| \| scaffold14851_996202_SNP | 996202 | C | T |
| S_9185659 \| \| scaffold14851_996206_SNP | 996206 | A | G |
| S_9185698 \| \| scaffold14851_997055_SNP | 997055 | G | A |
| S_9185700 \| \| scaffold14851_997074_SNP | 997074 | A | G |
| S_9185847 \| \| scaffold14851_998830_SNP | 998830 | A | C |
| S_9185899 \| \| scaffold14851_999634_SNP | 999634 | G | T |
| S_9185932 \| \| scaffold14851_1000178_SNP | 1000178 | G | T |
| scaffold14851_1011547_SNP | 1011547 | T | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| scaffold14851_1011548_SNP | 1011548 | T | G |
| S_9190670 \| \| scaffold14851_1011554_SNP | 1011554 | T | G |
| S_9190671 \| \| scaffold14851_1011558_SNP | 1011558 | T | A |
| S_9190928 \| \| scaffold14851_1014512_SNP | 1014512 | T | A |
| S_9190929 \| \| scaffold14851_1014518_SNP | 1014518 | T | G |
| S_9190976 \| \| scaffold14851_1015253_SNP | 1015253 | C | T |
| S_9191042 \| \| scaffold14851_1016117_SNP | 1016117 | A | T |
| S_9191046 \| \| scaffold14851_1016186_SNP | 1016186 | T | A |
| S_9191048 \| \| scaffold14851_1016219_SNP | 1016219 | G | A |
| S_9191086 \| \| scaffold14851_1017283_SNP | 1017283 | T | A |
| S_9191230 \| \| scaffold14851_1018995_SNP | 1018995 | C | A |
| S_9191233 \| \| scaffold14851_1019005_SNP | 1019005 | T | G |
| S_9191234 \| \| scaffold14851_1019008_SNP | 1019008 | T | G |
| S_9191257 \| \| scaffold14851_1019557_SNP | 1019557 | A | G |
| S_9191259 \| \| scaffold14851_1019578_SNP | 1019578 | C | A |
| S_9191262 \| \| scaffold14851_1019633_SNP | 1019633 | A | G |
| S_9191263 \| \| scaffold14851_1019646_SNP | 1019646 | C | T |
| S_9191385 \| \| scaffold14851_1020806_SNP | 1020806 | A | G |
| S_9191609 \| \| scaffold14851_1023684_SNP | 1023684 | A | G |
| S_9191611 \| \| scaffold14851_1023725_SNP | 1023725 | A | G |
| S_9192020 \| \| scaffold14851_1030502_SNP | 1030502 | C | T |
| S_9192311 \| \| scaffold14851_1036589_SNP | 1036589 | C | T |
| S_9192317 \| \| scaffold14851_1036761_SNP | 1036761 | T | C |
| S_9192321 \| \| scaffold14851_1036939_SNP | 1036939 | C | A |
| S_9192336 \| \| scaffold14851_1037109_SNP | 1037109 | A | G |
| S_9192339 \| \| scaffold14851_1037167_SNP | 1037167 | A | G |
| S_9192455 \| \| scaffold14851_1038752_SNP | 1038752 | G | T |
| S_9192493 \| \| scaffold14851_1039411_SNP | 1039411 | A | G |
| S_9192494 \| \| scaffold14851_1039427_SNP | 1039427 | G | C |
| S_9192663 \| \| scaffold14851_1041651_SNP | 1041651 | G | A |
| S_9192694 \| \| scaffold14851_1042229_SNP | 1042229 | C | A |
| S_9192737 \| \| scaffold14851_1043155_SNP | 1043155 | C | G |
| S_9192738 \| \| scaffold14851_1043160_SNP | 1043160 | G | T |
| S_9192739 \| \| scaffold14851_1043220_SNP | 1043220 | C | A |
| S_9192741 \| \| scaffold14851_1043226_SNP | 1043226 | G | T |
| S_9192749 \| \| scaffold14851_1043337_SNP | 1043337 | A | G |
| S_9192794 \| \| scaffold14851_1043561_SNP | 1043561 | G | T |
| S_9193313 \| \| scaffold14851_1049711_SNP | 1049711 | G | A |
| S_9193486 \| \| scaffold14851_1052442_SNP | 1052442 | C | G |
| S_9193514 \| \| scaffold14851_1052776_SNP | 1052776 | G | C |
| S_9193535 \| \| scaffold14851_1053009_SNP | 1053009 | T | A |
| S_9193536 \| \| scaffold14851_1053013_SNP | 1053013 | G | T |
| S_9193543 \| \| scaffold14851_1053083_SNP | 1053083 | C | G |
| S_9193544 \| \| scaffold14851_1053092_SNP | 1053092 | T | A |
| S_9193545 \| \| scaffold14851_1053106_SNP | 1053106 | T | A |
| S_9193551 \| \| scaffold14851_1053192_SNP | 1053192 | C | A |
| S_9193555 \| \| scaffold14851_1053228_SNP | 1053228 | T | A |
| S_9193658 \| \| scaffold14851_1054986_SNP | 1054986 | G | T |
| S_9193684 \| \| scaffold14851_1055854_SNP | 1055854 | T | C |
| S_9193702 \| \| scaffold14851_1056116_SNP | 1056116 | A | G |
| S_9193706 \| \| scaffold14851_1056236_SNP | 1056236 | T | A |
| S_9193746 \| \| scaffold14851_1056630_SNP | 1056630 | A | G |
| S_9193865 \| \| scaffold14851_1058208_SNP | 1058208 | T | C |
| S_9194606 \| \| scaffold14851_1067404_SNP | 1067404 | T | A |
| S_9194706 \| \| scaffold14851_1068807_SNP | 1068807 | A | C |
| S_9194708 \| \| scaffold14851_1068832_SNP | 1068832 | C | A |
| S_9194720 \| \| scaffold14851_1069093_SNP | 1069093 | T | G |
| S_9194721 \| \| scaffold14851_1069118_SNP | 1069118 | A | T |
| S_9194722 \| \| scaffold14851_1069122_SNP | 1069122 | T | A |
| S_9194723 \| \| scaffold14851_1069168_SNP | 1069168 | A | C |
| S_9194730 \| \| scaffold14851_1069349_SNP | 1069349 | G | T |
| S_9194913 \| \| scaffold14851_1072101_SNP | 1072101 | C | T |
| S_9194926 \| \| scaffold14851_1072306_SNP | 1072306 | T | G |
| S_9194970 \| \| scaffold14851_1072503_SNP | 1072503 | T | C |
| S_9195108 \| \| scaffold14851_1073728_SNP | 1073728 | C | T |
| S_9195180 \| \| scaffold14851_1074610_SNP | 1074610 | A | T |
| S_9195213 \| \| scaffold14851_1075177_SNP | 1075177 | T | C |
| S_9195249 \| \| scaffold14851_1075746_SNP | 1075746 | T | A |
| S_9195292 \| \| scaffold14851_1075913_SNP | 1075913 | C | T |
| S_9195303 \| \| scaffold14851_1076002_SNP | 1076002 | G | A |
| S_9195357 \| \| scaffold14851_1076695_SNP | 1076695 | G | T |
| S_9195362 \| \| scaffold14851_1076792_SNP | 1076792 | A | G |
| S_9195366 \| \| scaffold14851_1076820_SNP | 1076820 | A | G |
| S_9195368 \| \| scaffold14851_1076842_SNP | 1076842 | C | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9195370 \|\| scaffold14851_1076850_SNP | 1076850 | A | G |
| S_9195371 \|\| scaffold14851_1076879_SNP | 1076879 | A | G |
| S_9195435 \|\| scaffold14851_1078084_SNP | 1078084 | G | A |
| S_9195546 \|\| scaffold14851_1079943_SNP | 1079943 | G | A |
| S_9195550 \|\| scaffold14851_1080058_SNP | 1080058 | C | T |
| S_9195552 \|\| scaffold14851_1080091_SNP | 1080091 | T | G |
| S_9195554 \|\| scaffold14851_1080111_SNP | 1080111 | A | C |
| S_9195574 \|\| scaffold14851_1080367_SNP | 1080367 | C | T |
| S_9195578 \|\| scaffold14851_1080389_SNP | 1080389 | C | T |
| S_9195579 \|\| scaffold14851_1080405_SNP | 1080405 | G | C |
| S_9195584 \|\| scaffold14851_1080511_SNP | 1080511 | G | A |
| S_9195640 \|\| scaffold14851_1081289_SNP | 1081289 | A | C |
| S_9195664 \|\| scaffold14851_1081751_SNP | 1081751 | G | A |
| S_9195668 \|\| scaffold14851_1081913_SNP | 1081913 | C | T |
| S_9195682 \|\| scaffold14851_1082198_SNP | 1082198 | A | G |
| S_9195759 \|\| scaffold14851_1082895_SNP | 1082895 | T | C |
| S_9195775 \|\| scaffold14851_1083013_SNP | 1083013 | T | C |
| S_9195965 \|\| scaffold14851_1085185_SNP | 1085185 | G | T |
| S_9196240 \|\| scaffold14851_1089739_SNP | 1089739 | G | A |
| S_9196242 \|\| scaffold14851_1089748_SNP | 1089748 | T | C |
| S_9196249 \|\| scaffold14851_1089852_SNP | 1089852 | C | G |
| S_9196256 \|\| scaffold14851_1089939_SNP | 1089939 | T | A |
| S_9196258 \|\| scaffold14851_1089958_SNP | 1089958 | C | T |
| scaffold14851_1091765_SNP | 1091765 | A | G |
| S_9196517 \|\| scaffold14851_1092396_SNP | 1092396 | A | C |
| S_9196532 \|\| scaffold14851_1092527_SNP | 1092527 | T | C |
| S_9196533 \|\| scaffold14851_1092555_SNP | 1092555 | G | A |
| S_9196545 \|\| scaffold14851_1092675_SNP | 1092675 | T | C |
| S_9196561 \|\| scaffold14851_1092838_SNP | 1092838 | G | T |
| S_9196590 \|\| scaffold14851_1093305_SNP | 1093305 | A | G |
| S_9196595 \|\| scaffold14851_1093367_SNP | 1093367 | G | A |
| S_9196598 \|\| scaffold14851_1093465_SNP | 1093465 | C | T |
| S_9196603 \|\| scaffold14851_1093519_SNP | 1093519 | A | G |
| S_9196604 \|\| scaffold14851_1093541_SNP | 1093541 | T | C |
| S_9196611 \|\| scaffold14851_1093695_SNP | 1093695 | T | C |
| S_9196619 \|\| scaffold14851_1093878_SNP | 1093878 | A | G |
| S_9196633 \|\| scaffold14851_1094081_SNP | 1094081 | T | G |
| S_9196647 \|\| scaffold14851_1094296_SNP | 1094296 | A | T |
| S_9196656 \|\| scaffold14851_1094426_SNP | 1094426 | A | G |
| S_9196657 \|\| scaffold14851_1094461_SNP | 1094461 | G | A |
| S_9196962 \|\| scaffold14851_1098075_SNP | 1098075 | A | T |
| S_9197251 \|\| scaffold14851_1102315_SNP | 1102315 | C | G |
| S_9197389 \|\| scaffold14851_1104823_SNP | 1104823 | G | A |
| S_9197453 \|\| scaffold14851_1105851_SNP | 1105851 | G | T |
| S_9197462 \|\| scaffold14851_1106068_SNP | 1106068 | G | A |
| S_9197509 \|\| scaffold14851_1106855_SNP | 1106855 | C | T |
| S_9197554 \|\| scaffold14851_1107383_SNP | 1107383 | A | G |
| S_9197556 \|\| scaffold14851_1107397_SNP | 1107397 | A | G |
| S_9197561 \|\| scaffold14851_1107507_SNP | 1107507 | T | C |
| S_9197566 \|\| scaffold14851_1107635_SNP | 1107635 | A | C |
| S_9197602 \|\| scaffold14851_1108152_SNP | 1108152 | A | T |
| S_9197614 \|\| scaffold14851_1108266_SNP | 1108266 | G | A |
| S_9197679 \|\| scaffold14851_1109181_SNP | 1109181 | C | T |
| S_9197736 \|\| scaffold14851_1110040_SNP | 1110040 | C | T |
| S_9197737 \|\| scaffold14851_1110044_SNP | 1110044 | C | T |
| S_9197741 \|\| scaffold14851_1110122_SNP | 1110122 | A | G |
| S_9197742 \|\| scaffold14851_1110129_SNP | 1110129 | A | G |
| S_9197750 \|\| scaffold14851_1110236_SNP | 1110236 | C | T |
| S_9197761 \|\| scaffold14851_1110351_SNP | 1110351 | C | T |
| S_9197806 \|\| scaffold14851_1111128_SNP | 1111128 | C | T |
| S_9197820 \|\| scaffold14851_1111301_SNP | 1111301 | T | C |
| S_9197830 \|\| scaffold14851_1111410_SNP | 1111410 | A | G |
| S_9197862 \|\| scaffold14851_1111637_SNP | 1111637 | C | A |
| S_9197865 \|\| scaffold14851_1111687_SNP | 1111687 | G | T |
| S_9197866 \|\| scaffold14851_1111705_SNP | 1111705 | G | A |
| S_9197882 \|\| scaffold14851_1112129_SNP | 1112129 | A | G |
| S_9197883 \|\| scaffold14851_1112135_SNP | 1112135 | G | T |
| S_9197900 \|\| scaffold14851_1112362_SNP | 1112362 | T | C |
| S_9197901 \|\| scaffold14851_1112367_SNP | 1112367 | A | G |
| S_9197903 \|\| scaffold14851_1112396_SNP | 1112396 | C | T |
| S_9197904 \|\| scaffold14851_1112418_SNP | 1112418 | T | C |
| S_9197914 \|\| scaffold14851_1112537_SNP | 1112537 | A | T |
| S_9197924 \|\| scaffold14851_1112762_SNP | 1112762 | G | T |
| S_9197926 \|\| scaffold14851_1112778_SNP | 1112778 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9197989 \| \| scaffold14851_1113318_SNP | 1113318 | A | G |
| S_9197992 \| \| scaffold14851_1113365_SNP | 1113365 | C | A |
| S_9198006 \| \| scaffold14851_1113685_SNP | 1113685 | T | C |
| S_9198021 \| \| scaffold14851_1113890_SNP | 1113890 | C | G |
| S_9198022 \| \| scaffold14851_1113905_SNP | 1113905 | G | T |
| S_9198027 \| \| scaffold14851_1113973_SNP | 1113973 | T | A |
| S_9198034 \| \| scaffold14851_1114083_SNP | 1114083 | G | A |
| S_9198048 \| \| scaffold14851_1114212_SNP | 1114212 | T | C |
| S_9198060 \| \| scaffold14851_1114354_SNP | 1114354 | G | C |
| S_9198073 \| \| scaffold14851_1114577_SNP | 1114577 | A | T |
| S_9198074 \| \| scaffold14851_1114579_SNP | 1114579 | T | G |
| S_9198075 \| \| scaffold14851_1114606_SNP | 1114606 | A | G |
| S_9198081 \| \| scaffold14851_1114670_SNP | 1114670 | T | C |
| S_9198083 \| \| scaffold14851_1114683_SNP | 1114683 | C | T |
| S_9198117 \| \| scaffold14851_1115264_SNP | 1115264 | G | A |
| S_9198165 \| \| scaffold14851_1115710_SNP | 1115710 | T | G |
| S_9198175 \| \| scaffold14851_1115766_SNP | 1115766 | G | T |
| S_9198270 \| \| scaffold14851_1117306_SNP | 1117306 | T | A |
| S_9198274 \| \| scaffold14851_1117339_SNP | 1117339 | C | A |
| S_9198325 \| \| scaffold14851_1118002_SNP | 1118002 | C | T |
| S_9198350 \| \| scaffold14851_1118349_SNP | 1118349 | C | G |
| S_9198647 \| \| scaffold14851_1123215_SNP | 1123215 | T | C |
| S_9198690 \| \| scaffold14851_1124110_SNP | 1124110 | T | A |
| S_9198739 \| \| scaffold14851_1125069_SNP | 1125069 | T | C |
| S_9198742 \| \| scaffold14851_1125140_SNP | 1125140 | C | A |
| S_9198745 \| \| scaffold14851_1125186_SNP | 1125186 | C | T |
| S_9198747 \| \| scaffold14851_1125196_SNP | 1125196 | C | T |
| S_9198770 \| \| scaffold14851_1125390_SNP | 1125390 | T | A |
| S_9198832 \| \| scaffold14851_1126309_SNP | 1126309 | C | T |
| S_9199099 \| \| scaffold14851_1130920_SNP | 1130920 | A | G |
| S_9199138 \| \| scaffold14851_1131501_SNP | 1131501 | T | C |
| S_9199173 \| \| scaffold14851_1132052_SNP | 1132052 | A | G |
| S_9199225 \| \| scaffold14851_1134075_SNP | 1134075 | A | T |
| S_9199293 \| \| scaffold14851_1135883_SNP | 1135883 | A | T |
| S_9199320 \| \| scaffold14851_1136275_SNP | 1136275 | T | C |
| S_9199370 \| \| scaffold14851_1136800_SNP | 1136800 | G | A |
| S_9199895 \| \| scaffold14851_1142182_SNP | 1142182 | G | A |
| S_9199896 \| \| scaffold14851_1142204_SNP | 1142204 | C | G |
| S_9199897 \| \| scaffold14851_1142218_SNP | 1142218 | C | G |
| S_9200445 \| \| scaffold14851_1146799_SNP | 1146799 | T | C |
| S_9200448 \| \| scaffold14851_1146811_SNP | 1146811 | C | G |
| S_9200478 \| \| scaffold14851_1147028_SNP | 1147028 | C | A |
| S_9200559 \| \| scaffold14851_1148194_SNP | 1148194 | A | T |
| S_9200697 \| \| scaffold14851_1148656_SNP | 1148656 | T | G |
| S_9200827 \| \| scaffold14851_1149245_SNP | 1149245 | T | C |
| scaffold14851_1151185_SNP | 1151185 | T | C |
| scaffold14851_1153152_SNP | 1153152 | T | G |
| S_9201895 \| \| scaffold14851_1153622_SNP | 1153622 | G | T |
| S_9201899 \| \| scaffold14851_1153639_SNP | 1153639 | T | A |
| S_9201926 \| \| scaffold14851_1153766_SNP | 1153766 | A | T |
| S_9201955 \| \| scaffold14851_1153896_SNP | 1153896 | A | G |
| S_9208205 \| \| scaffold14851_1173113_SNP | 1173113 | A | C |
| scaffold14851_1173267_SNP | 1173267 | A | G |
| S_9209058 \| \| scaffold14851_1179184_SNP | 1179184 | T | A |
| S_9209156 \| \| scaffold14851_1179507_SNP | 1179507 | A | G |
| S_9209159 \| \| scaffold14851_1179541_SNP | 1179541 | G | A |
| S_9209162 \| \| scaffold14851_1179561_SNP | 1179561 | A | G |
| S_9210444 \| \| scaffold14851_1186275_SNP | 1186275 | T | G |
| S_9210573 \| \| scaffold14851_1186740_SNP | 1186740 | A | T |
| S_9210609 \| \| scaffold14851_1186872_SNP | 1186872 | T | C |
| S_9210618 \| \| scaffold14851_1186932_SNP | 1186932 | T | A |
| S_9210621 \| \| scaffold14851_1186975_SNP | 1186975 | A | G |
| scaffold14851_1187445_SNP | 1187445 | T | A |
| S_9210893 \| \| scaffold14851_1187869_SNP | 1187869 | T | C |
| S_9210930 \| \| scaffold14851_1188108_SNP | 1188108 | A | G |
| S_9210931 \| \| scaffold14851_1188109_SNP | 1188109 | A | G |
| S_9210947 \| \| scaffold14851_1188216_SNP | 1188216 | T | C |
| S_9210949 \| \| scaffold14851_1188239_SNP | 1188239 | A | C |
| S_9210963 \| \| scaffold14851_1188358_SNP | 1188358 | C | A |
| S_9210964 \| \| scaffold14851_1188368_SNP | 1188368 | A | G |
| S_9210965 \| \| scaffold14851_1188369_SNP | 1188369 | A | T |
| S_9211586 \| \| scaffold14851_1189820_SNP | 1189820 | G | T |
| S_9211625 \| \| scaffold14851_1190038_SNP | 1190038 | G | A |
| S_9211628 \| \| scaffold14851_1190045_SNP | 1190045 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9211925 \| \| scaffold14851_1191719_SNP | 1191719 | G | A |
| S_9212158 \| \| scaffold14851_1192272_SNP | 1192272 | T | G |
| S_9212217 \| \| scaffold14851_1192576_SNP | 1192576 | C | T |
| scaffold14851_1192712_SNP | 1192712 | A | C |
| S_9212239 \| \| scaffold14851_1192716_SNP | 1192716 | C | T |
| S_9212308 \| \| scaffold14851_1194480_SNP | 1194480 | C | T |
| S_9212370 \| \| scaffold14851_1194966_SNP | 1194966 | C | T |
| S_9212374 \| \| scaffold14851_1195056_SNP | 1195056 | A | G |
| scaffold14851_1195080_SNP | 1195080 | C | T |
| scaffold14851_1195095_SNP | 1195095 | C | A |
| S_9212391 \| \| scaffold14851_1195194_SNP | 1195194 | C | T |
| S_9212394 \| \| scaffold14851_1195208_SNP | 1195208 | C | A |
| S_9212491 \| \| scaffold14851_1196481_SNP | 1196481 | G | T |
| S_9212643 \| \| scaffold14851_1198088_SNP | 1198088 | A | T |
| S_9212644 \| \| scaffold14851_1198094_SNP | 1198094 | G | A |
| S_9212648 \| \| scaffold14851_1198166_SNP | 1198166 | A | C |
| S_9212782 \| \| scaffold14851_1198881_SNP | 1198881 | G | A |
| S_9212785 \| \| scaffold14851_1198946_SNP | 1198946 | T | C |
| S_9213927 \| \| scaffold14851_1203232_SNP | 1203232 | A | G |
| S_9213960 \| \| scaffold14851_1203591_SNP | 1203591 | G | C |
| S_9213962 \| \| scaffold14851_1203600_SNP | 1203600 | A | G |
| S_9213996 \| \| scaffold14851_1204080_SNP | 1204080 | A | G |
| S_9213997 \| \| scaffold14851_1204087_SNP | 1204087 | C | T |
| S_9214005 \| \| scaffold14851_1204279_SNP | 1204279 | C | A |
| S_9214006 \| \| scaffold14851_1204280_SNP | 1204280 | C | A |
| S_9214056 \| \| scaffold14851_1204969_SNP | 1204969 | A | T |
| S_9214076 \| \| scaffold14851_1205205_SNP | 1205205 | C | G |
| scaffold14851_1205522_SNP | 1205522 | A | T |
| S_9214138 \| \| scaffold14851_1205824_SNP | 1205824 | A | G |
| S_9214141 \| \| scaffold14851_1205902_SNP | 1205902 | T | G |
| S_9214142 \| \| scaffold14851_1205903_SNP | 1205903 | G | T |
| S_9214169 \| \| scaffold14851_1206504_SNP | 1206504 | T | C |
| S_9214192 \| \| scaffold14851_1206821_SNP | 1206821 | T | C |
| S_9214193 \| \| scaffold14851_1206822_SNP | 1206822 | G | A |
| S_9214195 \| \| scaffold14851_1206858_SNP | 1206858 | G | A |
| S_9214211 \| \| scaffold14851_1207277_SNP | 1207277 | C | G |
| S_9214243 \| \| scaffold14851_1207642_SNP | 1207642 | A | G |
| S_9214244 \| \| scaffold14851_1207648_SNP | 1207648 | T | C |
| S_9214261 \| \| scaffold14851_1207902_SNP | 1207902 | G | A |
| S_9214265 \| \| scaffold14851_1207971_SNP | 1207971 | A | T |
| S_9214266 \| \| scaffold14851_1207991_SNP | 1207991 | G | T |
| S_9214275 \| \| scaffold14851_1208169_SNP | 1208169 | A | C |
| S_9214277 \| \| scaffold14851_1208204_SNP | 1208204 | A | C |
| S_9214280 \| \| scaffold14851_1208228_SNP | 1208228 | C | T |
| S_9214283 \| \| scaffold14851_1208298_SNP | 1208298 | C | A |
| S_9214410 \| \| scaffold14851_1209871_SNP | 1209871 | C | T |
| S_9214444 \| \| scaffold14851_1210239_SNP | 1210239 | G | T |
| scaffold14851_1211484_SNP | 1211484 | T | C |
| S_9214559 \| \| scaffold14851_1211758_SNP | 1211758 | C | T |
| S_9214560 \| \| scaffold14851_1211764_SNP | 1211764 | A | T |
| S_9214579 \| \| scaffold14851_1211986_SNP | 1211986 | A | C |
| S_9214583 \| \| scaffold14851_1212028_SNP | 1212028 | G | A |
| S_9214584 \| \| scaffold14851_1212036_SNP | 1212036 | C | T |
| S_9214590 \| \| scaffold14851_1212163_SNP | 1212163 | G | A |
| S_9214613 \| \| scaffold14851_1212345_SNP | 1212345 | A | C |
| S_9214620 \| \| scaffold14851_1212426_SNP | 1212426 | C | A |
| S_9214672 \| \| scaffold14851_1213012_SNP | 1213012 | T | G |
| S_9214673 \| \| scaffold14851_1213026_SNP | 1213026 | G | A |
| S_9214743 \| \| scaffold14851_1213836_SNP | 1213836 | A | C |
| S_9214745 \| \| scaffold14851_1213849_SNP | 1213849 | C | A |
| S_9214747 \| \| scaffold14851_1213861_SNP | 1213861 | T | A |
| S_9214748 \| \| scaffold14851_1213871_SNP | 1213871 | C | A |
| S_9214782 \| \| scaffold14851_1214565_SNP | 1214565 | T | C |
| S_9214783 \| \| scaffold14851_1214578_SNP | 1214578 | G | A |
| S_9214784 \| \| scaffold14851_1214582_SNP | 1214582 | C | T |
| S_9214798 \| \| scaffold14851_1214769_SNP | 1214769 | G | A |
| S_9214805 \| \| scaffold14851_1214811_SNP | 1214811 | C | T |
| S_9214823 \| \| scaffold14851_1214915_SNP | 1214915 | T | C |
| S_9214843 \| \| scaffold14851_1215349_SNP | 1215349 | A | G |
| S_9214844 \| \| scaffold14851_1215360_SNP | 1215360 | T | C |
| S_9214846 \| \| scaffold14851_1215386_SNP | 1215386 | C | T |
| S_9214851 \| \| scaffold14851_1215442_SNP | 1215442 | A | T |
| S_9214852 \| \| scaffold14851_1215447_SNP | 1215447 | G | A |
| S_9214853 \| \| scaffold14851_1215449_SNP | 1215449 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9215276 \| \| scaffold14851_1217283_SNP | 1217283 | T | A |
| S_9215277 \| \| scaffold14851_1217327_SNP | 1217327 | C | T |
| S_9215279 \| \| scaffold14851_1217346_SNP | 1217346 | A | T |
| S_9215280 \| \| scaffold14851_1217359_SNP | 1217359 | A | G |
| S_9215282 \| \| scaffold14851_1217440_SNP | 1217440 | A | G |
| S_9215348 \| \| scaffold14851_1219322_SNP | 1219322 | A | T |
| S_9215398 \| \| scaffold14851_1220185_SNP | 1220185 | G | A |
| S_9215404 \| \| scaffold14851_1220280_SNP | 1220280 | T | C |
| S_9215407 \| \| scaffold14851_1220366_SNP | 1220366 | G | C |
| S_9215415 \| \| scaffold14851_1220493_SNP | 1220493 | T | A |
| S_9215431 \| \| scaffold14851_1220656_SNP | 1220656 | C | T |
| S_9215436 \| \| scaffold14851_1220687_SNP | 1220687 | G | A |
| S_9215450 \| \| scaffold14851_1220948_SNP | 1220948 | G | A |
| S_9215451 \| \| scaffold14851_1220949_SNP | 1220949 | A | T |
| S_9215459 \| \| scaffold14851_1221030_SNP | 1221030 | C | A |
| S_9215460 \| \| scaffold14851_1221042_SNP | 1221042 | C | T |
| S_9215462 \| \| scaffold14851_1221059_SNP | 1221059 | G | A |
| S_9215494 \| \| scaffold14851_1221598_SNP | 1221598 | A | C |
| S_9215533 \| \| scaffold14851_1221851_SNP | 1221851 | A | T |
| S_9215534 \| \| scaffold14851_1221860_SNP | 1221860 | G | A |
| S_9215584 \| \| scaffold14851_1222952_SNP | 1222952 | G | A |
| S_9215609 \| \| scaffold14851_1223332_SNP | 1223332 | C | T |
| S_9215614 \| \| scaffold14851_1223400_SNP | 1223400 | A | C |
| S_9215620 \| \| scaffold14851_1223415_SNP | 1223415 | A | T |
| S_9215632 \| \| scaffold14851_1223483_SNP | 1223483 | A | G |
| S_9215654 \| \| scaffold14851_1223575_SNP | 1223575 | T | C |
| S_9215657 \| \| scaffold14851_1223592_SNP | 1223592 | C | G |
| S_9215698 \| \| scaffold14851_1223831_SNP | 1223831 | C | T |
| S_9215699 \| \| scaffold14851_1223852_SNP | 1223852 | T | C |
| S_9215700 \| \| scaffold14851_1223860_SNP | 1223860 | A | C |
| S_9215704 \| \| scaffold14851_1223922_SNP | 1223922 | A | G |
| S_9215710 \| \| scaffold14851_1224013_SNP | 1224013 | C | A |
| S_9215712 \| \| scaffold14851_1224067_SNP | 1224067 | T | C |
| S_9215725 \| \| scaffold14851_1224388_SNP | 1224388 | T | C |
| S_9215728 \| \| scaffold14851_1224399_SNP | 1224399 | C | T |
| S_9215737 \| \| scaffold14851_1224603_SNP | 1224603 | G | C |
| S_9215800 \| \| scaffold14851_1224976_SNP | 1224976 | A | G |
| S_9215817 \| \| scaffold14851_1225015_SNP | 1225015 | T | C |
| S_9215935 \| \| scaffold14851_1226631_SNP | 1226631 | A | T |
| S_9215937 \| \| scaffold14851_1226646_SNP | 1226646 | G | A |
| S_9215951 \| \| scaffold14851_1226839_SNP | 1226839 | A | T |
| S_9215952 \| \| scaffold14851_1226841_SNP | 1226841 | A | C |
| S_9215957 \| \| scaffold14851_1227055_SNP | 1227055 | C | T |
| S_9215966 \| \| scaffold14851_1227151_SNP | 1227151 | T | A |
| S_9215972 \| \| scaffold14851_1227266_SNP | 1227266 | T | A |
| S_9215982 \| \| scaffold14851_1227592_SNP | 1227592 | G | A |
| S_9215999 \| \| scaffold14851_1227868_SNP | 1227868 | C | T |
| S_9216002 \| \| scaffold14851_1227878_SNP | 1227878 | C | T |
| S_9216023 \| \| scaffold14851_1228078_SNP | 1228078 | T | G |
| S_9216024 \| \| scaffold14851_1228086_SNP | 1228086 | C | T |
| S_9216031 \| \| scaffold14851_1228156_SNP | 1228156 | A | C |
| S_9216057 \| \| scaffold14851_1228424_SNP | 1228424 | G | T |
| S_9216087 \| \| scaffold14851_1228756_SNP | 1228756 | C | T |
| S_9216139 \| \| scaffold14851_1229274_SNP | 1229274 | A | C |
| S_9216163 \| \| scaffold14851_1229877_SNP | 1229877 | T | G |
| S_9216322 \| \| scaffold14851_1232000_SNP | 1232000 | C | G |
| S_9216340 \| \| scaffold14851_1232279_SNP | 1232279 | A | G |
| S_9216351 \| \| scaffold14851_1232435_SNP | 1232435 | C | T |
| S_9216376 \| \| scaffold14851_1232759_SNP | 1232759 | T | C |
| S_9216554 \| \| scaffold14851_1234995_SNP | 1234995 | A | T |
| S_9216568 \| \| scaffold14851_1235336_SNP | 1235336 | T | G |
| S_9216695 \| \| scaffold14851_1236463_SNP | 1236463 | G | C |
| S_9216699 \| \| scaffold14851_1236515_SNP | 1236515 | T | C |
| S_9216701 \| \| scaffold14851_1236557_SNP | 1236557 | G | T |
| S_9216800 \| \| scaffold14851_1238035_SNP | 1238035 | T | A |
| S_9216807 \| \| scaffold14851_1238136_SNP | 1238136 | C | T |
| S_9216818 \| \| scaffold14851_1238289_SNP | 1238289 | T | C |
| S_9216819 \| \| scaffold14851_1238290_SNP | 1238290 | T | A |
| S_9216820 \| \| scaffold14851_1238291_SNP | 1238291 | G | T |
| S_9216821 \| \| scaffold14851_1238292_SNP | 1238292 | T | A |
| S_9216828 \| \| scaffold14851_1238364_SNP | 1238364 | T | G |
| S_9216831 \| \| scaffold14851_1238447_SNP | 1238447 | C | T |
| S_9216868 \| \| scaffold14851_1238751_SNP | 1238751 | C | T |
| S_9216871 \| \| scaffold14851_1238840_SNP | 1238840 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9216872 \| \| scaffold14851_1238849_SNP | 1238849 | G | A |
| S_9216873 \| \| scaffold14851_1238872_SNP | 1238872 | A | T |
| S_9216956 \| \| scaffold14851_1239813_SNP | 1239813 | A | T |
| S_9216984 \| \| scaffold14851_1240287_SNP | 1240287 | T | C |
| S_9216998 \| \| scaffold14851_1240500_SNP | 1240500 | T | G |
| S_9217004 \| \| scaffold14851_1240553_SNP | 1240553 | C | T |
| S_9217125 \| \| scaffold14851_1242320_SNP | 1242320 | C | T |
| S_9217158 \| \| scaffold14851_1242743_SNP | 1242743 | G | A |
| S_9217159 \| \| scaffold14851_1242757_SNP | 1242757 | G | A |
| S_9217175 \| \| scaffold14851_1243124_SNP | 1243124 | A | G |
| S_9217183 \| \| scaffold14851_1243299_SNP | 1243299 | T | G |
| S_9217185 \| \| scaffold14851_1243310_SNP | 1243310 | G | A |
| S_9217186 \| \| scaffold14851_1243316_SNP | 1243316 | C | A |
| S_9217187 \| \| scaffold14851_1243323_SNP | 1243323 | A | G |
| S_9217189 \| \| scaffold14851_1243357_SNP | 1243357 | C | A |
| S_9217191 \| \| scaffold14851_1243410_SNP | 1243410 | T | C |
| S_9217200 \| \| scaffold14851_1243487_SNP | 1243487 | C | T |
| S_9217205 \| \| scaffold14851_1243560_SNP | 1243560 | T | C |
| S_9217210 \| \| scaffold14851_1243595_SNP | 1243595 | T | G |
| scaffold14851_1244047_SNP | 1244047 | C | A |
| S_9217277 \| \| scaffold14851_1244083_SNP | 1244083 | A | G |
| S_9217291 \| \| scaffold14851_1244288_SNP | 1244288 | T | C |
| S_9217292 \| \| scaffold14851_1244295_SNP | 1244295 | C | G |
| S_9217325 \| \| scaffold14851_1244827_SNP | 1244827 | C | T |
| S_9217326 \| \| scaffold14851_1244828_SNP | 1244828 | T | G |
| S_9217327 \| \| scaffold14851_1244829_SNP | 1244829 | A | T |
| S_9217351 \| \| scaffold14851_1245187_SNP | 1245187 | A | C |
| S_9217370 \| \| scaffold14851_1245634_SNP | 1245634 | T | C |
| S_9217409 \| \| scaffold14851_1246039_SNP | 1246039 | C | T |
| S_9217421 \| \| scaffold14851_1246261_SNP | 1246261 | T | A |
| S_9217467 \| \| scaffold14851_1246928_SNP | 1246928 | G | A |
| S_9217491 \| \| scaffold14851_1247295_SNP | 1247295 | C | A |
| S_9217503 \| \| scaffold14851_1247613_SNP | 1247613 | G | A |
| S_9217516 \| \| scaffold14851_1247829_SNP | 1247829 | G | A |
| S_9217521 \| \| scaffold14851_1247921_SNP | 1247921 | A | T |
| S_9217542 \| \| scaffold14851_1248287_SNP | 1248287 | T | C |
| S_9217548 \| \| scaffold14851_1248403_SNP | 1248403 | C | A |
| S_9217555 \| \| scaffold14851_1248453_SNP | 1248453 | C | T |
| S_9217556 \| \| scaffold14851_1248464_SNP | 1248464 | G | T |
| S_9217567 \| \| scaffold14851_1248633_SNP | 1248633 | T | C |
| S_9217570 \| \| scaffold14851_1248677_SNP | 1248677 | G | A |
| S_9217573 \| \| scaffold14851_1248687_SNP | 1248687 | C | T |
| S_9217574 \| \| scaffold14851_1248700_SNP | 1248700 | G | A |
| S_9217575 \| \| scaffold14851_1248732_SNP | 1248732 | C | T |
| S_9217581 \| \| scaffold14851_1248763_SNP | 1248763 | A | G |
| S_9217586 \| \| scaffold14851_1248818_SNP | 1248818 | G | A |
| S_9217593 \| \| scaffold14851_1248914_SNP | 1248914 | C | T |
| S_9217596 \| \| scaffold14851_1248941_SNP | 1248941 | A | G |
| S_9217598 \| \| scaffold14851_1249013_SNP | 1249013 | T | C |
| S_9217600 \| \| scaffold14851_1249041_SNP | 1249041 | G | A |
| S_9217648 \| \| scaffold14851_1249235_SNP | 1249235 | T | C |
| S_9217691 \| \| scaffold14851_1249638_SNP | 1249638 | G | A |
| S_9217692 \| \| scaffold14851_1249639_SNP | 1249639 | A | C |
| S_9217767 \| \| scaffold14851_1250773_SNP | 1250773 | G | A |
| S_9217779 \| \| scaffold14851_1250923_SNP | 1250923 | T | A |
| S_9217906 \| \| scaffold14851_1252888_SNP | 1252888 | T | A |
| S_9217914 \| \| scaffold14851_1253043_SNP | 1253043 | T | A |
| S_9217930 \| \| scaffold14851_1253314_SNP | 1253314 | G | A |
| S_9217933 \| \| scaffold14851_1253357_SNP | 1253357 | G | T |
| S_9217949 \| \| scaffold14851_1253676_SNP | 1253676 | G | T |
| S_9217959 \| \| scaffold14851_1253830_SNP | 1253830 | T | C |
| S_9217968 \| \| scaffold14851_1254021_SNP | 1254021 | T | G |
| S_9217970 \| \| scaffold14851_1254088_SNP | 1254088 | A | C |
| S_9217985 \| \| scaffold14851_1254482_SNP | 1254482 | T | G |
| S_9218008 \| \| scaffold14851_1254703_SNP | 1254703 | T | C |
| S_9218009 \| \| scaffold14851_1254704_SNP | 1254704 | C | T |
| S_9218157 \| \| scaffold14851_1255379_SNP | 1255379 | T | C |
| S_9218163 \| \| scaffold14851_1255425_SNP | 1255425 | A | G |
| S_9218164 \| \| scaffold14851_1255437_SNP | 1255437 | G | A |
| S_9218178 \| \| scaffold14851_1255482_SNP | 1255482 | T | C |
| S_9218184 \| \| scaffold14851_1255500_SNP | 1255500 | C | A |
| S_9218185 \| \| scaffold14851_1255513_SNP | 1255513 | C | A |
| S_9218240 \| \| scaffold14851_1256488_SNP | 1256488 | A | G |
| S_9218263 \| \| scaffold14851_1256865_SNP | 1256865 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9218408 \| \| scaffold14851_1259035_SNP | 1259035 | A | G |
| S_9218424 \| \| scaffold14851_1259244_SNP | 1259244 | C | T |
| S_9218437 \| \| scaffold14851_1259401_SNP | 1259401 | A | G |
| S_9218448 \| \| scaffold14851_1259569_SNP | 1259569 | G | A |
| S_9218467 \| \| scaffold14851_1259937_SNP | 1259937 | T | C |
| S_9218470 \| \| scaffold14851_1259957_SNP | 1259957 | T | C |
| S_9218481 \| \| scaffold14851_1260152_SNP | 1260152 | T | C |
| S_9218491 \| \| scaffold14851_1260413_SNP | 1260413 | T | C |
| S_9218523 \| \| scaffold14851_1260678_SNP | 1260678 | G | C |
| S_9218530 \| \| scaffold14851_1260760_SNP | 1260760 | T | C |
| S_9218540 \| \| scaffold14851_1261097_SNP | 1261097 | C | T |
| S_9218561 \| \| scaffold14851_1261375_SNP | 1261375 | A | G |
| S_9218578 \| \| scaffold14851_1261579_SNP | 1261579 | A | G |
| S_9218589 \| \| scaffold14851_1261777_SNP | 1261777 | A | G |
| S_9218595 \| \| scaffold14851_1261835_SNP | 1261835 | G | A |
| S_9218598 \| \| scaffold14851_1261872_SNP | 1261872 | T | G |
| S_9218610 \| \| scaffold14851_1262109_SNP | 1262109 | C | T |
| S_9218686 \| \| scaffold14851_1263214_SNP | 1263214 | A | G |
| S_9218705 \| \| scaffold14851_1263523_SNP | 1263523 | G | T |
| S_9218708 \| \| scaffold14851_1263598_SNP | 1263598 | A | G |
| S_9218710 \| \| scaffold14851_1263637_SNP | 1263637 | C | T |
| S_9218732 \| \| scaffold14851_1263913_SNP | 1263913 | C | T |
| S_9218758 \| \| scaffold14851_1264352_SNP | 1264352 | G | A |
| S_9218796 \| \| scaffold14851_1265033_SNP | 1265033 | C | T |
| S_9218923 \| \| scaffold14851_1266288_SNP | 1266288 | A | T |
| S_9218950 \| \| scaffold14851_1266632_SNP | 1266632 | C | G |
| S_9219005 \| \| scaffold14851_1267392_SNP | 1267392 | T | A |
| S_9219058 \| \| scaffold14851_1268209_SNP | 1268209 | G | A |
| S_9219109 \| \| scaffold14851_1268680_SNP | 1268680 | C | G |
| S_9219119 \| \| scaffold14851_1268741_SNP | 1268741 | T | C |
| S_9219124 \| \| scaffold14851_1268871_SNP | 1268871 | G | A |
| S_9219132 \| \| scaffold14851_1269098_SNP | 1269098 | T | A |
| S_9219137 \| \| scaffold14851_1269140_SNP | 1269140 | A | T |
| S_9219156 \| \| scaffold14851_1269505_SNP | 1269505 | G | C |
| S_9219291 \| \| scaffold14851_1271263_SNP | 1271263 | G | A |
| S_9219372 \| \| scaffold14851_1272434_SNP | 1272434 | T | A |
| S_9219374 \| \| scaffold14851_1272449_SNP | 1272449 | C | T |
| S_9219383 \| \| scaffold14851_1272519_SNP | 1272519 | C | A |
| S_9219540 \| \| scaffold14851_1273691_SNP | 1273691 | T | C |
| S_9219559 \| \| scaffold14851_1273854_SNP | 1273854 | T | C |
| S_9219626 \| \| scaffold14851_1274003_SNP | 1274003 | T | A |
| S_9219627 \| \| scaffold14851_1274005_SNP | 1274005 | A | T |
| S_9219628 \| \| scaffold14851_1274018_SNP | 1274018 | A | C |
| S_9219630 \| \| scaffold14851_1274078_SNP | 1274078 | G | T |
| S_9219638 \| \| scaffold14851_1274379_SNP | 1274379 | A | T |
| S_9219643 \| \| scaffold14851_1274453_SNP | 1274453 | G | A |
| S_9219648 \| \| scaffold14851_1274510_SNP | 1274510 | C | G |
| S_9219655 \| \| scaffold14851_1274615_SNP | 1274615 | T | C |
| S_9219656 \| \| scaffold14851_1274620_SNP | 1274620 | C | T |
| S_9219659 \| \| scaffold14851_1274695_SNP | 1274695 | G | T |
| S_9219662 \| \| scaffold14851_1274721_SNP | 1274721 | T | A |
| S_9219664 \| \| scaffold14851_1274766_SNP | 1274766 | T | C |
| S_9219667 \| \| scaffold14851_1274772_SNP | 1274772 | A | T |
| S_9219671 \| \| scaffold14851_1274837_SNP | 1274837 | A | T |
| S_9219677 \| \| scaffold14851_1275001_SNP | 1275001 | G | A |
| S_9219679 \| \| scaffold14851_1275021_SNP | 1275021 | T | C |
| S_9219682 \| \| scaffold14851_1275024_SNP | 1275024 | G | C |
| S_9219683 \| \| scaffold14851_1275037_SNP | 1275037 | T | C |
| S_9219692 \| \| scaffold14851_1275188_SNP | 1275188 | G | A |
| S_9219693 \| \| scaffold14851_1275201_SNP | 1275201 | C | T |
| S_9219696 \| \| scaffold14851_1275243_SNP | 1275243 | C | T |
| S_9219697 \| \| scaffold14851_1275313_SNP | 1275313 | C | T |
| S_9219735 \| \| scaffold14851_1275808_SNP | 1275808 | T | A |
| S_9219742 \| \| scaffold14851_1275898_SNP | 1275898 | G | A |
| S_9219761 \| \| scaffold14851_1276244_SNP | 1276244 | A | G |
| S_9219768 \| \| scaffold14851_1276420_SNP | 1276420 | C | T |
| S_9219777 \| \| scaffold14851_1276497_SNP | 1276497 | T | C |
| S_9219784 \| \| scaffold14851_1276550_SNP | 1276550 | C | T |
| S_9219786 \| \| scaffold14851_1276571_SNP | 1276571 | T | A |
| S_9219801 \| \| scaffold14851_1276693_SNP | 1276693 | A | T |
| S_9219850 \| \| scaffold14851_1277056_SNP | 1277056 | T | C |
| S_9219885 \| \| scaffold14851_1277608_SNP | 1277608 | C | T |
| S_9219891 \| \| scaffold14851_1277625_SNP | 1277625 | A | T |
| S_9219904 \| \| scaffold14851_1277753_SNP | 1277753 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9219922 \|\| scaffold14851_1278097_SNP | 1278097 | T | C |
| S_9219923 \|\| scaffold14851_1278129_SNP | 1278129 | A | C |
| S_9219940 \|\| scaffold14851_1278416_SNP | 1278416 | T | C |
| S_9219942 \|\| scaffold14851_1278461_SNP | 1278461 | A | G |
| S_9219945 \|\| scaffold14851_1278487_SNP | 1278487 | C | A |
| S_9219969 \|\| scaffold14851_1278841_SNP | 1278841 | C | T |
| S_9220013 \|\| scaffold14851_1279759_SNP | 1279759 | C | A |
| S_9220016 \|\| scaffold14851_1279839_SNP | 1279839 | T | A |
| S_9220060 \|\| scaffold14851_1280548_SNP | 1280548 | A | T |
| S_9220078 \|\| scaffold14851_1280889_SNP | 1280889 | G | A |
| S_9220087 \|\| scaffold14851_1281042_SNP | 1281042 | G | A |
| S_9220089 \|\| scaffold14851_1281065_SNP | 1281065 | C | T |
| S_9220102 \|\| scaffold14851_1281254_SNP | 1281254 | A | T |
| S_9220106 \|\| scaffold14851_1281361_SNP | 1281361 | G | A |
| S_9220108 \|\| scaffold14851_1281375_SNP | 1281375 | C | G |
| S_9220115 \|\| scaffold14851_1281471_SNP | 1281471 | A | T |
| S_9220116 \|\| scaffold14851_1281511_SNP | 1281511 | G | A |
| S_9220118 \|\| scaffold14851_1281570_SNP | 1281570 | A | T |
| S_9220241 \|\| scaffold14851_1282237_SNP | 1282237 | A | T |
| S_9220243 \|\| scaffold14851_1282294_SNP | 1282294 | T | C |
| S_9220267 \|\| scaffold14851_1282730_SNP | 1282730 | A | G |
| S_9220276 \|\| scaffold14851_1282870_SNP | 1282870 | C | T |
| S_9220279 \|\| scaffold14851_1282928_SNP | 1282928 | C | G |
| S_9220290 \|\| scaffold14851_1283151_SNP | 1283151 | G | A |
| S_9220291 \|\| scaffold14851_1283163_SNP | 1283163 | A | T |
| S_9220311 \|\| scaffold14851_1283614_SNP | 1283614 | T | C |
| S_9220312 \|\| scaffold14851_1283621_SNP | 1283621 | T | C |
| S_9220315 \|\| scaffold14851_1283660_SNP | 1283660 | C | A |
| S_9220327 \|\| scaffold14851_1283786_SNP | 1283786 | A | G |
| S_9220329 \|\| scaffold14851_1283798_SNP | 1283798 | T | C |
| S_9220334 \|\| scaffold14851_1283846_SNP | 1283846 | G | A |
| S_9220414 \|\| scaffold14851_1284927_SNP | 1284927 | T | C |
| S_9220415 \|\| scaffold14851_1284941_SNP | 1284941 | G | A |
| S_9220417 \|\| scaffold14851_1284986_SNP | 1284986 | G | A |
| S_9220419 \|\| scaffold14851_1285005_SNP | 1285005 | G | A |
| S_9220424 \|\| scaffold14851_1285048_SNP | 1285048 | A | T |
| S_9220432 \|\| scaffold14851_1285175_SNP | 1285175 | G | C |
| S_9220507 \|\| scaffold14851_1285883_SNP | 1285883 | A | G |
| S_9220508 \|\| scaffold14851_1285920_SNP | 1285920 | A | T |
| S_9220646 \|\| scaffold14851_1294237_SNP | 1294237 | C | A |
| S_9220647 \|\| scaffold14851_1294247_SNP | 1294247 | G | A |
| S_9220660 \|\| scaffold14851_1294381_SNP | 1294381 | G | T |
| S_9220669 \|\| scaffold14851_1294492_SNP | 1294492 | G | T |
| S_9220706 \|\| scaffold14851_1295135_SNP | 1295135 | G | A |
| S_9220884 \|\| scaffold14851_1297253_SNP | 1297253 | C | T |
| S_9220893 \|\| scaffold14851_1297423_SNP | 1297423 | C | G |
| S_9220939 \|\| scaffold14851_1298211_SNP | 1298211 | G | A |
| S_9220962 \|\| scaffold14851_1298695_SNP | 1298695 | C | T |
| S_9220968 \|\| scaffold14851_1298905_SNP | 1298905 | G | C |
| S_9221027 \|\| scaffold14851_1300002_SNP | 1300002 | C | A |
| S_9221031 \|\| scaffold14851_1300013_SNP | 1300013 | A | T |
| S_9221067 \|\| scaffold14851_1300379_SNP | 1300379 | G | A |
| S_9221158 \|\| scaffold14851_1301161_SNP | 1301161 | A | C |
| S_9221206 \|\| scaffold14851_1301863_SNP | 1301863 | G | C |
| S_9221208 \|\| scaffold14851_1301882_SNP | 1301882 | T | C |
| S_9221211 \|\| scaffold14851_1301937_SNP | 1301937 | C | T |
| S_9221294 \|\| scaffold14851_1303770_SNP | 1303770 | G | T |
| S_9221297 \|\| scaffold14851_1303875_SNP | 1303875 | T | A |
| S_9221307 \|\| scaffold14851_1304049_SNP | 1304049 | T | G |
| S_9221308 \|\| scaffold14851_1304058_SNP | 1304058 | A | C |
| S_9221316 \|\| scaffold14851_1304289_SNP | 1304289 | A | G |
| S_9221323 \|\| scaffold14851_1304413_SNP | 1304413 | T | C |
| S_9221337 \|\| scaffold14851_1304599_SNP | 1304599 | T | G |
| S_9221358 \|\| scaffold14851_1304992_SNP | 1304992 | T | A |
| S_9221361 \|\| scaffold14851_1305049_SNP | 1305049 | T | G |
| S_9221449 \|\| scaffold14851_1305691_SNP | 1305691 | T | C |
| S_9221452 \|\| scaffold14851_1305714_SNP | 1305714 | A | C |
| S_9221470 \|\| scaffold14851_1306007_SNP | 1306007 | C | A |
| S_9221471 \|\| scaffold14851_1306013_SNP | 1306013 | G | A |
| S_9221474 \|\| scaffold14851_1306026_SNP | 1306026 | C | A |
| S_9221488 \|\| scaffold14851_1306260_SNP | 1306260 | A | T |
| S_9221491 \|\| scaffold14851_1306276_SNP | 1306276 | G | C |
| S_9221500 \|\| scaffold14851_1306389_SNP | 1306389 | A | G |
| S_9221505 \|\| scaffold14851_1306451_SNP | 1306451 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9221506 \| \| scaffold14851_1306453_SNP | 1306453 | A | C |
| S_9221650 \| \| scaffold14851_1308202_SNP | 1308202 | T | A |
| S_9221752 \| \| scaffold14851_1309305_SNP | 1309305 | T | C |
| S_9221810 \| \| scaffold14851_1309757_SNP | 1309757 | A | G |
| S_9221891 \| \| scaffold14851_1311077_SNP | 1311077 | T | C |
| S_9221946 \| \| scaffold14851_1311766_SNP | 1311766 | C | A |
| S_9221952 \| \| scaffold14851_1311833_SNP | 1311833 | C | T |
| S_9221989 \| \| scaffold14851_1312240_SNP | 1312240 | C | T |
| S_9222055 \| \| scaffold14851_1312709_SNP | 1312709 | C | A |
| S_9222056 \| \| scaffold14851_1312741_SNP | 1312741 | C | T |
| S_9222121 \| \| scaffold14851_1313280_SNP | 1313280 | T | C |
| S_9222124 \| \| scaffold14851_1313305_SNP | 1313305 | G | A |
| S_9222141 \| \| scaffold14851_1313439_SNP | 1313439 | T | G |
| S_9222142 \| \| scaffold14851_1313453_SNP | 1313453 | A | G |
| S_9222157 \| \| scaffold14851_1313594_SNP | 1313594 | A | G |
| S_9222160 \| \| scaffold14851_1313627_SNP | 1313627 | A | G |
| S_9222161 \| \| scaffold14851_1313649_SNP | 1313649 | G | T |
| S_9222181 \| \| scaffold14851_1313782_SNP | 1313782 | C | T |
| S_9222197 \| \| scaffold14851_1313981_SNP | 1313981 | T | C |
| S_9222199 \| \| scaffold14851_1314016_SNP | 1314016 | T | A |
| S_9222200 \| \| scaffold14851_1314017_SNP | 1314017 | T | A |
| S_9222201 \| \| scaffold14851_1314018_SNP | 1314018 | T | A |
| S_9222204 \| \| scaffold14851_1314057_SNP | 1314057 | C | A |
| S_9222228 \| \| scaffold14851_1314339_SNP | 1314339 | C | T |
| S_9222230 \| \| scaffold14851_1314364_SNP | 1314364 | A | G |
| S_9222234 \| \| scaffold14851_1314395_SNP | 1314395 | C | T |
| S_9222238 \| \| scaffold14851_1314427_SNP | 1314427 | C | T |
| S_9222244 \| \| scaffold14851_1314475_SNP | 1314475 | C | A |
| S_9222254 \| \| scaffold14851_1314631_SNP | 1314631 | C | A |
| S_9222261 \| \| scaffold14851_1314692_SNP | 1314692 | A | G |
| S_9222296 \| \| scaffold14851_1315247_SNP | 1315247 | C | T |
| S_9222368 \| \| scaffold14851_1316584_SNP | 1316584 | G | A |
| S_9222401 \| \| scaffold14851_1316863_SNP | 1316863 | C | G |
| S_9222402 \| \| scaffold14851_1316869_SNP | 1316869 | C | T |
| S_9222414 \| \| scaffold14851_1316986_SNP | 1316986 | A | C |
| S_9222463 \| \| scaffold14851_1317481_SNP | 1317481 | G | A |
| S_9222474 \| \| scaffold14851_1317639_SNP | 1317639 | C | T |
| S_9222475 \| \| scaffold14851_1317652_SNP | 1317652 | G | T |
| S_9222486 \| \| scaffold14851_1317812_SNP | 1317812 | A | G |
| S_9222497 \| \| scaffold14851_1317995_SNP | 1317995 | G | A |
| S_9222513 \| \| scaffold14851_1318349_SNP | 1318349 | G | T |
| S_9222514 \| \| scaffold14851_1318351_SNP | 1318351 | C | G |
| S_9222515 \| \| scaffold14851_1318378_SNP | 1318378 | G | T |
| S_9222519 \| \| scaffold14851_1318413_SNP | 1318413 | A | G |
| S_9222535 \| \| scaffold14851_1318536_SNP | 1318536 | T | G |
| S_9222553 \| \| scaffold14851_1318645_SNP | 1318645 | T | C |
| S_9222554 \| \| scaffold14851_1318646_SNP | 1318646 | G | C |
| S_9222575 \| \| scaffold14851_1318907_SNP | 1318907 | G | A |
| S_9222579 \| \| scaffold14851_1318960_SNP | 1318960 | C | T |
| S_9222635 \| \| scaffold14851_1319563_SNP | 1319563 | A | G |
| S_9222641 \| \| scaffold14851_1319612_SNP | 1319612 | T | C |
| S_9222646 \| \| scaffold14851_1319705_SNP | 1319705 | A | T |
| S_9222648 \| \| scaffold14851_1319718_SNP | 1319718 | A | G |
| S_9222683 \| \| scaffold14851_1320290_SNP | 1320290 | G | A |
| S_9222699 \| \| scaffold14851_1320622_SNP | 1320622 | G | A |
| S_9222700 \| \| scaffold14851_1320648_SNP | 1320648 | T | C |
| S_9222767 \| \| scaffold14851_1321499_SNP | 1321499 | T | C |
| S_9222779 \| \| scaffold14851_1321524_SNP | 1321524 | T | A |
| S_9222799 \| \| scaffold14851_1321767_SNP | 1321767 | A | T |
| S_9222801 \| \| scaffold14851_1321800_SNP | 1321800 | A | G |
| S_9222802 \| \| scaffold14851_1321830_SNP | 1321830 | C | T |
| S_9223035 \| \| scaffold14851_1326020_SNP | 1326020 | G | A |
| S_9223046 \| \| scaffold14851_1326214_SNP | 1326214 | C | T |
| S_9223054 \| \| scaffold14851_1326289_SNP | 1326289 | A | G |
| S_9223412 \| \| scaffold14851_1328391_SNP | 1328391 | T | C |
| S_9223432 \| \| scaffold14851_1328515_SNP | 1328515 | T | C |
| scaffold14851_1329982_SNP | 1329982 | T | G |
| S_9223820 \| \| scaffold14851_1331147_SNP | 1331147 | T | A |
| scaffold14851_1334237_SNP | 1334237 | G | T |
| S_9224208 \| \| scaffold14851_1334289_SNP | 1334289 | A | C |
| scaffold14851_1334313_SNP | 1334313 | T | G |
| S_9224215 \| \| scaffold14851_1334398_SNP | 1334398 | G | A |
| S_9224271 \| \| scaffold14851_1335088_SNP | 1335088 | A | C |
| S_9224272 \| \| scaffold14851_1335094_SNP | 1335094 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9224301 \| \| scaffold14851_1335509_SNP | 1335509 | C | G |
| S_9224454 \| \| scaffold14851_1336879_SNP | 1336879 | C | T |
| S_9224740 \| \| scaffold14851_1339636_SNP | 1339636 | A | G |
| S_9224785 \| \| scaffold14851_1339829_SNP | 1339829 | T | A |
| S_9224786 \| \| scaffold14851_1339867_SNP | 1339867 | A | G |
| S_9224802 \| \| scaffold14851_1340064_SNP | 1340064 | T | A |
| S_9224830 \| \| scaffold14851_1340584_SNP | 1340584 | T | C |
| S_9224867 \| \| scaffold14851_1340946_SNP | 1340946 | G | A |
| S_9224878 \| \| scaffold14851_1341131_SNP | 1341131 | G | A |
| S_9224911 \| \| scaffold14851_1341572_SNP | 1341572 | A | G |
| S_9224977 \| \| scaffold14851_1342439_SNP | 1342439 | T | C |
| S_9224987 \| \| scaffold14851_1342588_SNP | 1342588 | T | A |
| S_9224988 \| \| scaffold14851_1342593_SNP | 1342593 | A | G |
| S_9224993 \| \| scaffold14851_1342681_SNP | 1342681 | C | T |
| S_9225020 \| \| scaffold14851_1343087_SNP | 1343087 | G | T |
| S_9225064 \| \| scaffold14851_1343487_SNP | 1343487 | C | A |
| S_9225077 \| \| scaffold14851_1343729_SNP | 1343729 | C | G |
| S_9225084 \| \| scaffold14851_1343850_SNP | 1343850 | A | G |
| S_9225085 \| \| scaffold14851_1343887_SNP | 1343887 | G | A |
| S_9225091 \| \| scaffold14851_1344060_SNP | 1344060 | G | A |
| S_9225092 \| \| scaffold14851_1344062_SNP | 1344062 | T | C |
| S_9225100 \| \| scaffold14851_1344257_SNP | 1344257 | A | T |
| S_9225123 \| \| scaffold14851_1344636_SNP | 1344636 | T | G |
| S_9225124 \| \| scaffold14851_1344648_SNP | 1344648 | C | T |
| S_9225126 \| \| scaffold14851_1344681_SNP | 1344681 | T | C |
| S_9225127 \| \| scaffold14851_1344695_SNP | 1344695 | A | G |
| S_9225147 \| \| scaffold14851_1345087_SNP | 1345087 | T | A |
| S_9225332 \| \| scaffold14851_1347124_SNP | 1347124 | T | G |
| S_9225377 \| \| scaffold14851_1347613_SNP | 1347613 | T | C |
| S_9225384 \| \| scaffold14851_1347827_SNP | 1347827 | C | G |
| S_9225385 \| \| scaffold14851_1347836_SNP | 1347836 | C | T |
| S_9225400 \| \| scaffold14851_1348074_SNP | 1348074 | G | C |
| S_9225405 \| \| scaffold14851_1348161_SNP | 1348161 | T | C |
| S_9225406 \| \| scaffold14851_1348165_SNP | 1348165 | C | G |
| S_9225408 \| \| scaffold14851_1348216_SNP | 1348216 | A | C |
| S_9225410 \| \| scaffold14851_1348222_SNP | 1348222 | G | A |
| S_9225475 \| \| scaffold14851_1348790_SNP | 1348790 | A | G |
| S_9225477 \| \| scaffold14851_1348823_SNP | 1348823 | A | C |
| S_9225503 \| \| scaffold14851_1349218_SNP | 1349218 | A | T |
| scaffold14851_1349324_SNP | 1349324 | T | A |
| S_9225520 \| \| scaffold14851_1349523_SNP | 1349523 | G | C |
| S_9225521 \| \| scaffold14851_1349544_SNP | 1349544 | A | G |
| S_9225523 \| \| scaffold14851_1349622_SNP | 1349622 | C | T |
| S_9225565 \| \| scaffold14851_1349902_SNP | 1349902 | C | G |
| S_9225610 \| \| scaffold14851_1350440_SNP | 1350440 | T | A |
| S_9225614 \| \| scaffold14851_1350515_SNP | 1350515 | T | A |
| S_9225673 \| \| scaffold14851_1351371_SNP | 1351371 | C | T |
| S_9225675 \| \| scaffold14851_1351422_SNP | 1351422 | T | C |
| S_9225728 \| \| scaffold14851_1352177_SNP | 1352177 | G | A |
| S_9225735 \| \| scaffold14851_1352531_SNP | 1352531 | G | A |
| S_9225739 \| \| scaffold14851_1352611_SNP | 1352611 | T | C |
| S_9225742 \| \| scaffold14851_1352736_SNP | 1352736 | G | A |
| S_9225743 \| \| scaffold14851_1352763_SNP | 1352763 | C | G |
| S_9225752 \| \| scaffold14851_1352848_SNP | 1352848 | C | A |
| S_9225753 \| \| scaffold14851_1352858_SNP | 1352858 | C | T |
| scaffold14851_1353037_SNP | 1353037 | T | G |
| scaffold14851_1353039_SNP | 1353039 | G | C |
| scaffold14851_1353041_SNP | 1353041 | T | G |
| S_9226010 \| \| scaffold14851_1355276_SNP | 1355276 | A | G |
| S_9226012 \| \| scaffold14851_1355281_SNP | 1355281 | G | A |
| S_9226033 \| \| scaffold14851_1355691_SNP | 1355691 | G | A |
| S_9226034 \| \| scaffold14851_1355695_SNP | 1355695 | A | G |
| S_9226045 \| \| scaffold14851_1355840_SNP | 1355840 | G | T |
| S_9226046 \| \| scaffold14851_1355841_SNP | 1355841 | T | C |
| S_9226047 \| \| scaffold14851_1355845_SNP | 1355845 | T | G |
| S_9226120 \| \| scaffold14851_1356917_SNP | 1356917 | T | C |
| S_9226121 \| \| scaffold14851_1356964_SNP | 1356964 | A | G |
| S_9226152 \| \| scaffold14851_1357315_SNP | 1357315 | G | T |
| S_9226156 \| \| scaffold14851_1357375_SNP | 1357375 | G | T |
| S_9226167 \| \| scaffold14851_1357561_SNP | 1357561 | A | C |
| S_9226171 \| \| scaffold14851_1357638_SNP | 1357638 | T | C |
| S_9226176 \| \| scaffold14851_1357680_SNP | 1357680 | A | G |
| S_9226211 \| \| scaffold14851_1358305_SNP | 1358305 | G | A |
| S_9226214 \| \| scaffold14851_1358336_SNP | 1358336 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9226229 \| \| scaffold14851_1358567_SNP | 1358567 | A | T |
| S_9226230 \| \| scaffold14851_1358591_SNP | 1358591 | G | A |
| S_9226248 \| \| scaffold14851_1358805_SNP | 1358805 | A | G |
| S_9226250 \| \| scaffold14851_1358880_SNP | 1358880 | G | A |
| S_9226267 \| \| scaffold14851_1359376_SNP | 1359376 | G | T |
| S_9226319 \| \| scaffold14851_1359816_SNP | 1359816 | A | T |
| S_9226321 \| \| scaffold14851_1359891_SNP | 1359891 | G | T |
| S_9226332 \| \| scaffold14851_1360045_SNP | 1360045 | C | A |
| S_9226334 \| \| scaffold14851_1360111_SNP | 1360111 | A | T |
| S_9226337 \| \| scaffold14851_1360177_SNP | 1360177 | C | T |
| S_9226340 \| \| scaffold14851_1360195_SNP | 1360195 | G | T |
| S_9226363 \| \| scaffold14851_1360489_SNP | 1360489 | C | T |
| S_9226374 \| \| scaffold14851_1360625_SNP | 1360625 | T | C |
| S_9226393 \| \| scaffold14851_1360890_SNP | 1360890 | C | T |
| S_9226394 \| \| scaffold14851_1360891_SNP | 1360891 | A | T |
| S_9226396 \| \| scaffold14851_1360902_SNP | 1360902 | C | T |
| S_9226397 \| \| scaffold14851_1360912_SNP | 1360912 | T | G |
| S_9226434 \| \| scaffold14851_1361179_SNP | 1361179 | T | G |
| S_9226445 \| \| scaffold14851_1361301_SNP | 1361301 | G | C |
| S_9226446 \| \| scaffold14851_1361331_SNP | 1361331 | G | C |
| S_9226467 \| \| scaffold14851_1361728_SNP | 1361728 | T | C |
| S_9226492 \| \| scaffold14851_1362063_SNP | 1362063 | G | T |
| S_9226495 \| \| scaffold14851_1362123_SNP | 1362123 | T | C |
| S_9226519 \| \| scaffold14851_1362428_SNP | 1362428 | T | G |
| S_9226535 \| \| scaffold14851_1362639_SNP | 1362639 | G | A |
| S_9226541 \| \| scaffold14851_1362727_SNP | 1362727 | T | A |
| S_9226669 \| \| scaffold14851_1363706_SNP | 1363706 | T | G |
| S_9226670 \| \| scaffold14851_1363722_SNP | 1363722 | G | A |
| S_9226690 \| \| scaffold14851_1364120_SNP | 1364120 | T | C |
| S_9226723 \| \| scaffold14851_1364577_SNP | 1364577 | G | A |
| S_9226724 \| \| scaffold14851_1364626_SNP | 1364626 | G | A |
| S_9226732 \| \| scaffold14851_1364776_SNP | 1364776 | A | T |
| S_9226733 \| \| scaffold14851_1364778_SNP | 1364778 | A | G |
| S_9226818 \| \| scaffold14851_1365813_SNP | 1365813 | T | C |
| S_9226824 \| \| scaffold14851_1365964_SNP | 1365964 | G | C |
| S_9226826 \| \| scaffold14851_1365982_SNP | 1365982 | T | C |
| S_9226827 \| \| scaffold14851_1365983_SNP | 1365983 | C | A |
| S_9226848 \| \| scaffold14851_1366281_SNP | 1366281 | A | G |
| S_9226873 \| \| scaffold14851_1366698_SNP | 1366698 | G | A |
| S_9226887 \| \| scaffold14851_1366923_SNP | 1366923 | C | G |
| S_9226888 \| \| scaffold14851_1366925_SNP | 1366925 | G | A |
| S_9226895 \| \| scaffold14851_1366994_SNP | 1366994 | A | G |
| S_9226899 \| \| scaffold14851_1367048_SNP | 1367048 | C | A |
| S_9226902 \| \| scaffold14851_1367079_SNP | 1367079 | A | G |
| S_9226907 \| \| scaffold14851_1367106_SNP | 1367106 | G | A |
| S_9226910 \| \| scaffold14851_1367145_SNP | 1367145 | C | T |
| S_9226923 \| \| scaffold14851_1367558_SNP | 1367558 | A | G |
| scaffold14851_1368643_SNP | 1368643 | C | A |
| S_9227106 \| \| scaffold14851_1369099_SNP | 1369099 | C | T |
| S_9227107 \| \| scaffold14851_1369125_SNP | 1369125 | G | A |
| S_9227170 \| \| scaffold14851_1369834_SNP | 1369834 | G | A |
| S_9227192 \| \| scaffold14851_1370505_SNP | 1370505 | C | T |
| S_9227266 \| \| scaffold14851_1372078_SNP | 1372078 | G | A |
| S_9227272 \| \| scaffold14851_1372192_SNP | 1372192 | T | G |
| S_9227274 \| \| scaffold14851_1372207_SNP | 1372207 | T | G |
| S_9227277 \| \| scaffold14851_1372339_SNP | 1372339 | G | A |
| S_9227354 \| \| scaffold14851_1373134_SNP | 1373134 | G | A |
| S_9227355 \| \| scaffold14851_1373155_SNP | 1373155 | A | C |
| S_9227359 \| \| scaffold14851_1373212_SNP | 1373212 | T | G |
| S_9227366 \| \| scaffold14851_1373279_SNP | 1373279 | C | T |
| $_9227369 \| \| scaffold14851_1373300_SNP | 1373300 | C | T |
| S_9227378 \| \| scaffold14851_1373469_SNP | 1373469 | G | A |
| S_9227379 \| \| scaffold14851_1373474_SNP | 1373474 | G | A |
| S_9227389 \| \| scaffold14851_1373604_SNP | 1373604 | T | C |
| S_9227390 \| \| scaffold14851_1373613_SNP | 1373613 | T | G |
| S_9227391 \| \| scaffold14851_1373629_SNP | 1373629 | A | T |
| S_9227392 \| \| scaffold14851_1373632_SNP | 1373632 | C | T |
| S_9227418 \| \| scaffold14851_1373986_SNP | 1373986 | G | T |
| S_9227420 \| \| scaffold14851_1374010_SNP | 1374010 | A | T |
| S_9227421 \| \| scaffold14851_1374013_SNP | 1374013 | T | A |
| scaffold14851_1375979_SNP | 1375979 | T | C |
| S_9227947 \| \| scaffold14851_1376087_SNP | 1376087 | T | C |
| S_9227948 \| \| scaffold14851_1376088_SNP | 1376088 | T | A |
| S_9227974 \| \| scaffold14851_1376662_SNP | 1376662 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9227975 \| \| scaffold14851_1376668_SNP | 1376668 | G | A |
| S_9227982 \| \| scaffold14851_1376758_SNP | 1376758 | T | A |
| S_9227987 \| \| scaffold14851_1376811_SNP | 1376811 | T | A |
| S_9227988 \| \| scaffold14851_1376812_SNP | 1376812 | T | A |
| S_9227993 \| \| scaffold14851_1376848_SNP | 1376848 | G | C |
| S_9228020 \| \| scaffold14851_1377148_SNP | 1377148 | C | A |
| scaffold14851_1377159_SNP | 1377159 | C | T |
| S_9228035 \| \| scaffold14851_1377316_SNP | 1377316 | T | C |
| S_9228040 \| \| scaffold14851_1377372_SNP | 1377372 | G | T |
| S_9228041 \| \| scaffold14851_1377373_SNP | 1377373 | C | T |
| S_9228042 \| \| scaffold14851_1377384_SNP | 1377384 | C | G |
| S_9229225 \| \| scaffold14851_1382823_SNP | 1382823 | T | C |
| S_9229887 \| \| scaffold14851_1385532_SNP | 1385532 | T | G |
| S_9229888 \| \| scaffold14851_1385534_SNP | 1385534 | A | G |
| S_9229889 \| \| scaffold14851_1385542_SNP | 1385542 | G | A |
| S_9229890 \| \| scaffold14851_1385543_SNP | 1385543 | C | T |
| S_9229959 \| \| scaffold14851_1386056_SNP | 1386056 | G | T |
| S_9230055 \| \| scaffold14851_1386581_SNP | 1386581 | G | A |
| S_9230461 \| \| scaffold14851_1388398_SNP | 1388398 | T | C |
| S_9231206 \| \| scaffold14851_1392344_SNP | 1392344 | A | T |
| S_9231216 \| \| scaffold14851_1392461_SNP | 1392461 | G | A |
| S_9231219 \| \| scaffold14851_1392493_SNP | 1392493 | A | G |
| S_9231220 \| \| scaffold14851_1392503_SNP | 1392503 | T | C |
| S_9231289 \| \| scaffold14851_1393478_SNP | 1393478 | T | G |
| S_9231290 \| \| scaffold14851_1393525_SNP | 1393525 | C | G |
| S_9231291 \| \| scaffold14851_1393568_SNP | 1393568 | T | C |
| S_9231329 \| \| scaffold14851_1394583_SNP | 1394583 | G | A |
| S_9231330 \| \| scaffold14851_1394601_SNP | 1394601 | T | A |
| S_9231331 \| \| scaffold14851_1394613_SNP | 1394613 | G | T |
| S_9231362 \| \| scaffold14851_1394991_SNP | 1394991 | A | G |
| S_9231364 \| \| scaffold14851_1395001_SNP | 1395001 | A | C |
| S_9231365 \| \| scaffold14851_1395006_SNP | 1395006 | G | A |
| S_9231367 \| \| scaffold14851_1395030_SNP | 1395030 | A | C |
| S_9231370 \| \| scaffold14851_1395063_SNP | 1395063 | C | T |
| S_9231373 \| \| scaffold14851_1395081_SNP | 1395081 | C | T |
| S_9231389 \| \| scaffold14851_1395246_SNP | 1395246 | G | C |
| S_9231396 \| \| scaffold14851_1395323_SNP | 1395323 | T | C |
| S_9231481 \| \| scaffold14851_1396440_SNP | 1396440 | C | A |
| S_9231484 \| \| scaffold14851_1396457_SNP | 1396457 | C | T |
| S_9231499 \| \| scaffold14851_1396650_SNP | 1396650 | A | T |
| S_9231634 \| \| scaffold14851_1397510_SNP | 1397510 | T | C |
| S_9231680 \| \| scaffold14851_1397899_SNP | 1397899 | A | T |
| S_9231681 \| \| scaffold14851_1397940_SNP | 1397940 | G | A |
| S_9231682 \| \| scaffold14851_1397969_SNP | 1397969 | C | T |
| S_9231708 \| \| scaffold14851_1398215_SNP | 1398215 | T | G |
| scaffold14851_1398239_SNP | 1398239 | A | C |
| S_9231734 \| \| scaffold14851_1398498_SNP | 1398498 | A | G |
| S_9231762 \| \| scaffold14851_1398848_SNP | 1398848 | C | A |
| S_9231816 \| \| scaffold14851_1399569_SNP | 1399569 | T | C |
| S_9231819 \| \| scaffold14851_1399629_SNP | 1399629 | G | C |
| S_9231889 \| \| scaffold14851_1400675_SNP | 1400675 | C | A |
| S_9231891 \| \| scaffold14851_1400702_SNP | 1400702 | C | T |
| S_9231904 \| \| scaffold14851_1400962_SNP | 1400962 | T | C |
| S_9231911 \| \| scaffold14851_1401034_SNP | 1401034 | G | A |
| S_9231917 \| \| scaffold14851_1401085_SNP | 1401085 | G | A |
| S_9231942 \| \| scaffold14851_1401388_SNP | 1401388 | T | C |
| S_9231943 \| \| scaffold14851_1401393_SNP | 1401393 | G | A |
| S_9231949 \| \| scaffold14851_1401423_SNP | 1401423 | A | T |
| S_9231977 \| \| scaffold14851_1401760_SNP | 1401760 | G | T |
| S_9232047 \| \| scaffold14851_1402997_SNP | 1402997 | A | G |
| S_9232069 \| \| scaffold14851_1403216_SNP | 1403216 | A | C |
| S_9232071 \| \| scaffold14851_1403220_SNP | 1403220 | A | T |
| S_9232102 \| \| scaffold14851_1403685_SNP | 1403685 | T | C |
| S_9232108 \| \| scaffold14851_1403717_SNP | 1403717 | G | A |
| S_9232134 \| \| scaffold14851_1403993_SNP | 1403993 | T | C |
| S_9232139 \| \| scaffold14851_1404167_SNP | 1404167 | G | A |
| S_9232140 \| \| scaffold14851_1404170_SNP | 1404170 | A | T |
| S_9232151 \| \| scaffold14851_1404292_SNP | 1404292 | A | G |
| S_9232167 \| \| scaffold14851_1404527_SNP | 1404527 | A | T |
| S_9232175 \| \| scaffold14851_1404592_SNP | 1404592 | A | T |
| S_9232189 \| \| scaffold14851_1404733_SNP | 1404733 | T | C |
| S_9232190 \| \| scaffold14851_1404734_SNP | 1404734 | C | A |
| S_9232191 \| \| scaffold14851_1404737_SNP | 1404737 | G | T |
| S_9232208 \| \| scaffold14851_1404953_SNP | 1404953 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9232234 \| \| scaffold14851_1405317_SNP | 1405317 | C | T |
| S_9232245 \| \| scaffold14851_1405401_SNP | 1405401 | A | T |
| S_9232270 \| \| scaffold14851_1406221_SNP | 1406221 | G | C |
| S_9232271 \| \| scaffold14851_1406222_SNP | 1406222 | A | G |
| S_9232272 \| \| scaffold14851_1406225_SNP | 1406225 | G | A |
| scaffold14851_1407693_SNP | 1407693 | G | A |
| S_9232330 \| \| scaffold14851_1407728_SNP | 1407728 | T | A |
| S_9232332 \| \| scaffold14851_1407773_SNP | 1407773 | A | C |
| S_9232337 \| \| scaffold14851_1407829_SNP | 1407829 | A | G |
| S_9232338 \| \| scaffold14851_1407867_SNP | 1407867 | C | A |
| S_9232370 \| \| scaffold14851_1408419_SNP | 1408419 | G | A |
| S_9232371 \| \| scaffold14851_1408425_SNP | 1408425 | G | A |
| S_9232372 \| \| scaffold14851_1408434_SNP | 1408434 | C | G |
| S_9232377 \| \| scaffold14851_1408459_SNP | 1408459 | C | T |
| S_9232748 \| \| scaffold14851_1410756_SNP | 1410756 | A | C |
| S_9233112 \| \| scaffold14851_1413280_SNP | 1413280 | T | G |
| S_9234372 \| \| scaffold14851_1421352_SNP | 1421352 | C | T |
| S_9234410 \| \| scaffold14851_1422064_SNP | 1422064 | A | T |
| S_9234421 \| \| scaffold14851_1422202_SNP | 1422202 | T | C |
| S_9234428 \| \| scaffold14851_1422324_SNP | 1422324 | G | A |
| S_9234450 \| \| scaffold14851_1422591_SNP | 1422591 | A | T |
| S_9234489 \| \| scaffold14851_1423178_SNP | 1423178 | T | C |
| S_9234495 \| \| scaffold14851_1423231_SNP | 1423231 | T | C |
| S_9234498 \| \| scaffold14851_1423257_SNP | 1423257 | C | T |
| S_9234499 \| \| scaffold14851_1423258_SNP | 1423258 | A | T |
| S_9234517 \| \| scaffold14851_1423500_SNP | 1423500 | G | T |
| S_9234524 \| \| scaffold14851_1423629_SNP | 1423629 | C | G |
| S_9234537 \| \| scaffold14851_1423765_SNP | 1423765 | T | G |
| S_9234538 \| \| scaffold14851_1423772_SNP | 1423772 | T | G |
| S_9234539 \| \| scaffold14851_1423803_SNP | 1423803 | C | G |
| S_9234546 \| \| scaffold14851_1423864_SNP | 1423864 | C | A |
| S_9234547 \| \| scaffold14851_1423872_SNP | 1423872 | A | C |
| S_9234549 \| \| scaffold14851_1423945_SNP | 1423945 | C | T |
| S_9234551 \| \| scaffold14851_1423958_SNP | 1423958 | T | G |
| S_9234557 \| \| scaffold14851_1424172_SNP | 1424172 | A | C |
| S_9234568 \| \| scaffold14851_1424377_SNP | 1424377 | T | C |
| S_9234581 \| \| scaffold14851_1424447_SNP | 1424447 | G | C |
| S_9234582 \| \| scaffold14851_1424453_SNP | 1424453 | G | A |
| S_9234584 \| \| scaffold14851_1424514_SNP | 1424514 | G | T |
| S_9234713 \| \| scaffold14851_1426533_SNP | 1426533 | G | T |
| S_9235159 \| \| scaffold14851_1428816_SNP | 1428816 | T | A |
| S_9235428 \| \| scaffold14851_1432236_SNP | 1432236 | T | C |
| S_9235454 \| \| scaffold14851_1432586_SNP | 1432586 | T | G |
| S_9235515 \| \| scaffold14851_1432708_SNP | 1432708 | G | A |
| scaffold14851_1432762_SNP | 1432762 | A | G |
| S_9235527 \| \| scaffold14851_1432800_SNP | 1432800 | G | A |
| scaffold14851_1432836_SNP | 1432836 | C | T |
| S_9235534 \| \| scaffold14851_1432860_SNP | 1432860 | G | A |
| S_9235603 \| \| scaffold14851_1433924_SNP | 1433924 | G | T |
| scaffold14851_1434111_SNP | 1434111 | T | C |
| S_9235654 \| \| scaffold14851_1434269_SNP | 1434269 | C | T |
| S_9235659 \| \| scaffold14851_1434328_SNP | 1434328 | C | T |
| S_9235667 \| \| scaffold14851_1434619_SNP | 1434619 | C | A |
| S_9235671 \| \| scaffold14851_1434676_SNP | 1434676 | C | T |
| S_9235673 \| \| scaffold14851_1434706_SNP | 1434706 | G | T |
| S_9235685 \| \| scaffold14851_1434765_SNP | 1434765 | A | G |
| S_9235758 \| \| scaffold14851_1435682_SNP | 1435682 | A | C |
| S_9235774 \| \| scaffold14851_1435938_SNP | 1435938 | G | T |
| S_9235789 \| \| scaffold14851_1436255_SNP | 1436255 | T | C |
| S_9235795 \| \| scaffold14851_1436357_SNP | 1436357 | T | C |
| S_9235798 \| \| scaffold14851_1436398_SNP | 1436398 | G | A |
| S_9235803 \| \| scaffold14851_1436440_SNP | 1436440 | G | C |
| S_9235809 \| \| scaffold14851_1436480_SNP | 1436480 | A | C |
| S_9235811 \| \| scaffold14851_1436490_SNP | 1436490 | G | A |
| S_9235813 \| \| scaffold14851_1436519_SNP | 1436519 | C | G |
| S_9235825 \| \| scaffold14851_1436683_SNP | 1436683 | T | C |
| S_9235826 \| \| scaffold14851_1436690_SNP | 1436690 | A | T |
| S_9235873 \| \| scaffold14851_1437454_SNP | 1437454 | G | C |
| S_9235899 \| \| scaffold14851_1438016_SNP | 1438016 | A | C |
| S_9235900 \| \| scaffold14851_1438017_SNP | 1438017 | T | C |
| S_9235933 \| \| scaffold14851_1438267_SNP | 1438267 | A | G |
| S_9235949 \| \| scaffold14851_1438320_SNP | 1438320 | G | A |
| S_9236018 \| \| scaffold14851_1438563_SNP | 1438563 | T | C |
| S_9236020 \| \| scaffold14851_1438587_SNP | 1438587 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9236023 \| \| scaffold14851_1438611_SNP | 1438611 | C | T |
| S_9236106 \| \| scaffold14851_1439832_SNP | 1439832 | G | T |
| scaffold14851_1440164_SNP | 1440164 | G | A |
| S_9236352 \| \| scaffold14851_1446359_SNP | 1446359 | C | T |
| S_9236355 \| \| scaffold14851_1446398_SNP | 1446398 | A | G |
| S_9236713 \| \| scaffold14851_1448268_SNP | 1448268 | T | C |
| S_9237471 \| \| scaffold14851_1451613_SNP | 1451613 | C | T |
| scaffold14851_1452914_SNP | 1452914 | A | G |
| scaffold14851_1453652_SNP | 1453652 | C | G |
| S_9237971 \| \| scaffold14851_1456302_SNP | 1456302 | C | T |
| S_9238375 \| \| scaffold14851_1458563_SNP | 1458563 | A | G |
| S_9238505 \| \| scaffold14851_1460326_SNP | 1460326 | A | G |
| S_9238507 \| \| scaffold14851_1460352_SNP | 1460352 | G | A |
| S_9238555 \| \| scaffold14851_1460575_SNP | 1460575 | A | G |
| S_9238556 \| \| scaffold14851_1460604_SNP | 1460604 | C | T |
| S_9238589 \| \| scaffold14851_1460838_SNP | 1460838 | A | G |
| S_9238590 \| \| scaffold14851_1460839_SNP | 1460839 | G | T |
| S_9238603 \| \| scaffold14851_1460918_SNP | 1460918 | A | C |
| S_9238610 \| \| scaffold14851_1461034_SNP | 1461034 | T | C |
| S_9238630 \| \| scaffold14851_1461202_SNP | 1461202 | A | C |
| S_9238632 \| \| scaffold14851_1461213_SNP | 1461213 | A | G |
| S_9238642 \| \| scaffold14851_1461333_SNP | 1461333 | C | G |
| S_9238776 \| \| scaffold14851_1462030_SNP | 1462030 | A | T |
| S_9238818 \| \| scaffold14851_1462206_SNP | 1462206 | T | C |
| S_9238826 \| \| scaffold14851_1462309_SNP | 1462309 | G | A |
| S_9238862 \| \| scaffold14851_1462681_SNP | 1462681 | A | T |
| S_9238881 \| \| scaffold14851_1462810_SNP | 1462810 | A | G |
| S_9238887 \| \| scaffold14851_1462909_SNP | 1462909 | T | C |
| S_9238929 \| \| scaffold14851_1463174_SNP | 1463174 | T | G |
| S_9239018 \| \| scaffold14851_1463656_SNP | 1463656 | G | A |
| S_9239021 \| \| scaffold14851_1463690_SNP | 1463690 | C | T |
| S_9239030 \| \| scaffold14851_1463743_SNP | 1463743 | A | G |
| S_9239048 \| \| scaffold14851_1463881_SNP | 1463881 | A | C |
| S_9239049 \| \| scaffold14851_1463907_SNP | 1463907 | C | T |
| S_9239071 \| \| scaffold14851_1464042_SNP | 1464042 | T | C |
| S_9239080 \| \| scaffold14851_1464084_SNP | 1464084 | A | G |
| S_9239158 \| \| scaffold14851_1464325_SNP | 1464325 | G | A |
| S_9239159 \| \| scaffold14851_1464326_SNP | 1464326 | G | A |
| S_9239210 \| \| scaffold14851_1464838_SNP | 1464838 | G | A |
| S_9239214 \| \| scaffold14851_1464867_SNP | 1464867 | T | C |
| S_9239335 \| \| scaffold14851_1465983_SNP | 1465983 | A | C |
| S_9239373 \| \| scaffold14851_1466431_SNP | 1466431 | G | C |
| S_9239664 \| \| scaffold14851_1469269_SNP | 1469269 | A | G |
| S_9239684 \| \| scaffold14851_1469529_SNP | 1469529 | C | A |
| S_9239739 \| \| scaffold14851_1470067_SNP | 1470067 | T | A |
| S_9239763 \| \| scaffold14851_1470311_SNP | 1470311 | G | A |
| S_9239776 \| \| scaffold14851_1470467_SNP | 1470467 | T | C |
| S_9240145 \| \| scaffold14851_1476109_SNP | 1476109 | G | T |
| S_9240157 \| \| scaffold14851_1476240_SNP | 1476240 | T | A |
| S_9240159 \| \| scaffold14851_1476289_SNP | 1476289 | A | G |
| S_9240161 \| \| scaffold14851_1476294_SNP | 1476294 | G | A |
| S_9240168 \| \| scaffold14851_1476424_SNP | 1476424 | C | A |
| S_9240169 \| \| scaffold14851_1476429_SNP | 1476429 | T | A |
| S_9240193 \| \| scaffold14851_1476656_SNP | 1476656 | G | T |
| S_9240195 \| \| scaffold14851_1476684_SNP | 1476684 | G | A |
| S_9240245 \| \| scaffold14851_1477786_SNP | 1477786 | G | A |
| S_9240248 \| \| scaffold14851_1477810_SNP | 1477810 | C | T |
| S_9240256 \| \| scaffold14851_1477986_SNP | 1477986 | T | C |
| S_9240258 \| \| scaffold14851_1477995_SNP | 1477995 | A | T |
| S_9240263 \| \| scaffold14851_1478084_SNP | 1478084 | A | G |
| S_9240264 \| \| scaffold14851_1478088_SNP | 1478088 | T | C |
| S_9240265 \| \| scaffold14851_1478103_SNP | 1478103 | C | T |
| S_9240287 \| \| scaffold14851_1478369_SNP | 1478369 | C | T |
| S_9240358 \| \| scaffold14851_1478729_SNP | 1478729 | A | G |
| S_9240443 \| \| scaffold14851_1481936_SNP | 1481936 | A | T |
| S_9240448 \| \| scaffold14851_1481975_SNP | 1481975 | C | G |
| S_9240453 \| \| scaffold14851_1482023_SNP | 1482023 | C | T |
| S_9240457 \| \| scaffold14851_1482078_SNP | 1482078 | A | G |
| S_9240460 \| \| scaffold14851_1482122_SNP | 1482122 | T | C |
| S_9240477 \| \| scaffold14851_1482339_SNP | 1482339 | A | G |
| S_9240481 \| \| scaffold14851_1482440_SNP | 1482440 | T | A |
| S_9240667 \| \| scaffold14851_1484512_SNP | 1484512 | G | T |
| S_9240669 \| \| scaffold14851_1484579_SNP | 1484579 | A | C |
| S_9240670 \| \| scaffold14851_1484588_SNP | 1484588 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9240671 \| \| scaffold14851_1484589_SNP | 1484589 | C | T |
| S_9240674 \| \| scaffold14851_1484658_SNP | 1484658 | C | T |
| S_9240720 \| \| scaffold14851_1485017_SNP | 1485017 | G | A |
| S_9240751 \| \| scaffold14851_1485360_SNP | 1485360 | C | G |
| S_9240763 \| \| scaffold14851_1485478_SNP | 1485478 | T | G |
| S_9240767 \| \| scaffold14851_1485572_SNP | 1485572 | C | T |
| S_9240768 \| \| scaffold14851_1485577_SNP | 1485577 | C | A |
| S_9240770 \| \| scaffold14851_1485595_SNP | 1485595 | C | G |
| S_9240771 \| \| scaffold14851_1485599_SNP | 1485599 | G | A |
| S_9240778 \| \| scaffold14851_1485795_SNP | 1485795 | G | T |
| S_9240780 \| \| scaffold14851_1485823_SNP | 1485823 | A | G |
| S_9240785 \| \| scaffold14851_1485858_SNP | 1485858 | G | A |
| S_9240786 \| \| scaffold14851_1485871_SNP | 1485871 | A | G |
| S_9240802 \| \| scaffold14851_1486143_SNP | 1486143 | C | A |
| S_9240807 \| \| scaffold14851_1486272_SNP | 1486272 | G | A |
| S_9240810 \| \| scaffold14851_1486291_SNP | 1486291 | G | A |
| S_9240874 \| \| scaffold14851_1487263_SNP | 1487263 | A | C |
| S_9240875 \| \| scaffold14851_1487290_SNP | 1487290 | G | A |
| S_9240876 \| \| scaffold14851_1487304_SNP | 1487304 | C | T |
| S_9240877 \| \| scaffold14851_1487319_SNP | 1487319 | C | A |
| S_9240892 \| \| scaffold14851_1487650_SNP | 1487650 | C | T |
| S_9240904 \| \| scaffold14851_1487850_SNP | 1487850 | G | A |
| S_9240939 \| \| scaffold14851_1488246_SNP | 1488246 | C | T |
| S_9240944 \| \| scaffold14851_1488409_SNP | 1488409 | T | C |
| S_9240950 \| \| scaffold14851_1488609_SNP | 1488609 | C | T |
| S_9240955 \| \| scaffold14851_1488683_SNP | 1488683 | T | C |
| S_9240964 \| \| scaffold14851_1488924_SNP | 1488924 | A | G |
| S_9240966 \| \| scaffold14851_1488957_SNP | 1488957 | C | A |
| S_9240975 \| \| scaffold14851_1489088_SNP | 1489088 | C | T |
| S_9240977 \| \| scaffold14851_1489102_SNP | 1489102 | G | A |
| S_9240987 \| \| scaffold14851_1489337_SNP | 1489337 | A | T |
| S_9241004 \| \| scaffold14851_1489605_SNP | 1489605 | C | A |
| S_9241045 \| \| scaffold14851_1490074_SNP | 1490074 | A | G |
| S_9241048 \| \| scaffold14851_1490109_SNP | 1490109 | T | G |
| S_9241059 \| \| scaffold14851_1490262_SNP | 1490262 | C | T |
| S_9241323 \| \| scaffold14851_1493545_SNP | 1493545 | C | T |
| S_9241394 \| \| scaffold14851_1494115_SNP | 1494115 | C | T |
| S_9241395 \| \| scaffold14851_1494132_SNP | 1494132 | A | T |
| S_9241433 \| \| scaffold14851_1494634_SNP | 1494634 | A | C |
| S_9241437 \| \| scaffold14851_1494687_SNP | 1494687 | C | A |
| S_9241439 \| \| scaffold14851_1494709_SNP | 1494709 | T | A |
| S_9241443 \| \| scaffold14851_1494760_SNP | 1494760 | C | T |
| S_9241579 \| \| scaffold14851_1496371_SNP | 1496371 | T | C |
| S_9241602 \| \| scaffold14851_1496535_SNP | 1496535 | G | T |
| S_9241690 \| \| scaffold14851_1497996_SNP | 1497996 | T | G |
| S_9241759 \| \| scaffold14851_1499285_SNP | 1499285 | A | G |
| S_9241762 \| \| scaffold14851_1499374_SNP | 1499374 | A | G |
| S_9241770 \| \| scaffold14851_1499462_SNP | 1499462 | T | A |
| S_9241845 \| \| scaffold14851_1500275_SNP | 1500275 | G | T |
| S_9241850 \| \| scaffold14851_1500313_SNP | 1500313 | G | A |
| S_9241900 \| \| scaffold14851_1500841_SNP | 1500841 | T | C |
| S_9242026 \| \| scaffold14851_1502925_SNP | 1502925 | A | T |
| S_9242027 \| \| scaffold14851_1502931_SNP | 1502931 | G | A |
| S_9242133 \| \| scaffold14851_1504504_SNP | 1504504 | A | T |
| S_9242164 \| \| scaffold14851_1505009_SNP | 1505009 | C | T |
| S_9242309 \| \| scaffold14851_1506409_SNP | 1506409 | G | T |
| S_9242328 \| \| scaffold14851_1506805_SNP | 1506805 | T | C |
| S_9242410 \| \| scaffold14851_1508069_SNP | 1508069 | C | T |
| S_9242413 \| \| scaffold14851_1508246_SNP | 1508246 | A | T |
| S_9242474 \| \| scaffold14851_1509238_SNP | 1509238 | T | C |
| S_9242641 \| \| scaffold14851_1511000_SNP | 1511000 | T | A |
| S_9242656 \| \| scaffold14851_1511089_SNP | 1511089 | A | G |
| S_9242659 \| \| scaffold14851_1511144_SNP | 1511144 | T | C |
| S_9242662 \| \| scaffold14851_1511231_SNP | 1511231 | C | G |
| S_9242955 \| \| scaffold14851_1514683_SNP | 1514683 | C | A |
| S_9242962 \| \| scaffold14851_1514755_SNP | 1514755 | C | T |
| S_9243056 \| \| scaffold14851_1515364_SNP | 1515364 | A | T |
| S_9243057 \| \| scaffold14851_1515390_SNP | 1515390 | T | C |
| S_9243168 \| \| scaffold14851_1516205_SNP | 1516205 | A | C |
| S_9243410 \| \| scaffold14851_1519267_SNP | 1519267 | C | T |
| S_9243527 \| \| scaffold14851_1520827_SNP | 1520827 | C | T |
| S_9243617 \| \| scaffold14851_1522082_SNP | 1522082 | T | C |
| S_9243626 \| \| scaffold14851_1522239_SNP | 1522239 | T | C |
| S_9243627 \| \| scaffold14851_1522338_SNP | 1522338 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9243647 \| \| scaffold14851_1522857_SNP | 1522857 | G | A |
| S_9243652 \| \| scaffold14851_1522896_SNP | 1522896 | A | G |
| S_9243815 \| \| scaffold14851_1525044_SNP | 1525044 | G | C |
| S_9243961 \| \| scaffold14851_1526854_SNP | 1526854 | C | T |
| S_9243965 \| \| scaffold14851_1526941_SNP | 1526941 | T | C |
| S_9244271 \| \| scaffold14851_1530748_SNP | 1530748 | C | G |
| S_9244282 \| \| scaffold14851_1530857_SNP | 1530857 | T | A |
| S_9244459 \| \| scaffold14851_1533444_SNP | 1533444 | T | C |
| S_9244751 \| \| scaffold14851_1538081_SNP | 1538081 | C | G |
| S_9244861 \| \| scaffold14851_1539563_SNP | 1539563 | G | A |
| S_9244863 \| \| scaffold14851_1539570_SNP | 1539570 | A | T |
| S_9244865 \| \| scaffold14851_1539580_SNP | 1539580 | A | C |
| S_9244911 \| \| scaffold14851_1540031_SNP | 1540031 | A | G |
| S_9244945 \| \| scaffold14851_1540407_SNP | 1540407 | T | C |
| S_9244974 \| \| scaffold14851_1540718_SNP | 1540718 | G | T |
| S_9245015 \| \| scaffold14851_1541140_SNP | 1541140 | G | A |
| S_9245016 \| \| scaffold14851_1541191_SNP | 1541191 | T | C |
| S_9245190 \| \| scaffold14851_1542926_SNP | 1542926 | C | A |
| S_9245191 \| \| scaffold14851_1542927_SNP | 1542927 | C | A |
| S_9245229 \| \| scaffold14851_1543119_SNP | 1543119 | G | A |
| S_9245513 \| \| scaffold14851_1547395_SNP | 1547395 | A | T |
| S_9245587 \| \| scaffold14851_1548502_SNP | 1548502 | G | T |
| S_9245638 \| \| scaffold14851_1548934_SNP | 1548934 | C | T |
| S_9245794 \| \| scaffold14851_1550460_SNP | 1550460 | G | C |
| S_9245806 \| \| scaffold14851_1550536_SNP | 1550536 | C | T |
| S_9245979 \| \| scaffold14851_1553133_SNP | 1553133 | G | A |
| S_9245980 \| \| scaffold14851_1553138_SNP | 1553138 | G | A |
| S_9246037 \| \| scaffold14851_1554096_SNP | 1554096 | A | C |
| S_9246039 \| \| scaffold14851_1554140_SNP | 1554140 | C | G |
| S_9246202 \| \| scaffold14851_1555907_SNP | 1555907 | T | G |
| S_9246503 \| \| scaffold14851_1559470_SNP | 1559470 | T | A |
| S_9246527 \| \| scaffold14851_1559835_SNP | 1559835 | T | C |
| S_9247566 \| \| scaffold14851_1571303_SNP | 1571303 | T | C |
| S_9247568 \| \| scaffold14851_1571305_SNP | 1571305 | T | A |
| S_9247621 \| \| scaffold14851_1571950_SNP | 1571950 | C | T |
| S_9247914 \| \| scaffold14851_1575761_SNP | 1575761 | T | G |
| S_9247921 \| \| scaffold14851_1575892_SNP | 1575892 | G | T |
| S_9248129 \| \| scaffold14851_1578539_SNP | 1578539 | G | A |
| S_9248135 \| \| scaffold14851_1578649_SNP | 1578649 | T | G |
| S_9248220 \| \| scaffold14851_1580050_SNP | 1580050 | T | A |
| S_9248221 \| \| scaffold14851_1580072_SNP | 1580072 | G | A |
| S_9248258 \| \| scaffold14851_1580715_SNP | 1580715 | C | A |
| S_9248305 \| \| scaffold14851_1581417_SNP | 1581417 | A | T |
| S_9248310 \| \| scaffold14851_1581457_SNP | 1581457 | A | G |
| S_9248323 \| \| scaffold14851_1581727_SNP | 1581727 | T | A |
| S_9248349 \| \| scaffold14851_1582132_SNP | 1582132 | A | G |
| S_9248437 \| \| scaffold14851_1582955_SNP | 1582955 | T | A |
| S_9248481 \| \| scaffold14851_1583528_SNP | 1583528 | G | A |
| S_9248512 \| \| scaffold14851_1583892_SNP | 1583892 | G | A |
| S_9248536 \| \| scaffold14851_1584095_SNP | 1584095 | A | G |
| S_9248538 \| \| scaffold14851_1584121_SNP | 1584121 | G | C |
| S_9248739 \| \| scaffold14851_1586983_SNP | 1586983 | A | T |
| S_9248741 \| \| scaffold14851_1587019_SNP | 1587019 | T | C |
| S_9248746 \| \| scaffold14851_1587068_SNP | 1587068 | A | G |
| S_9248771 \| \| scaffold14851_1587358_SNP | 1587358 | T | C |
| S_9248782 \| \| scaffold14851_1587580_SNP | 1587580 | G | A |
| S_9248828 \| \| scaffold14851_1588933_SNP | 1588933 | G | T |
| S_9248830 \| \| scaffold14851_1588945_SNP | 1588945 | A | T |
| S_9248839 \| \| scaffold14851_1589138_SNP | 1589138 | T | C |
| S_9248871 \| \| scaffold14851_1589375_SNP | 1589375 | T | C |
| S_9248872 \| \| scaffold14851_1589388_SNP | 1589388 | C | T |
| S_9249024 \| \| scaffold14851_1591794_SNP | 1591794 | G | A |
| S_9249243 \| \| scaffold14851_1593263_SNP | 1593263 | T | A |
| S_9249272 \| \| scaffold14851_1594159_SNP | 1594159 | T | G |
| S_9249288 \| \| scaffold14851_1594345_SNP | 1594345 | T | G |
| S_9249349 \| \| scaffold14851_1595271_SNP | 1595271 | G | A |
| S_9249356 \| \| scaffold14851_1595396_SNP | 1595396 | T | C |
| S_9249357 \| \| scaffold14851_1595398_SNP | 1595398 | G | T |
| S_9249369 \| \| scaffold14851_1595528_SNP | 1595528 | A | G |
| S_9249372 \| \| scaffold14851_1595553_SNP | 1595553 | G | T |
| S_9249377 \| \| scaffold14851_1595709_SNP | 1595709 | T | G |
| S_9249380 \| \| scaffold14851_1595765_SNP | 1595765 | C | T |
| S_9249381 \| \| scaffold14851_1595777_SNP | 1595777 | A | G |
| S_9249383 \| \| scaffold14851_1595787_SNP | 1595787 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9249388 \| \| scaffold14851_1595812_SNP | 1595812 | T | C |
| S_9249511 \| \| scaffold14851_1597279_SNP | 1597279 | A | G |
| S_9249512 \| \| scaffold14851_1597314_SNP | 1597314 | T | C |
| S_9249514 \| \| scaffold14851_1597342_SNP | 1597342 | T | A |
| S_9249541 \| \| scaffold14851_1597752_SNP | 1597752 | G | A |
| S_9249542 \| \| scaffold14851_1597753_SNP | 1597753 | C | T |
| S_9249543 \| \| scaffold14851_1597772_SNP | 1597772 | C | A |
| S_9249548 \| \| scaffold14851_1597918_SNP | 1597918 | T | A |
| S_9249549 \| \| scaffold14851_1597919_SNP | 1597919 | G | A |
| S_9249611 \| \| scaffold14851_1598945_SNP | 1598945 | A | C |
| S_9249621 \| \| scaffold14851_1599159_SNP | 1599159 | T | G |
| S_9249622 \| \| scaffold14851_1599185_SNP | 1599185 | G | A |
| S_9249624 \| \| scaffold14851_1599198_SNP | 1599198 | G | A |
| S_9249649 \| \| scaffold14851_1599655_SNP | 1599655 | T | G |
| S_9249659 \| \| scaffold14851_1599841_SNP | 1599841 | T | A |
| S_9249673 \| \| scaffold14851_1600196_SNP | 1600196 | C | A |
| S_9249704 \| \| scaffold14851_1600623_SNP | 1600623 | T | G |
| S_9249709 \| \| scaffold14851_1600695_SNP | 1600695 | T | A |
| S_9249710 \| \| scaffold14851_1600697_SNP | 1600697 | A | T |
| S_9249711 \| \| scaffold14851_1600698_SNP | 1600698 | A | T |
| S_9249712 \| \| scaffold14851_1600724_SNP | 1600724 | T | G |
| S_9249713 \| \| scaffold14851_1600735_SNP | 1600735 | G | A |
| S_9249751 \| \| scaffold14851_1601342_SNP | 1601342 | T | A |
| S_9249883 \| \| scaffold14851_1603645_SNP | 1603645 | G | T |
| S_9249923 \| \| scaffold14851_1604186_SNP | 1604186 | A | T |
| S_9249949 \| \| scaffold14851_1604783_SNP | 1604783 | G | T |
| S_9249980 \| \| scaffold14851_1605161_SNP | 1605161 | G | A |
| S_9249983 \| \| scaffold14851_1605192_SNP | 1605192 | C | G |
| S_9250021 \| \| scaffold14851_1605645_SNP | 1605645 | A | G |
| S_9250023 \| \| scaffold14851_1605664_SNP | 1605664 | A | G |
| S_9250035 \| \| scaffold14851_1606036_SNP | 1606036 | G | C |
| S_9250044 \| \| scaffold14851_1606158_SNP | 1606158 | G | A |
| S_9250089 \| \| scaffold14851_1606913_SNP | 1606913 | T | C |
| S_9250171 \| \| scaffold14851_1608816_SNP | 1608816 | A | T |
| S_9250264 \| \| scaffold14851_1610206_SNP | 1610206 | T | A |
| S_9250266 \| \| scaffold14851_1610208_SNP | 1610208 | C | T |
| S_9250267 \| \| scaffold14851_1610210_SNP | 1610210 | A | G |
| S_9250268 \| \| scaffold14851_1610220_SNP | 1610220 | G | A |
| S_9250271 \| \| scaffold14851_1610346_SNP | 1610346 | C | A |
| S_9250308 \| \| scaffold14851_1610762_SNP | 1610762 | A | G |
| S_9250310 \| \| scaffold14851_1610790_SNP | 1610790 | T | G |
| S_9250334 \| \| scaffold14851_1611232_SNP | 1611232 | G | T |
| S_9250335 \| \| scaffold14851_1611235_SNP | 1611235 | T | C |
| S_9250337 \| \| scaffold14851_1611253_SNP | 1611253 | T | A |
| S_9250339 \| \| scaffold14851_1611292_SNP | 1611292 | G | A |
| S_9250435 \| \| scaffold14851_1611736_SNP | 1611736 | T | A |
| S_9250455 \| \| scaffold14851_1612052_SNP | 1612052 | A | T |
| S_9250456 \| \| scaffold14851_1612054_SNP | 1612054 | T | A |
| S_9250472 \| \| scaffold14851_1612310_SNP | 1612310 | A | G |
| S_9250474 \| \| scaffold14851_1612385_SNP | 1612385 | C | T |
| S_9250483 \| \| scaffold14851_1612634_SNP | 1612634 | A | C |
| S_9250493 \| \| scaffold14851_1612756_SNP | 1612756 | C | G |
| S_9250495 \| \| scaffold14851_1612797_SNP | 1612797 | G | T |
| S_9250498 \| \| scaffold14851_1612831_SNP | 1612831 | A | T |
| S_9250505 \| \| scaffold14851_1612930_SNP | 1612930 | G | T |
| S_9250517 \| \| scaffold14851_1613154_SNP | 1613154 | C | A |
| S_9250533 \| \| scaffold14851_1613300_SNP | 1613300 | G | A |
| S_9250535 \| \| scaffold14851_1613334_SNP | 1613334 | G | A |
| S_9250553 \| \| scaffold14851_1613585_SNP | 1613585 | T | G |
| S_9250564 \| \| scaffold14851_1613695_SNP | 1613695 | T | G |
| S_9250572 \| \| scaffold14851_1613757_SNP | 1613757 | C | T |
| S_9250578 \| \| scaffold14851_1613835_SNP | 1613835 | A | C |
| S_9250579 \| \| scaffold14851_1613845_SNP | 1613845 | C | T |
| S_9250583 \| \| scaffold14851_1613869_SNP | 1613869 | C | G |
| S_9250590 \| \| scaffold14851_1613963_SNP | 1613963 | A | G |
| S_9250599 \| \| scaffold14851_1614247_SNP | 1614247 | G | A |
| S_9250602 \| \| scaffold14851_1614263_SNP | 1614263 | A | G |
| S_9250608 \| \| scaffold14851_1614276_SNP | 1614276 | A | T |
| S_9250633 \| \| scaffold14851_1614745_SNP | 1614745 | T | A |
| S_9250665 \| \| scaffold14851_1615194_SNP | 1615194 | A | C |
| S_9250831 \| \| scaffold14851_1617491_SNP | 1617491 | T | A |
| S_9250838 \| \| scaffold14851_1617656_SNP | 1617656 | T | C |
| S_9250839 \| \| scaffold14851_1617673_SNP | 1617673 | A | G |
| S_9250867 \| \| scaffold14851_1618148_SNP | 1618148 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9250877 \| \| scaffold14851_1618341_SNP | 1618341 | T | A |
| S_9250878 \| \| scaffold14851_1618351_SNP | 1618351 | G | T |
| S_9250881 \| \| scaffold14851_1618395_SNP | 1618395 | A | G |
| S_9250895 \| \| scaffold14851_1618664_SNP | 1618664 | G | A |
| S_9250904 \| \| scaffold14851_1618771_SNP | 1618771 | T | G |
| S_9250905 \| \| scaffold14851_1618780_SNP | 1618780 | C | A |
| S_9250906 \| \| scaffold14851_1618799_SNP | 1618799 | C | T |
| S_9250913 \| \| scaffold14851_1618989_SNP | 1618989 | A | T |
| S_9250925 \| \| scaffold14851_1619213_SNP | 1619213 | A | G |
| S_9250936 \| \| scaffold14851_1619489_SNP | 1619489 | C | T |
| S_9250943 \| \| scaffold14851_1619516_SNP | 1619516 | T | A |
| S_9250947 \| \| scaffold14851_1619562_SNP | 1619562 | G | A |
| S_9250952 \| \| scaffold14851_1619659_SNP | 1619659 | C | T |
| S_9250953 \| \| scaffold14851_1619677_SNP | 1619677 | A | C |
| S_9250960 \| \| scaffold14851_1619767_SNP | 1619767 | A | C |
| S_9250967 \| \| scaffold14851_1619805_SNP | 1619805 | T | A |
| S_9250976 \| \| scaffold14851_1619899_SNP | 1619899 | C | T |
| S_9251008 \| \| scaffold14851_1620436_SNP | 1620436 | G | A |
| S_9251018 \| \| scaffold14851_1620603_SNP | 1620603 | A | C |
| S_9251033 \| \| scaffold14851_1620827_SNP | 1620827 | G | C |
| S_9251042 \| \| scaffold14851_1620946_SNP | 1620946 | A | G |
| S_9251052 \| \| scaffold14851_1621155_SNP | 1621155 | G | A |
| S_9251193 \| \| scaffold14851_1622276_SNP | 1622276 | T | C |
| S_9251198 \| \| scaffold14851_1622328_SNP | 1622328 | G | A |
| S_9251199 \| \| scaffold14851_1622334_SNP | 1622334 | C | A |
| S_9251218 \| \| scaffold14851_1622650_SNP | 1622650 | C | T |
| S_9251307 \| \| scaffold14851_1624103_SNP | 1624103 | C | T |
| S_9251399 \| \| scaffold14851_1625223_SNP | 1625223 | G | A |
| S_9251404 \| \| scaffold14851_1625350_SNP | 1625350 | A | C |
| S_9251422 \| \| scaffold14851_1625460_SNP | 1625460 | A | G |
| S_9251424 \| \| scaffold14851_1625514_SNP | 1625514 | G | T |
| S_9251467 \| \| scaffold14851_1626715_SNP | 1626715 | G | A |
| S_9251474 \| \| scaffold14851_1626798_SNP | 1626798 | G | A |
| S_9251591 \| \| scaffold14851_1629456_SNP | 1629456 | T | G |
| S_9251597 \| \| scaffold14851_1629499_SNP | 1629499 | G | C |
| S_9251610 \| \| scaffold14851_1629634_SNP | 1629634 | A | T |
| S_9251613 \| \| scaffold14851_1629667_SNP | 1629667 | G | C |
| S_9251620 \| \| scaffold14851_1629854_SNP | 1629854 | C | G |
| S_9251621 \| \| scaffold14851_1629864_SNP | 1629864 | C | A |
| S_9251625 \| \| scaffold14851_1629911_SNP | 1629911 | G | C |
| S_9251665 \| \| scaffold14851_1630829_SNP | 1630829 | A | C |
| S_9251706 \| \| scaffold14851_1631383_SNP | 1631383 | A | G |
| S_9251708 \| \| scaffold14851_1631429_SNP | 1631429 | A | T |
| S_9251727 \| \| scaffold14851_1631795_SNP | 1631795 | C | T |
| S_9251769 \| \| scaffold14851_1631944_SNP | 1631944 | G | A |
| S_9251770 \| \| scaffold14851_1631951_SNP | 1631951 | G | A |
| S_9251773 \| \| scaffold14851_1632015_SNP | 1632015 | C | T |
| S_9251805 \| \| scaffold14851_1632596_SNP | 1632596 | A | T |
| S_9251817 \| \| scaffold14851_1632731_SNP | 1632731 | A | G |
| S_9251826 \| \| scaffold14851_1632938_SNP | 1632938 | G | A |
| S_9251830 \| \| scaffold14851_1633018_SNP | 1633018 | A | C |
| S_9251831 \| \| scaffold14851_1633021_SNP | 1633021 | G | A |
| S_9251832 \| \| scaffold14851_1633046_SNP | 1633046 | G | A |
| S_9251857 \| \| scaffold14851_1633510_SNP | 1633510 | G | T |
| S_9251860 \| \| scaffold14851_1633526_SNP | 1633526 | A | T |
| S_9251955 \| \| scaffold14851_1635136_SNP | 1635136 | G | A |
| S_9251960 \| \| scaffold14851_1635218_SNP | 1635218 | T | A |
| S_9251962 \| \| scaffold14851_1635258_SNP | 1635258 | T | A |
| S_9251964 \| \| scaffold14851_1635274_SNP | 1635274 | A | G |
| S_9252097 \| \| scaffold14851_1637178_SNP | 1637178 | T | C |
| S_9252099 \| \| scaffold14851_1637196_SNP | 1637196 | T | G |
| S_9252102 \| \| scaffold14851_1637232_SNP | 1637232 | G | C |
| S_9252114 \| \| scaffold14851_1637446_SNP | 1637446 | T | A |
| S_9252163 \| \| scaffold14851_1638000_SNP | 1638000 | A | G |
| S_9252166 \| \| scaffold14851_1638021_SNP | 1638021 | C | T |
| S_9252168 \| \| scaffold14851_1638040_SNP | 1638040 | G | C |
| S_9252201 \| \| scaffold14851_1638579_SNP | 1638579 | T | A |
| S_9252310 \| \| scaffold14851_1639901_SNP | 1639901 | T | G |
| S_9252442 \| \| scaffold14851_1641179_SNP | 1641179 | C | T |
| S_9252466 \| \| scaffold14851_1641686_SNP | 1641686 | A | G |
| S_9252467 \| \| scaffold14851_1641687_SNP | 1641687 | A | T |
| S_9252468 \| \| scaffold14851_1641690_SNP | 1641690 | A | G |
| S_9252471 \| \| scaffold14851_1641724_SNP | 1641724 | A | C |
| S_9252479 \| \| scaffold14851_1641823_SNP | 1641823 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9252483 \| \| scaffold14851_1641871_SNP | 1641871 | T | C |
| S_9252523 \| \| scaffold14851_1642494_SNP | 1642494 | G | T |
| S_9252541 \| \| scaffold14851_1642853_SNP | 1642853 | T | A |
| S_9252551 \| \| scaffold14851_1643163_SNP | 1643163 | A | G |
| S_9252552 \| \| scaffold14851_1643164_SNP | 1643164 | G | A |
| S_9252607 \| \| scaffold14851_1643530_SNP | 1643530 | C | T |
| S_9252630 \| \| scaffold14851_1643599_SNP | 1643599 | G | A |
| S_9252672 \| \| scaffold14851_1643932_SNP | 1643932 | T | G |
| S_9252673 \| \| scaffold14851_1643934_SNP | 1643934 | T | G |
| S_9252674 \| \| scaffold14851_1643935_SNP | 1643935 | G | C |
| S_9252734 \| \| scaffold14851_1644935_SNP | 1644935 | C | T |
| S_9252768 \| \| scaffold14851_1645344_SNP | 1645344 | T | A |
| S_9252795 \| \| scaffold14851_1645850_SNP | 1645850 | C | G |
| S_9252802 \| \| scaffold14851_1646019_SNP | 1646019 | C | T |
| S_9252804 \| \| scaffold14851_1646055_SNP | 1646055 | G | T |
| S_9252820 \| \| scaffold14851_1646379_SNP | 1646379 | T | A |
| S_9252849 \| \| scaffold14851_1646739_SNP | 1646739 | C | T |
| S_9252871 \| \| scaffold14851_1647086_SNP | 1647086 | T | G |
| S_9252872 \| \| scaffold14851_1647087_SNP | 1647087 | G | A |
| S_9252873 \| \| scaffold14851_1647088_SNP | 1647088 | A | T |
| S_9252949 \| \| scaffold14851_1648299_SNP | 1648299 | A | T |
| S_9252973 \| \| scaffold14851_1648641_SNP | 1648641 | A | G |
| S_9253049 \| \| scaffold14851_1649545_SNP | 1649545 | T | C |
| S_9253068 \| \| scaffold14851_1649819_SNP | 1649819 | A | G |
| S_9253081 \| \| scaffold14851_1650088_SNP | 1650088 | T | A |
| S_9253082 \| \| scaffold14851_1650089_SNP | 1650089 | C | A |
| S_9253092 \| \| scaffold14851_1650264_SNP | 1650264 | T | C |
| S_9253097 \| \| scaffold14851_1650335_SNP | 1650335 | A | C |
| S_9253099 \| \| scaffold14851_1650342_SNP | 1650342 | T | A |
| S_9253103 \| \| scaffold14851_1650477_SNP | 1650477 | A | C |
| S_9253105 \| \| scaffold14851_1650544_SNP | 1650544 | A | G |
| S_9253107 \| \| scaffold14851_1650572_SNP | 1650572 | T | C |
| S_9253142 \| \| scaffold14851_1650963_SNP | 1650963 | C | T |
| S_9253188 \| \| scaffold14851_1651783_SNP | 1651783 | T | C |
| S_9253216 \| \| scaffold14851_1652187_SNP | 1652187 | T | C |
| S_9253239 \| \| scaffold14851_1652436_SNP | 1652436 | T | A |
| S_9253240 \| \| scaffold14851_1652444_SNP | 1652444 | G | A |
| S_9253241 \| \| scaffold14851_1652446_SNP | 1652446 | A | G |
| S_9253300 \| \| scaffold14851_1652938_SNP | 1652938 | A | G |
| S_9253379 \| \| scaffold14851_1653892_SNP | 1653892 | A | G |
| S_9253386 \| \| scaffold14851_1653942_SNP | 1653942 | T | G |
| S_9253413 \| \| scaffold14851_1654264_SNP | 1654264 | A | G |
| S_9253445 \| \| scaffold14851_1654663_SNP | 1654663 | T | A |
| S_9253446 \| \| scaffold14851_1654664_SNP | 1654664 | A | C |
| S_9253479 \| \| scaffold14851_1655093_SNP | 1655093 | G | T |
| S_9253494 \| \| scaffold14851_1655335_SNP | 1655335 | A | C |
| S_9253510 \| \| scaffold14851_1655661_SNP | 1655661 | G | A |
| S_9253632 \| \| scaffold14851_1656712_SNP | 1656712 | G | A |
| S_9253638 \| \| scaffold14851_1656834_SNP | 1656834 | G | A |
| S_9253640 \| \| scaffold14851_1656917_SNP | 1656917 | A | C |
| S_9253662 \| \| scaffold14851_1657352_SNP | 1657352 | A | T |
| S_9253663 \| \| scaffold14851_1657353_SNP | 1657353 | A | T |
| S_9253664 \| \| scaffold14851_1657354_SNP | 1657354 | A | T |
| S_9253665 \| \| scaffold14851_1657355_SNP | 1657355 | A | T |
| S_9253698 \| \| scaffold14851_1657826_SNP | 1657826 | G | A |
| S_9253700 \| \| scaffold14851_1657908_SNP | 1657908 | C | A |
| S_9253701 \| \| scaffold14851_1657913_SNP | 1657913 | T | C |
| S_9253706 \| \| scaffold14851_1658094_SNP | 1658094 | G | A |
| S_9253777 \| \| scaffold14851_1658345_SNP | 1658345 | C | T |
| S_9253795 \| \| scaffold14851_1658854_SNP | 1658854 | T | C |
| S_9253796 \| \| scaffold14851_1658868_SNP | 1658868 | T | G |
| S_9253801 \| \| scaffold14851_1658989_SNP | 1658989 | G | A |
| S_9254051 \| \| scaffold14851_1660241_SNP | 1660241 | C | G |
| S_9254058 \| \| scaffold14851_1660368_SNP | 1660368 | A | T |
| S_9254082 \| \| scaffold14851_1660725_SNP | 1660725 | G | T |
| S_9254083 \| \| scaffold14851_1660743_SNP | 1660743 | A | G |
| S_9254086 \| \| scaffold14851_1660839_SNP | 1660839 | A | C |
| S_9254087 \| \| scaffold14851_1660840_SNP | 1660840 | T | A |
| S_9254101 \| \| scaffold14851_1661034_SNP | 1661034 | T | G |
| S_9254105 \| \| scaffold14851_1661105_SNP | 1661105 | C | T |
| S_9254130 \| \| scaffold14851_1661446_SNP | 1661446 | A | C |
| S_9254158 \| \| scaffold14851_1661813_SNP | 1661813 | G | A |
| S_9254252 \| \| scaffold14851_1663311_SNP | 1663311 | C | A |
| S_9254253 \| \| scaffold14851_1663382_SNP | 1663382 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9254254 \| \| scaffold14851_1663414_SNP | 1663414 | A | G |
| S_9254256 \| \| scaffold14851_1663518_SNP | 1663518 | T | G |
| S_9254354 \| \| scaffold14851_1665429_SNP | 1665429 | G | T |
| S_9254358 \| \| scaffold14851_1665524_SNP | 1665524 | C | A |
| S_9254359 \| \| scaffold14851_1665584_SNP | 1665584 | G | A |
| S_9254360 \| \| scaffold14851_1665613_SNP | 1665613 | C | T |
| S_9254439 \| \| scaffold14851_1666983_SNP | 1666983 | C | G |
| S_9254440 \| \| scaffold14851_1666984_SNP | 1666984 | T | G |
| S_9254464 \| \| scaffold14851_1667306_SNP | 1667306 | G | T |
| S_9254475 \| \| scaffold14851_1667642_SNP | 1667642 | C | A |
| scaffold14851_1668181_SNP | 1668181 | A | G |
| S_9254564 \| \| scaffold14851_1668994_SNP | 1668994 | C | T |
| S_9254725 \| \| scaffold14851_1669936_SNP | 1669936 | G | A |
| S_9254794 \| \| scaffold14851_1670218_SNP | 1670218 | T | A |
| S_9254799 \| \| scaffold14851_1670391_SNP | 1670391 | A | G |
| S_9254837 \| \| scaffold14851_1670866_SNP | 1670866 | A | C |
| S_9254939 \| \| scaffold14851_1672327_SNP | 1672327 | T | C |
| S_9254955 \| \| scaffold14851_1672528_SNP | 1672528 | T | C |
| S_9254965 \| \| scaffold14851_1672660_SNP | 1672660 | C | A |
| S_9255039 \| \| scaffold14851_1673468_SNP | 1673468 | T | C |
| S_9255040 \| \| scaffold14851_1673482_SNP | 1673482 | A | G |
| S_9255043 \| \| scaffold14851_1673541_SNP | 1673541 | G | A |
| S_9255044 \| \| scaffold14851_1673552_SNP | 1673552 | G | T |
| S_9255045 \| \| scaffold14851_1673573_SNP | 1673573 | C | T |
| S_9255052 \| \| scaffold14851_1673632_SNP | 1673632 | A | G |
| S_9255056 \| \| scaffold14851_1673671_SNP | 1673671 | C | T |
| S_9255114 \| \| scaffold14851_1674426_SNP | 1674426 | G | A |
| S_9255198 \| \| scaffold14851_1675304_SNP | 1675304 | G | T |
| S_9255234 \| \| scaffold14851_1675635_SNP | 1675635 | T | A |
| S_9255246 \| \| scaffold14851_1675847_SNP | 1675847 | T | C |
| S_9255247 \| \| scaffold14851_1675884_SNP | 1675884 | C | T |
| S_9255248 \| \| scaffold14851_1675903_SNP | 1675903 | A | G |
| S_9255270 \| \| scaffold14851_1676295_SNP | 1676295 | A | G |
| S_9255297 \| \| scaffold14851_1676682_SNP | 1676682 | G | T |
| S_9255303 \| \| scaffold14851_1676753_SNP | 1676753 | T | C |
| S_9255309 \| \| scaffold14851_1676852_SNP | 1676852 | A | G |
| S_9255310 \| \| scaffold14851_1676870_SNP | 1676870 | T | A |
| S_9255321 \| \| scaffold14851_1677077_SNP | 1677077 | A | G |
| S_9255354 \| \| scaffold14851_1677520_SNP | 1677520 | T | C |
| S_9255363 \| \| scaffold14851_1677609_SNP | 1677609 | C | G |
| S_9255393 \| \| scaffold14851_1678108_SNP | 1678108 | C | A |
| S_9255463 \| \| scaffold14851_1679079_SNP | 1679079 | G | A |
| S_9255471 \| \| scaffold14851_1679227_SNP | 1679227 | G | C |
| S_9255496 \| \| scaffold14851_1679631_SNP | 1679631 | A | T |
| S_9255577 \| \| scaffold14851_1680766_SNP | 1680766 | A | G |
| S_9255595 \| \| scaffold14851_1680996_SNP | 1680996 | G | A |
| S_9255634 \| \| scaffold14851_1681553_SNP | 1681553 | T | C |
| S_9255650 \| \| scaffold14851_1681790_SNP | 1681790 | G | A |
| S_9255652 \| \| scaffold14851_1681816_SNP | 1681816 | G | A |
| S_9255731 \| \| scaffold14851_1682908_SNP | 1682908 | T | G |
| S_9255747 \| \| scaffold14851_1683151_SNP | 1683151 | T | C |
| scaffold14851_1684248_SNP | 1684248 | A | G |
| S_9256073 \| \| scaffold14851_1684969_SNP | 1684969 | T | C |
| S_9256631 \| \| scaffold14851_1689187_SNP | 1689187 | T | G |
| S_9256636 \| \| scaffold14851_1689207_SNP | 1689207 | C | T |
| S_9256637 \| \| scaffold14851_1689216_SNP | 1689216 | T | A |
| S_9256638 \| \| scaffold14851_1689217_SNP | 1689217 | G | C |
| S_9256661 \| \| scaffold14851_1689705_SNP | 1689705 | G | A |
| S_9257787 \| \| scaffold14851_1695773_SNP | 1695773 | A | T |
| S_9257790 \| \| scaffold14851_1695811_SNP | 1695811 | T | C |
| S_9257792 \| \| scaffold14851_1695858_SNP | 1695858 | A | G |
| S_9257793 \| \| scaffold14851_1695863_SNP | 1695863 | G | T |
| S_9257800 \| \| scaffold14851_1695974_SNP | 1695974 | G | C |
| S_9257810 \| \| scaffold14851_1696077_SNP | 1696077 | G | C |
| S_9257811 \| \| scaffold14851_1696111_SNP | 1696111 | A | G |
| S_9257852 \| \| scaffold14851_1696367_SNP | 1696367 | A | G |
| S_9257854 \| \| scaffold14851_1696389_SNP | 1696389 | G | A |
| scaffold14851_1697212_SNP | 1697212 | C | T |
| S_9257987 \| \| scaffold14851_1697459_SNP | 1697459 | G | A |
| S_9258024 \| \| scaffold14851_1697846_SNP | 1697846 | G | A |
| S_9258026 \| \| scaffold14851_1697854_SNP | 1697854 | T | C |
| S_9258027 \| \| scaffold14851_1697860_SNP | 1697860 | T | G |
| S_9258332 \| \| scaffold14851_1703418_SNP | 1703418 | G | A |
| S_9258348 \| \| scaffold14851_1703704_SNP | 1703704 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9258352 \| \| scaffold14851_1703718_SNP | 1703718 | T | C |
| scaffold14851_1703742_SNP | 1703742 | A | G |
| S_9258379 \| \| scaffold14851_1703786_SNP | 1703786 | C | T |
| S_9258396 \| \| scaffold14851_1703928_SNP | 1703928 | G | T |
| S_9258397 \| \| scaffold14851_1703929_SNP | 1703929 | T | A |
| S_9258411 \| \| scaffold14851_1704124_SNP | 1704124 | T | C |
| S_9258419 \| \| scaffold14851_1704278_SNP | 1704278 | G | A |
| S_9258438 \| \| scaffold14851_1704499_SNP | 1704499 | G | A |
| S_9258439 \| \| scaffold14851_1704540_SNP | 1704540 | T | C |
| S_9258449 \| \| scaffold14851_1704822_SNP | 1704822 | G | A |
| S_9258504 \| \| scaffold14851_1705704_SNP | 1705704 | T | A |
| S_9258508 \| \| scaffold14851_1705773_SNP | 1705773 | T | G |
| S_9258521 \| \| scaffold14851_1706004_SNP | 1706004 | T | G |
| S_9258525 \| \| scaffold14851_1706066_SNP | 1706066 | T | G |
| S_9258526 \| \| scaffold14851_1706093_SNP | 1706093 | G | T |
| S_9258529 \| \| scaffold14851_1706167_SNP | 1706167 | T | A |
| S_9258530 \| \| scaffold14851_1706168_SNP | 1706168 | A | T |
| S_9258539 \| \| scaffold14851_1706319_SNP | 1706319 | C | T |
| S_9258576 \| \| scaffold14851_1706786_SNP | 1706786 | T | A |
| S_9258588 \| \| scaffold14851_1706999_SNP | 1706999 | C | G |
| S_9258596 \| \| scaffold14851_1707152_SNP | 1707152 | T | G |
| S_9258610 \| \| scaffold14851_1707387_SNP | 1707387 | A | T |
| S_9258620 \| \| scaffold14851_1707616_SNP | 1707616 | C | T |
| S_9258716 \| \| scaffold14851_1709316_SNP | 1709316 | C | T |
| S_9258719 \| \| scaffold14851_1709326_SNP | 1709326 | C | T |
| S_9258720 \| \| scaffold14851_1709332_SNP | 1709332 | A | C |
| S_9258732 \| \| scaffold14851_1709500_SNP | 1709500 | G | A |
| S_9258746 \| \| scaffold14851_1709797_SNP | 1709797 | G | A |
| S_9258774 \| \| scaffold14851_1710179_SNP | 1710179 | A | C |
| S_9258807 \| \| scaffold14851_1710342_SNP | 1710342 | C | G |
| S_9258824 \| \| scaffold14851_1710360_SNP | 1710360 | G | T |
| S_9258856 \| \| scaffold14851_1710463_SNP | 1710463 | G | A |
| S_9258901 \| \| scaffold14851_1710795_SNP | 1710795 | A | C |
| S_9258902 \| \| scaffold14851_1710801_SNP | 1710801 | C | G |
| S_9258925 \| \| scaffold14851_1711183_SNP | 1711183 | C | T |
| S_9258974 \| \| scaffold14851_1711854_SNP | 1711854 | C | G |
| S_9258981 \| \| scaffold14851_1711927_SNP | 1711927 | T | G |
| S_9258993 \| \| scaffold14851_1712091_SNP | 1712091 | C | T |
| S_9259002 \| \| scaffold14851_1712126_SNP | 1712126 | C | T |
| S_9259003 \| \| scaffold14851_1712128_SNP | 1712128 | T | G |
| S_9259013 \| \| scaffold14851_1712328_SNP | 1712328 | T | A |
| S_9259020 \| \| scaffold14851_1712455_SNP | 1712455 | T | G |
| S_9259029 \| \| scaffold14851_1712613_SNP | 1712613 | G | C |
| S_9259030 \| \| scaffold14851_1712616_SNP | 1712616 | G | A |
| S_9259031 \| \| scaffold14851_1712634_SNP | 1712634 | C | G |
| S_9259034 \| \| scaffold14851_1712676_SNP | 1712676 | A | G |
| S_9259226 \| \| scaffold14851_1716026_SNP | 1716026 | C | T |
| scaffold14851_1716095_SNP | 1716095 | A | G |
| S_9259237 \| \| scaffold14851_1716125_SNP | 1716125 | C | A |
| S_9259239 \| \| scaffold14851_1716192_SNP | 1716192 | A | C |
| S_9259240 \| \| scaffold14851_1716209_SNP | 1716209 | G | A |
| S_9259641 \| \| scaffold14851_1717922_SNP | 1717922 | C | T |
| S_9259747 \| \| scaffold14851_1718916_SNP | 1718916 | C | A |
| S_9259766 \| \| scaffold14851_1719319_SNP | 1719319 | T | G |
| S_9259816 \| \| scaffold14851_1720163_SNP | 1720163 | A | G |
| S_9259817 \| \| scaffold14851_1720165_SNP | 1720165 | G | A |
| S_9259821 \| \| scaffold14851_1720216_SNP | 1720216 | T | A |
| S_9259822 \| \| scaffold14851_1720223_SNP | 1720223 | A | T |
| S_9259823 \| \| scaffold14851_1720270_SNP | 1720270 | T | A |
| S_9259867 \| \| scaffold14851_1720349_SNP | 1720349 | G | A |
| S_9259868 \| \| scaffold14851_1720357_SNP | 1720357 | A | T |
| S_9259884 \| \| scaffold14851_1720546_SNP | 1720546 | G | A |
| S_9259893 \| \| scaffold14851_1720581_SNP | 1720581 | T | C |
| S_9259894 \| \| scaffold14851_1720603_SNP | 1720603 | T | C |
| S_9260025 \| \| scaffold14851_1722173_SNP | 1722173 | T | C |
| S_9260054 \| \| scaffold14851_1722432_SNP | 1722432 | C | T |
| S_9260068 \| \| scaffold14851_1722647_SNP | 1722647 | G | A |
| S_9260100 \| \| scaffold14851_1723182_SNP | 1723182 | G | A |
| S_9260171 \| \| scaffold14851_1724077_SNP | 1724077 | G | A |
| S_9260172 \| \| scaffold14851_1724102_SNP | 1724102 | A | T |
| S_9260180 \| \| scaffold14851_1724292_SNP | 1724292 | T | G |
| S_9260206 \| \| scaffold14851_1724645_SNP | 1724645 | C | T |
| S_9260254 \| \| scaffold14851_1725491_SNP | 1725491 | G | T |
| S_9260278 \| \| scaffold14851_1725734_SNP | 1725734 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9260329 \| \| scaffold14851_1728455_SNP | 1728455 | A | G |
| S_9260362 \| \| scaffold14851_1728875_SNP | 1728875 | A | T |
| S_9260452 \| \| scaffold14851_1731054_SNP | 1731054 | T | G |
| S_9260562 \| \| scaffold14851_1732497_SNP | 1732497 | A | G |
| S_9260580 \| \| scaffold14851_1732691_SNP | 1732691 | T | A |
| S_9260582 \| \| scaffold14851_1732717_SNP | 1732717 | A | G |
| S_9260702 \| \| scaffold14851_1733721_SNP | 1733721 | T | C |
| S_9260712 \| \| scaffold14851_1733765_SNP | 1733765 | A | T |
| S_9260751 \| \| scaffold14851_1734095_SNP | 1734095 | T | A |
| S_9260807 \| \| scaffold14851_1734466_SNP | 1734466 | C | A |
| S_9260841 \| \| scaffold14851_1734822_SNP | 1734822 | G | T |
| S_9260842 \| \| scaffold14851_1734837_SNP | 1734837 | A | C |
| S_9260854 \| \| scaffold14851_1734953_SNP | 1734953 | A | G |
| S_9260856 \| \| scaffold14851_1734980_SNP | 1734980 | C | T |
| scaffold14851_1736002_SNP | 1736002 | A | G |
| S_9261169 \| \| scaffold14851_1738526_SNP | 1738526 | T | C |
| scaffold14851_1740383_SNP | 1740383 | G | A |
| S_9261972 \| \| scaffold14851_1754305_SNP | 1754305 | C | G |
| S_9261998 \| \| scaffold14851_1754671_SNP | 1754671 | C | A |
| S_9262970 \| \| scaffold14851_1766482_SNP | 1766482 | C | T |
| S_9262973 \| \| scaffold14851_1766496_SNP | 1766496 | A | C |
| S_9262974 \| \| scaffold14851_1766582_SNP | 1766582 | G | T |
| S_9262975 \| \| scaffold14851_1766597_SNP | 1766597 | T | A |
| S_9262983 \| \| scaffold14851_1766761_SNP | 1766761 | G | T |
| scaffold14851_1772496_SNP | 1772496 | C | A |
| S_9263864 \| \| scaffold14851_1776015_SNP | 1776015 | T | C |
| S_9263940 \| \| scaffold14851_1776324_SNP | 1776324 | T | C |
| S_9263942 \| \| scaffold14851_1776336_SNP | 1776336 | G | A |
| S_9264655 \| \| scaffold14851_1785873_SNP | 1785873 | G | A |
| S_9264659 \| \| scaffold14851_1785894_SNP | 1785894 | C | T |
| S_9266134 \| \| scaffold14851_1793879_SNP | 1793879 | G | A |
| S_9266758 \| \| scaffold14851_1804064_SNP | 1804064 | T | C |
| S_9267122 \| \| scaffold14851_1807971_SNP | 1807971 | G | T |
| S_9267123 \| \| scaffold14851_1807975_SNP | 1807975 | A | G |
| S_9267439 \| \| scaffold14851_1818198_SNP | 1818198 | G | A |
| S_9267440 \| \| scaffold14851_1818199_SNP | 1818199 | A | C |
| S_9268028 \| \| scaffold14851_1819554_SNP | 1819554 | T | C |
| S_9268051 \| \| scaffold14851_1819646_SNP | 1819646 | A | G |
| S_9270880 \| \| scaffold14851_1825354_SNP | 1825354 | G | C |
| scaffold14851_1826898_SNP | 1826898 | G | C |
| S_9271010 \| \| scaffold14851_1826951_SNP | 1826951 | A | G |
| S_9271091 \| \| scaffold14851_1827651_SNP | 1827651 | A | C |
| S_9271092 \| \| scaffold14851_1827661_SNP | 1827661 | A | T |
| scaffold14851_1833052_SNP | 1833052 | C | A |
| scaffold14851_1835539_SNP | 1835539 | T | A |
| S_9272079 \| \| scaffold14851_1842680_SNP | 1842680 | T | C |
| S_9272080 \| \| scaffold14851_1842683_SNP | 1842683 | T | A |
| S_9272081 \| \| scaffold14851_1842727_SNP | 1842727 | C | G |
| S_9272300 \| \| scaffold14851_1844397_SNP | 1844397 | T | A |
| S_9272904 \| \| scaffold14851_1852534_SNP | 1852534 | C | T |
| S_9272908 \| \| scaffold14851_1852617_SNP | 1852617 | A | G |
| S_9274550 \| \| scaffold14851_1868867_SNP | 1868867 | G | A |
| scaffold14851_1876904_SNP | 1876904 | G | T |
| S_9276112 \| \| scaffold14851_1876951_SNP | 1876951 | C | T |
| S_9276113 \| \| scaffold14851_1876960_SNP | 1876960 | T | C |
| S_9276115 \| \| scaffold14851_1876977_SNP | 1876977 | A | G |
| scaffold14851_1881812_SNP | 1881812 | C | G |
| scaffold14851_1881814_SNP | 1881814 | T | A |
| S_9276876 \| \| scaffold14851_1882129_SNP | 1882129 | G | A |
| S_9276897 \| \| scaffold14851_1882477_SNP | 1882477 | C | T |
| scaffold14851_1895610_SNP | 1895610 | G | A |
| scaffold14851_1895625_SNP | 1895625 | T | C |
| scaffold14851_1895640_SNP | 1895640 | C | T |
| scaffold14851_1896426_SNP | 1896426 | G | A |
| S_9277550 \| \| scaffold14851_1896501_SNP | 1896501 | G | A |
| scaffold14851_1896810_SNP | 1896810 | C | T |
| scaffold14851_1896837_SNP | 1896837 | C | T |
| scaffold14851_1896852_SNP | 1896852 | T | C |
| S_9277992 \| \| scaffold14851_1908339_SNP | 1908339 | A | T |
| S_9278022 \| \| scaffold14851_1909107_SNP | 1909107 | A | G |
| S_9278276 \| \| scaffold14851_1912006_SNP | 1912006 | A | G |
| S_9278278 \| \| scaffold14851_1912056_SNP | 1912056 | A | T |
| S_9278333 \| \| scaffold14851_1912512_SNP | 1912512 | G | A |
| S_9278803 \| \| scaffold14851_1921165_SNP | 1921165 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9278820 \| \| scaffold14851_1921424_SNP | 1921424 | C | T |
| S_9278823 \| \| scaffold14851_1921449_SNP | 1921449 | A | T |
| S_9278825 \| \| scaffold14851_1921476_SNP | 1921476 | C | T |
| S_9278827 \| \| scaffold14851_1921478_SNP | 1921478 | T | C |
| scaffold14851_1986576_SNP | 1986576 | A | C |
| S_9290163 \| \| scaffold14851_2038378_SNP | 2038378 | C | G |
| S_9290440 \| \| scaffold14851_2041386_SNP | 2041386 | T | G |
| S_9291805 \| \| scaffold14851_2053134_SNP | 2053134 | T | C |
| S_9291830 \| \| scaffold14851_2053459_SNP | 2053459 | A | T |
| S_9291833 \| \| scaffold14851_2053505_SNP | 2053505 | G | C |
| scaffold14851_2056437_SNP | 2056437 | A | C |
| S_9292436 \| \| scaffold14851_2066380_SNP | 2066380 | C | T |
| scaffold14851_2077720_SNP | 2077720 | G | C |
| S_9294188 \| \| scaffold14851_2082270_SNP | 2082270 | T | G |
| scaffold14851_2084769_SNP | 2084769 | A | G |
| S_9294564 \| \| scaffold14851_2086113_SNP | 2086113 | G | T |
| S_9294778 \| \| scaffold14851_2088811_SNP | 2088811 | C | A |
| S_9294846 \| \| scaffold14851_2089752_SNP | 2089752 | C | T |
| S_9294877 \| \| scaffold14851_2090179_SNP | 2090179 | C | T |
| S_9294887 \| \| scaffold14851_2090460_SNP | 2090460 | G | A |
| S_9295484 \| \| scaffold14851_2098022_SNP | 2098022 | C | G |
| S_9295567 \| \| scaffold14851_2098976_SNP | 2098976 | A | G |
| S_9296181 \| \| scaffold14851_2107264_SNP | 2107264 | C | G |
| S_9296195 \| \| scaffold14851_2107482_SNP | 2107482 | G | A |
| S_9296295 \| \| scaffold14851_2108717_SNP | 2108717 | A | T |
| S_9296301 \| \| scaffold14851_2108883_SNP | 2108883 | G | A |
| S_9296306 \| \| scaffold14851_2108959_SNP | 2108959 | G | T |
| S_9296334 \| \| scaffold14851_2109382_SNP | 2109382 | C | G |
| S_9296351 \| \| scaffold14851_2109648_SNP | 2109648 | T | A |
| S_9296352 \| \| scaffold14851_2109649_SNP | 2109649 | A | C |
| S_9296409 \| \| scaffold14851_2110091_SNP | 2110091 | G | T |
| S_9296415 \| \| scaffold14851_2110167_SNP | 2110167 | A | G |
| S_9296489 \| \| scaffold14851_2110822_SNP | 2110822 | T | A |
| S_9296508 \| \| scaffold14851_2111315_SNP | 2111315 | T | A |
| S_9296575 \| \| scaffold14851_2112384_SNP | 2112384 | T | A |
| S_9296649 \| \| scaffold14851_2113337_SNP | 2113337 | T | C |
| S_9296711 \| \| scaffold14851_2114130_SNP | 2114130 | A | T |
| S_9296877 \| \| scaffold14851_2115877_SNP | 2115877 | C | T |
| S_9297012 \| \| scaffold14851_2118750_SNP | 2118750 | A | T |
| S_9297061 \| \| scaffold14851_2118945_SNP | 2118945 | G | A |
| S_9297083 \| \| scaffold14851_2118973_SNP | 2118973 | A | G |
| S_9297096 \| \| scaffold14851_2119035_SNP | 2119035 | G | A |
| S_9297177 \| \| scaffold14851_2120237_SNP | 2120237 | G | T |
| S_9297222 \| \| scaffold14851_2120708_SNP | 2120708 | G | A |
| S_9297285 \| \| scaffold14851_2121257_SNP | 2121257 | A | T |
| S_9297439 \| \| scaffold14851_2122997_SNP | 2122997 | C | A |
| S_9297452 \| \| scaffold14851_2123274_SNP | 2123274 | A | G |
| S_9297455 \| \| scaffold14851_2123300_SNP | 2123300 | A | G |
| S_9297502 \| \| scaffold14851_2123906_SNP | 2123906 | A | G |
| S_9297530 \| \| scaffold14851_2124275_SNP | 2124275 | G | A |
| S_9297536 \| \| scaffold14851_2124334_SNP | 2124334 | T | G |
| S_9297612 \| \| scaffold14851_2125595_SNP | 2125595 | T | A |
| S_9297750 \| \| scaffold14851_2127037_SNP | 2127037 | G | A |
| S_9297828 \| \| scaffold14851_2127824_SNP | 2127824 | T | A |
| S_9297890 \| \| scaffold14851_2128723_SNP | 2128723 | C | A |
| S_9297893 \| \| scaffold14851_2128740_SNP | 2128740 | A | T |
| S_9299027 \| \| scaffold14851_2144751_SNP | 2144751 | T | C |
| S_9299042 \| \| scaffold14851_2144959_SNP | 2144959 | C | A |
| S_9299061 \| \| scaffold14851_2145097_SNP | 2145097 | C | G |
| S_9299064 \| \| scaffold14851_2145113_SNP | 2145113 | T | A |
| S_9299098 \| \| scaffold14851_2145415_SNP | 2145415 | T | G |
| S_9299110 \| \| scaffold14851_2145555_SNP | 2145555 | T | C |
| S_9299119 \| \| scaffold14851_2145654_SNP | 2145654 | C | T |
| S_9299159 \| \| scaffold14851_2145941_SNP | 2145941 | G | T |
| S_9299166 \| \| scaffold14851_2146007_SNP | 2146007 | C | T |
| S_9299180 \| \| scaffold14851_2146100_SNP | 2146100 | A | T |
| S_9299213 \| \| scaffold14851_2146417_SNP | 2146417 | T | A |
| S_9299215 \| \| scaffold14851_2146436_SNP | 2146436 | C | T |
| S_9299235 \| \| scaffold14851_2146591_SNP | 2146591 | C | T |
| S_9299239 \| \| scaffold14851_2146633_SNP | 2146633 | G | A |
| S_9299280 \| \| scaffold14851_2147405_SNP | 2147405 | G | T |
| S_9299347 \| \| scaffold14851_2147968_SNP | 2147968 | T | G |
| S_9299452 \| \| scaffold14851_2150039_SNP | 2150039 | A | G |
| S_9299455 \| \| scaffold14851_2150077_SNP | 2150077 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|------|------|------|------|
| S_9299643 \| \| scaffold14851_2152028_SNP | 2152028 | C | T |
| S_9299716 \| \| scaffold14851_2152766_SNP | 2152766 | A | G |
| S_9299951 \| \| scaffold14851_2155425_SNP | 2155425 | T | G |
| S_9300063 \| \| scaffold14851_2157600_SNP | 2157600 | C | A |
| S_9300092 \| \| scaffold14851_2157976_SNP | 2157976 | C | T |
| S_9300107 \| \| scaffold14851_2158080_SNP | 2158080 | A | G |
| S_9300116 \| \| scaffold14851_2158212_SNP | 2158212 | T | C |
| S_9300120 \| \| scaffold14851_2158240_SNP | 2158240 | G | T |
| S_9300157 \| \| scaffold14851_2158706_SNP | 2158706 | C | T |
| S_9300158 \| \| scaffold14851_2158716_SNP | 2158716 | G | A |
| S_9300292 \| \| scaffold14851_2160548_SNP | 2160548 | T | C |
| S_9300314 \| \| scaffold14851_2161052_SNP | 2161052 | T | A |
| S_9300430 \| \| scaffold14851_2162914_SNP | 2162914 | G | T |
| S_9300462 \| \| scaffold14851_2163342_SNP | 2163342 | A | T |
| S_9300463 \| \| scaffold14851_2163346_SNP | 2163346 | A | G |
| S_9300674 \| \| scaffold14851_2166722_SNP | 2166722 | T | G |
| S_9300813 \| \| scaffold14851_2168856_SNP | 2168856 | G | T |
| S_9301186 \| \| scaffold14851_2174869_SNP | 2174869 | C | T |
| S_9301512 \| \| scaffold14851_2179528_SNP | 2179528 | C | T |
| S_9301568 \| \| scaffold14851_2180811_SNP | 2180811 | T | G |
| S_9301614 \| \| scaffold14851_2181689_SNP | 2181689 | G | A |
| S_9301750 \| \| scaffold14851_2183786_SNP | 2183786 | T | G |
| S_9301904 \| \| scaffold14851_2185186_SNP | 2185186 | T | G |
| S_9302305 \| \| scaffold14851_2189058_SNP | 2189058 | T | C |
| S_9302438 \| \| scaffold14851_2191052_SNP | 2191052 | T | G |
| S_9302476 \| \| scaffold14851_2191624_SNP | 2191624 | T | A |
| S_9302591 \| \| scaffold14851_2193113_SNP | 2193113 | A | G |
| S_9302790 \| \| scaffold14851_2195521_SNP | 2195521 | C | T |
| S_9302793 \| \| scaffold14851_2195577_SNP | 2195577 | C | T |
| S_9302798 \| \| scaffold14851_2195646_SNP | 2195646 | G | T |
| S_9302881 \| \| scaffold14851_2196960_SNP | 2196960 | G | A |
| S_9302882 \| \| scaffold14851_2196961_SNP | 2196961 | C | T |
| S_9302935 \| \| scaffold14851_2197636_SNP | 2197636 | C | T |
| S_9302960 \| \| scaffold14851_2197864_SNP | 2197864 | G | C |
| S_9302990 \| \| scaffold14851_2198179_SNP | 2198179 | T | G |
| S_9303097 \| \| scaffold14851_2199762_SNP | 2199762 | A | C |
| S_9303289 \| \| scaffold14851_2202804_SNP | 2202804 | A | T |
| S_9303293 \| \| scaffold14851_2202895_SNP | 2202895 | C | T |
| S_9303348 \| \| scaffold14851_2203980_SNP | 2203980 | T | C |
| S_9303354 \| \| scaffold14851_2204042_SNP | 2204042 | T | G |
| S_9303596 \| \| scaffold14851_2205712_SNP | 2205712 | A | G |
| S_9303651 \| \| scaffold14851_2206350_SNP | 2206350 | A | G |
| S_9304195 \| \| scaffold14851_2214640_SNP | 2214640 | G | A |
| S_9304211 \| \| scaffold14851_2214952_SNP | 2214952 | C | A |
| S_9304804 \| \| scaffold14851_2222811_SNP | 2222811 | C | T |
| S_9305584 \| \| scaffold14851_2232931_SNP | 2232931 | C | G |
| S_9305632 \| \| scaffold14851_2233518_SNP | 2233518 | A | T |
| S_9305677 \| \| scaffold14851_2234447_SNP | 2234447 | G | A |
| S_9305808 \| \| scaffold14851_2236162_SNP | 2236162 | G | C |
| S_9305869 \| \| scaffold14851_2237449_SNP | 2237449 | T | G |
| S_9305923 \| \| scaffold14851_2238077_SNP | 2238077 | A | G |
| S_9306165 \| \| scaffold14851_2241148_SNP | 2241148 | G | A |
| S_9306167 \| \| scaffold14851_2241216_SNP | 2241216 | T | C |
| S_9306179 \| \| scaffold14851_2241503_SNP | 2241503 | A | G |
| S_9306185 \| \| scaffold14851_2241524_SNP | 2241524 | G | A |
| S_9306266 \| \| scaffold14851_2242345_SNP | 2242345 | G | A |
| S_9306333 \| \| scaffold14851_2243328_SNP | 2243328 | G | C |
| S_9306398 \| \| scaffold14851_2244225_SNP | 2244225 | T | C |
| S_9306448 \| \| scaffold14851_2244811_SNP | 2244811 | T | C |
| S_9306471 \| \| scaffold14851_2245069_SNP | 2245069 | C | T |
| S_9306547 \| \| scaffold14851_2246314_SNP | 2246314 | C | T |
| S_9306595 \| \| scaffold14851_2246921_SNP | 2246921 | C | A |
| S_9306625 \| \| scaffold14851_2247412_SNP | 2247412 | G | A |
| S_9306634 \| \| scaffold14851_2247609_SNP | 2247609 | G | A |
| S_9306697 \| \| scaffold14851_2248527_SNP | 2248527 | C | T |
| S_9306708 \| \| scaffold14851_2248596_SNP | 2248596 | C | T |
| S_9306736 \| \| scaffold14851_2248958_SNP | 2248958 | G | A |
| S_9306775 \| \| scaffold14851_2249568_SNP | 2249568 | A | G |
| S_9306797 \| \| scaffold14851_2249844_SNP | 2249844 | G | C |
| S_9306848 \| \| scaffold14851_2250715_SNP | 2250715 | G | T |
| S_9306866 \| \| scaffold14851_2250909_SNP | 2250909 | C | G |
| S_9306913 \| \| scaffold14851_2251531_SNP | 2251531 | G | T |
| S_9306976 \| \| scaffold14851_2252295_SNP | 2252295 | C | G |
| S_9306979 \| \| scaffold14851_2252349_SNP | 2252349 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9306983 \|\| scaffold14851_2252397_SNP | 2252397 | A | G |
| S_9307003 \|\| scaffold14851_2252625_SNP | 2252625 | C | A |
| S_9307008 \|\| scaffold14851_2252667_SNP | 2252667 | G | C |
| S_9307022 \|\| scaffold14851_2252985_SNP | 2252985 | A | T |
| S_9307064 \|\| scaffold14851_2253729_SNP | 2253729 | C | T |
| S_9307145 \|\| scaffold14851_2254726_SNP | 2254726 | C | G |
| S_9307159 \|\| scaffold14851_2254952_SNP | 2254952 | G | C |
| S_9307243 \|\| scaffold14851_2255336_SNP | 2255336 | T | C |
| S_9307244 \|\| scaffold14851_2255342_SNP | 2255342 | A | T |
| S_9307289 \|\| scaffold14851_2256026_SNP | 2256026 | C | T |
| S_9307309 \|\| scaffold14851_2256329_SNP | 2256329 | G | A |
| S_9307315 \|\| scaffold14851_2256447_SNP | 2256447 | T | C |
| S_9307318 \|\| scaffold14851_2256468_SNP | 2256468 | G | C |
| S_9307334 \|\| scaffold14851_2256795_SNP | 2256795 | A | T |
| S_9307394 \|\| scaffold14851_2257607_SNP | 2257607 | G | A |
| S_9307488 \|\| scaffold14851_2258552_SNP | 2258552 | G | A |
| S_9307597 \|\| scaffold14851_2260546_SNP | 2260546 | G | T |
| S_9307650 \|\| scaffold14851_2261250_SNP | 2261250 | C | G |
| S_9307655 \|\| scaffold14851_2261357_SNP | 2261357 | T | A |
| S_9307658 \|\| scaffold14851_2261371_SNP | 2261371 | C | T |
| S_9307659 \|\| scaffold14851_2261373_SNP | 2261373 | G | C |
| S_9307727 \|\| scaffold14851_2261913_SNP | 2261913 | G | A |
| S_9307729 \|\| scaffold14851_2261923_SNP | 2261923 | A | G |
| S_9307730 \|\| scaffold14851_2261929_SNP | 2261929 | G | T |
| S_9307753 \|\| scaffold14851_2262222_SNP | 2262222 | G | A |
| S_9307757 \|\| scaffold14851_2262255_SNP | 2262255 | A | C |
| S_9307840 \|\| scaffold14851_2262709_SNP | 2262709 | A | G |
| S_9307896 \|\| scaffold14851_2263028_SNP | 2263028 | G | C |
| S_9307897 \|\| scaffold14851_2263037_SNP | 2263037 | A | G |
| S_9307932 \|\| scaffold14851_2263339_SNP | 2263339 | G | T |
| S_9307960 \|\| scaffold14851_2263640_SNP | 2263640 | C | A |
| S_9307972 \|\| scaffold14851_2263868_SNP | 2263868 | A | T |
| S_9307986 \|\| scaffold14851_2263992_SNP | 2263992 | A | T |
| S_9307999 \|\| scaffold14851_2264165_SNP | 2264165 | A | G |
| S_9308027 \|\| scaffold14851_2264251_SNP | 2264251 | T | G |
| S_9308030 \|\| scaffold14851_2264319_SNP | 2264319 | T | A |
| S_9308033 \|\| scaffold14851_2264352_SNP | 2264352 | T | A |
| S_9308034 \|\| scaffold14851_2264378_SNP | 2264378 | A | T |
| S_9308061 \|\| scaffold14851_2264832_SNP | 2264832 | A | T |
| S_9308063 \|\| scaffold14851_2264892_SNP | 2264892 | A | C |
| S_9308064 \|\| scaffold14851_2264930_SNP | 2264930 | A | C |
| S_9308065 \|\| scaffold14851_2264961_SNP | 2264961 | T | A |
| S_9308103 \|\| scaffold14851_2265482_SNP | 2265482 | T | C |
| S_9308105 \|\| scaffold14851_2265496_SNP | 2265496 | T | C |
| S_9308110 \|\| scaffold14851_2265594_SNP | 2265594 | C | A |
| S_9308117 \|\| scaffold14851_2265770_SNP | 2265770 | A | G |
| S_9308120 \|\| scaffold14851_2265807_SNP | 2265807 | T | G |
| S_9308160 \|\| scaffold14851_2266205_SNP | 2266205 | A | G |
| S_9308161 \|\| scaffold14851_2266207_SNP | 2266207 | T | C |
| S_9308162 \|\| scaffold14851_2266226_SNP | 2266226 | C | T |
| S_9308177 \|\| scaffold14851_2266477_SNP | 2266477 | T | A |
| S_9308178 \|\| scaffold14851_2266479_SNP | 2266479 | T | A |
| S_9308301 \|\| scaffold14851_2268103_SNP | 2268103 | C | A |
| S_9308304 \|\| scaffold14851_2268239_SNP | 2268239 | A | G |
| S_9308307 \|\| scaffold14851_2268256_SNP | 2268256 | A | C |
| S_9308308 \|\| scaffold14851_2268275_SNP | 2268275 | A | T |
| S_9308309 \|\| scaffold14851_2268277_SNP | 2268277 | T | C |
| S_9308314 \|\| scaffold14851_2268326_SNP | 2268326 | A | T |
| S_9308316 \|\| scaffold14851_2268353_SNP | 2268353 | T | C |
| S_9308322 \|\| scaffold14851_2268479_SNP | 2268479 | G | C |
| S_9308341 \|\| scaffold14851_2268863_SNP | 2268863 | T | G |
| S_9308355 \|\| scaffold14851_2269103_SNP | 2269103 | T | A |
| S_9308371 \|\| scaffold14851_2269228_SNP | 2269228 | G | A |
| S_9308398 \|\| scaffold14851_2269555_SNP | 2269555 | C | T |
| S_9308400 \|\| scaffold14851_2269575_SNP | 2269575 | G | T |
| S_9308428 \|\| scaffold14851_2270023_SNP | 2270023 | G | A |
| S_9308442 \|\| scaffold14851_2270186_SNP | 2270186 | C | T |
| S_9308443 \|\| scaffold14851_2270253_SNP | 2270253 | A | C |
| S_9308456 \|\| scaffold14851_2270388_SNP | 2270388 | A | G |
| S_9308457 \|\| scaffold14851_2270410_SNP | 2270410 | A | T |
| S_9308461 \|\| scaffold14851_2270506_SNP | 2270506 | A | T |
| S_9308486 \|\| scaffold14851_2270747_SNP | 2270747 | G | A |
| S_9308506 \|\| scaffold14851_2270891_SNP | 2270891 | T | C |
| S_9308508 \|\| scaffold14851_2270920_SNP | 2270920 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9308514 \| \| scaffold14851_2271088_SNP | 2271088 | C | T |
| S_9308517 \| \| scaffold14851_2271150_SNP | 2271150 | A | G |
| S_9308518 \| \| scaffold14851_2271167_SNP | 2271167 | C | A |
| S_9308521 \| \| scaffold14851_2271185_SNP | 2271185 | C | G |
| S_9308541 \| \| scaffold14851_2271534_SNP | 2271534 | T | C |
| S_9308557 \| \| scaffold14851_2271723_SNP | 2271723 | A | G |
| S_9308622 \| \| scaffold14851_2272863_SNP | 2272863 | T | C |
| S_9308677 \| \| scaffold14851_2273774_SNP | 2273774 | T | C |
| S_9308709 \| \| scaffold14851_2274579_SNP | 2274579 | G | A |
| S_9308717 \| \| scaffold14851_2274799_SNP | 2274799 | G | A |
| S_9308723 \| \| scaffold14851_2274853_SNP | 2274853 | G | A |
| S_9308724 \| \| scaffold14851_2274875_SNP | 2274875 | T | C |
| S_9308735 \| \| scaffold14851_2275042_SNP | 2275042 | G | A |
| S_9308795 \| \| scaffold14851_2276044_SNP | 2276044 | G | A |
| S_9308799 \| \| scaffold14851_2276090_SNP | 2276090 | G | A |
| S_9308840 \| \| scaffold14851_2276940_SNP | 2276940 | C | A |
| S_9308843 \| \| scaffold14851_2276972_SNP | 2276972 | T | C |
| S_9308851 \| \| scaffold14851_2277102_SNP | 2277102 | T | G |
| S_9308855 \| \| scaffold14851_2277153_SNP | 2277153 | A | G |
| S_9308871 \| \| scaffold14851_2277337_SNP | 2277337 | G | T |
| S_9308895 \| \| scaffold14851_2277679_SNP | 2277679 | T | A |
| S_9308903 \| \| scaffold14851_2277809_SNP | 2277809 | T | C |
| S_9308928 \| \| scaffold14851_2278104_SNP | 2278104 | C | G |
| S_9308930 \| \| scaffold14851_2278183_SNP | 2278183 | G | A |
| S_9308955 \| \| scaffold14851_2278758_SNP | 2278758 | T | G |
| S_9309027 \| \| scaffold14851_2279469_SNP | 2279469 | C | T |
| S_9309030 \| \| scaffold14851_2279530_SNP | 2279530 | G | A |
| S_9309032 \| \| scaffold14851_2279543_SNP | 2279543 | A | C |
| S_9309441 \| \| scaffold14851_2283514_SNP | 2283514 | T | A |
| S_9309510 \| \| scaffold14851_2284564_SNP | 2284564 | T | C |
| S_9309640 \| \| scaffold14851_2286278_SNP | 2286278 | A | G |
| S_9309667 \| \| scaffold14851_2286530_SNP | 2286530 | C | T |
| S_9309692 \| \| scaffold14851_2286852_SNP | 2286852 | C | T |
| S_9309754 \| \| scaffold14851_2287853_SNP | 2287853 | T | G |
| S_9309841 \| \| scaffold14851_2288997_SNP | 2288997 | T | A |
| S_9309858 \| \| scaffold14851_2289422_SNP | 2289422 | T | C |
| S_9309888 \| \| scaffold14851_2290039_SNP | 2290039 | G | A |
| S_9309926 \| \| scaffold14851_2290488_SNP | 2290488 | A | T |
| S_9309982 \| \| scaffold14851_2291244_SNP | 2291244 | T | G |
| S_9310033 \| \| scaffold14851_2291801_SNP | 2291801 | T | C |
| S_9310065 \| \| scaffold14851_2292160_SNP | 2292160 | T | G |
| S_9310070 \| \| scaffold14851_2292254_SNP | 2292254 | T | A |
| S_9310088 \| \| scaffold14851_2292561_SNP | 2292561 | C | T |
| S_9310129 \| \| scaffold14851_2293132_SNP | 2293132 | G | A |
| S_9310162 \| \| scaffold14851_2293581_SNP | 2293581 | G | A |
| S_9310173 \| \| scaffold14851_2293796_SNP | 2293796 | A | T |
| S_9310174 \| \| scaffold14851_2293809_SNP | 2293809 | G | T |
| S_9310216 \| \| scaffold14851_2294678_SNP | 2294678 | A | G |
| S_9310218 \| \| scaffold14851_2294688_SNP | 2294688 | A | C |
| S_9310229 \| \| scaffold14851_2294838_SNP | 2294838 | T | C |
| S_9310280 \| \| scaffold14851_2295164_SNP | 2295164 | C | T |
| S_9310346 \| \| scaffold14851_2295705_SNP | 2295705 | T | C |
| S_9310348 \| \| scaffold14851_2295707_SNP | 2295707 | C | T |
| S_9310423 \| \| scaffold14851_2296463_SNP | 2296463 | G | A |
| S_9310533 \| \| scaffold14851_2297703_SNP | 2297703 | C | A |
| S_9310536 \| \| scaffold14851_2297722_SNP | 2297722 | G | T |
| S_9310539 \| \| scaffold14851_2297870_SNP | 2297870 | G | A |
| S_9310580 \| \| scaffold14851_2298468_SNP | 2298468 | C | A |
| S_9310597 \| \| scaffold14851_2298572_SNP | 2298572 | T | G |
| S_9310601 \| \| scaffold14851_2298585_SNP | 2298585 | G | T |
| scaffold14851_2298855_SNP | 2298855 | T | C |
| scaffold14851_2298869_SNP | 2298869 | T | C |
| S_9310661 \| \| scaffold14851_2299217_SNP | 2299217 | T | A |
| S_9310748 \| \| scaffold14851_2299638_SNP | 2299638 | T | C |
| S_9310751 \| \| scaffold14851_2299661_SNP | 2299661 | G | C |
| S_9310762 \| \| scaffold14851_2299870_SNP | 2299870 | G | A |
| S_9310763 \| \| scaffold14851_2299878_SNP | 2299878 | G | T |
| S_9310768 \| \| scaffold14851_2299917_SNP | 2299917 | C | T |
| S_9310809 \| \| scaffold14851_2300590_SNP | 2300590 | C | T |
| S_9310837 \| \| scaffold14851_2300968_SNP | 2300968 | T | G |
| S_9310861 \| \| scaffold14851_2301239_SNP | 2301239 | T | A |
| S_9310926 \| \| scaffold14851_2302239_SNP | 2302239 | A | C |
| S_9310930 \| \| scaffold14851_2302264_SNP | 2302264 | C | T |
| S_9310949 \| \| scaffold14851_2302423_SNP | 2302423 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9310956 \| \| scaffold14851_2302486_SNP | 2302486 | T | G |
| S_9310964 \| \| scaffold14851_2302612_SNP | 2302612 | A | C |
| S_9310969 \| \| scaffold14851_2302713_SNP | 2302713 | G | C |
| S_9310973 \| \| scaffold14851_2302823_SNP | 2302823 | T | C |
| S_9310992 \| \| scaffold14851_2302980_SNP | 2302980 | G | A |
| S_9311010 \| \| scaffold14851_2303269_SNP | 2303269 | T | C |
| S_9311046 \| \| scaffold14851_2303787_SNP | 2303787 | G | A |
| S_9311196 \| \| scaffold14851_2305090_SNP | 2305090 | A | G |
| S_9311224 \| \| scaffold14851_2305525_SNP | 2305525 | C | T |
| S_9311351 \| \| scaffold14851_2307052_SNP | 2307052 | C | T |
| S_9311394 \| \| scaffold14851_2307522_SNP | 2307522 | G | A |
| S_9311405 \| \| scaffold14851_2307639_SNP | 2307639 | C | G |
| S_9311596 \| \| scaffold14851_2308906_SNP | 2308906 | T | C |
| S_9311775 \| \| scaffold14851_2311522_SNP | 2311522 | G | A |
| S_9311784 \| \| scaffold14851_2311649_SNP | 2311649 | A | G |
| S_9311898 \| \| scaffold14851_2312482_SNP | 2312482 | G | T |
| S_9313770 \| \| scaffold14851_2329449_SNP | 2329449 | C | T |
| S_9314320 \| \| scaffold14851_2333859_SNP | 2333859 | A | C |
| scaffold14851_2335527_SNP | 2335527 | G | C |
| S_9314591 \| \| scaffold14851_2335619_SNP | 2335619 | A | C |
| S_9314608 \| \| scaffold14851_2335716_SNP | 2335716 | C | T |
| S_9314710 \| \| scaffold14851_2336532_SNP | 2336532 | G | A |
| S_9314729 \| \| scaffold14851_2336757_SNP | 2336757 | T | G |
| S_9314755 \| \| scaffold14851_2337187_SNP | 2337187 | T | C |
| S_9314757 \| \| scaffold14851_2337201_SNP | 2337201 | A | G |
| S_9314779 \| \| scaffold14851_2337395_SNP | 2337395 | G | A |
| S_9314780 \| \| scaffold14851_2337396_SNP | 2337396 | T | A |
| S_9314784 \| \| scaffold14851_2337424_SNP | 2337424 | T | C |
| S_9314785 \| \| scaffold14851_2337431_SNP | 2337431 | G | A |
| S_9314810 \| \| scaffold14851_2337646_SNP | 2337646 | C | T |
| S_9314817 \| \| scaffold14851_2337676_SNP | 2337676 | C | T |
| S_9314819 \| \| scaffold14851_2337687_SNP | 2337687 | T | C |
| S_9314825 \| \| scaffold14851_2337737_SNP | 2337737 | G | A |
| S_9314896 \| \| scaffold14851_2337967_SNP | 2337967 | C | T |
| S_9314898 \| \| scaffold14851_2337975_SNP | 2337975 | C | T |
| S_9314914 \| \| scaffold14851_2338081_SNP | 2338081 | A | G |
| S_9314927 \| \| scaffold14851_2338210_SNP | 2338210 | T | C |
| S_9314936 \| \| scaffold14851_2338268_SNP | 2338268 | G | A |
| S_9314942 \| \| scaffold14851_2338343_SNP | 2338343 | T | A |
| S_9314976 \| \| scaffold14851_2338655_SNP | 2338655 | A | G |
| S_9314984 \| \| scaffold14851_2338707_SNP | 2338707 | A | G |
| S_9315012 \| \| scaffold14851_2338951_SNP | 2338951 | G | A |
| S_9315058 \| \| scaffold14851_2339259_SNP | 2339259 | C | T |
| S_9315110 \| \| scaffold14851_2339567_SNP | 2339567 | T | C |
| S_9315111 \| \| scaffold14851_2339568_SNP | 2339568 | C | T |
| S_9315121 \| \| scaffold14851_2339609_SNP | 2339609 | G | A |
| S_9315136 \| \| scaffold14851_2339781_SNP | 2339781 | A | G |
| S_9315160 \| \| scaffold14851_2339997_SNP | 2339997 | C | A |
| S_9315171 \| \| scaffold14851_2340069_SNP | 2340069 | A | G |
| S_9315174 \| \| scaffold14851_2340077_SNP | 2340077 | G | T |
| S_9315180 \| \| scaffold14851_2340128_SNP | 2340128 | C | A |
| S_9315184 \| \| scaffold14851_2340148_SNP | 2340148 | G | A |
| S_9315200 \| \| scaffold14851_2340281_SNP | 2340281 | A | G |
| S_9315221 \| \| scaffold14851_2340417_SNP | 2340417 | C | A |
| S_9315231 \| \| scaffold14851_2340483_SNP | 2340483 | A | G |
| S_9315234 \| \| scaffold14851_2340496_SNP | 2340496 | G | A |
| scaffold14851_2340646_SNP | 2340646 | C | T |
| S_9315261 \| \| scaffold14851_2340670_SNP | 2340670 | G | T |
| S_9315264 \| \| scaffold14851_2340690_SNP | 2340690 | G | A |
| scaffold14851_2340733_SNP | 2340733 | G | A |
| S_9315303 \| \| scaffold14851_2340813_SNP | 2340813 | C | T |
| S_9315424 \| \| scaffold14851_2341301_SNP | 2341301 | G | T |
| S_9315425 \| \| scaffold14851_2341309_SNP | 2341309 | A | G |
| S_9315488 \| \| scaffold14851_2342043_SNP | 2342043 | C | G |
| S_9315496 \| \| scaffold14851_2342096_SNP | 2342096 | G | A |
| S_9315497 \| \| scaffold14851_2342108_SNP | 2342108 | G | A |
| S_9315508 \| \| scaffold14851_2342288_SNP | 2342288 | G | A |
| S_9315510 \| \| scaffold14851_2342340_SNP | 2342340 | G | A |
| S_9315517 \| \| scaffold14851_2342451_SNP | 2342451 | C | T |
| S_9315522 \| \| scaffold14851_2342488_SNP | 2342488 | C | A |
| scaffold14851_2348330_SNP | 2348330 | G | C |
| S_9316562 \| \| scaffold14851_2350636_SNP | 2350636 | C | T |
| S_9316680 \| \| scaffold14851_2352233_SNP | 2352233 | C | A |
| S_9316759 \| \| scaffold14851_2353228_SNP | 2353228 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9316859 \| \| scaffold14851_2354642_SNP | 2354642 | G | T |
| S_9316866 \| \| scaffold14851_2354762_SNP | 2354762 | G | A |
| S_9316875 \| \| scaffold14851_2354898_SNP | 2354898 | T | A |
| S_9316907 \| \| scaffold14851_2355386_SNP | 2355386 | T | A |
| S_9316930 \| \| scaffold14851_2355735_SNP | 2355735 | G | A |
| S_9316931 \| \| scaffold14851_2355778_SNP | 2355778 | G | A |
| S_9317062 \| \| scaffold14851_2356934_SNP | 2356934 | T | G |
| S_9317098 \| \| scaffold14851_2357552_SNP | 2357552 | G | A |
| S_9317124 \| \| scaffold14851_2358186_SNP | 2358186 | T | A |
| S_9317185 \| \| scaffold14851_2358931_SNP | 2358931 | C | T |
| S_9317266 \| \| scaffold14851_2360155_SNP | 2360155 | G | A |
| S_9317414 \| \| scaffold14851_2361750_SNP | 2361750 | A | T |
| S_9317436 \| \| scaffold14851_2362244_SNP | 2362244 | T | C |
| S_9317944 \| \| scaffold14851_2368683_SNP | 2368683 | G | A |
| S_9318180 \| \| scaffold14851_2372287_SNP | 2372287 | G | C |
| S_9318183 \| \| scaffold14851_2372320_SNP | 2372320 | T | C |
| S_9318647 \| \| scaffold14851_2379298_SNP | 2379298 | C | A |
| S_9318654 \| \| scaffold14851_2379460_SNP | 2379460 | A | G |
| S_9318656 \| \| scaffold14851_2379471_SNP | 2379471 | T | C |
| S_9319108 \| \| scaffold14851_2385426_SNP | 2385426 | T | C |
| S_9319205 \| \| scaffold14851_2386348_SNP | 2386348 | G | A |
| S_9319249 \| \| scaffold14851_2387442_SNP | 2387442 | C | T |
| S_9319254 \| \| scaffold14851_2387544_SNP | 2387544 | G | A |
| S_9319256 \| \| scaffold14851_2387591_SNP | 2387591 | T | A |
| S_9319257 \| \| scaffold14851_2387593_SNP | 2387593 | C | T |
| S_9319262 \| \| scaffold14851_2387655_SNP | 2387655 | C | T |
| S_9319277 \| \| scaffold14851_2388003_SNP | 2388003 | C | A |
| S_9319337 \| \| scaffold14851_2388920_SNP | 2388920 | G | T |
| S_9319371 \| \| scaffold14851_2389262_SNP | 2389262 | G | T |
| S_9319712 \| \| scaffold14851_2393947_SNP | 2393947 | C | T |
| S_9320216 \| \| scaffold14851_2400340_SNP | 2400340 | A | G |
| S_9320346 \| \| scaffold14851_2402129_SNP | 2402129 | C | A |
| S_9320439 \| \| scaffold14851_2403477_SNP | 2403477 | T | C |
| S_9320556 \| \| scaffold14851_2405131_SNP | 2405131 | A | T |
| S_9320572 \| \| scaffold14851_2405365_SNP | 2405365 | C | A |
| S_9320621 \| \| scaffold14851_2405858_SNP | 2405858 | G | T |
| S_9321087 \| \| scaffold14851_2410727_SNP | 2410727 | T | G |
| S_9321110 \| \| scaffold14851_2410962_SNP | 2410962 | A | C |
| S_9321689 \| \| scaffold14851_2419952_SNP | 2419952 | C | A |
| S_9321706 \| \| scaffold14851_2420103_SNP | 2420103 | C | A |
| S_9321711 \| \| scaffold14851_2420228_SNP | 2420228 | A | G |
| S_9321713 \| \| scaffold14851_2420354_SNP | 2420354 | C | T |
| S_9321715 \| \| scaffold14851_2420363_SNP | 2420363 | G | T |
| S_9321716 \| \| scaffold14851_2420379_SNP | 2420379 | G | A |
| S_9321735 \| \| scaffold14851_2420670_SNP | 2420670 | G | T |
| S_9321736 \| \| scaffold14851_2420671_SNP | 2420671 | C | T |
| S_9321743 \| \| scaffold14851_2420778_SNP | 2420778 | G | A |
| S_9321744 \| \| scaffold14851_2420781_SNP | 2420781 | A | G |
| S_9321746 \| \| scaffold14851_2420841_SNP | 2420841 | G | A |
| S_9321837 \| \| scaffold14851_2421255_SNP | 2421255 | T | C |
| S_9321848 \| \| scaffold14851_2421455_SNP | 2421455 | C | T |
| S_9322077 \| \| scaffold14851_2423423_SNP | 2423423 | A | G |
| S_9322078 \| \| scaffold14851_2423442_SNP | 2423442 | A | T |
| S_9322079 \| \| scaffold14851_2423443_SNP | 2423443 | T | C |
| S_9322102 \| \| scaffold14851_2423678_SNP | 2423678 | G | C |
| S_9322109 \| \| scaffold14851_2423866_SNP | 2423866 | T | A |
| S_9322124 \| \| scaffold14851_2424105_SNP | 2424105 | C | T |
| S_9322142 \| \| scaffold14851_2424488_SNP | 2424488 | A | T |
| S_9322175 \| \| scaffold14851_2425019_SNP | 2425019 | T | G |
| S_9322185 \| \| scaffold14851_2425110_SNP | 2425110 | C | A |
| S_9322239 \| \| scaffold14851_2425768_SNP | 2425768 | A | T |
| S_9322240 \| \| scaffold14851_2425794_SNP | 2425794 | G | C |
| S_9322381 \| \| scaffold14851_2428146_SNP | 2428146 | C | T |
| S_9322384 \| \| scaffold14851_2428161_SNP | 2428161 | A | C |
| S_9322403 \| \| scaffold14851_2428243_SNP | 2428243 | A | T |
| S_9322404 \| \| scaffold14851_2428244_SNP | 2428244 | A | T |
| S_9322413 \| \| scaffold14851_2428426_SNP | 2428426 | A | G |
| S_9322481 \| \| scaffold14851_2429958_SNP | 2429958 | T | C |
| S_9322483 \| \| scaffold14851_2429998_SNP | 2429998 | A | G |
| S_9322491 \| \| scaffold14851_2430249_SNP | 2430249 | T | C |
| S_9322562 \| \| scaffold14851_2430532_SNP | 2430532 | A | T |
| S_9322563 \| \| scaffold14851_2430537_SNP | 2430537 | A | G |
| S_9322671 \| \| scaffold14851_2431904_SNP | 2431904 | G | C |
| S_9322712 \| \| scaffold14851_2432805_SNP | 2432805 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9322736 \| \| scaffold14851_2433104_SNP | 2433104 | C | G |
| S_9322740 \| \| scaffold14851_2433148_SNP | 2433148 | A | T |
| S_9322741 \| \| scaffold14851_2433149_SNP | 2433149 | A | C |
| S_9322742 \| \| scaffold14851_2433161_SNP | 2433161 | A | T |
| S_9322744 \| \| scaffold14851_2433214_SNP | 2433214 | G | A |
| S_9322856 \| \| scaffold14851_2434419_SNP | 2434419 | C | A |
| S_9322859 \| \| scaffold14851_2434443_SNP | 2434443 | C | A |
| S_9323036 \| \| scaffold14851_2436340_SNP | 2436340 | A | C |
| S_9323070 \| \| scaffold14851_2436650_SNP | 2436650 | G | A |
| S_9323073 \| \| scaffold14851_2436662_SNP | 2436662 | T | A |
| S_9323085 \| \| scaffold14851_2436843_SNP | 2436843 | T | A |
| S_9323164 \| \| scaffold14851_2437569_SNP | 2437569 | G | A |
| S_9323179 \| \| scaffold14851_2437768_SNP | 2437768 | C | T |
| S_9323194 \| \| scaffold14851_2438023_SNP | 2438023 | T | A |
| S_9323220 \| \| scaffold14851_2438444_SNP | 2438444 | G | A |
| S_9323225 \| \| scaffold14851_2438482_SNP | 2438482 | A | C |
| S_9323234 \| \| scaffold14851_2438585_SNP | 2438585 | A | G |
| S_9323287 \| \| scaffold14851_2439500_SNP | 2439500 | A | G |
| S_9323288 \| \| scaffold14851_2439508_SNP | 2439508 | T | G |
| S_9323290 \| \| scaffold14851_2439513_SNP | 2439513 | G | A |
| S_9323331 \| \| scaffold14851_2440337_SNP | 2440337 | A | G |
| S_9323332 \| \| scaffold14851_2440344_SNP | 2440344 | T | G |
| S_9323334 \| \| scaffold14851_2440360_SNP | 2440360 | T | A |
| S_9323335 \| \| scaffold14851_2440384_SNP | 2440384 | T | C |
| S_9323341 \| \| scaffold14851_2440657_SNP | 2440657 | A | C |
| S_9323344 \| \| scaffold14851_2440671_SNP | 2440671 | A | T |
| S_9323360 \| \| scaffold14851_2440942_SNP | 2440942 | G | A |
| S_9323411 \| \| scaffold14851_2441924_SNP | 2441924 | T | G |
| S_9323499 \| \| scaffold14851_2443221_SNP | 2443221 | T | C |
| S_9323514 \| \| scaffold14851_2443489_SNP | 2443489 | A | G |
| S_9323566 \| \| scaffold14851_2444330_SNP | 2444330 | C | T |
| S_9323580 \| \| scaffold14851_2444477_SNP | 2444477 | T | C |
| S_9323588 \| \| scaffold14851_2444631_SNP | 2444631 | C | T |
| S_9323589 \| \| scaffold14851_2444632_SNP | 2444632 | G | T |
| S_9323591 \| \| scaffold14851_2444669_SNP | 2444669 | A | G |
| S_9323592 \| \| scaffold14851_2444680_SNP | 2444680 | T | C |
| S_9323702 \| \| scaffold14851_2445913_SNP | 2445913 | G | C |
| S_9323721 \| \| scaffold14851_2446171_SNP | 2446171 | C | T |
| S_9323726 \| \| scaffold14851_2446235_SNP | 2446235 | T | G |
| S_9323730 \| \| scaffold14851_2446279_SNP | 2446279 | C | A |
| S_9323735 \| \| scaffold14851_2446332_SNP | 2446332 | T | C |
| S_9323740 \| \| scaffold14851_2446378_SNP | 2446378 | T | G |
| S_9323741 \| \| scaffold14851_2446397_SNP | 2446397 | T | C |
| S_9323768 \| \| scaffold14851_2446756_SNP | 2446756 | A | T |
| S_9323784 \| \| scaffold14851_2446953_SNP | 2446953 | A | T |
| S_9323944 \| \| scaffold14851_2449023_SNP | 2449023 | T | A |
| S_9323952 \| \| scaffold14851_2449104_SNP | 2449104 | C | A |
| S_9323990 \| \| scaffold14851_2449625_SNP | 2449625 | A | G |
| S_9324011 \| \| scaffold14851_2449909_SNP | 2449909 | C | A |
| S_9324053 \| \| scaffold14851_2450530_SNP | 2450530 | A | T |
| S_9324086 \| \| scaffold14851_2451254_SNP | 2451254 | G | A |
| S_9324154 \| \| scaffold14851_2452219_SNP | 2452219 | A | T |
| S_9324187 \| \| scaffold14851_2452523_SNP | 2452523 | A | C |
| S_9324424 \| \| scaffold14851_2453522_SNP | 2453522 | A | T |
| S_9324425 \| \| scaffold14851_2453530_SNP | 2453530 | G | A |
| S_9324436 \| \| scaffold14851_2453722_SNP | 2453722 | T | C |
| S_9324442 \| \| scaffold14851_2453811_SNP | 2453811 | G | A |
| S_9324527 \| \| scaffold14851_2454693_SNP | 2454693 | T | C |
| S_9324528 \| \| scaffold14851_2454704_SNP | 2454704 | C | T |
| S_9324530 \| \| scaffold14851_2454741_SNP | 2454741 | A | G |
| S_9324547 \| \| scaffold14851_2454880_SNP | 2454880 | T | C |
| S_9324559 \| \| scaffold14851_2455025_SNP | 2455025 | C | T |
| S_9324635 \| \| scaffold14851_2455921_SNP | 2455921 | C | T |
| S_9324698 \| \| scaffold14851_2458015_SNP | 2458015 | A | T |
| S_9324733 \| \| scaffold14851_2458579_SNP | 2458579 | T | C |
| S_9324735 \| \| scaffold14851_2458600_SNP | 2458600 | G | T |
| S_9324777 \| \| scaffold14851_2459100_SNP | 2459100 | T | C |
| S_9324794 \| \| scaffold14851_2459382_SNP | 2459382 | G | T |
| S_9324802 \| \| scaffold14851_2459482_SNP | 2459482 | A | G |
| S_9324911 \| \| scaffold14851_2460686_SNP | 2460686 | A | G |
| S_9324916 \| \| scaffold14851_2460788_SNP | 2460788 | T | A |
| S_9324940 \| \| scaffold14851_2461341_SNP | 2461341 | T | A |
| S_9324968 \| \| scaffold14851_2461688_SNP | 2461688 | A | G |
| S_9324975 \| \| scaffold14851_2461793_SNP | 2461793 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9324981 \| \| scaffold14851_2461971_SNP | 2461971 | C | T |
| S_9324982 \| \| scaffold14851_2461988_SNP | 2461988 | A | G |
| S_9324985 \| \| scaffold14851_2462024_SNP | 2462024 | C | G |
| S_9325002 \| \| scaffold14851_2462253_SNP | 2462253 | T | C |
| S_9325067 \| \| scaffold14851_2462724_SNP | 2462724 | A | C |
| S_9325083 \| \| scaffold14851_2462984_SNP | 2462984 | C | A |
| S_9325097 \| \| scaffold14851_2463178_SNP | 2463178 | T | C |
| S_9325100 \| \| scaffold14851_2463246_SNP | 2463246 | C | A |
| S_9325123 \| \| scaffold14851_2463619_SNP | 2463619 | T | G |
| S_9325132 \| \| scaffold14851_2463765_SNP | 2463765 | C | T |
| S_9325139 \| \| scaffold14851_2463822_SNP | 2463822 | T | C |
| S_9325147 \| \| scaffold14851_2464030_SNP | 2464030 | T | C |
| S_9325150 \| \| scaffold14851_2464070_SNP | 2464070 | C | A |
| S_9325188 \| \| scaffold14851_2464774_SNP | 2464774 | A | C |
| S_9325213 \| \| scaffold14851_2465114_SNP | 2465114 | G | C |
| S_9325221 \| \| scaffold14851_2465216_SNP | 2465216 | C | T |
| S_9325222 \| \| scaffold14851_2465249_SNP | 2465249 | A | G |
| S_9325252 \| \| scaffold14851_2465715_SNP | 2465715 | G | T |
| S_9325281 \| \| scaffold14851_2465920_SNP | 2465920 | C | T |
| S_9325296 \| \| scaffold14851_2466161_SNP | 2466161 | T | C |
| S_9325297 \| \| scaffold14851_2466162_SNP | 2466162 | G | T |
| S_9325301 \| \| scaffold14851_2466197_SNP | 2466197 | A | G |
| S_9325325 \| \| scaffold14851_2466479_SNP | 2466479 | C | T |
| S_9325330 \| \| scaffold14851_2466530_SNP | 2466530 | A | G |
| S_9325348 \| \| scaffold14851_2466769_SNP | 2466769 | C | T |
| S_9325361 \| \| scaffold14851_2466902_SNP | 2466902 | A | C |
| S_9325362 \| \| scaffold14851_2466909_SNP | 2466909 | A | C |
| S_9325367 \| \| scaffold14851_2466938_SNP | 2466938 | A | T |
| S_9325440 \| \| scaffold14851_2467894_SNP | 2467894 | C | T |
| scaffold14851_2467940_SNP | 2467940 | T | C |
| S_9325505 \| \| scaffold14851_2468475_SNP | 2468475 | G | A |
| S_9325541 \| \| scaffold14851_2468875_SNP | 2468875 | C | A |
| S_9325544 \| \| scaffold14851_2468917_SNP | 2468917 | T | G |
| S_9325566 \| \| scaffold14851_2469145_SNP | 2469145 | G | A |
| S_9325586 \| \| scaffold14851_2469351_SNP | 2469351 | T | A |
| S_9325614 \| \| scaffold14851_2469819_SNP | 2469819 | T | G |
| S_9325626 \| \| scaffold14851_2470035_SNP | 2470035 | G | A |
| S_9325633 \| \| scaffold14851_2470148_SNP | 2470148 | T | G |
| S_9325645 \| \| scaffold14851_2470316_SNP | 2470316 | A | C |
| S_9325662 \| \| scaffold14851_2470700_SNP | 2470700 | T | A |
| S_9325693 \| \| scaffold14851_2471112_SNP | 2471112 | G | A |
| S_9325694 \| \| scaffold14851_2471117_SNP | 2471117 | G | C |
| S_9325704 \| \| scaffold14851_2471391_SNP | 2471391 | C | G |
| S_9325705 \| \| scaffold14851_2471401_SNP | 2471401 | A | T |
| S_9325706 \| \| scaffold14851_2471402_SNP | 2471402 | T | G |
| S_9325707 \| \| scaffold14851_2471407_SNP | 2471407 | A | G |
| S_9325708 \| \| scaffold14851_2471429_SNP | 2471429 | T | C |
| S_9325709 \| \| scaffold14851_2471454_SNP | 2471454 | T | A |
| S_9325710 \| \| scaffold14851_2471469_SNP | 2471469 | A | T |
| S_9325712 \| \| scaffold14851_2471487_SNP | 2471487 | A | T |
| S_9325716 \| \| scaffold14851_2471543_SNP | 2471543 | A | T |
| S_9325717 \| \| scaffold14851_2471548_SNP | 2471548 | G | A |
| S_9325720 \| \| scaffold14851_2471564_SNP | 2471564 | T | G |
| S_9325723 \| \| scaffold14851_2471586_SNP | 2471586 | T | C |
| S_9325731 \| \| scaffold14851_2471629_SNP | 2471629 | C | A |
| S_9325744 \| \| scaffold14851_2471819_SNP | 2471819 | G | A |
| S_9325759 \| \| scaffold14851_2472105_SNP | 2472105 | T | G |
| S_9325767 \| \| scaffold14851_2472200_SNP | 2472200 | A | C |
| S_9325768 \| \| scaffold14851_2472204_SNP | 2472204 | T | C |
| S_9325769 \| \| scaffold14851_2472224_SNP | 2472224 | C | T |
| S_9325778 \| \| scaffold14851_2472442_SNP | 2472442 | A | G |
| S_9325779 \| \| scaffold14851_2472444_SNP | 2472444 | A | T |
| S_9325780 \| \| scaffold14851_2472457_SNP | 2472457 | G | T |
| S_9325906 \| \| scaffold14851_2473752_SNP | 2473752 | T | A |
| S_9325934 \| \| scaffold14851_2474072_SNP | 2474072 | T | G |
| S_9325935 \| \| scaffold14851_2474073_SNP | 2474073 | C | A |
| S_9325936 \| \| scaffold14851_2474074_SNP | 2474074 | A | G |
| S_9326037 \| \| scaffold14851_2476611_SNP | 2476611 | T | C |
| S_9326043 \| \| scaffold14851_2476746_SNP | 2476746 | C | A |
| S_9326052 \| \| scaffold14851_2476816_SNP | 2476816 | A | T |
| S_9326057 \| \| scaffold14851_2476920_SNP | 2476920 | C | T |
| scaffold14851_2476921_SNP | 2476921 | G | T |
| S_9326100 \| \| scaffold14851_2477300_SNP | 2477300 | T | G |
| S_9326105 \| \| scaffold14851_2477375_SNP | 2477375 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9326117 \|\| scaffold14851_2477563_SNP | 2477563 | A | G |
| S_9326131 \|\| scaffold14851_2477719_SNP | 2477719 | A | C |
| S_9326172 \|\| scaffold14851_2478437_SNP | 2478437 | A | C |
| S_9326219 \|\| scaffold14851_2478992_SNP | 2478992 | A | C |
| S_9326312 \|\| scaffold14851_2480134_SNP | 2480134 | T | C |
| S_9326405 \|\| scaffold14851_2481518_SNP | 2481518 | T | C |
| S_9326451 \|\| scaffold14851_2482318_SNP | 2482318 | T | A |
| S_9326458 \|\| scaffold14851_2482385_SNP | 2482385 | C | A |
| S_9326513 \|\| scaffold14851_2482505_SNP | 2482505 | A | G |
| S_9326539 \|\| scaffold14851_2482763_SNP | 2482763 | G | A |
| S_9326557 \|\| scaffold14851_2483051_SNP | 2483051 | G | A |
| S_9326558 \|\| scaffold14851_2483054_SNP | 2483054 | T | G |
| S_9326575 \|\| scaffold14851_2483337_SNP | 2483337 | T | A |
| S_9326578 \|\| scaffold14851_2483344_SNP | 2483344 | A | G |
| S_9326604 \|\| scaffold14851_2483603_SNP | 2483603 | G | A |
| S_9326621 \|\| scaffold14851_2483957_SNP | 2483957 | T | C |
| S_9326637 \|\| scaffold14851_2484215_SNP | 2484215 | A | T |
| S_9326638 \|\| scaffold14851_2484224_SNP | 2484224 | C | T |
| S_9326734 \|\| scaffold14851_2485450_SNP | 2485450 | C | G |
| S_9326742 \|\| scaffold14851_2485575_SNP | 2485575 | G | C |
| S_9326745 \|\| scaffold14851_2485611_SNP | 2485611 | A | T |
| S_9326817 \|\| scaffold14851_2486714_SNP | 2486714 | C | A |
| S_9326832 \|\| scaffold14851_2486984_SNP | 2486984 | T | C |
| S_9326837 \|\| scaffold14851_2487015_SNP | 2487015 | G | A |
| S_9326838 \|\| scaffold14851_2487016_SNP | 2487016 | A | G |
| S_9326839 \|\| scaffold14851_2487018_SNP | 2487018 | G | A |
| S_9326868 \|\| scaffold14851_2487498_SNP | 2487498 | G | A |
| S_9326889 \|\| scaffold14851_2487994_SNP | 2487994 | C | G |
| S_9326890 \|\| scaffold14851_2487996_SNP | 2487996 | G | C |
| S_9326891 \|\| scaffold14851_2488091_SNP | 2488091 | A | G |
| S_9326976 \|\| scaffold14851_2489479_SNP | 2489479 | G | A |
| S_9326997 \|\| scaffold14851_2489920_SNP | 2489920 | T | C |
| S_9327500 \|\| scaffold14851_2493193_SNP | 2493193 | T | C |
| scaffold14851_2493941_SNP | 2493941 | C | T |
| S_9327899 \|\| scaffold14851_2496056_SNP | 2496056 | T | C |
| S_9328167 \|\| scaffold14851_2497716_SNP | 2497716 | C | A |
| S_9328174 \|\| scaffold14851_2497773_SNP | 2497773 | G | A |
| S_9329064 \|\| scaffold14851_2503991_SNP | 2503991 | T | C |
| S_9329069 \|\| scaffold14851_2504020_SNP | 2504020 | T | G |
| S_9329081 \|\| scaffold14851_2504156_SNP | 2504156 | A | C |
| S_9329113 \|\| scaffold14851_2504564_SNP | 2504564 | G | T |
| S_9329114 \|\| scaffold14851_2504567_SNP | 2504567 | G | T |
| S_9329121 \|\| scaffold14851_2504669_SNP | 2504669 | C | A |
| S_9329122 \|\| scaffold14851_2504678_SNP | 2504678 | T | C |
| S_9329125 \|\| scaffold14851_2504757_SNP | 2504757 | G | C |
| S_9329128 \|\| scaffold14851_2504813_SNP | 2504813 | G | A |
| S_9329129 \|\| scaffold14851_2504816_SNP | 2504816 | A | G |
| S_9329219 \|\| scaffold14851_2505714_SNP | 2505714 | C | A |
| S_9329221 \|\| scaffold14851_2505722_SNP | 2505722 | G | C |
| S_9329222 \|\| scaffold14851_2505728_SNP | 2505728 | T | G |
| S_9329238 \|\| scaffold14851_2505861_SNP | 2505861 | T | G |
| S_9329239 \|\| scaffold14851_2505882_SNP | 2505882 | G | C |
| S_9329298 \|\| scaffold14851_2506792_SNP | 2506792 | G | T |
| S_9329301 \|\| scaffold14851_2506827_SNP | 2506827 | C | T |
| S_9329303 \|\| scaffold14851_2506899_SNP | 2506899 | A | T |
| S_9329304 \|\| scaffold14851_2506904_SNP | 2506904 | A | C |
| S_9329326 \|\| scaffold14851_2507127_SNP | 2507127 | C | T |
| S_9329328 \|\| scaffold14851_2507151_SNP | 2507151 | T | A |
| S_9329329 \|\| scaffold14851_2507159_SNP | 2507159 | G | C |
| S_9329429 \|\| scaffold14851_2508372_SNP | 2508372 | C | A |
| S_9329430 \|\| scaffold14851_2508429_SNP | 2508429 | A | G |
| S_9329456 \|\| scaffold14851_2508893_SNP | 2508893 | A | G |
| S_9329457 \|\| scaffold14851_2508930_SNP | 2508930 | C | G |
| S_9329459 \|\| scaffold14851_2508961_SNP | 2508961 | G | C |
| S_9329460 \|\| scaffold14851_2508965_SNP | 2508965 | T | C |
| S_9329477 \|\| scaffold14851_2509322_SNP | 2509322 | C | A |
| S_9329514 \|\| scaffold14851_2509913_SNP | 2509913 | T | G |
| S_9329515 \|\| scaffold14851_2509939_SNP | 2509939 | G | C |
| S_9329518 \|\| scaffold14851_2510111_SNP | 2510111 | A | G |
| S_9329519 \|\| scaffold14851_2510152_SNP | 2510152 | A | G |
| S_9329524 \|\| scaffold14851_2510222_SNP | 2510222 | A | C |
| S_9329526 \|\| scaffold14851_2510240_SNP | 2510240 | A | T |
| S_9329540 \|\| scaffold14851_2510497_SNP | 2510497 | A | C |
| S_9329607 \|\| scaffold14851_2511078_SNP | 2511078 | C | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9329651 \| \| scaffold14851_2511451_SNP | 2511451 | A | G |
| S_9329673 \| \| scaffold14851_2511689_SNP | 2511689 | T | G |
| S_9329755 \| \| scaffold14851_2512987_SNP | 2512987 | C | A |
| S_9329856 \| \| scaffold14851_2514069_SNP | 2514069 | C | T |
| S_9330018 \| \| scaffold14851_2516126_SNP | 2516126 | C | A |
| S_9330089 \| \| scaffold14851_2516710_SNP | 2516710 | T | G |
| S_9330100 \| \| scaffold14851_2516776_SNP | 2516776 | A | C |
| S_9330181 \| \| scaffold14851_2518257_SNP | 2518257 | T | C |
| S_9330219 \| \| scaffold14851_2518953_SNP | 2518953 | C | A |
| S_9330229 \| \| scaffold14851_2519176_SNP | 2519176 | T | A |
| S_9330240 \| \| scaffold14851_2519386_SNP | 2519386 | G | A |
| S_9330247 \| \| scaffold14851_2519478_SNP | 2519478 | T | G |
| S_9330250 \| \| scaffold14851_2519489_SNP | 2519489 | T | G |
| S_9330397 \| \| scaffold14851_2521501_SNP | 2521501 | G | A |
| S_9330398 \| \| scaffold14851_2521510_SNP | 2521510 | A | G |
| S_9330405 \| \| scaffold14851_2521658_SNP | 2521658 | T | C |
| S_9330406 \| \| scaffold14851_2521661_SNP | 2521661 | A | G |
| S_9330418 \| \| scaffold14851_2521850_SNP | 2521850 | C | T |
| S_9330429 \| \| scaffold14851_2521990_SNP | 2521990 | T | G |
| S_9330430 \| \| scaffold14851_2522006_SNP | 2522006 | G | T |
| scaffold14851_2522091_SNP | 2522091 | A | G |
| S_9330529 \| \| scaffold14851_2522749_SNP | 2522749 | G | A |
| S_9330530 \| \| scaffold14851_2522787_SNP | 2522787 | T | C |
| S_9330545 \| \| scaffold14851_2523023_SNP | 2523023 | A | G |
| S_9330551 \| \| scaffold14851_2523091_SNP | 2523091 | G | A |
| S_9330552 \| \| scaffold14851_2523093_SNP | 2523093 | G | C |
| S_9330556 \| \| scaffold14851_2523138_SNP | 2523138 | G | A |
| S_9330557 \| \| scaffold14851_2523181_SNP | 2523181 | A | T |
| S_9330558 \| \| scaffold14851_2523190_SNP | 2523190 | A | G |
| S_9330559 \| \| scaffold14851_2523205_SNP | 2523205 | G | A |
| S_9330560 \| \| scaffold14851_2523220_SNP | 2523220 | A | G |
| S_9330576 \| \| scaffold14851_2523384_SNP | 2523384 | C | G |
| S_9330601 \| \| scaffold14851_2523554_SNP | 2523554 | C | G |
| S_9330603 \| \| scaffold14851_2523594_SNP | 2523594 | A | T |
| S_9330610 \| \| scaffold14851_2523747_SNP | 2523747 | A | G |
| S_9330688 \| \| scaffold14851_2524868_SNP | 2524868 | G | T |
| S_9330692 \| \| scaffold14851_2524919_SNP | 2524919 | T | C |
| S_9330695 \| \| scaffold14851_2524935_SNP | 2524935 | T | C |
| S_9330699 \| \| scaffold14851_2525010_SNP | 2525010 | C | T |
| S_9330701 \| \| scaffold14851_2525042_SNP | 2525042 | C | T |
| S_9330708 \| \| scaffold14851_2525094_SNP | 2525094 | C | T |
| S_9330728 \| \| scaffold14851_2525352_SNP | 2525352 | G | C |
| S_9330731 \| \| scaffold14851_2525363_SNP | 2525363 | G | C |
| S_9330733 \| \| scaffold14851_2525368_SNP | 2525368 | G | A |
| S_9330734 \| \| scaffold14851_2525370_SNP | 2525370 | G | A |
| S_9330778 \| \| scaffold14851_2525945_SNP | 2525945 | T | C |
| S_9330799 \| \| scaffold14851_2526179_SNP | 2526179 | T | C |
| S_9330812 \| \| scaffold14851_2526524_SNP | 2526524 | A | C |
| S_9330894 \| \| scaffold14851_2527635_SNP | 2527635 | G | A |
| S_9330899 \| \| scaffold14851_2527750_SNP | 2527750 | A | T |
| S_9330907 \| \| scaffold14851_2527819_SNP | 2527819 | C | A |
| S_9330911 \| \| scaffold14851_2527864_SNP | 2527864 | T | G |
| S_9331004 \| \| scaffold14851_2528991_SNP | 2528991 | A | G |
| S_9331083 \| \| scaffold14851_2529846_SNP | 2529846 | A | T |
| S_9331085 \| \| scaffold14851_2529966_SNP | 2529966 | C | A |
| S_9331106 \| \| scaffold14851_2530681_SNP | 2530681 | T | G |
| S_9331116 \| \| scaffold14851_2530797_SNP | 2530797 | C | T |
| S_9331249 \| \| scaffold14851_2532490_SNP | 2532490 | C | G |
| S_9331290 \| \| scaffold14851_2533230_SNP | 2533230 | T | A |
| S_9331296 \| \| scaffold14851_2533379_SNP | 2533379 | C | T |
| S_9331312 \| \| scaffold14851_2533568_SNP | 2533568 | A | T |
| S_9331328 \| \| scaffold14851_2533774_SNP | 2533774 | C | A |
| S_9331373 \| \| scaffold14851_2534192_SNP | 2534192 | T | C |
| S_9331377 \| \| scaffold14851_2534360_SNP | 2534360 | T | C |
| S_9331420 \| \| scaffold14851_2535256_SNP | 2535256 | A | G |
| S_9331441 \| \| scaffold14851_2535693_SNP | 2535693 | T | C |
| S_9331447 \| \| scaffold14851_2535863_SNP | 2535863 | C | A |
| S_9331454 \| \| scaffold14851_2536065_SNP | 2536065 | A | C |
| S_9331466 \| \| scaffold14851_2536215_SNP | 2536215 | T | C |
| S_9331521 \| \| scaffold14851_2537548_SNP | 2537548 | T | C |
| S_9331535 \| \| scaffold14851_2537709_SNP | 2537709 | C | T |
| S_9331547 \| \| scaffold14851_2537876_SNP | 2537876 | C | G |
| S_9331549 \| \| scaffold14851_2537909_SNP | 2537909 | G | C |
| S_9331551 \| \| scaffold14851_2537955_SNP | 2537955 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9331587 \| \| scaffold14851_2538205_SNP | 2538205 | T | G |
| S_9331614 \| \| scaffold14851_2538606_SNP | 2538606 | T | C |
| S_9331615 \| \| scaffold14851_2538608_SNP | 2538608 | G | A |
| S_9331617 \| \| scaffold14851_2538628_SNP | 2538628 | C | A |
| S_9331642 \| \| scaffold14851_2539059_SNP | 2539059 | C | T |
| S_9331815 \| \| scaffold14851_2540909_SNP | 2540909 | T | C |
| S_9331836 \| \| scaffold14851_2541147_SNP | 2541147 | A | G |
| S_9331853 \| \| scaffold14851_2541337_SNP | 2541337 | G | A |
| S_9331856 \| \| scaffold14851_2541368_SNP | 2541368 | A | T |
| S_9331916 \| \| scaffold14851_2542061_SNP | 2542061 | C | T |
| S_9331944 \| \| scaffold14851_2542730_SNP | 2542730 | T | C |
| S_9331948 \| \| scaffold14851_2542788_SNP | 2542788 | C | T |
| S_9331977 \| \| scaffold14851_2543164_SNP | 2543164 | T | A |
| S_9332105 \| \| scaffold14851_2544694_SNP | 2544694 | T | C |
| S_9332179 \| \| scaffold14851_2545871_SNP | 2545871 | G | A |
| S_9332192 \| \| scaffold14851_2546072_SNP | 2546072 | G | C |
| S_9332203 \| \| scaffold14851_2546263_SNP | 2546263 | T | C |
| S_9332265 \| \| scaffold14851_2546668_SNP | 2546668 | T | C |
| S_9332309 \| \| scaffold14851_2547017_SNP | 2547017 | T | C |
| S_9332311 \| \| scaffold14851_2547028_SNP | 2547028 | G | A |
| S_9332420 \| \| scaffold14851_2548969_SNP | 2548969 | A | G |
| S_9332424 \| \| scaffold14851_2549021_SNP | 2549021 | T | C |
| $_9332425 \| \| scaffold14851_2549036_SNP | 2549036 | G | A |
| S_9332427 \| \| scaffold14851_2549089_SNP | 2549089 | C | T |
| S_9332452 \| \| scaffold14851_2549242_SNP | 2549242 | A | G |
| S_9332453 \| \| scaffold14851_2549254_SNP | 2549254 | A | G |
| S_9332511 \| \| scaffold14851_2550221_SNP | 2550221 | G | A |
| S_9332518 \| \| scaffold14851_2550280_SNP | 2550280 | A | T |
| S_9332539 \| \| scaffold14851_2550500_SNP | 2550500 | A | T |
| S_9332548 \| \| scaffold14851_2550629_SNP | 2550629 | A | G |
| S_9332643 \| \| scaffold14851_2552435_SNP | 2552435 | C | T |
| S_9332870 \| \| scaffold14851_2554734_SNP | 2554734 | C | G |
| S_9332931 \| \| scaffold14851_2555596_SNP | 2555596 | G | T |
| S_9333093 \| \| scaffold14851_2557735_SNP | 2557735 | A | G |
| S_9333209 \| \| scaffold14851_2559530_SNP | 2559530 | C | A |
| S_9333278 \| \| scaffold14851_2560651_SNP | 2560651 | T | G |
| S_9333396 \| \| scaffold14851_2562023_SNP | 2562023 | G | A |
| S_9333546 \| \| scaffold14851_2564291_SNP | 2564291 | A | T |
| S_9333669 \| \| scaffold14851_2565886_SNP | 2565886 | C | T |
| S_9333680 \| \| scaffold14851_2566171_SNP | 2566171 | C | T |
| S_9333720 \| \| scaffold14851_2566563_SNP | 2566563 | A | G |
| S_9333723 \| \| scaffold14851_2566578_SNP | 2566578 | C | T |
| S_9333727 \| \| scaffold14851_2566692_SNP | 2566692 | G | C |
| S_9333728 \| \| scaffold14851_2566695_SNP | 2566695 | C | G |
| S_9333789 \| \| scaffold14851_2567776_SNP | 2567776 | G | A |
| S_9333791 \| \| scaffold14851_2567829_SNP | 2567829 | G | T |
| S_9333794 \| \| scaffold14851_2567913_SNP | 2567913 | T | C |
| S_9333992 \| \| scaffold14851_2571365_SNP | 2571365 | T | G |
| S_9334030 \| \| scaffold14851_2571716_SNP | 2571716 | A | G |
| S_9334368 \| \| scaffold14851_2577430_SNP | 2577430 | G | T |
| S_9334490 \| \| scaffold14851_2578646_SNP | 2578646 | T | A |
| S_9334681 \| \| scaffold14851_2581676_SNP | 2581676 | A | G |
| $_9334688 \| \| scaffold14851_2581918_SNP | 2581918 | G | A |
| S_9334690 \| \| scaffold14851_2581925_SNP | 2581925 | T | A |
| S_9334691 \| \| scaffold14851_2581927_SNP | 2581927 | T | A |
| S_9334722 \| \| scaffold14851_2582034_SNP | 2582034 | C | T |
| S_9334789 \| \| scaffold14851_2583086_SNP | 2583086 | T | A |
| S_9335504 \| \| scaffold14851_2593171_SNP | 2593171 | G | T |
| S_9335529 \| \| scaffold14851_2593286_SNP | 2593286 | G | A |
| S_9335531 \| \| scaffold14851_2593313_SNP | 2593313 | C | A |
| S_9335571 \| \| scaffold14851_2593954_SNP | 2593954 | A | G |
| S_9335687 \| \| scaffold14851_2595432_SNP | 2595432 | G | A |
| S_9335878 \| \| scaffold14851_2599531_SNP | 2599531 | C | A |
| S_9335914 \| \| scaffold14851_2599931_SNP | 2599931 | G | C |
| S_9335916 \| \| scaffold14851_2599950_SNP | 2599950 | G | T |
| S_9336119 \| \| scaffold14851_2605224_SNP | 2605224 | T | A |
| S_9337265 \| \| scaffold14851_2617714_SNP | 2617714 | T | A |
| S_9337345 \| \| scaffold14851_2618724_SNP | 2618724 | G | A |
| S_9338568 \| \| scaffold14851_2635690_SNP | 2635690 | T | C |
| S_9338717 \| \| scaffold14851_2637861_SNP | 2637861 | A | T |
| S_9339171 \| \| scaffold14851_2644707_SNP | 2644707 | T | C |
| S_9339177 \| \| scaffold14851_2644742_SNP | 2644742 | A | T |
| S_9339179 \| \| scaffold14851_2644781_SNP | 2644781 | C | T |
| S_9339180 \| \| scaffold14851_2644782_SNP | 2644782 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9339181 \| \| scaffold14851_2644783_SNP | 2644783 | C | T |
| S_9339182 \| \| scaffold14851_2644800_SNP | 2644800 | A | C |
| S_9339215 \| \| scaffold14851_2644893_SNP | 2644893 | G | A |
| S_9339248 \| \| scaffold14851_2645036_SNP | 2645036 | C | T |
| S_9339260 \| \| scaffold14851_2645092_SNP | 2645092 | C | T |
| S_9339274 \| \| scaffold14851_2645177_SNP | 2645177 | A | C |
| S_9339462 \| \| scaffold14851_2647319_SNP | 2647319 | A | T |
| S_9339472 \| \| scaffold14851_2647449_SNP | 2647449 | C | T |
| S_9339533 \| \| scaffold14851_2648147_SNP | 2648147 | A | T |
| S_9339534 \| \| scaffold14851_2648174_SNP | 2648174 | C | T |
| S_9339539 \| \| scaffold14851_2648265_SNP | 2648265 | A | G |
| S_9339614 \| \| scaffold14851_2648503_SNP | 2648503 | A | G |
| S_9339652 \| \| scaffold14851_2648591_SNP | 2648591 | A | T |
| S_9339653 \| \| scaffold14851_2648592_SNP | 2648592 | A | T |
| S_9339654 \| \| scaffold14851_2648593_SNP | 2648593 | A | T |
| S_9339656 \| \| scaffold14851_2648595_SNP | 2648595 | G | T |
| S_9339684 \| \| scaffold14851_2648817_SNP | 2648817 | C | A |
| S_9340072 \| \| scaffold14851_2654380_SNP | 2654380 | T | C |
| S_9340121 \| \| scaffold14851_2655252_SNP | 2655252 | A | G |
| S_9340154 \| \| scaffold14851_2655830_SNP | 2655830 | A | T |
| scaffold14851_2655831_SNP | 2655831 | T | A |
| scaffold14851_2655832_SNP | 2655832 | A | T |
| S_9340159 \| \| scaffold14851_2655881_SNP | 2655881 | T | G |
| S_9340164 \| \| scaffold14851_2655953_SNP | 2655953 | A | G |
| S_9340170 \| \| scaffold14851_2656050_SNP | 2656050 | C | T |
| S_9340184 \| \| scaffold14851_2656267_SNP | 2656267 | C | T |
| S_9340187 \| \| scaffold14851_2656281_SNP | 2656281 | T | A |
| S_9340267 \| \| scaffold14851_2656944_SNP | 2656944 | T | A |
| S_9340328 \| \| scaffold14851_2658091_SNP | 2658091 | T | A |
| S_9340366 \| \| scaffold14851_2658634_SNP | 2658634 | A | T |
| S_9340367 \| \| scaffold14851_2658635_SNP | 2658635 | C | T |
| S_9340368 \| \| scaffold14851_2658655_SNP | 2658655 | G | C |
| S_9340390 \| \| scaffold14851_2659143_SNP | 2659143 | C | T |
| S_9340400 \| \| scaffold14851_2659248_SNP | 2659248 | A | C |
| S_9340401 \| \| scaffold14851_2659253_SNP | 2659253 | G | A |
| S_9340403 \| \| scaffold14851_2659260_SNP | 2659260 | T | C |
| S_9340405 \| \| scaffold14851_2659294_SNP | 2659294 | C | T |
| S_9340406 \| \| scaffold14851_2659304_SNP | 2659304 | C | T |
| S_9340466 \| \| scaffold14851_2659590_SNP | 2659590 | A | G |
| S_9340474 \| \| scaffold14851_2659648_SNP | 2659648 | C | T |
| S_9340496 \| \| scaffold14851_2659862_SNP | 2659862 | G | T |
| S_9340505 \| \| scaffold14851_2659947_SNP | 2659947 | C | T |
| S_9340527 \| \| scaffold14851_2660339_SNP | 2660339 | G | T |
| S_9340530 \| \| scaffold14851_2660422_SNP | 2660422 | A | G |
| S_9340552 \| \| scaffold14851_2660721_SNP | 2660721 | A | G |
| S_9340555 \| \| scaffold14851_2660758_SNP | 2660758 | T | G |
| S_9340587 \| \| scaffold14851_2661423_SNP | 2661423 | T | C |
| S_9340591 \| \| scaffold14851_2661480_SNP | 2661480 | T | A |
| S_9340599 \| \| scaffold14851_2661594_SNP | 2661594 | C | T |
| S_9340603 \| \| scaffold14851_2661688_SNP | 2661688 | C | T |
| S_9340606 \| \| scaffold14851_2661731_SNP | 2661731 | T | G |
| S_9340621 \| \| scaffold14851_2661874_SNP | 2661874 | T | G |
| scaffold14851_2662318_SNP | 2662318 | A | G |
| scaffold14851_2662320_SNP | 2662320 | G | T |
| scaffold14851_2662321_SNP | 2662321 | T | G |
| scaffold14851_2662322_SNP | 2662322 | G | A |
| S_9340649 \| \| scaffold14851_2662427_SNP | 2662427 | C | T |
| S_9340655 \| \| scaffold14851_2662623_SNP | 2662623 | A | G |
| S_9340660 \| \| scaffold14851_2662650_SNP | 2662650 | C | A |
| S_9340665 \| \| scaffold14851_2662723_SNP | 2662723 | C | A |
| S_9340668 \| \| scaffold14851_2662772_SNP | 2662772 | C | G |
| S_9340689 \| \| scaffold14851_2663154_SNP | 2663154 | G | A |
| S_9340714 \| \| scaffold14851_2663578_SNP | 2663578 | G | C |
| S_9340765 \| \| scaffold14851_2664576_SNP | 2664576 | G | C |
| S_9340769 \| \| scaffold14851_2664648_SNP | 2664648 | C | T |
| S_9340770 \| \| scaffold14851_2664650_SNP | 2664650 | A | C |
| S_9340802 \| \| scaffold14851_2665252_SNP | 2665252 | A | G |
| S_9340803 \| \| scaffold14851_2665257_SNP | 2665257 | T | C |
| S_9340804 \| \| scaffold14851_2665261_SNP | 2665261 | T | G |
| S_9340828 \| \| scaffold14851_2665888_SNP | 2665888 | A | G |
| S_9340830 \| \| scaffold14851_2665986_SNP | 2665986 | A | G |
| S_9340834 \| \| scaffold14851_2666131_SNP | 2666131 | T | C |
| S_9340836 \| \| scaffold14851_2666164_SNP | 2666164 | C | T |
| S_9340868 \| \| scaffold14851_2666501_SNP | 2666501 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9340900 \| \| scaffold14851_2667058_SNP | 2667058 | C | A |
| S_9340921 \| \| scaffold14851_2667530_SNP | 2667530 | C | G |
| S_9340934 \| \| scaffold14851_2667749_SNP | 2667749 | C | T |
| S_9341227 \| \| scaffold14851_2672251_SNP | 2672251 | A | T |
| S_9341273 \| \| scaffold14851_2673148_SNP | 2673148 | A | C |
| S_9341281 \| \| scaffold14851_2673228_SNP | 2673228 | G | A |
| S_9341282 \| \| scaffold14851_2673229_SNP | 2673229 | C | A |
| S_9341285 \| \| scaffold14851_2673291_SNP | 2673291 | T | C |
| S_9341312 \| \| scaffold14851_2673576_SNP | 2673576 | T | A |
| S_9341327 \| \| scaffold14851_2673716_SNP | 2673716 | A | G |
| S_9341328 \| \| scaffold14851_2673724_SNP | 2673724 | G | A |
| S_9341347 \| \| scaffold14851_2674093_SNP | 2674093 | A | C |
| S_9341348 \| \| scaffold14851_2674095_SNP | 2674095 | A | G |
| S_9341371 \| \| scaffold14851_2674708_SNP | 2674708 | A | G |
| S_9341373 \| \| scaffold14851_2674725_SNP | 2674725 | T | C |
| S_9341394 \| \| scaffold14851_2675107_SNP | 2675107 | C | T |
| S_9341396 \| \| scaffold14851_2675131_SNP | 2675131 | C | T |
| S_9341400 \| \| scaffold14851_2675198_SNP | 2675198 | C | T |
| S_9341401 \| \| scaffold14851_2675204_SNP | 2675204 | A | G |
| S_9341436 \| \| scaffold14851_2675826_SNP | 2675826 | A | G |
| S_9341444 \| \| scaffold14851_2676077_SNP | 2676077 | T | A |
| S_9341453 \| \| scaffold14851_2676142_SNP | 2676142 | C | A |
| S_9341466 \| \| scaffold14851_2676487_SNP | 2676487 | A | T |
| S_9341497 \| \| scaffold14851_2676957_SNP | 2676957 | A | T |
| S_9341499 \| \| scaffold14851_2676991_SNP | 2676991 | C | T |
| S_9341503 \| \| scaffold14851_2677177_SNP | 2677177 | A | C |
| S_9341579 \| \| scaffold14851_2678333_SNP | 2678333 | T | G |
| S_9341657 \| \| scaffold14851_2679052_SNP | 2679052 | T | A |
| S_9341818 \| \| scaffold14851_2680986_SNP | 2680986 | T | G |
| S_9341899 \| \| scaffold14851_2681850_SNP | 2681850 | A | T |
| S_9342122 \| \| scaffold14851_2684803_SNP | 2684803 | G | T |
| S_9342123 \| \| scaffold14851_2684807_SNP | 2684807 | T | G |
| S_9342124 \| \| scaffold14851_2684813_SNP | 2684813 | G | A |
| S_9342127 \| \| scaffold14851_2684862_SNP | 2684862 | A | T |
| S_9342134 \| \| scaffold14851_2685060_SNP | 2685060 | A | G |
| S_9342137 \| \| scaffold14851_2685098_SNP | 2685098 | T | G |
| S_9342196 \| \| scaffold14851_2685591_SNP | 2685591 | G | A |
| S_9342233 \| \| scaffold14851_2686133_SNP | 2686133 | A | G |
| S_9342263 \| \| scaffold14851_2686460_SNP | 2686460 | T | C |
| S_9342285 \| \| scaffold14851_2686657_SNP | 2686657 | C | T |
| S_9342286 \| \| scaffold14851_2686661_SNP | 2686661 | A | G |
| S_9342328 \| \| scaffold14851_2687289_SNP | 2687289 | G | A |
| S_9342401 \| \| scaffold14851_2687798_SNP | 2687798 | T | C |
| S_9342460 \| \| scaffold14851_2688668_SNP | 2688668 | A | T |
| S_9342486 \| \| scaffold14851_2688831_SNP | 2688831 | A | C |
| S_9342567 \| \| scaffold14851_2690027_SNP | 2690027 | A | G |
| S_9342659 \| \| scaffold14851_2691488_SNP | 2691488 | T | A |
| S_9342661 \| \| scaffold14851_2691490_SNP | 2691490 | T | C |
| S_9342743 \| \| scaffold14851_2692715_SNP | 2692715 | G | A |
| S_9342777 \| \| scaffold14851_2693149_SNP | 2693149 | C | G |
| S_9342780 \| \| scaffold14851_2693264_SNP | 2693264 | T | G |
| S_9342854 \| \| scaffold14851_2694135_SNP | 2694135 | T | C |
| S_9342855 \| \| scaffold14851_2694136_SNP | 2694136 | C | T |
| S_9342859 \| \| scaffold14851_2694269_SNP | 2694269 | T | C |
| S_9342861 \| \| scaffold14851_2694284_SNP | 2694284 | G | A |
| S_9342862 \| \| scaffold14851_2694296_SNP | 2694296 | T | C |
| S_9342869 \| \| scaffold14851_2694429_SNP | 2694429 | T | G |
| S_9342900 \| \| scaffold14851_2694544_SNP | 2694544 | G | T |
| S_9342908 \| \| scaffold14851_2694619_SNP | 2694619 | A | T |
| S_9342913 \| \| scaffold14851_2694642_SNP | 2694642 | C | T |
| S_9342914 \| \| scaffold14851_2694685_SNP | 2694685 | T | C |
| S_9342918 \| \| scaffold14851_2694858_SNP | 2694858 | A | T |
| S_9343067 \| \| scaffold14851_2696490_SNP | 2696490 | T | C |
| S_9343096 \| \| scaffold14851_2696836_SNP | 2696836 | A | T |
| S_9343106 \| \| scaffold14851_2697041_SNP | 2697041 | C | T |
| scaffold14851_2697670_SNP | 2697670 | G | T |
| S_9343159 \| \| scaffold14851_2697763_SNP | 2697763 | A | C |
| S_9343203 \| \| scaffold14851_2698419_SNP | 2698419 | G | T |
| S_9343205 \| \| scaffold14851_2698440_SNP | 2698440 | T | A |
| S_9343239 \| \| scaffold14851_2699024_SNP | 2699024 | C | T |
| S_9344946 \| \| scaffold14851_2704836_SNP | 2704836 | A | G |
| S_9344960 \| \| scaffold14851_2704901_SNP | 2704901 | G | A |
| S_9345033 \| \| scaffold14851_2705368_SNP | 2705368 | A | T |
| S_9345035 \| \| scaffold14851_2705418_SNP | 2705418 | T | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9345238 \| \| scaffold14851_2707018_SNP | 2707018 | T | C |
| S_9345332 \| \| scaffold14851_2707681_SNP | 2707681 | C | A |
| S_9345366 \| \| scaffold14851_2708289_SNP | 2708289 | C | T |
| S_9345384 \| \| scaffold14851_2708444_SNP | 2708444 | C | T |
| S_9345389 \| \| scaffold14851_2708493_SNP | 2708493 | C | A |
| S_9345393 \| \| scaffold14851_2708524_SNP | 2708524 | T | C |
| S_9345404 \| \| scaffold14851_2708678_SNP | 2708678 | T | C |
| S_9345412 \| \| scaffold14851_2708838_SNP | 2708838 | A | G |
| S_9345413 \| \| scaffold14851_2708844_SNP | 2708844 | G | T |
| S_9345414 \| \| scaffold14851_2708850_SNP | 2708850 | A | G |
| S_9345419 \| \| scaffold14851_2708945_SNP | 2708945 | G | C |
| S_9345466 \| \| scaffold14851_2709537_SNP | 2709537 | A | C |
| S_9345467 \| \| scaffold14851_2709538_SNP | 2709538 | G | A |
| S_9345488 \| \| scaffold14851_2709826_SNP | 2709826 | T | G |
| S_9345496 \| \| scaffold14851_2709901_SNP | 2709901 | A | G |
| S_9345530 \| \| scaffold14851_2710331_SNP | 2710331 | C | T |
| S_9345532 \| \| scaffold14851_2710340_SNP | 2710340 | G | A |
| S_9345534 \| \| scaffold14851_2710348_SNP | 2710348 | A | T |
| S_9345535 \| \| scaffold14851_2710349_SNP | 2710349 | G | A |
| S_9345630 \| \| scaffold14851_2711280_SNP | 2711280 | T | C |
| S_9345631 \| \| scaffold14851_2711281_SNP | 2711281 | G | T |
| S_9345683 \| \| scaffold14851_2711655_SNP | 2711655 | G | T |
| S_9345713 \| \| scaffold14851_2712187_SNP | 2712187 | T | C |
| S_9345795 \| \| scaffold14851_2712553_SNP | 2712553 | T | C |
| S_9345804 \| \| scaffold14851_2712691_SNP | 2712691 | T | G |
| S_9345807 \| \| scaffold14851_2712718_SNP | 2712718 | A | C |
| S_9345809 \| \| scaffold14851_2712723_SNP | 2712723 | G | A |
| S_9345929 \| \| scaffold14851_2714590_SNP | 2714590 | A | C |
| S_9345945 \| \| scaffold14851_2714741_SNP | 2714741 | A | T |
| S_9345988 \| \| scaffold14851_2715251_SNP | 2715251 | G | A |
| S_9346047 \| \| scaffold14851_2715905_SNP | 2715905 | T | C |
| S_9346070 \| \| scaffold14851_2716105_SNP | 2716105 | C | T |
| S_9346083 \| \| scaffold14851_2716348_SNP | 2716348 | A | G |
| S_9346084 \| \| scaffold14851_2716377_SNP | 2716377 | C | T |
| S_9346128 \| \| scaffold14851_2717016_SNP | 2717016 | A | T |
| S_9346214 \| \| scaffold14851_2718020_SNP | 2718020 | A | G |
| S_9346369 \| \| scaffold14851_2719718_SNP | 2719718 | C | G |
| S_9346403 \| \| scaffold14851_2719943_SNP | 2719943 | C | A |
| S_9346480 \| \| scaffold14851_2720936_SNP | 2720936 | G | A |
| S_9346496 \| \| scaffold14851_2721123_SNP | 2721123 | C | T |
| S_9346498 \| \| scaffold14851_2721130_SNP | 2721130 | A | G |
| S_9346513 \| \| scaffold14851_2721520_SNP | 2721520 | G | A |
| S_9346560 \| \| scaffold14851_2722772_SNP | 2722772 | C | G |
| S_9346562 \| \| scaffold14851_2722776_SNP | 2722776 | C | T |
| S_9346577 \| \| scaffold14851_2722919_SNP | 2722919 | G | T |
| S_9346578 \| \| scaffold14851_2722953_SNP | 2722953 | T | C |
| S_9346585 \| \| scaffold14851_2723015_SNP | 2723015 | C | A |
| S_9346629 \| \| scaffold14851_2723743_SNP | 2723743 | G | A |
| S_9346641 \| \| scaffold14851_2724100_SNP | 2724100 | A | C |
| S_9346649 \| \| scaffold14851_2724253_SNP | 2724253 | T | A |
| S_9346760 \| \| scaffold14851_2725336_SNP | 2725336 | C | G |
| S_9346769 \| \| scaffold14851_2725480_SNP | 2725480 | G | C |
| S_9346773 \| \| scaffold14851_2725589_SNP | 2725589 | T | C |
| S_9346870 \| \| scaffold14851_2726713_SNP | 2726713 | C | T |
| S_9346873 \| \| scaffold14851_2726779_SNP | 2726779 | A | T |
| S_9346874 \| \| scaffold14851_2726784_SNP | 2726784 | T | G |
| S_9346886 \| \| scaffold14851_2726919_SNP | 2726919 | C | G |
| S_9346914 \| \| scaffold14851_2727230_SNP | 2727230 | G | A |
| S_9346966 \| \| scaffold14851_2727940_SNP | 2727940 | T | G |
| S_9346973 \| \| scaffold14851_2728007_SNP | 2728007 | T | C |
| S_9346976 \| \| scaffold14851_2728020_SNP | 2728020 | G | A |
| S_9347039 \| \| scaffold14851_2728891_SNP | 2728891 | T | C |
| S_9347068 \| \| scaffold14851_2729346_SNP | 2729346 | A | T |
| S_9347097 \| \| scaffold14851_2729782_SNP | 2729782 | C | A |
| S_9347130 \| \| scaffold14851_2730110_SNP | 2730110 | C | G |
| S_9347131 \| \| scaffold14851_2730111_SNP | 2730111 | A | T |
| S_9347160 \| \| scaffold14851_2730202_SNP | 2730202 | C | T |
| S_9347169 \| \| scaffold14851_2730356_SNP | 2730356 | G | A |
| S_9347170 \| \| scaffold14851_2730364_SNP | 2730364 | C | T |
| S_9347195 \| \| scaffold14851_2730619_SNP | 2730619 | A | G |
| S_9347200 \| \| scaffold14851_2730652_SNP | 2730652 | T | C |
| S_9347207 \| \| scaffold14851_2730712_SNP | 2730712 | G | C |
| S_9347208 \| \| scaffold14851_2730714_SNP | 2730714 | T | A |
| S_9347210 \| \| scaffold14851_2730725_SNP | 2730725 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9347212 \| \| scaffold14851_2730731_SNP | 2730731 | A | G |
| S_9347215 \| \| scaffold14851_2730780_SNP | 2730780 | A | G |
| S_9347242 \| \| scaffold14851_2731046_SNP | 2731046 | T | C |
| S_9347249 \| \| scaffold14851_2731162_SNP | 2731162 | A | G |
| S_9347287 \| \| scaffold14851_2731352_SNP | 2731352 | A | T |
| S_9347293 \| \| scaffold14851_2731386_SNP | 2731386 | A | T |
| S_9347294 \| \| scaffold14851_2731393_SNP | 2731393 | A | G |
| S_9347500 \| \| scaffold14851_2734484_SNP | 2734484 | G | T |
| S_9347527 \| \| scaffold14851_2734834_SNP | 2734834 | A | T |
| S_9347621 \| \| scaffold14851_2735463_SNP | 2735463 | A | T |
| S_9347622 \| \| scaffold14851_2735470_SNP | 2735470 | C | A |
| S_9347696 \| \| scaffold14851_2735664_SNP | 2735664 | G | T |
| S_9347716 \| \| scaffold14851_2735924_SNP | 2735924 | T | C |
| S_9347735 \| \| scaffold14851_2736357_SNP | 2736357 | T | A |
| S_9347750 \| \| scaffold14851_2736602_SNP | 2736602 | T | C |
| S_9347756 \| \| scaffold14851_2736703_SNP | 2736703 | C | T |
| S_9347759 \| \| scaffold14851_2736740_SNP | 2736740 | A | T |
| S_9347768 \| \| scaffold14851_2736864_SNP | 2736864 | G | C |
| S_9347772 \| \| scaffold14851_2736926_SNP | 2736926 | T | C |
| S_9347776 \| \| scaffold14851_2736941_SNP | 2736941 | A | G |
| S_9347778 \| \| scaffold14851_2736964_SNP | 2736964 | G | C |
| S_9347787 \| \| scaffold14851_2737186_SNP | 2737186 | T | A |
| S_9347831 \| \| scaffold14851_2737606_SNP | 2737606 | A | C |
| S_9347833 \| \| scaffold14851_2737615_SNP | 2737615 | G | A |
| S_9347870 \| \| scaffold14851_2738184_SNP | 2738184 | G | C |
| S_9347876 \| \| scaffold14851_2738246_SNP | 2738246 | C | T |
| S_9347896 \| \| scaffold14851_2738685_SNP | 2738685 | A | G |
| S_9347915 \| \| scaffold14851_2738913_SNP | 2738913 | A | C |
| S_9347917 \| \| scaffold14851_2738974_SNP | 2738974 | T | C |
| S_9348034 \| \| scaffold14851_2740295_SNP | 2740295 | G | A |
| S_9348035 \| \| scaffold14851_2740307_SNP | 2740307 | G | T |
| S_9348161 \| \| scaffold14851_2742211_SNP | 2742211 | A | T |
| S_9348162 \| \| scaffold14851_2742219_SNP | 2742219 | G | T |
| S_9348166 \| \| scaffold14851_2742276_SNP | 2742276 | T | A |
| S_9348167 \| \| scaffold14851_2742277_SNP | 2742277 | T | A |
| S_9348196 \| \| scaffold14851_2742755_SNP | 2742755 | G | A |
| S_9348212 \| \| scaffold14851_2743066_SNP | 2743066 | G | A |
| S_9348271 \| \| scaffold14851_2743282_SNP | 2743282 | C | A |
| S_9348311 \| \| scaffold14851_2744206_SNP | 2744206 | C | T |
| S_9348337 \| \| scaffold14851_2744312_SNP | 2744312 | A | G |
| S_9348345 \| \| scaffold14851_2744424_SNP | 2744424 | A | G |
| S_9348354 \| \| scaffold14851_2744489_SNP | 2744489 | A | C |
| S_9348364 \| \| scaffold14851_2744590_SNP | 2744590 | A | G |
| S_9348400 \| \| scaffold14851_2744837_SNP | 2744837 | C | T |
| S_9348406 \| \| scaffold14851_2744891_SNP | 2744891 | T | C |
| S_9348430 \| \| scaffold14851_2745209_SNP | 2745209 | C | T |
| S_9348468 \| \| scaffold14851_2745673_SNP | 2745673 | T | C |
| S_9348491 \| \| scaffold14851_2745960_SNP | 2745960 | T | C |
| S_9348524 \| \| scaffold14851_2746646_SNP | 2746646 | T | A |
| S_9348566 \| \| scaffold14851_2747364_SNP | 2747364 | C | A |
| S_9348764 \| \| scaffold14851_2751095_SNP | 2751095 | G | A |
| S_9348792 \| \| scaffold14851_2751681_SNP | 2751681 | T | C |
| S_9348829 \| \| scaffold14851_2752339_SNP | 2752339 | T | C |
| S_9348845 \| \| scaffold14851_2752708_SNP | 2752708 | T | C |
| S_9348878 \| \| scaffold14851_2753033_SNP | 2753033 | T | C |
| S_9348909 \| \| scaffold14851_2753369_SNP | 2753369 | G | A |
| S_9348920 \| \| scaffold14851_2753482_SNP | 2753482 | C | T |
| S_9348930 \| \| scaffold14851_2753556_SNP | 2753556 | T | C |
| S_9348938 \| \| scaffold14851_2753631_SNP | 2753631 | A | T |
| S_9348945 \| \| scaffold14851_2753651_SNP | 2753651 | C | T |
| S_9348952 \| \| scaffold14851_2753728_SNP | 2753728 | A | C |
| S_9349011 \| \| scaffold14851_2754954_SNP | 2754954 | C | G |
| S_9349015 \| \| scaffold14851_2755020_SNP | 2755020 | T | C |
| S_9349016 \| \| scaffold14851_2755031_SNP | 2755031 | T | C |
| S_9349024 \| \| scaffold14851_2755150_SNP | 2755150 | A | G |
| S_9349027 \| \| scaffold14851_2755161_SNP | 2755161 | C | T |
| S_9349047 \| \| scaffold14851_2755363_SNP | 2755363 | C | G |
| S_9349049 \| \| scaffold14851_2755370_SNP | 2755370 | C | A |
| S_9349054 \| \| scaffold14851_2755436_SNP | 2755436 | C | A |
| S_9349081 \| \| scaffold14851_2755693_SNP | 2755693 | G | T |
| S_9349083 \| \| scaffold14851_2755706_SNP | 2755706 | C | T |
| S_9349093 \| \| scaffold14851_2755758_SNP | 2755758 | G | A |
| S_9349169 \| \| scaffold14851_2757249_SNP | 2757249 | T | A |
| scaffold14851_2757435_SNP | 2757435 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9349192 \|\| scaffold14851_2757477_SNP | 2757477 | T | C |
| S_9349213 \|\| scaffold14851_2757757_SNP | 2757757 | A | G |
| S_9349366 \|\| scaffold14851_2759398_SNP | 2759398 | T | C |
| S_9349375 \|\| scaffold14851_2759587_SNP | 2759587 | C | T |
| S_9349385 \|\| scaffold14851_2760011_SNP | 2760011 | G | C |
| S_9349400 \|\| scaffold14851_2760217_SNP | 2760217 | T | A |
| S_9349488 \|\| scaffold14851_2761518_SNP | 2761518 | C | T |
| S_9349526 \|\| scaffold14851_2762052_SNP | 2762052 | G | C |
| S_9349538 \|\| scaffold14851_2762163_SNP | 2762163 | G | A |
| S_9349540 \|\| scaffold14851_2762168_SNP | 2762168 | C | T |
| S_9349541 \|\| scaffold14851_2762176_SNP | 2762176 | A | C |
| S_9349558 \|\| scaffold14851_2762361_SNP | 2762361 | A | C |
| S_9349578 \|\| scaffold14851_2762672_SNP | 2762672 | C | A |
| S_9349588 \|\| scaffold14851_2762701_SNP | 2762701 | G | C |
| S_9349633 \|\| scaffold14851_2762876_SNP | 2762876 | T | C |
| S_9349651 \|\| scaffold14851_2763061_SNP | 2763061 | C | T |
| S_9349663 \|\| scaffold14851_2763304_SNP | 2763304 | T | A |
| S_9349665 \|\| scaffold14851_2763317_SNP | 2763317 | C | T |
| S_9349674 \|\| scaffold14851_2763423_SNP | 2763423 | T | C |
| S_9349691 \|\| scaffold14851_2763782_SNP | 2763782 | A | T |
| S_9349698 \|\| scaffold14851_2763882_SNP | 2763882 | G | A |
| S_9349771 \|\| scaffold14851_2764576_SNP | 2764576 | A | T |
| S_9349783 \|\| scaffold14851_2764813_SNP | 2764813 | A | C |
| S_9350121 \|\| scaffold14851_2769238_SNP | 2769238 | C | T |
| S_9350372 \|\| scaffold14851_2772534_SNP | 2772534 | G | A |
| S_9350396 \|\| scaffold14851_2772860_SNP | 2772860 | C | G |
| S_9350403 \|\| scaffold14851_2772941_SNP | 2772941 | C | A |
| S_9350423 \|\| scaffold14851_2773310_SNP | 2773310 | G | C |
| S_9350429 \|\| scaffold14851_2773402_SNP | 2773402 | C | A |
| S_9350458 \|\| scaffold14851_2773778_SNP | 2773778 | G | A |
| S_9350477 \|\| scaffold14851_2773978_SNP | 2773978 | G | T |
| S_9350479 \|\| scaffold14851_2774009_SNP | 2774009 | G | A |
| scaffold14851_2774034_SNP | 2774034 | A | C |
| S_9350485 \|\| scaffold14851_2774087_SNP | 2774087 | C | G |
| S_9350488 \|\| scaffold14851_2774142_SNP | 2774142 | C | T |
| S_9350557 \|\| scaffold14851_2775229_SNP | 2775229 | G | A |
| S_9350560 \|\| scaffold14851_2775270_SNP | 2775270 | G | A |
| S_9350562 \|\| scaffold14851_2775281_SNP | 2775281 | T | C |
| S_9350580 \|\| scaffold14851_2775625_SNP | 2775625 | T | A |
| S_9350601 \|\| scaffold14851_2776054_SNP | 2776054 | G | A |
| S_9350624 \|\| scaffold14851_2776491_SNP | 2776491 | A | G |
| S_9350693 \|\| scaffold14851_2777497_SNP | 2777497 | C | T |
| S_9350754 \|\| scaffold14851_2778059_SNP | 2778059 | A | T |
| S_9350771 \|\| scaffold14851_2778199_SNP | 2778199 | A | T |
| S_9350793 \|\| scaffold14851_2778569_SNP | 2778569 | A | G |
| S_9350794 \|\| scaffold14851_2778580_SNP | 2778580 | G | A |
| S_9350795 \|\| scaffold14851_2778586_SNP | 2778586 | T | C |
| S_9350831 \|\| scaffold14851_2779352_SNP | 2779352 | T | A |
| S_9350864 \|\| scaffold14851_2779580_SNP | 2779580 | G | T |
| S_9350936 \|\| scaffold14851_2780511_SNP | 2780511 | A | C |
| S_9350951 \|\| scaffold14851_2780693_SNP | 2780693 | T | C |
| S_9351004 \|\| scaffold14851_2781339_SNP | 2781339 | G | T |
| S_9351026 \|\| scaffold14851_2781694_SNP | 2781694 | T | G |
| S_9351045 \|\| scaffold14851_2782003_SNP | 2782003 | G | T |
| S_9351213 \|\| scaffold14851_2783850_SNP | 2783850 | T | G |
| S_9351227 \|\| scaffold14851_2784030_SNP | 2784030 | T | C |
| S_9351236 \|\| scaffold14851_2784175_SNP | 2784175 | A | G |
| S_9351238 \|\| scaffold14851_2784204_SNP | 2784204 | C | T |
| S_9351244 \|\| scaffold14851_2784365_SNP | 2784365 | A | T |
| S_9351246 \|\| scaffold14851_2784385_SNP | 2784385 | G | A |
| S_9351247 \|\| scaffold14851_2784391_SNP | 2784391 | C | T |
| S_9351251 \|\| scaffold14851_2784435_SNP | 2784435 | T | A |
| S_9351255 \|\| scaffold14851_2784530_SNP | 2784530 | T | C |
| S_9351301 \|\| scaffold14851_2784968_SNP | 2784968 | C | G |
| S_9351339 \|\| scaffold14851_2785702_SNP | 2785702 | T | A |
| S_9351370 \|\| scaffold14851_2785799_SNP | 2785799 | C | A |
| S_9351374 \|\| scaffold14851_2785894_SNP | 2785894 | G | T |
| S_9351378 \|\| scaffold14851_2785975_SNP | 2785975 | A | G |
| S_9351414 \|\| scaffold14851_2786359_SNP | 2786359 | C | T |
| S_9351419 \|\| scaffold14851_2786395_SNP | 2786395 | C | T |
| S_9351429 \|\| scaffold14851_2786528_SNP | 2786528 | G | A |
| S_9351458 \|\| scaffold14851_2786825_SNP | 2786825 | T | C |
| S_9351461 \|\| scaffold14851_2786846_SNP | 2786846 | T | C |
| S_9351497 \|\| scaffold14851_2787192_SNP | 2787192 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9351502 \|\| scaffold14851_2787227_SNP | 2787227 | A | T |
| S_9351526 \|\| scaffold14851_2787393_SNP | 2787393 | C | G |
| S_9351530 \|\| scaffold14851_2787424_SNP | 2787424 | T | C |
| S_9351636 \|\| scaffold14851_2788186_SNP | 2788186 | T | A |
| S_9351827 \|\| scaffold14851_2789196_SNP | 2789196 | T | G |
| S_9351935 \|\| scaffold14851_2790222_SNP | 2790222 | C | T |
| S_9351990 \|\| scaffold14851_2790632_SNP | 2790632 | G | A |
| S_9351993 \|\| scaffold14851_2790696_SNP | 2790696 | C | T |
| S_9352012 \|\| scaffold14851_2791137_SNP | 2791137 | A | G |
| S_9352014 \|\| scaffold14851_2791157_SNP | 2791157 | G | A |
| S_9352016 \|\| scaffold14851_2791217_SNP | 2791217 | C | T |
| S_9352039 \|\| scaffold14851_2791408_SNP | 2791408 | T | C |
| S_9352042 \|\| scaffold14851_2791437_SNP | 2791437 | C | T |
| S_9352043 \|\| scaffold14851_2791442_SNP | 2791442 | C | T |
| S_9352064 \|\| scaffold14851_2791879_SNP | 2791879 | C | T |
| S_9352107 \|\| scaffold14851_2792545_SNP | 2792545 | C | T |
| S_9352108 \|\| scaffold14851_2792548_SNP | 2792548 | C | T |
| S_9352147 \|\| scaffold14851_2793212_SNP | 2793212 | C | A |
| S_9352168 \|\| scaffold14851_2793460_SNP | 2793460 | A | G |
| S_9352187 \|\| scaffold14851_2793648_SNP | 2793648 | T | C |
| S_9352192 \|\| scaffold14851_2793701_SNP | 2793701 | A | G |
| S_9352262 \|\| scaffold14851_2794093_SNP | 2794093 | A | G |
| S_9352276 \|\| scaffold14851_2794196_SNP | 2794196 | T | C |
| S_9352279 \|\| scaffold14851_2794231_SNP | 2794231 | G | A |
| S_9352393 \|\| scaffold14851_2795631_SNP | 2795631 | G | A |
| S_9352451 \|\| scaffold14851_2796393_SNP | 2796393 | A | G |
| S_9352479 \|\| scaffold14851_2796861_SNP | 2796861 | A | T |
| S_9352480 \|\| scaffold14851_2796862_SNP | 2796862 | C | T |
| S_9352520 \|\| scaffold14851_2797268_SNP | 2797268 | C | T |
| S_9352559 \|\| scaffold14851_2797469_SNP | 2797469 | G | C |
| S_9352610 \|\| scaffold14851_2798100_SNP | 2798100 | T | G |
| S_9352644 \|\| scaffold14851_2798481_SNP | 2798481 | G | A |
| S_9352645 \|\| scaffold14851_2798482_SNP | 2798482 | G | T |
| S_9352728 \|\| scaffold14851_2799396_SNP | 2799396 | G | C |
| S_9352791 \|\| scaffold14851_2799570_SNP | 2799570 | C | T |
| S_9352854 \|\| scaffold14851_2800069_SNP | 2800069 | G | T |
| S_9352855 \|\| scaffold14851_2800100_SNP | 2800100 | T | G |
| S_9352858 \|\| scaffold14851_2800188_SNP | 2800188 | A | C |
| S_9352912 \|\| scaffold14851_2800872_SNP | 2800872 | G | C |
| S_9353254 \|\| scaffold14851_2805547_SNP | 2805547 | G | T |
| S_9353255 \|\| scaffold14851_2805549_SNP | 2805549 | A | T |
| S_9353363 \|\| scaffold14851_2806307_SNP | 2806307 | G | A |
| S_9353390 \|\| scaffold14851_2806537_SNP | 2806537 | A | T |
| S_9353407 \|\| scaffold14851_2806694_SNP | 2806694 | G | A |
| S_9353408 \|\| scaffold14851_2806695_SNP | 2806695 | G | T |
| S_9353409 \|\| scaffold14851_2806710_SNP | 2806710 | T | G |
| S_9353411 \|\| scaffold14851_2806785_SNP | 2806785 | C | T |
| S_9353412 \|\| scaffold14851_2806798_SNP | 2806798 | G | A |
| S_9353413 \|\| scaffold14851_2806801_SNP | 2806801 | C | T |
| S_9353414 \|\| scaffold14851_2806802_SNP | 2806802 | T | A |
| S_9353415 \|\| scaffold14851_2806803_SNP | 2806803 | C | T |
| S_9353416 \|\| scaffold14851_2806837_SNP | 2806837 | C | T |
| S_9353424 \|\| scaffold14851_2806943_SNP | 2806943 | C | T |
| S_9353430 \|\| scaffold14851_2807022_SNP | 2807022 | G | C |
| S_9353434 \|\| scaffold14851_2807084_SNP | 2807084 | C | G |
| S_9353438 \|\| scaffold14851_2807119_SNP | 2807119 | G | A |
| S_9353441 \|\| scaffold14851_2807186_SNP | 2807186 | A | G |
| S_9353452 \|\| scaffold14851_2807355_SNP | 2807355 | C | A |
| S_9353523 \|\| scaffold14851_2808625_SNP | 2808625 | G | T |
| S_9353587 \|\| scaffold14851_2809394_SNP | 2809394 | G | T |
| S_9353590 \|\| scaffold14851_2809469_SNP | 2809469 | T | A |
| S_9353597 \|\| scaffold14851_2809598_SNP | 2809598 | T | C |
| S_9353634 \|\| scaffold14851_2810178_SNP | 2810178 | C | G |
| S_9353647 \|\| scaffold14851_2810410_SNP | 2810410 | A | T |
| S_9353654 \|\| scaffold14851_2810463_SNP | 2810463 | T | C |
| scaffold14851_2810701_SNP | 2810701 | A | T |
| scaffold14851_2810702_SNP | 2810702 | T | G |
| S_9353667 \|\| scaffold14851_2810703_SNP | 2810703 | T | A |
| S_9353670 \|\| scaffold14851_2810818_SNP | 2810818 | G | A |
| S_9353671 \|\| scaffold14851_2810855_SNP | 2810855 | C | A |
| S_9353673 \|\| scaffold14851_2810889_SNP | 2810889 | A | G |
| S_9353686 \|\| scaffold14851_2811053_SNP | 2811053 | T | G |
| S_9353689 \|\| scaffold14851_2811091_SNP | 2811091 | G | T |
| scaffold14851_2811209_SNP | 2811209 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9353727 \| \| scaffold14851_2811725_SNP | 2811725 | T | A |
| S_9353744 \| \| scaffold14851_2811954_SNP | 2811954 | A | T |
| S_9353769 \| \| scaffold14851_2812436_SNP | 2812436 | C | A |
| S_9353782 \| \| scaffold14851_2812708_SNP | 2812708 | C | A |
| scaffold14851_2812883_SNP | 2812883 | G | T |
| scaffold14851_2812888_SNP | 2812888 | A | T |
| S_9353842 \| \| scaffold14851_2813466_SNP | 2813466 | G | A |
| S_9353978 \| \| scaffold14851_2814975_SNP | 2814975 | A | T |
| S_9354090 \| \| scaffold14851_2816483_SNP | 2816483 | A | G |
| S_9354105 \| \| scaffold14851_2816599_SNP | 2816599 | C | T |
| S_9354272 \| \| scaffold14851_2818677_SNP | 2818677 | G | A |
| S_9354361 \| \| scaffold14851_2819045_SNP | 2819045 | T | C |
| S_9354372 \| \| scaffold14851_2819293_SNP | 2819293 | T | A |
| S_9354373 \| \| scaffold14851_2819308_SNP | 2819308 | A | T |
| S_9354374 \| \| scaffold14851_2819338_SNP | 2819338 | C | A |
| S_9354379 \| \| scaffold14851_2819418_SNP | 2819418 | A | C |
| S_9354380 \| \| scaffold14851_2819419_SNP | 2819419 | G | A |
| S_9354381 \| \| scaffold14851_2819420_SNP | 2819420 | G | T |
| S_9354382 \| \| scaffold14851_2819438_SNP | 2819438 | C | G |
| S_9354405 \| \| scaffold14851_2820002_SNP | 2820002 | T | G |
| S_9354422 \| \| scaffold14851_2820202_SNP | 2820202 | T | A |
| S_9354433 \| \| scaffold14851_2820339_SNP | 2820339 | G | C |
| S_9354452 \| \| scaffold14851_2820692_SNP | 2820692 | T | A |
| S_9354454 \| \| scaffold14851_2820739_SNP | 2820739 | C | A |
| S_9354459 \| \| scaffold14851_2820890_SNP | 2820890 | A | T |
| S_9354464 \| \| scaffold14851_2821029_SNP | 2821029 | G | T |
| S_9354467 \| \| scaffold14851_2821082_SNP | 2821082 | G | A |
| S_9354470 \| \| scaffold14851_2821172_SNP | 2821172 | G | T |
| S_9354472 \| \| scaffold14851_2821216_SNP | 2821216 | C | T |
| S_9354520 \| \| scaffold14851_2821756_SNP | 2821756 | G | T |
| S_9354772 \| \| scaffold14851_2824670_SNP | 2824670 | G | T |
| S_9354821 \| \| scaffold14851_2825199_SNP | 2825199 | G | A |
| S_9354972 \| \| scaffold14851_2826018_SNP | 2826018 | G | T |
| S_9354988 \| \| scaffold14851_2826375_SNP | 2826375 | G | A |
| S_9354995 \| \| scaffold14851_2826497_SNP | 2826497 | T | A |
| S_9355218 \| \| scaffold14851_2828150_SNP | 2828150 | T | A |
| S_9355224 \| \| scaffold14851_2828270_SNP | 2828270 | A | G |
| S_9355279 \| \| scaffold14851_2829288_SNP | 2829288 | A | G |
| S_9355381 \| \| scaffold14851_2830646_SNP | 2830646 | A | G |
| S_9355421 \| \| scaffold14851_2831322_SNP | 2831322 | G | T |
| S_9355458 \| \| scaffold14851_2831933_SNP | 2831933 | T | C |
| S_9355505 \| \| scaffold14851_2832888_SNP | 2832888 | T | A |
| S_9355549 \| \| scaffold14851_2833432_SNP | 2833432 | A | T |
| S_9355570 \| \| scaffold14851_2833769_SNP | 2833769 | C | A |
| S_9355607 \| \| scaffold14851_2834265_SNP | 2834265 | G | C |
| S_9355609 \| \| scaffold14851_2834352_SNP | 2834352 | C | A |
| S_9355620 \| \| scaffold14851_2834531_SNP | 2834531 | A | C |
| S_9355643 \| \| scaffold14851_2834834_SNP | 2834834 | T | C |
| S_9355698 \| \| scaffold14851_2834988_SNP | 2834988 | G | T |
| S_9355700 \| \| scaffold14851_2835122_SNP | 2835122 | A | G |
| S_9355763 \| \| scaffold14851_2835901_SNP | 2835901 | A | T |
| S_9355781 \| \| scaffold14851_2836251_SNP | 2836251 | C | T |
| S_9355961 \| \| scaffold14851_2837856_SNP | 2837856 | A | C |
| S_9355985 \| \| scaffold14851_2838348_SNP | 2838348 | G | T |
| S_9356030 \| \| scaffold14851_2839257_SNP | 2839257 | G | A |
| S_9356077 \| \| scaffold14851_2839744_SNP | 2839744 | A | C |
| S_9356105 \| \| scaffold14851_2840033_SNP | 2840033 | A | T |
| S_9356127 \| \| scaffold14851_2840198_SNP | 2840198 | C | T |
| scaffold14851_2840379_SNP | 2840379 | C | T |
| S_9356209 \| \| scaffold14851_2840939_SNP | 2840939 | A | C |
| S_9356218 \| \| scaffold14851_2841025_SNP | 2841025 | C | T |
| S_9356220 \| \| scaffold14851_2841062_SNP | 2841062 | A | G |
| S_9356224 \| \| scaffold14851_2841138_SNP | 2841138 | T | C |
| S_9356225 \| \| scaffold14851_2841147_SNP | 2841147 | G | A |
| S_9356227 \| \| scaffold14851_2841156_SNP | 2841156 | T | G |
| S_9356230 \| \| scaffold14851_2841166_SNP | 2841166 | C | T |
| S_9356249 \| \| scaffold14851_2841518_SNP | 2841518 | G | A |
| S_9356258 \| \| scaffold14851_2841622_SNP | 2841622 | G | C |
| S_9356314 \| \| scaffold14851_2842440_SNP | 2842440 | G | A |
| S_9356418 \| \| scaffold14851_2843455_SNP | 2843455 | G | A |
| S_9356421 \| \| scaffold14851_2843459_SNP | 2843459 | G | C |
| S_9356423 \| \| scaffold14851_2843477_SNP | 2843477 | G | A |
| S_9356454 \| \| scaffold14851_2844191_SNP | 2844191 | C | A |
| S_9356464 \| \| scaffold14851_2844244_SNP | 2844244 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9356480 \| \| scaffold14851_2844377_SNP | 2844377 | G | A |
| S_9356502 \| \| scaffold14851_2844517_SNP | 2844517 | T | A |
| S_9356552 \| \| scaffold14851_2845055_SNP | 2845055 | G | T |
| S_9356574 \| \| scaffold14851_2845421_SNP | 2845421 | T | G |
| S_9356615 \| \| scaffold14851_2846143_SNP | 2846143 | A | T |
| S_9356617 \| \| scaffold14851_2846152_SNP | 2846152 | A | T |
| S_9356618 \| \| scaffold14851_2846157_SNP | 2846157 | C | A |
| S_9356770 \| \| scaffold14851_2847664_SNP | 2847664 | T | C |
| S_9356831 \| \| scaffold14851_2848762_SNP | 2848762 | A | G |
| S_9356832 \| \| scaffold14851_2848783_SNP | 2848783 | G | A |
| S_9356833 \| \| scaffold14851_2848791_SNP | 2848791 | C | T |
| S_9356834 \| \| scaffold14851_2848827_SNP | 2848827 | C | T |
| S_9356859 \| \| scaffold14851_2849143_SNP | 2849143 | T | C |
| S_9356914 \| \| scaffold14851_2849343_SNP | 2849343 | T | G |
| S_9356919 \| \| scaffold14851_2849413_SNP | 2849413 | G | A |
| S_9356922 \| \| scaffold14851_2849460_SNP | 2849460 | C | A |
| S_9356925 \| \| scaffold14851_2849514_SNP | 2849514 | A | T |
| S_9356930 \| \| scaffold14851_2849585_SNP | 2849585 | G | C |
| S_9356931 \| \| scaffold14851_2849593_SNP | 2849593 | C | G |
| S_9356933 \| \| scaffold14851_2849628_SNP | 2849628 | T | G |
| S_9356936 \| \| scaffold14851_2849645_SNP | 2849645 | A | C |
| S_9356938 \| \| scaffold14851_2849834_SNP | 2849834 | G | T |
| S_9356948 \| \| scaffold14851_2850010_SNP | 2850010 | T | A |
| S_9356953 \| \| scaffold14851_2850126_SNP | 2850126 | C | G |
| S_9356964 \| \| scaffold14851_2850319_SNP | 2850319 | A | G |
| S_9357026 \| \| scaffold14851_2851226_SNP | 2851226 | A | G |
| S_9357028 \| \| scaffold14851_2851235_SNP | 2851235 | C | T |
| S_9357031 \| \| scaffold14851_2851282_SNP | 2851282 | A | G |
| S_9357032 \| \| scaffold14851_2851283_SNP | 2851283 | A | T |
| S_9357061 \| \| scaffold14851_2851783_SNP | 2851783 | T | C |
| S_9357062 \| \| scaffold14851_2851792_SNP | 2851792 | T | C |
| S_9357063 \| \| scaffold14851_2851799_SNP | 2851799 | A | T |
| S_9357078 \| \| scaffold14851_2852015_SNP | 2852015 | T | C |
| S_9357086 \| \| scaffold14851_2852342_SNP | 2852342 | A | G |
| S_9357087 \| \| scaffold14851_2852356_SNP | 2852356 | G | A |
| S_9357088 \| \| scaffold14851_2852362_SNP | 2852362 | A | T |
| S_9357090 \| \| scaffold14851_2852385_SNP | 2852385 | G | C |
| S_9357092 \| \| scaffold14851_2852443_SNP | 2852443 | A | G |
| S_9357096 \| \| scaffold14851_2852495_SNP | 2852495 | A | G |
| S_9357101 \| \| scaffold14851_2852542_SNP | 2852542 | C | T |
| S_9357105 \| \| scaffold14851_2852617_SNP | 2852617 | A | T |
| S_9357116 \| \| scaffold14851_2852719_SNP | 2852719 | C | A |
| S_9357121 \| \| scaffold14851_2852778_SNP | 2852778 | A | C |
| S_9357127 \| \| scaffold14851_2852925_SNP | 2852925 | A | T |
| S_9357145 \| \| scaffold14851_2853172_SNP | 2853172 | C | T |
| S_9357197 \| \| scaffold14851_2853867_SNP | 2853867 | T | G |
| S_9357200 \| \| scaffold14851_2853877_SNP | 2853877 | T | G |
| S_9357206 \| \| scaffold14851_2853935_SNP | 2853935 | A | T |
| S_9357251 \| \| scaffold14851_2854130_SNP | 2854130 | C | A |
| scaffold14851_2854131_SNP | 2854131 | G | A |
| S_9357278 \| \| scaffold14851_2854354_SNP | 2854354 | A | G |
| S_9357305 \| \| scaffold14851_2854856_SNP | 2854856 | T | G |
| S_9357315 \| \| scaffold14851_2855014_SNP | 2855014 | G | T |
| S_9357331 \| \| scaffold14851_2855199_SNP | 2855199 | T | C |
| S_9357361 \| \| scaffold14851_2855416_SNP | 2855416 | G | A |
| S_9357366 \| \| scaffold14851_2855429_SNP | 2855429 | C | T |
| scaffold14851_2855492_SNP | 2855492 | T | C |
| S_9357393 \| \| scaffold14851_2855567_SNP | 2855567 | T | C |
| S_9357398 \| \| scaffold14851_2855608_SNP | 2855608 | A | G |
| S_9357604 \| \| scaffold14851_2858253_SNP | 2858253 | A | G |
| S_9357788 \| \| scaffold14851_2861107_SNP | 2861107 | C | G |
| S_9357833 \| \| scaffold14851_2861676_SNP | 2861676 | G | T |
| S_9357910 \| \| scaffold14851_2862036_SNP | 2862036 | G | A |
| S_9357980 \| \| scaffold14851_2862765_SNP | 2862765 | T | A |
| S_9357981 \| \| scaffold14851_2862774_SNP | 2862774 | T | G |
| S_9358054 \| \| scaffold14851_2863367_SNP | 2863367 | G | A |
| S_9358055 \| \| scaffold14851_2863409_SNP | 2863409 | T | C |
| S_9358064 \| \| scaffold14851_2863571_SNP | 2863571 | C | A |
| S_9358092 \| \| scaffold14851_2863924_SNP | 2863924 | C | T |
| S_9358128 \| \| scaffold14851_2864259_SNP | 2864259 | T | C |
| S_9358177 \| \| scaffold14851_2865015_SNP | 2865015 | G | A |
| S_9358239 \| \| scaffold14851_2865671_SNP | 2865671 | T | G |
| S_9358315 \| \| scaffold14851_2866139_SNP | 2866139 | G | A |
| S_9358354 \| \| scaffold14851_2866812_SNP | 2866812 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9358357 \| \| scaffold14851_2866901_SNP | 2866901 | C | A |
| S_9358360 \| \| scaffold14851_2866923_SNP | 2866923 | A | G |
| S_9358371 \| \| scaffold14851_2867306_SNP | 2867306 | C | T |
| S_9358475 \| \| scaffold14851_2868175_SNP | 2868175 | A | G |
| S_9358476 \| \| scaffold14851_2868183_SNP | 2868183 | A | T |
| S_9358477 \| \| scaffold14851_2868204_SNP | 2868204 | T | C |
| S_9358483 \| \| scaffold14851_2868356_SNP | 2868356 | G | A |
| S_9358485 \| \| scaffold14851_2868373_SNP | 2868373 | A | G |
| S_9358486 \| \| scaffold14851_2868408_SNP | 2868408 | G | A |
| S_9358488 \| \| scaffold14851_2868437_SNP | 2868437 | A | G |
| S_9358491 \| \| scaffold14851_2868450_SNP | 2868450 | T | C |
| S_9358493 \| \| scaffold14851_2868492_SNP | 2868492 | T | C |
| S_9358494 \| \| scaffold14851_2868528_SNP | 2868528 | A | G |
| S_9358497 \| \| scaffold14851_2868608_SNP | 2868608 | A | G |
| S_9358498 \| \| scaffold14851_2868637_SNP | 2868637 | G | A |
| S_9358520 \| \| scaffold14851_2869019_SNP | 2869019 | G | T |
| S_9358521 \| \| scaffold14851_2869047_SNP | 2869047 | C | T |
| S_9358525 \| \| scaffold14851_2869137_SNP | 2869137 | A | T |
| S_9358528 \| \| scaffold14851_2869159_SNP | 2869159 | A | G |
| S_9358530 \| \| scaffold14851_2869196_SNP | 2869196 | G | A |
| S_9358531 \| \| scaffold14851_2869206_SNP | 2869206 | C | T |
| S_9358533 \| \| scaffold14851_2869219_SNP | 2869219 | A | G |
| S_9358535 \| \| scaffold14851_2869317_SNP | 2869317 | A | G |
| S_9358559 \| \| scaffold14851_2869700_SNP | 2869700 | T | G |
| S_9358675 \| \| scaffold14851_2871091_SNP | 2871091 | A | C |
| S_9358685 \| \| scaffold14851_2871291_SNP | 2871291 | T | G |
| S_9358700 \| \| scaffold14851_2871537_SNP | 2871537 | C | G |
| S_9358865 \| \| scaffold14851_2873332_SNP | 2873332 | G | C |
| S_9358878 \| \| scaffold14851_2873593_SNP | 2873593 | C | G |
| S_9358899 \| \| scaffold14851_2873848_SNP | 2873848 | A | G |
| S_9358989 \| \| scaffold14851_2875168_SNP | 2875168 | T | A |
| S_9358996 \| \| scaffold14851_2875301_SNP | 2875301 | C | T |
| S_9359033 \| \| scaffold14851_2876107_SNP | 2876107 | T | A |
| S_9359098 \| \| scaffold14851_2877168_SNP | 2877168 | A | C |
| S_9359105 \| \| scaffold14851_2877261_SNP | 2877261 | C | T |
| S_9359315 \| \| scaffold14851_2880193_SNP | 2880193 | A | G |
| S_9359374 \| \| scaffold14851_2880871_SNP | 2880871 | C | A |
| S_9359378 \| \| scaffold14851_2880897_SNP | 2880897 | T | G |
| scaffold14851_2881268_SNP | 2881268 | T | C |
| S_9359425 \| \| scaffold14851_2881570_SNP | 2881570 | C | T |
| S_9359429 \| \| scaffold14851_2881615_SNP | 2881615 | G | T |
| S_9359442 \| \| scaffold14851_2881888_SNP | 2881888 | A | T |
| S_9359507 \| \| scaffold14851_2882608_SNP | 2882608 | T | C |
| S_9359527 \| \| scaffold14851_2882889_SNP | 2882889 | C | T |
| S_9359555 \| \| scaffold14851_2883387_SNP | 2883387 | G | C |
| S_9359669 \| \| scaffold14851_2884502_SNP | 2884502 | A | T |
| S_9359718 \| \| scaffold14851_2885198_SNP | 2885198 | C | A |
| S_9359722 \| \| scaffold14851_2885264_SNP | 2885264 | G | A |
| S_9359740 \| \| scaffold14851_2885472_SNP | 2885472 | G | A |
| S_9360158 \| \| scaffold14851_2888765_SNP | 2888765 | A | C |
| S_9360172 \| \| scaffold14851_2888902_SNP | 2888902 | C | G |
| S_9360248 \| \| scaffold14851_2890301_SNP | 2890301 | G | T |
| S_9360257 \| \| scaffold14851_2890523_SNP | 2890523 | C | A |
| S_9360282 \| \| scaffold14851_2890986_SNP | 2890986 | G | A |
| S_9360285 \| \| scaffold14851_2891029_SNP | 2891029 | G | A |
| S_9360296 \| \| scaffold14851_2891215_SNP | 2891215 | A | G |
| S_9360297 \| \| scaffold14851_2891226_SNP | 2891226 | T | G |
| S_9360299 \| \| scaffold14851_2891336_SNP | 2891336 | T | C |
| S_9360300 \| \| scaffold14851_2891344_SNP | 2891344 | T | A |
| S_9360502 \| \| scaffold14851_2893938_SNP | 2893938 | G | T |
| S_9360510 \| \| scaffold14851_2894062_SNP | 2894062 | A | G |
| S_9360557 \| \| scaffold14851_2894880_SNP | 2894880 | C | A |
| S_9360560 \| \| scaffold14851_2894930_SNP | 2894930 | G | C |
| S_9360564 \| \| scaffold14851_2895051_SNP | 2895051 | C | T |
| S_9360591 \| \| scaffold14851_2895493_SNP | 2895493 | T | C |
| S_9360592 \| \| scaffold14851_2895502_SNP | 2895502 | G | T |
| S_9360593 \| \| scaffold14851_2895513_SNP | 2895513 | T | C |
| S_9360609 \| \| scaffold14851_2895782_SNP | 2895782 | C | G |
| S_9360614 \| \| scaffold14851_2895878_SNP | 2895878 | C | T |
| S_9360670 \| \| scaffold14851_2896298_SNP | 2896298 | A | G |
| S_9360680 \| \| scaffold14851_2896518_SNP | 2896518 | C | T |
| S_9360685 \| \| scaffold14851_2896578_SNP | 2896578 | A | C |
| S_9360692 \| \| scaffold14851_2896724_SNP | 2896724 | A | G |
| S_9360693 \| \| scaffold14851_2896739_SNP | 2896739 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9360695 \| \| scaffold14851_2896774_SNP | 2896774 | A | G |
| S_9360696 \| \| scaffold14851_2896805_SNP | 2896805 | A | C |
| S_9360728 \| \| scaffold14851_2897183_SNP | 2897183 | G | A |
| S_9360729 \| \| scaffold14851_2897207_SNP | 2897207 | G | A |
| S_9360778 \| \| scaffold14851_2898010_SNP | 2898010 | G | A |
| S_9360791 \| \| scaffold14851_2898155_SNP | 2898155 | T | G |
| S_9360830 \| \| scaffold14851_2898747_SNP | 2898747 | G | T |
| S_9360847 \| \| scaffold14851_2899123_SNP | 2899123 | T | A |
| S_9360851 \| \| scaffold14851_2899169_SNP | 2899169 | A | G |
| S_9360971 \| \| scaffold14851_2901136_SNP | 2901136 | C | A |
| S_9361012 \| \| scaffold14851_2901790_SNP | 2901790 | G | A |
| S_9361036 \| \| scaffold14851_2901852_SNP | 2901852 | C | T |
| S_9361053 \| \| scaffold14851_2902192_SNP | 2902192 | T | C |
| S_9361144 \| \| scaffold14851_2903501_SNP | 2903501 | T | C |
| S_9361259 \| \| scaffold14851_2904869_SNP | 2904869 | T | A |
| S_9361272 \| \| scaffold14851_2904925_SNP | 2904925 | A | T |
| S_9361278 \| \| scaffold14851_2904942_SNP | 2904942 | G | A |
| S_9361313 \| \| scaffold14851_2905088_SNP | 2905088 | C | T |
| S_9361335 \| \| scaffold14851_2905446_SNP | 2905446 | G | A |
| S_9361338 \| \| scaffold14851_2905457_SNP | 2905457 | T | C |
| S_9361339 \| \| scaffold14851_2905478_SNP | 2905478 | C | A |
| S_9361347 \| \| scaffold14851_2905565_SNP | 2905565 | T | C |
| S_9361361 \| \| scaffold14851_2905788_SNP | 2905788 | A | C |
| S_9361436 \| \| scaffold14851_2907176_SNP | 2907176 | C | T |
| S_9361582 \| \| scaffold14851_2912143_SNP | 2912143 | T | C |
| S_9361603 \| \| scaffold14851_2912333_SNP | 2912333 | A | T |
| S_9361620 \| \| scaffold14851_2912487_SNP | 2912487 | G | A |
| S_9361637 \| \| scaffold14851_2912616_SNP | 2912616 | A | G |
| S_9361646 \| \| scaffold14851_2912667_SNP | 2912667 | T | C |
| S_9361865 \| \| scaffold14851_2915538_SNP | 2915538 | T | G |
| S_9361880 \| \| scaffold14851_2915801_SNP | 2915801 | A | G |
| S_9361881 \| \| scaffold14851_2915802_SNP | 2915802 | C | T |
| S_9362103 \| \| scaffold14851_2918292_SNP | 2918292 | C | T |
| S_9362169 \| \| scaffold14851_2919300_SNP | 2919300 | A | C |
| S_9362209 \| \| scaffold14851_2920105_SNP | 2920105 | C | T |
| S_9362268 \| \| scaffold14851_2921151_SNP | 2921151 | G | C |
| S_9362386 \| \| scaffold14851_2922760_SNP | 2922760 | T | A |
| S_9362390 \| \| scaffold14851_2922778_SNP | 2922778 | T | G |
| S_9362414 \| \| scaffold14851_2923164_SNP | 2923164 | G | A |
| S_9362427 \| \| scaffold14851_2923462_SNP | 2923462 | G | A |
| S_9362445 \| \| scaffold14851_2923832_SNP | 2923832 | C | T |
| S_9362460 \| \| scaffold14851_2924097_SNP | 2924097 | C | T |
| S_9362461 \| \| scaffold14851_2924102_SNP | 2924102 | C | T |
| S_9362483 \| \| scaffold14851_2924506_SNP | 2924506 | G | T |
| S_9362488 \| \| scaffold14851_2924637_SNP | 2924637 | G | C |
| S_9362490 \| \| scaffold14851_2924666_SNP | 2924666 | G | A |
| S_9362502 \| \| scaffold14851_2924840_SNP | 2924840 | G | C |
| S_9362504 \| \| scaffold14851_2924874_SNP | 2924874 | C | T |
| S_9362505 \| \| scaffold14851_2924881_SNP | 2924881 | C | T |
| S_9362571 \| \| scaffold14851_2925343_SNP | 2925343 | A | T |
| S_9362578 \| \| scaffold14851_2925400_SNP | 2925400 | C | T |
| S_9362587 \| \| scaffold14851_2925569_SNP | 2925569 | T | C |
| S_9362604 \| \| scaffold14851_2925677_SNP | 2925677 | T | A |
| S_9362632 \| \| scaffold14851_2926356_SNP | 2926356 | G | T |
| S_9362633 \| \| scaffold14851_2926386_SNP | 2926386 | A | G |
| S_9362652 \| \| scaffold14851_2926667_SNP | 2926667 | A | G |
| S_9362664 \| \| scaffold14851_2926877_SNP | 2926877 | A | G |
| S_9362666 \| \| scaffold14851_2927047_SNP | 2927047 | C | A |
| S_9362677 \| \| scaffold14851_2927142_SNP | 2927142 | A | G |
| S_9362703 \| \| scaffold14851_2927417_SNP | 2927417 | G | T |
| S_9362710 \| \| scaffold14851_2927579_SNP | 2927579 | C | T |
| S_9362711 \| \| scaffold14851_2927580_SNP | 2927580 | A | G |
| S_9362718 \| \| scaffold14851_2927652_SNP | 2927652 | T | C |
| S_9362728 \| \| scaffold14851_2927868_SNP | 2927868 | C | T |
| S_9362765 \| \| scaffold14851_2928348_SNP | 2928348 | C | G |
| S_9362788 \| \| scaffold14851_2928703_SNP | 2928703 | T | C |
| S_9362801 \| \| scaffold14851_2928949_SNP | 2928949 | G | A |
| S_9362830 \| \| scaffold14851_2929364_SNP | 2929364 | A | C |
| S_9362935 \| \| scaffold14851_2930843_SNP | 2930843 | A | G |
| S_9362957 \| \| scaffold14851_2931265_SNP | 2931265 | A | C |
| S_9362964 \| \| scaffold14851_2931433_SNP | 2931433 | C | A |
| S_9362974 \| \| scaffold14851_2931555_SNP | 2931555 | A | T |
| S_9362975 \| \| scaffold14851_2931569_SNP | 2931569 | A | T |
| S_9362980 \| \| scaffold14851_2931654_SNP | 2931654 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9362981 \| \| scaffold14851_2931694_SNP | 2931694 | G | A |
| S_9362982 \| \| scaffold14851_2931699_SNP | 2931699 | T | C |
| S_9362983 \| \| scaffold14851_2931707_SNP | 2931707 | G | C |
| S_9363005 \| \| scaffold14851_2932118_SNP | 2932118 | A | G |
| S_9363087 \| \| scaffold14851_2933256_SNP | 2933256 | A | G |
| S_9363140 \| \| scaffold14851_2934092_SNP | 2934092 | G | T |
| S_9363215 \| \| scaffold14851_2934986_SNP | 2934986 | T | A |
| S_9363230 \| \| scaffold14851_2935093_SNP | 2935093 | A | G |
| S_9363241 \| \| scaffold14851_2935127_SNP | 2935127 | G | T |
| S_9363368 \| \| scaffold14851_2936934_SNP | 2936934 | C | T |
| S_9363373 \| \| scaffold14851_2936950_SNP | 2936950 | T | C |
| S_9363376 \| \| scaffold14851_2937041_SNP | 2937041 | G | A |
| S_9363388 \| \| scaffold14851_2937139_SNP | 2937139 | T | C |
| S_9363392 \| \| scaffold14851_2937209_SNP | 2937209 | A | G |
| S_9363405 \| \| scaffold14851_2937373_SNP | 2937373 | T | C |
| S_9363409 \| \| scaffold14851_2937391_SNP | 2937391 | G | A |
| S_9363457 \| \| scaffold14851_2937864_SNP | 2937864 | T | C |
| S_9363535 \| \| scaffold14851_2939495_SNP | 2939495 | A | T |
| S_9363552 \| \| scaffold14851_2939875_SNP | 2939875 | C | A |
| S_9363559 \| \| scaffold14851_2940019_SNP | 2940019 | A | C |
| S_9363574 \| \| scaffold14851_2940363_SNP | 2940363 | C | A |
| S_9363699 \| \| scaffold14851_2941602_SNP | 2941602 | C | T |
| S_9363878 \| \| scaffold14851_2944910_SNP | 2944910 | G | T |
| S_9363923 \| \| scaffold14851_2945793_SNP | 2945793 | G | A |
| S_9363930 \| \| scaffold14851_2945849_SNP | 2945849 | A | C |
| S_9363957 \| \| scaffold14851_2946222_SNP | 2946222 | G | T |
| S_9364029 \| \| scaffold14851_2946806_SNP | 2946806 | G | A |
| S_9364033 \| \| scaffold14851_2946851_SNP | 2946851 | C | G |
| S_9364213 \| \| scaffold14851_2948844_SNP | 2948844 | T | A |
| S_9364215 \| \| scaffold14851_2948845_SNP | 2948845 | C | A |
| S_9364276 \| \| scaffold14851_2949559_SNP | 2949559 | T | G |
| S_9364302 \| \| scaffold14851_2949917_SNP | 2949917 | A | T |
| S_9364454 \| \| scaffold14851_2951185_SNP | 2951185 | A | C |
| S_9364459 \| \| scaffold14851_2951256_SNP | 2951256 | G | A |
| S_9364462 \| \| scaffold14851_2951271_SNP | 2951271 | A | T |
| S_9364496 \| \| scaffold14851_2951888_SNP | 2951888 | C | T |
| S_9364497 \| \| scaffold14851_2951894_SNP | 2951894 | A | T |
| S_9364510 \| \| scaffold14851_2951990_SNP | 2951990 | T | G |
| S_9364528 \| \| scaffold14851_2952118_SNP | 2952118 | C | G |
| S_9364538 \| \| scaffold14851_2952208_SNP | 2952208 | C | T |
| S_9364559 \| \| scaffold14851_2952393_SNP | 2952393 | A | C |
| S_9364573 \| \| scaffold14851_2952569_SNP | 2952569 | G | A |
| S_9364633 \| \| scaffold14851_2953413_SNP | 2953413 | A | C |
| S_9364644 \| \| scaffold14851_2953586_SNP | 2953586 | T | C |
| S_9364678 \| \| scaffold14851_2953955_SNP | 2953955 | C | T |
| scaffold14851_2954447_SNP | 2954447 | G | T |
| S_9364852 \| \| scaffold14851_2955280_SNP | 2955280 | C | T |
| S_9364988 \| \| scaffold14851_2956341_SNP | 2956341 | T | G |
| S_9364996 \| \| scaffold14851_2956441_SNP | 2956441 | A | G |
| S_9365079 \| \| scaffold14851_2957364_SNP | 2957364 | G | C |
| S_9365110 \| \| scaffold14851_2957651_SNP | 2957651 | T | C |
| S_9365242 \| \| scaffold14851_2959605_SNP | 2959605 | C | T |
| S_9365245 \| \| scaffold14851_2959660_SNP | 2959660 | A | G |
| S_9365256 \| \| scaffold14851_2959828_SNP | 2959828 | T | C |
| S_9365262 \| \| scaffold14851_2959882_SNP | 2959882 | A | T |
| S_9365268 \| \| scaffold14851_2960030_SNP | 2960030 | G | A |
| S_9365269 \| \| scaffold14851_2960035_SNP | 2960035 | G | A |
| S_9365385 \| \| scaffold14851_2962585_SNP | 2962585 | C | T |
| S_9365393 \| \| scaffold14851_2962849_SNP | 2962849 | C | A |
| S_9365416 \| \| scaffold14851_2963215_SNP | 2963215 | T | G |
| S_9365418 \| \| scaffold14851_2963234_SNP | 2963234 | T | G |
| S_9365448 \| \| scaffold14851_2963601_SNP | 2963601 | G | A |
| S_9365463 \| \| scaffold14851_2963772_SNP | 2963772 | C | T |
| S_9365574 \| \| scaffold14851_2965356_SNP | 2965356 | A | G |
| scaffold14851_2965623_SNP | 2965623 | A | G |
| S_9365848 \| \| scaffold14851_2967857_SNP | 2967857 | A | C |
| S_9365853 \| \| scaffold14851_2968158_SNP | 2968158 | A | G |
| S_9365877 \| \| scaffold14851_2968507_SNP | 2968507 | G | T |
| S_9365878 \| \| scaffold14851_2968516_SNP | 2968516 | G | C |
| S_9365887 \| \| scaffold14851_2968676_SNP | 2968676 | A | G |
| S_9365890 \| \| scaffold14851_2968862_SNP | 2968862 | A | G |
| S_9365892 \| \| scaffold14851_2968866_SNP | 2968866 | C | T |
| S_9365967 \| \| scaffold14851_2969812_SNP | 2969812 | T | C |
| S_9366054 \| \| scaffold14851_2970773_SNP | 2970773 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9366108 \| \| scaffold14851_2971276_SNP | 2971276 | G | A |
| S_9366184 \| \| scaffold14851_2971616_SNP | 2971616 | C | G |
| S_9366200 \| \| scaffold14851_2971910_SNP | 2971910 | T | G |
| S_9366201 \| \| scaffold14851_2971922_SNP | 2971922 | T | A |
| S_9366205 \| \| scaffold14851_2971970_SNP | 2971970 | T | G |
| S_9366241 \| \| scaffold14851_2972510_SNP | 2972510 | T | G |
| S_9366246 \| \| scaffold14851_2972586_SNP | 2972586 | C | T |
| S_9366265 \| \| scaffold14851_2972784_SNP | 2972784 | T | C |
| S_9366303 \| \| scaffold14851_2973254_SNP | 2973254 | G | A |
| S_9366392 \| \| scaffold14851_2973837_SNP | 2973837 | G | T |
| S_9366557 \| \| scaffold14851_2976268_SNP | 2976268 | T | C |
| S_9366568 \| \| scaffold14851_2976482_SNP | 2976482 | G | A |
| S_9366588 \| \| scaffold14851_2976751_SNP | 2976751 | C | A |
| S_9366608 \| \| scaffold14851_2976995_SNP | 2976995 | A | G |
| S_9366694 \| \| scaffold14851_2977963_SNP | 2977963 | C | A |
| S_9366696 \| \| scaffold14851_2977971_SNP | 2977971 | T | A |
| S_9366697 \| \| scaffold14851_2977976_SNP | 2977976 | A | T |
| S_9366744 \| \| scaffold14851_2978407_SNP | 2978407 | A | G |
| S_9366802 \| \| scaffold14851_2979208_SNP | 2979208 | G | A |
| S_9366804 \| \| scaffold14851_2979228_SNP | 2979228 | C | T |
| S_9366805 \| \| scaffold14851_2979229_SNP | 2979229 | G | C |
| S_9366806 \| \| scaffold14851_2979230_SNP | 2979230 | G | A |
| S_9366810 \| \| scaffold14851_2979312_SNP | 2979312 | A | G |
| S_9366812 \| \| scaffold14851_2979353_SNP | 2979353 | A | C |
| S_9366817 \| \| scaffold14851_2979416_SNP | 2979416 | G | T |
| S_9366818 \| \| scaffold14851_2979438_SNP | 2979438 | T | C |
| S_9366931 \| \| scaffold14851_2981169_SNP | 2981169 | A | C |
| S_9366934 \| \| scaffold14851_2981220_SNP | 2981220 | C | T |
| S_9366955 \| \| scaffold14851_2981420_SNP | 2981420 | C | A |
| S_9366967 \| \| scaffold14851_2981613_SNP | 2981613 | T | C |
| S_9366968 \| \| scaffold14851_2981631_SNP | 2981631 | A | C |
| S_9366971 \| \| scaffold14851_2981641_SNP | 2981641 | T | C |
| S_9367000 \| \| scaffold14851_2981988_SNP | 2981988 | A | G |
| S_9367068 \| \| scaffold14851_2983249_SNP | 2983249 | A | T |
| S_9367072 \| \| scaffold14851_2983266_SNP | 2983266 | T | C |
| S_9367075 \| \| scaffold14851_2983301_SNP | 2983301 | A | G |
| S_9367105 \| \| scaffold14851_2983791_SNP | 2983791 | G | A |
| S_9367151 \| \| scaffold14851_2984626_SNP | 2984626 | A | T |
| S_9367179 \| \| scaffold14851_2984866_SNP | 2984866 | G | A |
| S_9367181 \| \| scaffold14851_2984973_SNP | 2984973 | T | A |
| S_9367194 \| \| scaffold14851_2985385_SNP | 2985385 | T | G |
| S_9367264 \| \| scaffold14851_2985603_SNP | 2985603 | C | T |
| S_9367284 \| \| scaffold14851_2985882_SNP | 2985882 | G | T |
| S_9367290 \| \| scaffold14851_2986013_SNP | 2986013 | C | A |
| S_9367327 \| \| scaffold14851_2986640_SNP | 2986640 | G | A |
| S_9367328 \| \| scaffold14851_2986661_SNP | 2986661 | C | T |
| S_9367337 \| \| scaffold14851_2986762_SNP | 2986762 | A | C |
| S_9367339 \| \| scaffold14851_2986764_SNP | 2986764 | T | G |
| S_9367340 \| \| scaffold14851_2986809_SNP | 2986809 | G | C |
| S_9367346 \| \| scaffold14851_2986920_SNP | 2986920 | A | C |
| S_9367352 \| \| scaffold14851_2987038_SNP | 2987038 | T | C |
| S_9367375 \| \| scaffold14851_2987744_SNP | 2987744 | T | A |
| S_9367378 \| \| scaffold14851_2987746_SNP | 2987746 | T | G |
| S_9367476 \| \| scaffold14851_2989190_SNP | 2989190 | C | T |
| S_9367477 \| \| scaffold14851_2989206_SNP | 2989206 | T | C |
| S_9367478 \| \| scaffold14851_2989209_SNP | 2989209 | T | C |
| S_9367485 \| \| scaffold14851_2989306_SNP | 2989306 | G | C |
| S_9367500 \| \| scaffold14851_2989464_SNP | 2989464 | C | A |
| S_9367525 \| \| scaffold14851_2989632_SNP | 2989632 | C | T |
| S_9367533 \| \| scaffold14851_2989734_SNP | 2989734 | T | C |
| S_9367549 \| \| scaffold14851_2990122_SNP | 2990122 | A | G |
| S_9367562 \| \| scaffold14851_2990225_SNP | 2990225 | C | T |
| S_9367611 \| \| scaffold14851_2991127_SNP | 2991127 | A | G |
| S_9367627 \| \| scaffold14851_2991393_SNP | 2991393 | C | T |
| S_9367641 \| \| scaffold14851_2991573_SNP | 2991573 | G | A |
| S_9367713 \| \| scaffold14851_2992292_SNP | 2992292 | C | T |
| S_9367724 \| \| scaffold14851_2992502_SNP | 2992502 | G | C |
| S_9367814 \| \| scaffold14851_2994046_SNP | 2994046 | G | T |
| S_9367828 \| \| scaffold14851_2994241_SNP | 2994241 | G | T |
| S_9367844 \| \| scaffold14851_2994413_SNP | 2994413 | A | G |
| S_9367871 \| \| scaffold14851_2994926_SNP | 2994926 | C | T |
| S_9367947 \| \| scaffold14851_2995750_SNP | 2995750 | A | T |
| scaffold14851_2996299_SNP | 2996299 | C | T |
| S_9368075 \| \| scaffold14851_2996310_SNP | 2996310 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| scaffold14851_2996397_SNP | 2996397 | A | G |
| S_9368154 \| \| scaffold14851_2996494_SNP | 2996494 | C | T |
| S_9368159 \| \| scaffold14851_2996521_SNP | 2996521 | A | G |
| S_9368354 \| \| scaffold14851_2997819_SNP | 2997819 | G | A |
| S_9368375 \| \| scaffold14851_2998085_SNP | 2998085 | G | T |
| S_9368383 \| \| scaffold14851_2998219_SNP | 2998219 | T | C |
| S_9368469 \| \| scaffold14851_2999590_SNP | 2999590 | T | C |
| S_9368470 \| \| scaffold14851_2999603_SNP | 2999603 | A | G |
| S_9368482 \| \| scaffold14851_2999754_SNP | 2999754 | G | C |
| S_9368502 \| \| scaffold14851_2999938_SNP | 2999938 | A | C |
| S_9368503 \| \| scaffold14851_2999990_SNP | 2999990 | C | A |
| S_9368514 \| \| scaffold14851_3000216_SNP | 3000216 | C | T |
| S_9368524 \| \| scaffold14851_3000463_SNP | 3000463 | T | C |
| S_9368544 \| \| scaffold14851_3000811_SNP | 3000811 | G | C |
| S_9368545 \| \| scaffold14851_3000890_SNP | 3000890 | A | C |
| S_9368546 \| \| scaffold14851_3000891_SNP | 3000891 | T | A |
| S_9368608 \| \| scaffold14851_3001357_SNP | 3001357 | T | C |
| S_9368610 \| \| scaffold14851_3001378_SNP | 3001378 | A | G |
| S_9368627 \| \| scaffold14851_3001649_SNP | 3001649 | G | A |
| S_9368644 \| \| scaffold14851_3001974_SNP | 3001974 | C | A |
| S_9368658 \| \| scaffold14851_3002200_SNP | 3002200 | G | C |
| S_9368680 \| \| scaffold14851_3002488_SNP | 3002488 | C | T |
| S_9368702 \| \| scaffold14851_3002661_SNP | 3002661 | G | C |
| S_9368743 \| \| scaffold14851_3003359_SNP | 3003359 | T | C |
| S_9368765 \| \| scaffold14851_3003679_SNP | 3003679 | C | T |
| S_9368782 \| \| scaffold14851_3003885_SNP | 3003885 | C | T |
| S_9368784 \| \| scaffold14851_3003930_SNP | 3003930 | T | G |
| S_9368785 \| \| scaffold14851_3003958_SNP | 3003958 | C | T |
| S_9368792 \| \| scaffold14851_3003988_SNP | 3003988 | A | T |
| S_9368831 \| \| scaffold14851_3004596_SNP | 3004596 | C | T |
| S_9369045 \| \| scaffold14851_3006890_SNP | 3006890 | C | T |
| S_9369245 \| \| scaffold14851_3008833_SNP | 3008833 | A | T |
| S_9369360 \| \| scaffold14851_3009898_SNP | 3009898 | A | G |
| S_9369363 \| \| scaffold14851_3010005_SNP | 3010005 | T | C |
| S_9369411 \| \| scaffold14851_3010776_SNP | 3010776 | G | A |
| S_9369419 \| \| scaffold14851_3011067_SNP | 3011067 | G | A |
| S_9369586 \| \| scaffold14851_3013303_SNP | 3013303 | G | A |
| S_9369588 \| \| scaffold14851_3013340_SNP | 3013340 | G | T |
| S_9369592 \| \| scaffold14851_3013380_SNP | 3013380 | T | A |
| S_9369650 \| \| scaffold14851_3014297_SNP | 3014297 | T | A |
| S_9370265 \| \| scaffold14851_3026390_SNP | 3026390 | G | T |
| S_9370442 \| \| scaffold14851_3029582_SNP | 3029582 | C | T |
| S_9370494 \| \| scaffold14851_3030318_SNP | 3030318 | A | G |
| S_9370576 \| \| scaffold14851_3031716_SNP | 3031716 | A | C |
| S_9370589 \| \| scaffold14851_3031928_SNP | 3031928 | C | T |
| S_9370592 \| \| scaffold14851_3032005_SNP | 3032005 | G | C |
| S_9370625 \| \| scaffold14851_3032407_SNP | 3032407 | C | G |
| S_9370706 \| \| scaffold14851_3033532_SNP | 3033532 | A | G |
| S_9370727 \| \| scaffold14851_3033910_SNP | 3033910 | T | A |
| S_9370753 \| \| scaffold14851_3034434_SNP | 3034434 | A | G |
| S_9371103 \| \| scaffold14851_3037831_SNP | 3037831 | T | A |
| S_9371105 \| \| scaffold14851_3037848_SNP | 3037848 | A | C |
| S_9371257 \| \| scaffold14851_3039054_SNP | 3039054 | A | C |
| S_9371262 \| \| scaffold14851_3039180_SNP | 3039180 | T | C |
| S_9371388 \| \| scaffold14851_3040936_SNP | 3040936 | T | A |
| S_9371390 \| \| scaffold14851_3040950_SNP | 3040950 | A | T |
| S_9371394 \| \| scaffold14851_3041008_SNP | 3041008 | G | C |
| S_9371417 \| \| scaffold14851_3041295_SNP | 3041295 | G | A |
| S_9371587 \| \| scaffold14851_3043138_SNP | 3043138 | T | C |
| S_9371616 \| \| scaffold14851_3043753_SNP | 3043753 | G | T |
| S_9371639 \| \| scaffold14851_3043889_SNP | 3043889 | C | T |
| S_9371645 \| \| scaffold14851_3043973_SNP | 3043973 | A | G |
| S_9371998 \| \| scaffold14851_3047386_SNP | 3047386 | G | C |
| S_9372021 \| \| scaffold14851_3047696_SNP | 3047696 | A | T |
| S_9372052 \| \| scaffold14851_3048106_SNP | 3048106 | A | C |
| S_9372058 \| \| scaffold14851_3048151_SNP | 3048151 | C | T |
| S_9372115 \| \| scaffold14851_3048432_SNP | 3048432 | C | A |
| S_9372137 \| \| scaffold14851_3048870_SNP | 3048870 | A | C |
| S_9372261 \| \| scaffold14851_3049750_SNP | 3049750 | C | G |
| S_9372265 \| \| scaffold14851_3049787_SNP | 3049787 | A | G |
| S_9372277 \| \| scaffold14851_3049907_SNP | 3049907 | T | A |
| S_9372282 \| \| scaffold14851_3049996_SNP | 3049996 | G | A |
| S_9372318 \| \| scaffold14851_3050373_SNP | 3050373 | A | C |
| S_9372328 \| \| scaffold14851_3050537_SNP | 3050537 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9372338 \| \| scaffold14851_3050662_SNP | 3050662 | C | G |
| S_9372363 \| \| scaffold14851_3050962_SNP | 3050962 | G | T |
| S_9372381 \| \| scaffold14851_3051218_SNP | 3051218 | A | T |
| S_9372425 \| \| scaffold14851_3051779_SNP | 3051779 | T | A |
| S_9372480 \| \| scaffold14851_3052082_SNP | 3052082 | A | G |
| S_9372696 \| \| scaffold14851_3054983_SNP | 3054983 | C | T |
| S_9372740 \| \| scaffold14851_3055571_SNP | 3055571 | C | G |
| S_9372753 \| \| scaffold14851_3055717_SNP | 3055717 | C | G |
| S_9372755 \| \| scaffold14851_3055741_SNP | 3055741 | C | T |
| S_9372756 \| \| scaffold14851_3055768_SNP | 3055768 | T | G |
| S_9372757 \| \| scaffold14851_3055786_SNP | 3055786 | C | T |
| S_9372763 \| \| scaffold14851_3055881_SNP | 3055881 | G | C |
| S_9372766 \| \| scaffold14851_3055899_SNP | 3055899 | C | G |
| S_9372779 \| \| scaffold14851_3056011_SNP | 3056011 | C | T |
| S_9372780 \| \| scaffold14851_3056023_SNP | 3056023 | C | T |
| S_9372781 \| \| scaffold14851_3056029_SNP | 3056029 | G | A |
| S_9373084 \| \| scaffold14851_3058844_SNP | 3058844 | C | A |
| S_9373085 \| \| scaffold14851_3058845_SNP | 3058845 | G | C |
| S_9373092 \| \| scaffold14851_3058911_SNP | 3058911 | A | G |
| S_9373176 \| \| scaffold14851_3059947_SNP | 3059947 | G | A |
| S_9373206 \| \| scaffold14851_3060526_SNP | 3060526 | C | T |
| S_9373260 \| \| scaffold14851_3061425_SNP | 3061425 | G | T |
| S_9373416 \| \| scaffold14851_3063573_SNP | 3063573 | C | A |
| S_9373451 \| \| scaffold14851_3064083_SNP | 3064083 | A | C |
| S_9373997 \| \| scaffold14851_3070207_SNP | 3070207 | G | C |
| S_9374075 \| \| scaffold14851_3070734_SNP | 3070734 | C | T |
| S_9374076 \| \| scaffold14851_3070807_SNP | 3070807 | G | C |
| S_9374198 \| \| scaffold14851_3072605_SNP | 3072605 | G | A |
| S_9374208 \| \| scaffold14851_3072721_SNP | 3072721 | C | T |
| S_9374324 \| \| scaffold14851_3073648_SNP | 3073648 | G | A |
| S_9374342 \| \| scaffold14851_3074045_SNP | 3074045 | T | A |
| S_9374398 \| \| scaffold14851_3074884_SNP | 3074884 | G | T |
| S_9374399 \| \| scaffold14851_3074915_SNP | 3074915 | T | C |
| S_9374418 \| \| scaffold14851_3075130_SNP | 3075130 | A | G |
| S_9374479 \| \| scaffold14851_3076008_SNP | 3076008 | T | A |
| S_9374481 \| \| scaffold14851_3076032_SNP | 3076032 | A | C |
| S_9374482 \| \| scaffold14851_3076048_SNP | 3076048 | C | T |
| S_9374483 \| \| scaffold14851_3076061_SNP | 3076061 | C | T |
| S_9374505 \| \| scaffold14851_3076346_SNP | 3076346 | T | C |
| S_9374512 \| \| scaffold14851_3076447_SNP | 3076447 | T | G |
| S_9374523 \| \| scaffold14851_3076735_SNP | 3076735 | A | G |
| S_9374524 \| \| scaffold14851_3076738_SNP | 3076738 | T | G |
| S_9374525 \| \| scaffold14851_3076741_SNP | 3076741 | G | A |
| S_9374532 \| \| scaffold14851_3076835_SNP | 3076835 | C | T |
| S_9374534 \| \| scaffold14851_3076937_SNP | 3076937 | T | A |
| scaffold14851_3077420_SNP | 3077420 | A | C |
| S_9374602 \| \| scaffold14851_3077750_SNP | 3077750 | G | C |
| S_9374603 \| \| scaffold14851_3077752_SNP | 3077752 | T | A |
| S_9374609 \| \| scaffold14851_3077794_SNP | 3077794 | G | A |
| S_9374658 \| \| scaffold14851_3078430_SNP | 3078430 | C | A |
| S_9374666 \| \| scaffold14851_3078536_SNP | 3078536 | G | A |
| S_9374688 \| \| scaffold14851_3078770_SNP | 3078770 | A | G |
| S_9374690 \| \| scaffold14851_3078780_SNP | 3078780 | G | T |
| S_9374692 \| \| scaffold14851_3078806_SNP | 3078806 | T | C |
| S_9374716 \| \| scaffold14851_3079033_SNP | 3079033 | T | C |
| S_9374738 \| \| scaffold14851_3079229_SNP | 3079229 | T | A |
| S_9374739 \| \| scaffold14851_3079233_SNP | 3079233 | C | T |
| S_9374744 \| \| scaffold14851_3079266_SNP | 3079266 | T | C |
| S_9374883 \| \| scaffold14851_3080441_SNP | 3080441 | A | T |
| S_9374892 \| \| scaffold14851_3080594_SNP | 3080594 | C | T |
| S_9374932 \| \| scaffold14851_3081385_SNP | 3081385 | A | T |
| S_9374933 \| \| scaffold14851_3081392_SNP | 3081392 | A | T |
| S_9374974 \| \| scaffold14851_3082020_SNP | 3082020 | T | G |
| S_9375022 \| \| scaffold14851_3082863_SNP | 3082863 | A | T |
| S_9375027 \| \| scaffold14851_3082972_SNP | 3082972 | C | A |
| S_9375031 \| \| scaffold14851_3083025_SNP | 3083025 | C | T |
| S_9375032 \| \| scaffold14851_3083031_SNP | 3083031 | A | G |
| S_9375388 \| \| scaffold14851_3088167_SNP | 3088167 | A | G |
| S_9375667 \| \| scaffold14851_3091293_SNP | 3091293 | A | T |
| S_9375853 \| \| scaffold14851_3093870_SNP | 3093870 | T | C |
| S_9376049 \| \| scaffold14851_3095825_SNP | 3095825 | T | A |
| S_9376173 \| \| scaffold14851_3097508_SNP | 3097508 | T | C |
| S_9376174 \| \| scaffold14851_3097514_SNP | 3097514 | G | C |
| S_9376176 \| \| scaffold14851_3097524_SNP | 3097524 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9376194 \| \| scaffold14851_3097767_SNP | 3097767 | T | C |
| S_9376195 \| \| scaffold14851_3097778_SNP | 3097778 | A | G |
| S_9376196 \| \| scaffold14851_3097798_SNP | 3097798 | A | C |
| S_9376246 \| \| scaffold14851_3098201_SNP | 3098201 | A | G |
| S_9376249 \| \| scaffold14851_3098246_SNP | 3098246 | G | A |
| S_9376250 \| \| scaffold14851_3098249_SNP | 3098249 | G | A |
| S_9376252 \| \| scaffold14851_3098276_SNP | 3098276 | C | T |
| S_9376291 \| \| scaffold14851_3098613_SNP | 3098613 | G | C |
| S_9376300 \| \| scaffold14851_3098720_SNP | 3098720 | A | G |
| S_9376304 \| \| scaffold14851_3098762_SNP | 3098762 | C | T |
| S_9376308 \| \| scaffold14851_3098825_SNP | 3098825 | C | A |
| S_9376311 \| \| scaffold14851_3098834_SNP | 3098834 | C | T |
| S_9376314 \| \| scaffold14851_3098853_SNP | 3098853 | A | G |
| S_9376384 \| \| scaffold14851_3100124_SNP | 3100124 | C | T |
| S_9376399 \| \| scaffold14851_3100324_SNP | 3100324 | T | C |
| S_9376411 \| \| scaffold14851_3100460_SNP | 3100460 | A | G |
| S_9376451 \| \| scaffold14851_3100904_SNP | 3100904 | A | T |
| S_9376466 \| \| scaffold14851_3101148_SNP | 3101148 | T | G |
| S_9376470 \| \| scaffold14851_3101179_SNP | 3101179 | G | T |
| S_9376501 \| \| scaffold14851_3101581_SNP | 3101581 | T | C |
| S_9376516 \| \| scaffold14851_3101864_SNP | 3101864 | C | T |
| S_9376603 \| \| scaffold14851_3103060_SNP | 3103060 | G | T |
| S_9376622 \| \| scaffold14851_3103353_SNP | 3103353 | A | T |
| S_9376633 \| \| scaffold14851_3103473_SNP | 3103473 | G | A |
| S_9376641 \| \| scaffold14851_3103557_SNP | 3103557 | T | C |
| S_9376643 \| \| scaffold14851_3103601_SNP | 3103601 | T | C |
| S_9376648 \| \| scaffold14851_3103704_SNP | 3103704 | G | A |
| S_9376651 \| \| scaffold14851_3103759_SNP | 3103759 | A | G |
| S_9376709 \| \| scaffold14851_3104479_SNP | 3104479 | C | G |
| S_9376715 \| \| scaffold14851_3104548_SNP | 3104548 | T | A |
| S_9376716 \| \| scaffold14851_3104656_SNP | 3104656 | T | A |
| S_9376719 \| \| scaffold14851_3104682_SNP | 3104682 | A | C |
| S_9376734 \| \| scaffold14851_3104894_SNP | 3104894 | G | A |
| S_9376735 \| \| scaffold14851_3104900_SNP | 3104900 | A | G |
| S_9376738 \| \| scaffold14851_3104966_SNP | 3104966 | T | C |
| S_9376744 \| \| scaffold14851_3105003_SNP | 3105003 | C | T |
| S_9376746 \| \| scaffold14851_3105021_SNP | 3105021 | C | G |
| S_9376748 \| \| scaffold14851_3105033_SNP | 3105033 | C | T |
| S_9376774 \| \| scaffold14851_3105419_SNP | 3105419 | G | A |
| S_9376847 \| \| scaffold14851_3106421_SNP | 3106421 | A | G |
| S_9376848 \| \| scaffold14851_3106425_SNP | 3106425 | G | A |
| S_9376859 \| \| scaffold14851_3106575_SNP | 3106575 | A | C |
| S_9376860 \| \| scaffold14851_3106592_SNP | 3106592 | C | T |
| S_9376934 \| \| scaffold14851_3107718_SNP | 3107718 | T | G |
| S_9376938 \| \| scaffold14851_3107752_SNP | 3107752 | G | A |
| S_9376939 \| \| scaffold14851_3107770_SNP | 3107770 | A | T |
| S_9377002 \| \| scaffold14851_3108424_SNP | 3108424 | A | G |
| S_9377084 \| \| scaffold14851_3109691_SNP | 3109691 | C | T |
| S_9377111 \| \| scaffold14851_3110394_SNP | 3110394 | A | G |
| S_9377184 \| \| scaffold14851_3111478_SNP | 3111478 | C | T |
| S_9377188 \| \| scaffold14851_3111517_SNP | 3111517 | T | A |
| S_9377266 \| \| scaffold14851_3112037_SNP | 3112037 | T | G |
| S_9377271 \| \| scaffold14851_3112206_SNP | 3112206 | C | T |
| S_9377288 \| \| scaffold14851_3112483_SNP | 3112483 | A | T |
| S_9377328 \| \| scaffold14851_3113180_SNP | 3113180 | A | G |
| S_9377331 \| \| scaffold14851_3113191_SNP | 3113191 | G | T |
| S_9377332 \| \| scaffold14851_3113201_SNP | 3113201 | T | C |
| S_9377333 \| \| scaffold14851_3113225_SNP | 3113225 | C | T |
| S_9377336 \| \| scaffold14851_3113270_SNP | 3113270 | C | T |
| S_9377386 \| \| scaffold14851_3113788_SNP | 3113788 | A | T |
| S_9377399 \| \| scaffold14851_3113907_SNP | 3113907 | T | C |
| S_9377402 \| \| scaffold14851_3113934_SNP | 3113934 | A | G |
| S_9377403 \| \| scaffold14851_3113974_SNP | 3113974 | T | C |
| S_9377404 \| \| scaffold14851_3113975_SNP | 3113975 | T | A |
| S_9377619 \| \| scaffold14851_3116267_SNP | 3116267 | C | T |
| S_9377810 \| \| scaffold14851_3118243_SNP | 3118243 | A | C |
| S_9377846 \| \| scaffold14851_3118467_SNP | 3118467 | A | T |
| S_9377856 \| \| scaffold14851_3118582_SNP | 3118582 | A | C |
| S_9378050 \| \| scaffold14851_3122483_SNP | 3122483 | G | A |
| S_9378128 \| \| scaffold14851_3123249_SNP | 3123249 | C | A |
| S_9378153 \| \| scaffold14851_3123480_SNP | 3123480 | T | C |
| S_9378203 \| \| scaffold14851_3124381_SNP | 3124381 | G | A |
| S_9378204 \| \| scaffold14851_3124382_SNP | 3124382 | T | G |
| S_9378348 \| \| scaffold14851_3126921_SNP | 3126921 | A | C |

137

138

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9378424 \| \| scaffold14851_3127549_SNP | 3127549 | G | T |
| S_9378558 \| \| scaffold14851_3129297_SNP | 3129297 | A | G |
| S_9378615 \| \| scaffold14851_3130220_SNP | 3130220 | T | G |
| S_9378836 \| \| scaffold14851_3133610_SNP | 3133610 | G | T |
| S_9378936 \| \| scaffold14851_3134994_SNP | 3134994 | G | C |
| S_9379024 \| \| scaffold14851_3135929_SNP | 3135929 | A | C |
| S_9379092 \| \| scaffold14851_3136905_SNP | 3136905 | G | A |
| S_9379107 \| \| scaffold14851_3137096_SNP | 3137096 | T | A |
| S_9379236 \| \| scaffold14851_3138766_SNP | 3138766 | G | A |
| S_9379241 \| \| scaffold14851_3139041_SNP | 3139041 | C | A |
| S_9379242 \| \| scaffold14851_3139043_SNP | 3139043 | A | T |
| S_9379368 \| \| scaffold14851_3141043_SNP | 3141043 | G | A |
| S_9379369 \| \| scaffold14851_3141045_SNP | 3141045 | T | G |
| S_9379478 \| \| scaffold14851_3143383_SNP | 3143383 | C | T |
| S_9379622 \| \| scaffold14851_3144978_SNP | 3144978 | G | A |
| S_9379634 \| \| scaffold14851_3145254_SNP | 3145254 | A | G |
| S_9379758 \| \| scaffold14851_3147616_SNP | 3147616 | C | T |
| S_9380246 \| \| scaffold14851_3153795_SNP | 3153795 | T | G |
| S_9380503 \| \| scaffold14851_3157650_SNP | 3157650 | C | T |
| S_9380787 \| \| scaffold14851_3162327_SNP | 3162327 | T | C |
| S_9380797 \| \| scaffold14851_3162518_SNP | 3162518 | G | A |
| S_9381019 \| \| scaffold14851_3164913_SNP | 3164913 | C | T |
| S_9381135 \| \| scaffold14851_3165801_SNP | 3165801 | G | A |
| S_9381166 \| \| scaffold14851_3166212_SNP | 3166212 | A | G |
| S_9381181 \| \| scaffold14851_3166626_SNP | 3166626 | T | C |
| S_9381273 \| \| scaffold14851_3167686_SNP | 3167686 | T | A |
| S_9381274 \| \| scaffold14851_3167688_SNP | 3167688 | G | A |
| S_9381284 \| \| scaffold14851_3167859_SNP | 3167859 | T | G |
| S_9381295 \| \| scaffold14851_3167975_SNP | 3167975 | A | C |
| S_9381296 \| \| scaffold14851_3167982_SNP | 3167982 | T | A |
| S_9381302 \| \| scaffold14851_3168069_SNP | 3168069 | A | T |
| S_9381306 \| \| scaffold14851_3168176_SNP | 3168176 | T | C |
| S_9381327 \| \| scaffold14851_3168399_SNP | 3168399 | A | G |
| S_9381383 \| \| scaffold14851_3169143_SNP | 3169143 | T | G |
| S_9381431 \| \| scaffold14851_3169751_SNP | 3169751 | T | C |
| S_9381435 \| \| scaffold14851_3169844_SNP | 3169844 | G | A |
| S_9381444 \| \| scaffold14851_3169980_SNP | 3169980 | C | A |
| S_9381501 \| \| scaffold14851_3170788_SNP | 3170788 | A | C |
| S_9381692 \| \| scaffold14851_3172437_SNP | 3172437 | G | A |
| S_9381863 \| \| scaffold14851_3174371_SNP | 3174371 | T | C |
| S_9382017 \| \| scaffold14851_3176375_SNP | 3176375 | A | G |
| S_9382366 \| \| scaffold14851_3180712_SNP | 3180712 | G | T |
| S_9382385 \| \| scaffold14851_3180956_SNP | 3180956 | C | G |
| S_9382398 \| \| scaffold14851_3181232_SNP | 3181232 | G | C |
| S_9382625 \| \| scaffold14851_3184532_SNP | 3184532 | G | A |
| S_9382860 \| \| scaffold14851_3187670_SNP | 3187670 | A | C |
| S_9382985 \| \| scaffold14851_3189445_SNP | 3189445 | T | C |
| S_9382988 \| \| scaffold14851_3189469_SNP | 3189469 | C | A |
| S_9383123 \| \| scaffold14851_3191036_SNP | 3191036 | A | C |
| S_9383158 \| \| scaffold14851_3191700_SNP | 3191700 | A | G |
| S_9383187 \| \| scaffold14851_3192149_SNP | 3192149 | C | A |
| S_9383374 \| \| scaffold14851_3194799_SNP | 3194799 | G | T |
| S_9383750 \| \| scaffold14851_3199451_SNP | 3199451 | C | A |
| S_9383864 \| \| scaffold14851_3200472_SNP | 3200472 | G | T |
| S_9383969 \| \| scaffold14851_3202039_SNP | 3202039 | C | G |
| S_9384100 \| \| scaffold14851_3204154_SNP | 3204154 | T | G |
| S_9384190 \| \| scaffold14851_3205080_SNP | 3205080 | A | C |
| S_9384191 \| \| scaffold14851_3205084_SNP | 3205084 | A | G |
| S_9384192 \| \| scaffold14851_3205128_SNP | 3205128 | G | C |
| S_9384201 \| \| scaffold14851_3205289_SNP | 3205289 | G | T |
| S_9384215 \| \| scaffold14851_3205576_SNP | 3205576 | T | C |
| S_9384222 \| \| scaffold14851_3205699_SNP | 3205699 | G | A |
| S_9384395 \| \| scaffold14851_3208677_SNP | 3208677 | G | C |
| scaffold14851_3209553_SNP | 3209553 | T | A |
| S_9384473 \| \| scaffold14851_3209650_SNP | 3209650 | C | T |
| S_9384476 \| \| scaffold14851_3209663_SNP | 3209663 | T | C |
| S_9384480 \| \| scaffold14851_3209677_SNP | 3209677 | C | G |
| S_9384489 \| \| scaffold14851_3209760_SNP | 3209760 | A | T |
| S_9384510 \| \| scaffold14851_3209969_SNP | 3209969 | C | T |
| S_9384593 \| \| scaffold14851_3210501_SNP | 3210501 | T | G |
| S_9384624 \| \| scaffold14851_3210966_SNP | 3210966 | A | C |
| S_9384626 \| \| scaffold14851_3211011_SNP | 3211011 | C | T |
| S_9384629 \| \| scaffold14851_3211022_SNP | 3211022 | T | G |
| S_9384637 \| \| scaffold14851_3211088_SNP | 3211088 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9384641 \| \| scaffold14851_3211121_SNP | 3211121 | G | A |
| S_9384646 \| \| scaffold14851_3211165_SNP | 3211165 | G | A |
| S_9384648 \| \| scaffold14851_3211223_SNP | 3211223 | G | A |
| S_9384717 \| \| scaffold14851_3211718_SNP | 3211718 | C | T |
| S_9384722 \| \| scaffold14851_3211743_SNP | 3211743 | G | A |
| S_9384797 \| \| scaffold14851_3212722_SNP | 3212722 | A | C |
| S_9384870 \| \| scaffold14851_3213614_SNP | 3213614 | A | G |
| scaffold14851_3214577_SNP | 3214577 | A | G |
| scaffold14851_3215085_SNP | 3215085 | C | G |
| S_9385060 \| \| scaffold14851_3215169_SNP | 3215169 | G | A |
| S_9385130 \| \| scaffold14851_3215578_SNP | 3215578 | A | G |
| S_9385208 \| \| scaffold14851_3216086_SNP | 3216086 | A | G |
| S_9387052 \| \| scaffold14851_3243920_SNP | 3243920 | T | A |
| S_9387631 \| \| scaffold14851_3251814_SNP | 3251814 | T | A |
| scaffold 14851_3253492_SNP | 3253492 | G | A |
| S_9387816 \| \| scaffold14851_3253645_SNP | 3253645 | A | G |
| S_9387878 \| \| scaffold14851_3254638_SNP | 3254638 | C | A |
| S_9387889 \| \| scaffold14851_3254692_SNP | 3254692 | C | T |
| S_9388044 \| \| scaffold14851_3256488_SNP | 3256488 | A | C |
| S_9388502 \| \| scaffold14851_3261395_SNP | 3261395 | T | C |
| S_9388690 \| \| scaffold14851_3263201_SNP | 3263201 | A | G |
| S_9388835 \| \| scaffold14851_3265384_SNP | 3265384 | G | A |
| S_9388942 \| \| scaffold14851_3266571_SNP | 3266571 | A | C |
| S_9389107 \| \| scaffold14851_3267971_SNP | 3267971 | T | C |
| S_9389845 \| \| scaffold14851_3274672_SNP | 3274672 | T | A |
| S_9389885 \| \| scaffold14851_3275655_SNP | 3275655 | T | C |
| S_9393008 \| \| scaffold14851_3291351_SNP | 3291351 | T | C |
| S_9393172 \| \| scaffold14851_3293738_SNP | 3293738 | C | A |
| S_9393173 \| \| scaffold14851_3293739_SNP | 3293739 | A | G |
| S_9393208 \| \| scaffold14851_3293990_SNP | 3293990 | A | G |
| scaffold14851_3294505_SNP | 3294505 | C | A |
| scaffold14851_3296156_SNP | 3296156 | G | T |
| S_9394210 \| \| scaffold14851_3309134_SNP | 3309134 | C | A |
| S_9394450 \| \| scaffold14851_3312049_SNP | 3312049 | A | T |
| S_9394484 \| \| scaffold14851_3312293_SNP | 3312293 | C | T |
| S_9394499 \| \| scaffold14851_3312446_SNP | 3312446 | C | A |
| S_9394716 \| \| scaffold14851_3315637_SNP | 3315637 | T | C |
| S_9395016 \| \| scaffold14851_3319759_SNP | 3319759 | T | G |
| S_9395076 \| \| scaffold14851_3321787_SNP | 3321787 | G | C |
| S_9395132 \| \| scaffold14851_3322276_SNP | 3322276 | A | T |
| S_9395198 \| \| scaffold14851_3323073_SNP | 3323073 | G | C |
| S_9395230 \| \| scaffold14851_3323463_SNP | 3323463 | C | A |
| S_9395286 \| \| scaffold14851_3324332_SNP | 3324332 | T | C |
| S_9395330 \| \| scaffold14851_3324854_SNP | 3324854 | G | C |
| S_9395333 \| \| scaffold14851_3324938_SNP | 3324938 | C | T |
| scaffold14851_3325050_SNP | 3325050 | A | C |
| S_9395722 \| \| scaffold14851_3329053_SNP | 3329053 | T | A |
| S_9395877 \| \| scaffold14851_3331648_SNP | 3331648 | T | A |
| S_9395950 \| \| scaffold14851_3332802_SNP | 3332802 | G | T |
| S_9395960 \| \| scaffold14851_3332965_SNP | 3332965 | G | A |
| S_9395998 \| \| scaffold14851_3333589_SNP | 3333589 | A | G |
| S_9396019 \| \| scaffold14851_3333789_SNP | 3333789 | G | C |
| S_9396023 \| \| scaffold14851_3333888_SNP | 3333888 | T | A |
| S_9396028 \| \| scaffold14851_3333988_SNP | 3333988 | C | T |
| S_9396069 \| \| scaffold14851_3334576_SNP | 3334576 | C | T |
| S_9396070 \| \| scaffold14851_3334626_SNP | 3334626 | A | T |
| S_9396082 \| \| scaffold14851_3334878_SNP | 3334878 | C | A |
| S_9396098 \| \| scaffold14851_3335153_SNP | 3335153 | G | T |
| S_9396099 \| \| scaffold14851_3335159_SNP | 3335159 | C | G |
| S_9396128 \| \| scaffold14851_3335411_SNP | 3335411 | G | A |
| S_9396211 \| \| scaffold14851_3336371_SNP | 3336371 | C | T |
| S_9396215 \| \| scaffold14851_3336429_SNP | 3336429 | A | C |
| S_9396221 \| \| scaffold14851_3336531_SNP | 3336531 | G | T |
| S_9396268 \| \| scaffold14851_3337095_SNP | 3337095 | G | A |
| S_9396273 \| \| scaffold14851_3337166_SNP | 3337166 | T | G |
| S_9396301 \| \| scaffold14851_3337618_SNP | 3337618 | T | A |
| S_9396459 \| \| scaffold14851_3339009_SNP | 3339009 | G | T |
| S_9396474 \| \| scaffold14851_3339252_SNP | 3339252 | C | T |
| S_9396488 \| \| scaffold14851_3339283_SNP | 3339283 | G | A |
| S_9396543 \| \| scaffold14851_3339610_SNP | 3339610 | G | T |
| S_9396554 \| \| scaffold14851_3339891_SNP | 3339891 | G | A |
| S_9396572 \| \| scaffold14851_3340129_SNP | 3340129 | C | T |
| S_9396584 \| \| scaffold14851_3340413_SNP | 3340413 | C | G |
| S_9396603 \| \| scaffold14851_3340910_SNP | 3340910 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| scaffold14851_3342840_SNP | 3342840 | A | G |
| S_9396803 \| \| scaffold14851_3343553_SNP | 3343553 | C | T |
| S_9396882 \| \| scaffold14851_3344712_SNP | 3344712 | T | A |
| S_9396891 \| \| scaffold14851_3344841_SNP | 3344841 | T | A |
| S_9396893 \| \| scaffold14851_3344910_SNP | 3344910 | T | A |
| S_9396901 \| \| scaffold14851_3345087_SNP | 3345087 | A | T |
| S_9396902 \| \| scaffold14851_3345125_SNP | 3345125 | A | G |
| S_9396904 \| \| scaffold14851_3345151_SNP | 3345151 | G | C |
| S_9396911 \| \| scaffold14851_3345208_SNP | 3345208 | A | G |
| S_9396913 \| \| scaffold14851_3345239_SNP | 3345239 | A | C |
| S_9396922 \| \| scaffold14851_3345410_SNP | 3345410 | A | G |
| S_9396923 \| \| scaffold14851_3345411_SNP | 3345411 | C | G |
| S_9396926 \| \| scaffold14851_3345470_SNP | 3345470 | T | A |
| S_9396927 \| \| scaffold14851_3345534_SNP | 3345534 | C | T |
| S_9396930 \| \| scaffold14851_3345641_SNP | 3345641 | C | G |
| S_9396942 \| \| scaffold14851_3345826_SNP | 3345826 | C | T |
| S_9396944 \| \| scaffold14851_3345878_SNP | 3345878 | T | C |
| S_9397039 \| \| scaffold14851_3346673_SNP | 3346673 | G | A |
| S_9397055 \| \| scaffold14851_3346857_SNP | 3346857 | T | C |
| S_9397057 \| \| scaffold14851_3346880_SNP | 3346880 | A | C |
| S_9397096 \| \| scaffold14851_3347403_SNP | 3347403 | T | C |
| S_9397121 \| \| scaffold14851_3347758_SNP | 3347758 | A | G |
| S_9397125 \| \| scaffold14851_3347807_SNP | 3347807 | G | A |
| S_9397128 \| \| scaffold14851_3347840_SNP | 3347840 | T | C |
| S_9397138 \| \| scaffold14851_3347923_SNP | 3347923 | A | G |
| S_9397149 \| \| scaffold14851_3348062_SNP | 3348062 | T | C |
| S_9397154 \| \| scaffold14851_3348125_SNP | 3348125 | T | C |
| S_9397155 \| \| scaffold14851_3348165_SNP | 3348165 | T | A |
| S_9397164 \| \| scaffold14851_3348283_SNP | 3348283 | T | G |
| S_9397167 \| \| scaffold14851_3348313_SNP | 3348313 | A | G |
| S_9397200 \| \| scaffold14851_3348627_SNP | 3348627 | C | T |
| S_9397286 \| \| scaffold14851_3349891_SNP | 3349891 | C | T |
| scaffold14851_3350016_SNP | 3350016 | G | A |
| S_9397344 \| \| scaffold14851_3350388_SNP | 3350388 | G | A |
| S_9397353 \| \| scaffold14851_3350520_SNP | 3350520 | G | A |
| S_9397360 \| \| scaffold14851_3350635_SNP | 3350635 | A | G |
| S_9397362 \| \| scaffold14851_3350664_SNP | 3350664 | T | C |
| S_9397384 \| \| scaffold14851_3351047_SNP | 3351047 | A | G |
| S_9397434 \| \| scaffold14851_3351750_SNP | 3351750 | A | G |
| S_9397439 \| \| scaffold14851_3351848_SNP | 3351848 | A | T |
| S_9397450 \| \| scaffold14851_3352108_SNP | 3352108 | A | C |
| S_9397561 \| \| scaffold14851_3354889_SNP | 3354889 | T | C |
| S_9397624 \| \| scaffold14851_3355988_SNP | 3355988 | G | A |
| S_9397654 \| \| scaffold14851_3356275_SNP | 3356275 | G | A |
| S_9397661 \| \| scaffold14851_3356391_SNP | 3356391 | G | A |
| S_9397665 \| \| scaffold14851_3356423_SNP | 3356423 | T | A |
| S_9397679 \| \| scaffold14851_3356585_SNP | 3356585 | T | A |
| S_9397680 \| \| scaffold14851_3356590_SNP | 3356590 | T | G |
| S_9397732 \| \| scaffold14851_3357292_SNP | 3357292 | A | T |
| S_9397737 \| \| scaffold14851_3357307_SNP | 3357307 | T | A |
| S_9397785 \| \| scaffold14851_3357645_SNP | 3357645 | A | T |
| S_9397908 \| \| scaffold14851_3358922_SNP | 3358922 | T | C |
| S_9397949 \| \| scaffold14851_3359119_SNP | 3359119 | A | C |
| S_9397960 \| \| scaffold14851_3359387_SNP | 3359387 | C | T |
| S_9397961 \| \| scaffold14851_3359389_SNP | 3359389 | A | G |
| scaffold14851_3359424_SNP | 3359424 | G | A |
| S_9397985 \| \| scaffold14851_3359472_SNP | 3359472 | T | C |
| scaffold14851_3359478_SNP | 3359478 | G | A |
| S_9398037 \| \| scaffold14851_3359701_SNP | 3359701 | A | G |
| S_9398171 \| \| scaffold14851_3360634_SNP | 3360634 | C | A |
| S_9398180 \| \| scaffold14851_3360775_SNP | 3360775 | T | C |
| S_9398311 \| \| scaffold14851_3361765_SNP | 3361765 | T | G |
| S_9398313 \| \| scaffold14851_3361815_SNP | 3361815 | C | G |
| S_9398314 \| \| scaffold14851_3361901_SNP | 3361901 | A | C |
| S_9398315 \| \| scaffold14851_3361904_SNP | 3361904 | C | A |
| S_9398326 \| \| scaffold14851_3362064_SNP | 3362064 | A | T |
| S_9398334 \| \| scaffold14851_3362313_SNP | 3362313 | T | C |
| S_9398500 \| \| scaffold14851_3364136_SNP | 3364136 | C | A |
| S_9398543 \| \| scaffold14851_3364528_SNP | 3364528 | A | T |
| S_9398558 \| \| scaffold14851_3364848_SNP | 3364848 | A | G |
| S_9398602 \| \| scaffold14851_3365862_SNP | 3365862 | A | T |
| S_9398603 \| \| scaffold14851_3365886_SNP | 3365886 | A | G |
| S_9398609 \| \| scaffold14851_3366091_SNP | 3366091 | C | A |
| S_9398613 \| \| scaffold14851_3366186_SNP | 3366186 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9398840 \| \| scaffold14851_3368119_SNP | 3368119 | C | A |
| S_9398873 \| \| scaffold14851_3368636_SNP | 3368636 | T | C |
| S_9398902 \| \| scaffold14851_3368746_SNP | 3368746 | C | T |
| S_9398929 \| \| scaffold14851_3368858_SNP | 3368858 | G | A |
| S_9398940 \| \| scaffold14851_3369108_SNP | 3369108 | T | G |
| S_9398941 \| \| scaffold14851_3369170_SNP | 3369170 | A | T |
| S_9398942 \| \| scaffold14851_3369187_SNP | 3369187 | T | A |
| S_9398943 \| \| scaffold14851_3369199_SNP | 3369199 | A | G |
| S_9398944 \| \| scaffold14851_3369202_SNP | 3369202 | T | C |
| S_9398967 \| \| scaffold14851_3369589_SNP | 3369589 | C | T |
| S_9398968 \| \| scaffold14851_3369591_SNP | 3369591 | A | T |
| S_9399076 \| \| scaffold14851_3370981_SNP | 3370981 | A | G |
| S_9399108 \| \| scaffold14851_3371170_SNP | 3371170 | A | G |
| S_9399120 \| \| scaffold14851_3371253_SNP | 3371253 | A | G |
| S_9399139 \| \| scaffold14851_3371294_SNP | 3371294 | A | G |
| S_9399207 \| \| scaffold14851_3371508_SNP | 3371508 | C | G |
| S_9399221 \| \| scaffold14851_3371686_SNP | 3371686 | C | G |
| S_9399237 \| \| scaffold14851_3372023_SNP | 3372023 | C | A |
| S_9399238 \| \| scaffold14851_3372051_SNP | 3372051 | T | C |
| S_9399245 \| \| scaffold14851_3372215_SNP | 3372215 | A | G |
| S_9399336 \| \| scaffold14851_3373485_SNP | 3373485 | A | G |
| S_9399337 \| \| scaffold14851_3373493_SNP | 3373493 | T | G |
| S_9399350 \| \| scaffold14851_3373635_SNP | 3373635 | C | A |
| S_9399369 \| \| scaffold14851_3373913_SNP | 3373913 | A | G |
| S_9399440 \| \| scaffold14851_3374813_SNP | 3374813 | A | C |
| S_9399441 \| \| scaffold14851_3374814_SNP | 3374814 | T | A |
| S_9399442 \| \| scaffold14851_3374818_SNP | 3374818 | A | T |
| S_9399533 \| \| scaffold14851_3376211_SNP | 3376211 | T | A |
| S_9399567 \| \| scaffold14851_3376521_SNP | 3376521 | T | C |
| S_9399630 \| \| scaffold14851_3377372_SNP | 3377372 | T | A |
| S_9399635 \| \| scaffold14851_3377474_SNP | 3377474 | A | T |
| S_9399651 \| \| scaffold14851_3378068_SNP | 3378068 | G | A |
| S_9399685 \| \| scaffold14851_3378779_SNP | 3378779 | A | C |
| S_9399739 \| \| scaffold14851_3379256_SNP | 3379256 | C | T |
| S_9399765 \| \| scaffold14851_3379605_SNP | 3379605 | C | A |
| S_9399774 \| \| scaffold14851_3379755_SNP | 3379755 | A | C |
| S_9399776 \| \| scaffold14851_3379762_SNP | 3379762 | T | A |
| S_9399777 \| \| scaffold14851_3379771_SNP | 3379771 | C | T |
| S_9399785 \| \| scaffold14851_3379876_SNP | 3379876 | G | A |
| S_9399787 \| \| scaffold14851_3379911_SNP | 3379911 | A | C |
| S_9399788 \| \| scaffold14851_3379925_SNP | 3379925 | C | A |
| S_9399889 \| \| scaffold14851_3381619_SNP | 3381619 | T | A |
| S_9399934 \| \| scaffold14851_3382466_SNP | 3382466 | C | G |
| S_9399982 \| \| scaffold14851_3382961_SNP | 3382961 | A | G |
| S_9400023 \| \| scaffold14851_3383924_SNP | 3383924 | T | C |
| S_9400505 \| \| scaffold14851_3390515_SNP | 3390515 | A | T |
| S_9400506 \| \| scaffold14851_3390518_SNP | 3390518 | G | T |
| S_9400812 \| \| scaffold14851_3393541_SNP | 3393541 | G | A |
| S_9400947 \| \| scaffold14851_3395243_SNP | 3395243 | A | T |
| S_9401164 \| \| scaffold14851_3398357_SNP | 3398357 | A | T |
| S_9401179 \| \| scaffold14851_3398602_SNP | 3398602 | C | T |
| S_9401186 \| \| scaffold14851_3398855_SNP | 3398855 | T | A |
| S_9401253 \| \| scaffold14851_3400241_SNP | 3400241 | A | G |
| S_9401257 \| \| scaffold14851_3400315_SNP | 3400315 | T | G |
| S_9401417 \| \| scaffold14851_3403516_SNP | 3403516 | T | A |
| S_9401541 \| \| scaffold14851_3405524_SNP | 3405524 | T | C |
| S_9401552 \| \| scaffold14851_3405731_SNP | 3405731 | G | T |
| S_9401577 \| \| scaffold14851_3406217_SNP | 3406217 | C | T |
| S_9401667 \| \| scaffold14851_3406912_SNP | 3406912 | G | T |
| S_9401678 \| \| scaffold14851_3407045_SNP | 3407045 | T | A |
| S_9401681 \| \| scaffold14851_3407088_SNP | 3407088 | T | C |
| S_9401692 \| \| scaffold14851_3407354_SNP | 3407354 | G | T |
| S_9401716 \| \| scaffold14851_3407617_SNP | 3407617 | T | A |
| S_9401722 \| \| scaffold14851_3407759_SNP | 3407759 | G | A |
| S_9401726 \| \| scaffold14851_3407864_SNP | 3407864 | T | C |
| S_9401748 \| \| scaffold14851_3408232_SNP | 3408232 | C | A |
| S_9401749 \| \| scaffold14851_3408233_SNP | 3408233 | T | A |
| S_9401964 \| \| scaffold14851_3410069_SNP | 3410069 | C | T |
| S_9402093 \| \| scaffold14851_3411688_SNP | 3411688 | T | A |
| S_9402097 \| \| scaffold14851_3411791_SNP | 3411791 | G | C |
| S_9402110 \| \| scaffold14851_3412002_SNP | 3412002 | G | A |
| S_9402169 \| \| scaffold14851_3412973_SNP | 3412973 | A | G |
| S_9402175 \| \| scaffold14851_3413060_SNP | 3413060 | A | G |
| S_9402279 \| \| scaffold14851_3414188_SNP | 3414188 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9402508 \| \| scaffold14851_3416610_SNP | 3416610 | C | T |
| S_9402523 \| \| scaffold14851_3416729_SNP | 3416729 | G | T |
| scaffold14851_3417688_SNP | 3417688 | T | A |
| S_9402743 \| \| scaffold14851_3418503_SNP | 3418503 | C | T |
| S_9402956 \| \| scaffold14851_3421993_SNP | 3421993 | A | T |
| S_9402966 \| \| scaffold14851_3422088_SNP | 3422088 | A | G |
| S_9403277 \| \| scaffold14851_3425152_SNP | 3425152 | C | G |
| S_9403812 \| \| scaffold14851_3431887_SNP | 3431887 | C | A |
| S_9403881 \| \| scaffold14851_3434098_SNP | 3434098 | C | A |
| S_9403989 \| \| scaffold14851_3434786_SNP | 3434786 | T | A |
| S_9404249 \| \| scaffold14851_3438026_SNP | 3438026 | C | A |
| S_9404251 \| \| scaffold14851_3438043_SNP | 3438043 | G | A |
| S_9404271 \| \| scaffold14851_3438551_SNP | 3438551 | T | A |
| S_9404275 \| \| scaffold14851_3438626_SNP | 3438626 | G | T |
| S_9404520 \| \| scaffold14851_3441756_SNP | 3441756 | A | G |
| S_9404529 \| \| scaffold14851_3442000_SNP | 3442000 | G | T |
| S_9404540 \| \| scaffold14851_3442100_SNP | 3442100 | G | T |
| S_9404551 \| \| scaffold14851_3442273_SNP | 3442273 | C | G |
| S_9404600 \| \| scaffold14851_3442959_SNP | 3442959 | C | T |
| S_9404661 \| \| scaffold14851_3443791_SNP | 3443791 | T | C |
| S_9404675 \| \| scaffold14851_3444007_SNP | 3444007 | T | C |
| S_9404690 \| \| scaffold14851_3444158_SNP | 3444158 | G | A |
| S_9404810 \| \| scaffold14851_3445394_SNP | 3445394 | G | C |
| S_9404885 \| \| scaffold14851_3446579_SNP | 3446579 | G | A |
| S_9404899 \| \| scaffold14851_3446752_SNP | 3446752 | T | C |
| S_9404922 \| \| scaffold14851_3447079_SNP | 3447079 | A | C |
| S_9405086 \| \| scaffold14851_3448729_SNP | 3448729 | T | C |
| S_9405651 \| \| scaffold14851_3457834_SNP | 3457834 | A | G |
| S_9405654 \| \| scaffold14851_3457853_SNP | 3457853 | C | T |
| S_9405690 \| \| scaffold14851_3458438_SNP | 3458438 | A | C |
| S_9405709 \| \| scaffold14851_3458741_SNP | 3458741 | C | A |
| S_9405711 \| \| scaffold14851_3458772_SNP | 3458772 | G | T |
| S_9405733 \| \| scaffold14851_3459161_SNP | 3459161 | G | T |
| S_9405736 \| \| scaffold14851_3459215_SNP | 3459215 | T | G |
| S_9405749 \| \| scaffold14851_3459359_SNP | 3459359 | T | C |
| S_9405797 \| \| scaffold14851_3460012_SNP | 3460012 | T | C |
| S_9405869 \| \| scaffold14851_3460894_SNP | 3460894 | A | G |
| S_9405870 \| \| scaffold14851_3460905_SNP | 3460905 | A | C |
| S_9405886 \| \| scaffold14851_3461252_SNP | 3461252 | A | T |
| S_9405929 \| \| scaffold14851_3461771_SNP | 3461771 | A | T |
| S_9405932 \| \| scaffold14851_3461787_SNP | 3461787 | G | T |
| S_9406159 \| \| scaffold14851_3464589_SNP | 3464589 | C | T |
| S_9406173 \| \| scaffold14851_3464775_SNP | 3464775 | A | T |
| S_9406244 \| \| scaffold14851_3465436_SNP | 3465436 | T | C |
| S_9406271 \| \| scaffold14851_3465886_SNP | 3465886 | C | T |
| S_9406341 \| \| scaffold14851_3466776_SNP | 3466776 | T | C |
| S_9406373 \| \| scaffold14851_3466963_SNP | 3466963 | G | A |
| S_9406476 \| \| scaffold14851_3468039_SNP | 3468039 | C | T |
| S_9406489 \| \| scaffold14851_3468280_SNP | 3468280 | A | G |
| S_9406494 \| \| scaffold14851_3468463_SNP | 3468463 | A | G |
| S_9406524 \| \| scaffold14851_3468859_SNP | 3468859 | C | T |
| S_9406557 \| \| scaffold14851_3469208_SNP | 3469208 | G | T |
| S_9406646 \| \| scaffold14851_3470705_SNP | 3470705 | A | G |
| S_9406663 \| \| scaffold14851_3471002_SNP | 3471002 | A | T |
| S_9406694 \| \| scaffold14851_3471618_SNP | 3471618 | C | T |
| S_9406805 \| \| scaffold14851_3473654_SNP | 3473654 | C | A |
| S_9406856 \| \| scaffold14851_3474162_SNP | 3474162 | C | T |
| S_9406867 \| \| scaffold14851_3474253_SNP | 3474253 | A | G |
| S_9406885 \| \| scaffold14851_3474513_SNP | 3474513 | A | T |
| S_9406922 \| \| scaffold14851_3475184_SNP | 3475184 | A | G |
| S_9406930 \| \| scaffold14851_3475300_SNP | 3475300 | T | A |
| S_9406936 \| \| scaffold14851_3475440_SNP | 3475440 | G | C |
| S_9406952 \| \| scaffold14851_3475665_SNP | 3475665 | T | A |
| S_9406977 \| \| scaffold14851_3476021_SNP | 3476021 | A | G |
| S_9406995 \| \| scaffold14851_3476078_SNP | 3476078 | A | G |
| S_9407004 \| \| scaffold14851_3476236_SNP | 3476236 | G | T |
| S_9407005 \| \| scaffold14851_3476237_SNP | 3476237 | A | G |
| S_9407006 \| \| scaffold14851_3476238_SNP | 3476238 | T | A |
| S_9407010 \| \| scaffold14851_3476325_SNP | 3476325 | T | C |
| S_9407011 \| \| scaffold14851_3476326_SNP | 3476326 | T | A |
| S_9407081 \| \| scaffold14851_3477401_SNP | 3477401 | A | G |
| S_9407136 \| \| scaffold14851_3477989_SNP | 3477989 | G | A |
| S_9407160 \| \| scaffold14851_3478566_SNP | 3478566 | T | A |
| S_9407178 \| \| scaffold14851_3478931_SNP | 3478931 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9407198 \| \| scaffold14851_3479282_SNP | 3479282 | G | T |
| S_9407199 \| \| scaffold14851_3479288_SNP | 3479288 | C | T |
| S_9407201 \| \| scaffold14851_3479314_SNP | 3479314 | A | G |
| S_9407202 \| \| scaffold14851_3479318_SNP | 3479318 | C | T |
| S_9407208 \| \| scaffold14851_3479402_SNP | 3479402 | G | A |
| S_9407234 \| \| scaffold14851_3479638_SNP | 3479638 | A | G |
| S_9407257 \| \| scaffold14851_3479944_SNP | 3479944 | C | A |
| S_9407295 \| \| scaffold14851_3480554_SNP | 3480554 | G | C |
| S_9407296 \| \| scaffold14851_3480562_SNP | 3480562 | A | T |
| S_9407301 \| \| scaffold14851_3480687_SNP | 3480687 | C | T |
| S_9407324 \| \| scaffold14851_3480885_SNP | 3480885 | G | T |
| S_9407360 \| \| scaffold14851_3481353_SNP | 3481353 | T | A |
| S_9407368 \| \| scaffold14851_3481444_SNP | 3481444 | T | C |
| S_9407436 \| \| scaffold14851_3482195_SNP | 3482195 | A | C |
| S_9407477 \| \| scaffold14851_3482500_SNP | 3482500 | T | C |
| S_9407492 \| \| scaffold14851_3482616_SNP | 3482616 | T | C |
| S_9407533 \| \| scaffold14851_3482939_SNP | 3482939 | C | A |
| S_9407544 \| \| scaffold14851_3483028_SNP | 3483028 | T | C |
| S_9407557 \| \| scaffold14851_3483276_SNP | 3483276 | G | C |
| S_9407573 \| \| scaffold14851_3483470_SNP | 3483470 | G | A |
| S_9407585 \| \| scaffold14851_3483550_SNP | 3483550 | G | T |
| S_9407596 \| \| scaffold14851_3483700_SNP | 3483700 | G | T |
| S_9407603 \| \| scaffold14851_3483780_SNP | 3483780 | A | C |
| S_9407605 \| \| scaffold14851_3483788_SNP | 3483788 | G | A |
| S_9407664 \| \| scaffold14851_3484449_SNP | 3484449 | T | C |
| S_9407681 \| \| scaffold14851_3484663_SNP | 3484663 | C | A |
| S_9407684 \| \| scaffold14851_3484677_SNP | 3484677 | C | T |
| S_9407692 \| \| scaffold14851_3484720_SNP | 3484720 | T | C |
| S_9407697 \| \| scaffold14851_3484801_SNP | 3484801 | C | G |
| S_9407713 \| \| scaffold14851_3485144_SNP | 3485144 | A | C |
| S_9407715 \| \| scaffold14851_3485156_SNP | 3485156 | G | C |
| S_9407734 \| \| scaffold14851_3485496_SNP | 3485496 | C | G |
| S_9407743 \| \| scaffold14851_3485580_SNP | 3485580 | T | C |
| S_9407745 \| \| scaffold14851_3485588_SNP | 3485588 | A | G |
| S_9407747 \| \| scaffold14851_3485657_SNP | 3485657 | T | C |
| S_9407749 \| \| scaffold14851_3485670_SNP | 3485670 | G | C |
| S_9407778 \| \| scaffold14851_3486285_SNP | 3486285 | C | T |
| S_9407786 \| \| scaffold14851_3486375_SNP | 3486375 | G | A |
| S_9407815 \| \| scaffold14851_3486712_SNP | 3486712 | G | A |
| S_9407819 \| \| scaffold14851_3486766_SNP | 3486766 | A | G |
| S_9407823 \| \| scaffold14851_3486785_SNP | 3486785 | G | T |
| S_9407824 \| \| scaffold14851_3486841_SNP | 3486841 | T | C |
| S_9407972 \| \| scaffold14851_3488013_SNP | 3488013 | T | G |
| S_9407991 \| \| scaffold14851_3488354_SNP | 3488354 | G | A |
| S_9408007 \| \| scaffold14851_3489429_SNP | 3489429 | A | C |
| S_9408008 \| \| scaffold14851_3489503_SNP | 3489503 | G | A |
| S_9408030 \| \| scaffold14851_3489771_SNP | 3489771 | A | G |
| S_9408084 \| \| scaffold14851_3490235_SNP | 3490235 | C | T |
| S_9408118 \| \| scaffold14851_3490609_SNP | 3490609 | T | C |
| S_9408119 \| \| scaffold14851_3490618_SNP | 3490618 | G | C |
| S_9408121 \| \| scaffold14851_3490637_SNP | 3490637 | T | C |
| S_9408133 \| \| scaffold14851_3490822_SNP | 3490822 | T | G |
| S_9408186 \| \| scaffold14851_3491693_SNP | 3491693 | G | T |
| S_9408187 \| \| scaffold14851_3491708_SNP | 3491708 | T | G |
| S_9408216 \| \| scaffold14851_3491965_SNP | 3491965 | A | T |
| S_9408305 \| \| scaffold14851_3492694_SNP | 3492694 | A | G |
| S_9408383 \| \| scaffold14851_3493630_SNP | 3493630 | T | C |
| S_9408522 \| \| scaffold14851_3495344_SNP | 3495344 | T | C |
| S_9408524 \| \| scaffold14851_3495362_SNP | 3495362 | T | C |
| S_9408557 \| \| scaffold14851_3495645_SNP | 3495645 | C | T |
| S_9408693 \| \| scaffold14851_3497580_SNP | 3497580 | T | A |
| S_9408709 \| \| scaffold14851_3497705_SNP | 3497705 | T | G |
| S_9408732 \| \| scaffold14851_3498142_SNP | 3498142 | A | C |
| S_9408740 \| \| scaffold14851_3498288_SNP | 3498288 | G | T |
| S_9408743 \| \| scaffold14851_3498374_SNP | 3498374 | T | C |
| S_9408748 \| \| scaffold14851_3498449_SNP | 3498449 | T | A |
| S_9408753 \| \| scaffold14851_3498707_SNP | 3498707 | A | T |
| S_9408758 \| \| scaffold14851_3498874_SNP | 3498874 | A | C |
| S_9408761 \| \| scaffold14851_3498915_SNP | 3498915 | T | C |
| S_9408763 \| \| scaffold14851_3498926_SNP | 3498926 | G | A |
| S_9408768 \| \| scaffold14851_3499026_SNP | 3499026 | T | C |
| S_9408769 \| \| scaffold14851_3499049_SNP | 3499049 | T | A |
| S_9408791 \| \| scaffold14851_3499398_SNP | 3499398 | T | C |
| S_9408812 \| \| scaffold14851_3499758_SNP | 3499758 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9408858 \| \| scaffold14851_3500777_SNP | 3500777 | C | T |
| S_9409021 \| \| scaffold14851_3502376_SNP | 3502376 | A | C |
| S_9409024 \| \| scaffold14851_3502447_SNP | 3502447 | A | T |
| S_9409054 \| \| scaffold14851_3503033_SNP | 3503033 | C | T |
| S_9409061 \| \| scaffold14851_3503141_SNP | 3503141 | T | C |
| S_9409067 \| \| scaffold14851_3503239_SNP | 3503239 | A | G |
| S_9409076 \| \| scaffold14851_3503438_SNP | 3503438 | G | A |
| S_9409089 \| \| scaffold14851_3503536_SNP | 3503536 | T | G |
| S_9409091 \| \| scaffold14851_3503574_SNP | 3503574 | T | C |
| S_9409123 \| \| scaffold14851_3504088_SNP | 3504088 | G | A |
| S_9409189 \| \| scaffold14851_3505073_SNP | 3505073 | A | C |
| S_9409191 \| \| scaffold14851_3505100_SNP | 3505100 | A | T |
| S_9409192 \| \| scaffold14851_3505107_SNP | 3505107 | A | T |
| S_9409193 \| \| scaffold14851_3505114_SNP | 3505114 | C | A |
| S_9409195 \| \| scaffold14851_3505162_SNP | 3505162 | C | T |
| S_9409310 \| \| scaffold14851_3506058_SNP | 3506058 | C | T |
| S_9409312 \| \| scaffold14851_3506130_SNP | 3506130 | T | C |
| S_9409327 \| \| scaffold14851_3506387_SNP | 3506387 | T | C |
| S_9409328 \| \| scaffold14851_3506393_SNP | 3506393 | C | T |
| S_9409348 \| \| scaffold14851_3506775_SNP | 3506775 | T | G |
| S_9409449 \| \| scaffold14851_3508297_SNP | 3508297 | C | T |
| S_9409460 \| \| scaffold14851_3508474_SNP | 3508474 | G | C |
| S_9409461 \| \| scaffold14851_3508487_SNP | 3508487 | A | G |
| S_9409462 \| \| scaffold14851_3508526_SNP | 3508526 | T | A |
| S_9409686 \| \| scaffold14851_3511552_SNP | 3511552 | G | A |
| S_9409700 \| \| scaffold14851_3511873_SNP | 3511873 | T | A |
| S_9409707 \| \| scaffold14851_3511971_SNP | 3511971 | T | A |
| S_9409708 \| \| scaffold14851_3511986_SNP | 3511986 | A | T |
| S_9409718 \| \| scaffold14851_3512055_SNP | 3512055 | C | A |
| S_9409736 \| \| scaffold14851_3512219_SNP | 3512219 | C | T |
| S_9409757 \| \| scaffold14851_3512462_SNP | 3512462 | T | C |
| S_9409775 \| \| scaffold14851_3512755_SNP | 3512755 | C | T |
| S_9409785 \| \| scaffold14851_3512939_SNP | 3512939 | G | A |
| S_9409786 \| \| scaffold14851_3512943_SNP | 3512943 | T | C |
| S_9409789 \| \| scaffold14851_3513002_SNP | 3513002 | A | G |
| S_9409823 \| \| scaffold14851_3513510_SNP | 3513510 | T | A |
| S_9409842 \| \| scaffold14851_3513762_SNP | 3513762 | A | T |
| S_9409852 \| \| scaffold14851_3513879_SNP | 3513879 | C | A |
| S_9409858 \| \| scaffold14851_3513895_SNP | 3513895 | G | C |
| S_9409860 \| \| scaffold14851_3513917_SNP | 3513917 | C | T |
| S_9409862 \| \| scaffold14851_3513949_SNP | 3513949 | C | T |
| S_9409869 \| \| scaffold14851_3514091_SNP | 3514091 | G | C |
| S_9410026 \| \| scaffold14851_3516531_SNP | 3516531 | A | G |
| S_9410029 \| \| scaffold14851_3516597_SNP | 3516597 | T | A |
| S_9410128 \| \| scaffold14851_3517672_SNP | 3517672 | T | C |
| S_9410327 \| \| scaffold14851_3519661_SNP | 3519661 | G | C |
| S_9410329 \| \| scaffold14851_3519695_SNP | 3519695 | C | G |
| S_9410331 \| \| scaffold14851_3519735_SNP | 3519735 | T | C |
| S_9410332 \| \| scaffold14851_3519804_SNP | 3519804 | C | A |
| S_9410337 \| \| scaffold14851_3519911_SNP | 3519911 | G | T |
| S_9410338 \| \| scaffold14851_3519917_SNP | 3519917 | G | A |
| S_9410343 \| \| scaffold14851_3520003_SNP | 3520003 | A | G |
| S_9410344 \| \| scaffold14851_3520007_SNP | 3520007 | G | A |
| S_9410349 \| \| scaffold14851_3520068_SNP | 3520068 | A | G |
| S_9410361 \| \| scaffold14851_3520314_SNP | 3520314 | T | C |
| S_9410362 \| \| scaffold14851_3520355_SNP | 3520355 | T | C |
| S_9410363 \| \| scaffold14851_3520361_SNP | 3520361 | C | T |
| S_9410365 \| \| scaffold14851_3520375_SNP | 3520375 | T | A |
| S_9410375 \| \| scaffold14851_3520493_SNP | 3520493 | T | C |
| S_9410395 \| \| scaffold14851_3520648_SNP | 3520648 | G | A |
| S_9410437 \| \| scaffold14851_3521203_SNP | 3521203 | G | A |
| S_9410442 \| \| scaffold14851_3521246_SNP | 3521246 | A | G |
| S_9410447 \| \| scaffold14851_3521311_SNP | 3521311 | A | T |
| S_9410524 \| \| scaffold14851_3522344_SNP | 3522344 | G | T |
| S_9410525 \| \| scaffold14851_3522347_SNP | 3522347 | A | G |
| S_9410528 \| \| scaffold14851_3522424_SNP | 3522424 | T | G |
| S_9410529 \| \| scaffold14851_3522436_SNP | 3522436 | A | T |
| S_9410530 \| \| scaffold14851_3522441_SNP | 3522441 | T | C |
| S_9410532 \| \| scaffold14851_3522471_SNP | 3522471 | G | A |
| S_9410540 \| \| scaffold14851_3522678_SNP | 3522678 | C | A |
| S_9410553 \| \| scaffold14851_3522822_SNP | 3522822 | C | T |
| S_9410554 \| \| scaffold14851_3522827_SNP | 3522827 | A | T |
| S_9410620 \| \| scaffold14851_3524651_SNP | 3524651 | T | A |
| S_9410623 \| \| scaffold14851_3524697_SNP | 3524697 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9410626 \| \| scaffold14851_3524740_SNP | 3524740 | T | C |
| S_9410639 \| \| scaffold14851_3524899_SNP | 3524899 | C | T |
| S_9410648 \| \| scaffold14851_3525056_SNP | 3525056 | T | C |
| S_9410649 \| \| scaffold14851_3525078_SNP | 3525078 | T | C |
| S_9410659 \| \| scaffold14851_3525258_SNP | 3525258 | A | G |
| S_9410660 \| \| scaffold14851_3525286_SNP | 3525286 | G | A |
| S_9410662 \| \| scaffold14851_3525331_SNP | 3525331 | G | T |
| S_9410663 \| \| scaffold14851_3525379_SNP | 3525379 | T | C |
| S_9410664 \| \| scaffold14851_3525387_SNP | 3525387 | C | T |
| S_9410670 \| \| scaffold14851_3525530_SNP | 3525530 | T | G |
| S_9410671 \| \| scaffold14851_3525548_SNP | 3525548 | A | T |
| S_9410728 \| \| scaffold14851_3527247_SNP | 3527247 | A | T |
| S_9410731 \| \| scaffold14851_3527311_SNP | 3527311 | A | G |
| S_9410733 \| \| scaffold14851_3527320_SNP | 3527320 | A | G |
| S_9410881 \| \| scaffold14851_3529239_SNP | 3529239 | G | T |
| S_9410918 \| \| scaffold14851_3529629_SNP | 3529629 | A | G |
| S_9410922 \| \| scaffold14851_3529656_SNP | 3529656 | C | A |
| S_9410923 \| \| scaffold14851_3529701_SNP | 3529701 | A | C |
| S_9410933 \| \| scaffold14851_3529790_SNP | 3529790 | A | T |
| S_9410937 \| \| scaffold14851_3529815_SNP | 3529815 | G | T |
| S_9410950 \| \| scaffold14851_3529926_SNP | 3529926 | C | T |
| S_9410956 \| \| scaffold14851_3529988_SNP | 3529988 | A | G |
| S_9410959 \| \| scaffold14851_3530011_SNP | 3530011 | A | G |
| scaffold14851_3530067_SNP | 3530067 | C | A |
| S_9410971 \| \| scaffold14851_3530090_SNP | 3530090 | T | C |
| S_9410986 \| \| scaffold14851_3530186_SNP | 3530186 | A | C |
| S_9410987 \| \| scaffold14851_3530193_SNP | 3530193 | C | T |
| scaffold14851_3542611_SNP | 3542611 | A | G |
| scaffold14851_3542628_SNP | 3542628 | A | G |
| S_9411587 \| \| scaffold14851_3547934_SNP | 3547934 | T | G |
| S_9411589 \| \| scaffold14851_3547984_SNP | 3547984 | G | C |
| S_9411599 \| \| scaffold14851_3548267_SNP | 3548267 | C | G |
| S_9411615 \| \| scaffold14851_3548342_SNP | 3548342 | A | G |
| S_9412050 \| \| scaffold14851_3558197_SNP | 3558197 | C | T |
| S_9412053 \| \| scaffold14851_3558290_SNP | 3558290 | T | G |
| S_9412066 \| \| scaffold14851_3558461_SNP | 3558461 | G | A |
| S_9412070 \| \| scaffold14851_3558518_SNP | 3558518 | G | A |
| S_9412075 \| \| scaffold14851_3558653_SNP | 3558653 | G | A |
| S_9412080 \| \| scaffold14851_3558705_SNP | 3558705 | A | C |
| S_9412089 \| \| scaffold14851_3558812_SNP | 3558812 | C | A |
| scaffold14851_3558905_SNP | 3558905 | C | T |
| S_9412187 \| \| scaffold14851_3560575_SNP | 3560575 | A | C |
| S_9412192 \| \| scaffold14851_3560664_SNP | 3560664 | G | T |
| S_9412703 \| \| scaffold14851_3567546_SNP | 3567546 | T | G |
| S_9413315 \| \| scaffold14851_3586982_SNP | 3586982 | T | A |
| S_9415882 \| \| scaffold14851_3602699_SNP | 3602699 | G | A |
| S_9415883 \| \| scaffold14851_3602707_SNP | 3602707 | C | T |
| S_9415895 \| \| scaffold14851_3602929_SNP | 3602929 | C | T |
| S_9415924 \| \| scaffold14851_3603301_SNP | 3603301 | T | A |
| S_9415934 \| \| scaffold14851_3603496_SNP | 3603496 | C | A |
| S_9415940 \| \| scaffold14851_3603538_SNP | 3603538 | C | T |
| S_9416037 \| \| scaffold14851_3605186_SNP | 3605186 | C | A |
| S_9416040 \| \| scaffold14851_3605264_SNP | 3605264 | A | G |
| S_9416041 \| \| scaffold14851_3605268_SNP | 3605268 | T | C |
| S_9416154 \| \| scaffold14851_3606839_SNP | 3606839 | T | C |
| S_9416155 \| \| scaffold14851_3606840_SNP | 3606840 | T | C |
| S_9416159 \| \| scaffold14851_3606881_SNP | 3606881 | C | T |
| S_9416160 \| \| scaffold14851_3606883_SNP | 3606883 | C | G |
| S_9416165 \| \| scaffold14851_3606960_SNP | 3606960 | T | C |
| S_9416173 \| \| scaffold14851_3607122_SNP | 3607122 | T | C |
| S_9416175 \| \| scaffold14851_3607135_SNP | 3607135 | G | A |
| S_9416176 \| \| scaffold14851_3607147_SNP | 3607147 | G | C |
| S_9416227 \| \| scaffold14851_3608025_SNP | 3608025 | G | A |
| S_9416235 \| \| scaffold14851_3608142_SNP | 3608142 | G | A |
| S_9416236 \| \| scaffold14851_3608148_SNP | 3608148 | C | T |
| S_9416255 \| \| scaffold14851_3608392_SNP | 3608392 | A | G |
| S_9416257 \| \| scaffold14851_3608409_SNP | 3608409 | T | G |
| S_9416279 \| \| scaffold14851_3608504_SNP | 3608504 | G | A |
| S_9416354 \| \| scaffold14851_3608753_SNP | 3608753 | A | G |
| S_9416369 \| \| scaffold14851_3608975_SNP | 3608975 | A | T |
| S_9416377 \| \| scaffold14851_3609211_SNP | 3609211 | T | A |
| S_9416458 \| \| scaffold14851_3610262_SNP | 3610262 | A | G |
| S_9416478 \| \| scaffold14851_3610549_SNP | 3610549 | G | A |
| S_9416479 \| \| scaffold14851_3610552_SNP | 3610552 | C | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9416552 \| \| scaffold14851_3611611_SNP | 3611611 | T | A |
| S_9416575 \| \| scaffold14851_3611996_SNP | 3611996 | G | T |
| S_9416702 \| \| scaffold14851_3613178_SNP | 3613178 | G | T |
| S_9416707 \| \| scaffold14851_3613280_SNP | 3613280 | G | T |
| S_9416719 \| \| scaffold14851_3613566_SNP | 3613566 | T | C |
| S_9416722 \| \| scaffold14851_3613586_SNP | 3613586 | T | C |
| S_9416749 \| \| scaffold14851_3614094_SNP | 3614094 | T | G |
| S_9416789 \| \| scaffold14851_3614679_SNP | 3614679 | G | A |
| S_9416794 \| \| scaffold14851_3614760_SNP | 3614760 | G | T |
| S_9416870 \| \| scaffold14851_3616094_SNP | 3616094 | G | A |
| S_9416999 \| \| scaffold14851_3618066_SNP | 3618066 | A | G |
| S_9417021 \| \| scaffold14851_3618743_SNP | 3618743 | G | A |
| S_9417054 \| \| scaffold14851_3619883_SNP | 3619883 | A | G |
| S_9417063 \| \| scaffold14851_3620128_SNP | 3620128 | G | A |
| S_9417086 \| \| scaffold14851_3620453_SNP | 3620453 | A | G |
| S_9417104 \| \| scaffold14851_3620663_SNP | 3620663 | G | A |
| S_9417233 \| \| scaffold14851_3621912_SNP | 3621912 | T | G |
| S_9417239 \| \| scaffold14851_3622062_SNP | 3622062 | T | A |
| S_9417270 \| \| scaffold14851_3622517_SNP | 3622517 | C | G |
| S_9417276 \| \| scaffold14851_3622586_SNP | 3622586 | T | A |
| S_9417362 \| \| scaffold14851_3623244_SNP | 3623244 | C | T |
| S_9417365 \| \| scaffold14851_3623289_SNP | 3623289 | T | C |
| S_9417434 \| \| scaffold14851_3624480_SNP | 3624480 | G | T |
| S_9417450 \| \| scaffold14851_3624713_SNP | 3624713 | T | C |
| S_9417477 \| \| scaffold14851_3625069_SNP | 3625069 | T | A |
| S_9417478 \| \| scaffold14851_3625078_SNP | 3625078 | T | C |
| S_9417481 \| \| scaffold14851_3625124_SNP | 3625124 | C | T |
| S_9417483 \| \| scaffold14851_3625137_SNP | 3625137 | G | C |
| S_9417484 \| \| scaffold14851_3625150_SNP | 3625150 | G | A |
| S_9417489 \| \| scaffold14851_3625243_SNP | 3625243 | G | A |
| S_9417506 \| \| scaffold14851_3625526_SNP | 3625526 | G | A |
| S_9417523 \| \| scaffold14851_3625878_SNP | 3625878 | G | A |
| S_9417530 \| \| scaffold14851_3626026_SNP | 3626026 | T | A |
| S_9417550 \| \| scaffold14851_3626321_SNP | 3626321 | T | G |
| S_9417566 \| \| scaffold14851_3626623_SNP | 3626623 | T | A |
| S_9417596 \| \| scaffold14851_3627128_SNP | 3627128 | T | G |
| S_9417614 \| \| scaffold14851_3627447_SNP | 3627447 | A | G |
| S_9417688 \| \| scaffold14851_3628434_SNP | 3628434 | C | T |
| S_9417698 \| \| scaffold14851_3628614_SNP | 3628614 | C | A |
| S_9417699 \| \| scaffold14851_3628634_SNP | 3628634 | T | C |
| S_9417702 \| \| scaffold14851_3628669_SNP | 3628669 | A | C |
| S_9417714 \| \| scaffold14851_3628867_SNP | 3628867 | C | T |
| S_9417715 \| \| scaffold14851_3628875_SNP | 3628875 | A | C |
| S_9417820 \| \| scaffold14851_3630427_SNP | 3630427 | G | T |
| S_9417824 \| \| scaffold14851_3630480_SNP | 3630480 | T | C |
| S_9417887 \| \| scaffold14851_3631343_SNP | 3631343 | G | T |
| S_9417983 \| \| scaffold14851_3632190_SNP | 3632190 | A | G |
| S_9417987 \| \| scaffold14851_3632287_SNP | 3632287 | C | T |
| S_9418126 \| \| scaffold14851_3633424_SNP | 3633424 | C | T |
| S_9418147 \| \| scaffold14851_3633717_SNP | 3633717 | C | T |
| S_9418223 \| \| scaffold14851_3634845_SNP | 3634845 | T | C |
| S_9418264 \| \| scaffold14851_3635238_SNP | 3635238 | T | C |
| S_9418280 \| \| scaffold14851_3635512_SNP | 3635512 | C | T |
| S_9418310 \| \| scaffold14851_3635938_SNP | 3635938 | A | T |
| S_9418345 \| \| scaffold14851_3636418_SNP | 3636418 | T | C |
| scaffold14851_3636437_SNP | 3636437 | C | T |
| S_9418354 \| \| scaffold14851_3636547_SNP | 3636547 | A | T |
| scaffold14851_3636615_SNP | 3636615 | G | A |
| S_9418357 \| \| scaffold14851_3636629_SNP | 3636629 | T | C |
| S_9418358 \| \| scaffold14851_3636630_SNP | 3636630 | T | C |
| S_9418395 \| \| scaffold14851_3637084_SNP | 3637084 | C | T |
| S_9418453 \| \| scaffold14851_3637743_SNP | 3637743 | A | G |
| S_9418596 \| \| scaffold14851_3638843_SNP | 3638843 | A | T |
| S_9418605 \| \| scaffold14851_3638907_SNP | 3638907 | A | G |
| S_9418608 \| \| scaffold14851_3638917_SNP | 3638917 | T | A |
| S_9418736 \| \| scaffold14851_3640723_SNP | 3640723 | A | T |
| S_9418795 \| \| scaffold14851_3641666_SNP | 3641666 | G | A |
| S_9418797 \| \| scaffold14851_3641687_SNP | 3641687 | A | G |
| scaffold14851_3641811_SNP | 3641811 | G | T |
| S_9418837 \| \| scaffold14851_3642219_SNP | 3642219 | A | T |
| S_9418900 \| \| scaffold14851_3642962_SNP | 3642962 | A | G |
| S_9418901 \| \| scaffold14851_3642963_SNP | 3642963 | C | G |
| S_9418937 \| \| scaffold14851_3643482_SNP | 3643482 | G | A |
| S_9418938 \| \| scaffold14851_3643499_SNP | 3643499 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9418939 \| \| scaffold14851_3643502_SNP | 3643502 | T | C |
| S_9418997 \| \| scaffold14851_3644680_SNP | 3644680 | C | G |
| S_9419054 \| \| scaffold14851_3646116_SNP | 3646116 | G | A |
| S_9419075 \| \| scaffold14851_3646309_SNP | 3646309 | C | T |
| scaffold14851_3646339_SNP | 3646339 | A | T |
| scaffold14851_3646348_SNP | 3646348 | G | A |
| S_9419084 \| \| scaffold14851_3646398_SNP | 3646398 | A | C |
| S_9419116 \| \| scaffold14851_3646791_SNP | 3646791 | G | C |
| S_9419125 \| \| scaffold14851_3646998_SNP | 3646998 | T | A |
| S_9419164 \| \| scaffold14851_3647522_SNP | 3647522 | G | T |
| scaffold14851_3647661_SNP | 3647661 | C | T |
| S_9419177 \| \| scaffold14851_3647712_SNP | 3647712 | C | T |
| S_9419219 \| \| scaffold14851_3648060_SNP | 3648060 | G | C |
| S_9419250 \| \| scaffold14851_3648451_SNP | 3648451 | C | T |
| S_9419253 \| \| scaffold14851_3648457_SNP | 3648457 | G | A |
| S_9419259 \| \| scaffold14851_3648517_SNP | 3648517 | A | G |
| scaffold14851_3648544_SNP | 3648544 | G | A |
| S_9419325 \| \| scaffold14851_3649159_SNP | 3649159 | C | A |
| S_9419339 \| \| scaffold14851_3649389_SNP | 3649389 | C | G |
| S_9419345 \| \| scaffold14851_3649547_SNP | 3649547 | A | G |
| S_9419352 \| \| scaffold14851_3649688_SNP | 3649688 | T | C |
| S_9419356 \| \| scaffold14851_3649790_SNP | 3649790 | G | A |
| S_9419375 \| \| scaffold14851_3650256_SNP | 3650256 | G | A |
| S_9419377 \| \| scaffold14851_3650304_SNP | 3650304 | G | A |
| S_9419477 \| \| scaffold14851_3651572_SNP | 3651572 | G | A |
| S_9419539 \| \| scaffold14851_3652671_SNP | 3652671 | C | A |
| S_9419550 \| \| scaffold14851_3652738_SNP | 3652738 | T | G |
| scaffold14851_3652898_SNP | 3652898 | A | T |
| S_9419580 \| \| scaffold14851_3653172_SNP | 3653172 | G | A |
| S_9419585 \| \| scaffold14851_3653221_SNP | 3653221 | A | T |
| S_9419635 \| \| scaffold14851_3653786_SNP | 3653786 | G | A |
| scaffold14851_3654485_SNP | 3654485 | A | C |
| S_9419779 \| \| scaffold14851_3655191_SNP | 3655191 | C | A |
| S_9419780 \| \| scaffold14851_3655193_SNP | 3655193 | A | T |
| S_9419781 \| \| scaffold14851_3655307_SNP | 3655307 | A | T |
| S_9420017 \| \| scaffold14851_3658448_SNP | 3658448 | G | A |
| S_9420087 \| \| scaffold14851_3659762_SNP | 3659762 | G | T |
| S_9420093 \| \| scaffold14851_3659882_SNP | 3659882 | G | C |
| S_9420099 \| \| scaffold14851_3659930_SNP | 3659930 | T | G |
| scaffold14851_3660507_SNP | 3660507 | T | G |
| S_9420144 \| \| scaffold14851_3660829_SNP | 3660829 | T | G |
| S_9420147 \| \| scaffold14851_3660848_SNP | 3660848 | C | T |
| S_9420148 \| \| scaffold14851_3660899_SNP | 3660899 | A | G |
| S_9420150 \| \| scaffold14851_3660935_SNP | 3660935 | G | T |
| S_9420247 \| \| scaffold14851_3662526_SNP | 3662526 | G | A |
| S_9420271 \| \| scaffold14851_3662969_SNP | 3662969 | T | C |
| S_9420274 \| \| scaffold14851_3663056_SNP | 3663056 | T | C |
| S_9420305 \| \| scaffold14851_3663433_SNP | 3663433 | C | G |
| S_9420312 \| \| scaffold14851_3663492_SNP | 3663492 | C | T |
| S_9420314 \| \| scaffold14851_3663512_SNP | 3663512 | C | T |
| S_9420318 \| \| scaffold14851_3663572_SNP | 3663572 | G | A |
| S_9420330 \| \| scaffold14851_3663736_SNP | 3663736 | G | A |
| S_9420338 \| \| scaffold14851_3663799_SNP | 3663799 | C | T |
| S_9420380 \| \| scaffold14851_3664200_SNP | 3664200 | C | A |
| S_9420381 \| \| scaffold14851_3664204_SNP | 3664204 | G | T |
| S_9420392 \| \| scaffold14851_3664361_SNP | 3664361 | C | T |
| S_9420417 \| \| scaffold14851_3664536_SNP | 3664536 | G | T |
| S_9420456 \| \| scaffold14851_3665086_SNP | 3665086 | A | T |
| S_9420464 \| \| scaffold14851_3665221_SNP | 3665221 | T | C |
| S_9420480 \| \| scaffold14851_3665534_SNP | 3665534 | A | T |
| $_9420584 \| \| scaffold14851_3666827_SNP | 3666827 | G | C |
| S_9420585 \| \| scaffold14851_3666840_SNP | 3666840 | G | A |
| S_9420685 \| \| scaffold14851_3668306_SNP | 3668306 | C | T |
| S_9420703 \| \| scaffold14851_3668489_SNP | 3668489 | G | A |
| S_9420715 \| \| scaffold14851_3668684_SNP | 3668684 | A | C |
| S_9420772 \| \| scaffold14851_3669664_SNP | 3669664 | C | A |
| S_9420776 \| \| scaffold14851_3669726_SNP | 3669726 | T | C |
| S_9420778 \| \| scaffold14851_3669732_SNP | 3669732 | A | T |
| S_9420803 \| \| scaffold14851_3670051_SNP | 3670051 | C | T |
| S_9420810 \| \| scaffold14851_3670162_SNP | 3670162 | A | G |
| S_9420813 \| \| scaffold14851_3670268_SNP | 3670268 | A | G |
| S_9420820 \| \| scaffold14851_3670359_SNP | 3670359 | A | C |
| S_9420944 \| \| scaffold14851_3672306_SNP | 3672306 | C | T |
| S_9420992 \| \| scaffold14851_3673030_SNP | 3673030 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9420993 \| \| scaffold14851_3673076_SNP | 3673076 | C | T |
| scaffold14851_3674681_SNP | 3674681 | G | A |
| S_9421132 \| \| scaffold14851_3675604_SNP | 3675604 | T | C |
| S_9421188 \| \| scaffold14851_3676294_SNP | 3676294 | C | T |
| S_9421317 \| \| scaffold14851_3678288_SNP | 3678288 | A | G |
| S_9421338 \| \| scaffold14851_3678642_SNP | 3678642 | C | A |
| S_9421816 \| \| scaffold14851_3683608_SNP | 3683608 | G | T |
| scaffold14851_3685389_SNP | 3685389 | G | A |
| S_9422016 \| \| scaffold14851_3685610_SNP | 3685610 | G | A |
| S_9422373 \| \| scaffold14851_3690431_SNP | 3690431 | T | A |
| S_9422479 \| \| scaffold14851_3691942_SNP | 3691942 | T | A |
| scaffold14851_3694829_SNP | 3694829 | G | A |
| S_9422799 \| \| scaffold14851_3695158_SNP | 3695158 | G | A |
| scaffold14851_3695218_SNP | 3695218 | G | A |
| S_9422834 \| \| scaffold14851_3695381_SNP | 3695381 | T | C |
| S_9422843 \| \| scaffold14851_3695432_SNP | 3695432 | G | A |
| S_9422857 \| \| scaffold14851_3695594_SNP | 3695594 | A | G |
| S_9422859 \| \| scaffold14851_3695646_SNP | 3695646 | G | A |
| S_9422860 \| \| scaffold14851_3695734_SNP | 3695734 | A | C |
| S_9422864 \| \| scaffold14851_3695813_SNP | 3695813 | G | A |
| S_9422880 \| \| scaffold14851_3696003_SNP | 3696003 | T | A |
| S_9422883 \| \| scaffold14851_3696053_SNP | 3696053 | A | G |
| S_9422886 \| \| scaffold14851_3696084_SNP | 3696084 | A | G |
| scaffold14851_3697256_SNP | 3697256 | T | C |
| S_9423414 \| \| scaffold14851_3700760_SNP | 3700760 | C | T |
| scaffold14851_3701199_SNP | 3701199 | A | G |
| S_9423543 \| \| scaffold14851_3701612_SNP | 3701612 | C | T |
| S_9423554 \| \| scaffold14851_3701897_SNP | 3701897 | A | T |
| S_9424101 \| \| scaffold14851_3708680_SNP | 3708680 | T | C |
| S_9424222 \| \| scaffold14851_3710390_SNP | 3710390 | T | G |
| S_9424235 \| \| scaffold14851_3710613_SNP | 3710613 | C | T |
| S_9424276 \| \| scaffold14851_3711165_SNP | 3711165 | C | G |
| S_9424326 \| \| scaffold14851_3711868_SNP | 3711868 | G | A |
| S_9424334 \| \| scaffold14851_3711973_SNP | 3711973 | T | A |
| S_9424389 \| \| scaffold14851_3712708_SNP | 3712708 | G | A |
| S_9424433 \| \| scaffold14851_3713374_SNP | 3713374 | T | G |
| S_9424458 \| \| scaffold14851_3713722_SNP | 3713722 | A | C |
| S_9424510 \| \| scaffold14851_3714672_SNP | 3714672 | C | T |
| S_9424525 \| \| scaffold14851_3714865_SNP | 3714865 | T | C |
| S_9424543 \| \| scaffold14851_3715154_SNP | 3715154 | A | T |
| S_9424589 \| \| scaffold14851_3716032_SNP | 3716032 | C | A |
| S_9424646 \| \| scaffold14851_3717318_SNP | 3717318 | C | G |
| S_9424739 \| \| scaffold14851_3718583_SNP | 3718583 | A | G |
| S_9424746 \| \| scaffold14851_3718759_SNP | 3718759 | A | G |
| S_9424750 \| \| scaffold14851_3718839_SNP | 3718839 | G | A |
| S_9424751 \| \| scaffold14851_3718851_SNP | 3718851 | C | T |
| S_9424758 \| \| scaffold14851_3719059_SNP | 3719059 | G | A |
| S_9424761 \| \| scaffold14851_3719098_SNP | 3719098 | A | T |
| S_9424775 \| \| scaffold14851_3719511_SNP | 3719511 | C | A |
| S_9424776 \| \| scaffold14851_3719514_SNP | 3719514 | T | G |
| S_9424789 \| \| scaffold14851_3719673_SNP | 3719673 | T | C |
| S_9424790 \| \| scaffold14851_3719674_SNP | 3719674 | G | A |
| S_9424895 \| \| scaffold14851_3720699_SNP | 3720699 | A | G |
| S_9424928 \| \| scaffold14851_3721026_SNP | 3721026 | T | G |
| S_9424934 \| \| scaffold14851_3721067_SNP | 3721067 | G | T |
| S_9424958 \| \| scaffold14851_3721473_SNP | 3721473 | C | T |
| S_9425001 \| \| scaffold14851_3722066_SNP | 3722066 | A | T |
| S_9425030 \| \| scaffold14851_3722446_SNP | 3722446 | C | T |
| S_9425074 \| \| scaffold14851_3722737_SNP | 3722737 | A | C |
| S_9425075 \| \| scaffold14851_3722794_SNP | 3722794 | A | G |
| S_9425076 \| \| scaffold14851_3722797_SNP | 3722797 | T | C |
| S_9425077 \| \| scaffold14851_3722799_SNP | 3722799 | G | A |
| S_9425078 \| \| scaffold14851_3722803_SNP | 3722803 | C | T |
| S_9425083 \| \| scaffold14851_3722966_SNP | 3722966 | C | T |
| S_9425099 \| \| scaffold14851_3723167_SNP | 3723167 | G | A |
| S_9425103 \| \| scaffold14851_3723229_SNP | 3723229 | G | C |
| S_9425124 \| \| scaffold14851_3723492_SNP | 3723492 | T | A |
| S_9425138 \| \| scaffold14851_3723599_SNP | 3723599 | T | A |
| S_9425142 \| \| scaffold14851_3723633_SNP | 3723633 | A | G |
| S_9425743 \| \| scaffold14851_3726472_SNP | 3726472 | A | T |
| S_9425753 \| \| scaffold14851_3726553_SNP | 3726553 | A | G |
| S_9425756 \| \| scaffold14851_3726593_SNP | 3726593 | T | C |
| S_9425766 \| \| scaffold14851_3726858_SNP | 3726858 | T | A |
| S_9425778 \| \| scaffold14851_3727088_SNP | 3727088 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9425779 \| \| scaffold14851_3727091_SNP | 3727091 | A | C |
| S_9425781 \| \| scaffold14851_3727113_SNP | 3727113 | C | T |
| S_9426026 \| \| scaffold14851_3729363_SNP | 3729363 | G | A |
| S_9426084 \| \| scaffold14851_3729728_SNP | 3729728 | A | G |
| S_9426085 \| \| scaffold14851_3729733_SNP | 3729733 | G | A |
| S_9426138 \| \| scaffold14851_3730105_SNP | 3730105 | A | G |
| S_9426139 \| \| scaffold14851_3730119_SNP | 3730119 | A | G |
| S_9426165 \| \| scaffold14851_3730424_SNP | 3730424 | C | A |
| S_9426204 \| \| scaffold14851_3730808_SNP | 3730808 | C | T |
| S_9426215 \| \| scaffold14851_3730957_SNP | 3730957 | G | C |
| scaffold14851_3731126_SNP | 3731126 | G | C |
| scaffold14851_3731382_SNP | 3731382 | C | T |
| S_9426263 \| \| scaffold14851_3731449_SNP | 3731449 | C | T |
| S_9426267 \| \| scaffold14851_3731486_SNP | 3731486 | A | G |
| S_9426304 \| \| scaffold14851_3731894_SNP | 3731894 | G | C |
| S_9426452 \| \| scaffold14851_3732649_SNP | 3732649 | T | A |
| S_9426546 \| \| scaffold14851_3733754_SNP | 3733754 | A | T |
| S_9426553 \| \| scaffold14851_3733849_SNP | 3733849 | T | A |
| S_9426568 \| \| scaffold14851_3734197_SNP | 3734197 | A | G |
| S_9426596 \| \| scaffold14851_3734473_SNP | 3734473 | T | C |
| S_9426654 \| \| scaffold14851_3734846_SNP | 3734846 | T | C |
| S_9427004 \| \| scaffold14851_3740478_SNP | 3740478 | T | A |
| S_9427614 \| \| scaffold14851_3745822_SNP | 3745822 | T | G |
| S_9427615 \| \| scaffold14851_3745827_SNP | 3745827 | G | C |
| S_9427761 \| \| scaffold14851_3747168_SNP | 3747168 | G | A |
| S_9427807 \| \| scaffold14851_3747570_SNP | 3747570 | A | G |
| S_9427825 \| \| scaffold14851_3747815_SNP | 3747815 | T | A |
| S_9427837 \| \| scaffold14851_3747908_SNP | 3747908 | A | C |
| S_9428204 \| \| scaffold14851_3752523_SNP | 3752523 | C | A |
| S_9428242 \| \| scaffold14851_3752998_SNP | 3752998 | A | G |
| S_9428580 \| \| scaffold14851_3756956_SNP | 3756956 | T | C |
| S_9428617 \| \| scaffold14851_3757250_SNP | 3757250 | T | C |
| S_9428618 \| \| scaffold14851_3757254_SNP | 3757254 | T | C |
| S_9428646 \| \| scaffold14851_3757624_SNP | 3757624 | A | T |
| S_9428647 \| \| scaffold14851_3757630_SNP | 3757630 | G | C |
| S_9428648 \| \| scaffold14851_3757643_SNP | 3757643 | A | T |
| S_9428650 \| \| scaffold14851_3757684_SNP | 3757684 | T | A |
| S_9428661 \| \| scaffold14851_3757882_SNP | 3757882 | C | A |
| S_9428665 \| \| scaffold14851_3757916_SNP | 3757916 | T | A |
| S_9428668 \| \| scaffold14851_3757967_SNP | 3757967 | C | G |
| S_9428677 \| \| scaffold14851_3758128_SNP | 3758128 | A | G |
| S_9428776 \| \| scaffold14851_3759435_SNP | 3759435 | T | G |
| S_9428798 \| \| scaffold14851_3759760_SNP | 3759760 | A | G |
| S_9428825 \| \| scaffold14851_3760210_SNP | 3760210 | C | T |
| S_9428873 \| \| scaffold14851_3760873_SNP | 3760873 | A | G |
| S_9428894 \| \| scaffold14851_3761207_SNP | 3761207 | T | G |
| S_9428996 \| \| scaffold14851_3762993_SNP | 3762993 | C | T |
| S_9429006 \| \| scaffold14851_3763077_SNP | 3763077 | A | T |
| S_9429118 \| \| scaffold14851_3764349_SNP | 3764349 | G | A |
| S_9429134 \| \| scaffold14851_3764791_SNP | 3764791 | C | T |
| S_9429141 \| \| scaffold14851_3764863_SNP | 3764863 | C | T |
| S_9429144 \| \| scaffold14851_3764925_SNP | 3764925 | C | T |
| S_9429161 \| \| scaffold14851_3765248_SNP | 3765248 | G | A |
| S_9429163 \| \| scaffold14851_3765277_SNP | 3765277 | C | G |
| S_9429284 \| \| scaffold14851_3766331_SNP | 3766331 | A | C |
| S_9429301 \| \| scaffold14851_3766557_SNP | 3766557 | T | A |
| S_9429340 \| \| scaffold14851_3766967_SNP | 3766967 | T | A |
| S_9429342 \| \| scaffold14851_3767014_SNP | 3767014 | T | A |
| S_9429354 \| \| scaffold14851_3767343_SNP | 3767343 | T | C |
| S_9429364 \| \| scaffold14851_3767707_SNP | 3767707 | C | T |
| S_9429438 \| \| scaffold14851_3768942_SNP | 3768942 | A | G |
| S_9429457 \| \| scaffold14851_3769347_SNP | 3769347 | T | C |
| S_9429464 \| \| scaffold14851_3769442_SNP | 3769442 | G | T |
| S_9429466 \| \| scaffold14851_3769446_SNP | 3769446 | T | G |
| S_9429471 \| \| scaffold14851_3769504_SNP | 3769504 | A | G |
| S_9429472 \| \| scaffold14851_3769544_SNP | 3769544 | T | C |
| S_9429476 \| \| scaffold14851_3769659_SNP | 3769659 | A | G |
| S_9429482 \| \| scaffold14851_3769729_SNP | 3769729 | C | G |
| S_9429490 \| \| scaffold14851_3769963_SNP | 3769963 | T | C |
| S_9429509 \| \| scaffold14851_3770186_SNP | 3770186 | G | A |
| S_9429511 \| \| scaffold14851_3770204_SNP | 3770204 | G | C |
| S_9429512 \| \| scaffold14851_3770248_SNP | 3770248 | G | A |
| S_9429523 \| \| scaffold14851_3770460_SNP | 3770460 | T | G |
| S_9429540 \| \| scaffold14851_3770759_SNP | 3770759 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9429676 \|\| scaffold14851_3773529_SNP | 3773529 | C | T |
| S_9429707 \|\| scaffold14851_3773775_SNP | 3773775 | C | G |
| S_9429714 \|\| scaffold14851_3773874_SNP | 3773874 | G | A |
| S_9429715 \|\| scaffold14851_3773875_SNP | 3773875 | G | A |
| S_9429722 \|\| scaffold14851_3773926_SNP | 3773926 | A | C |
| S_9429740 \|\| scaffold14851_3774122_SNP | 3774122 | T | G |
| S_9429762 \|\| scaffold14851_3774546_SNP | 3774546 | A | G |
| S_9429763 \|\| scaffold14851_3774563_SNP | 3774563 | T | A |
| S_9429764 \|\| scaffold14851_3774564_SNP | 3774564 | T | A |
| S_9429784 \|\| scaffold14851_3775137_SNP | 3775137 | G | A |
| S_9429809 \|\| scaffold14851_3775498_SNP | 3775498 | A | T |
| S_9429810 \|\| scaffold14851_3775500_SNP | 3775500 | T | C |
| S_9429817 \|\| scaffold14851_3775605_SNP | 3775605 | T | A |
| S_9429821 \|\| scaffold14851_3775819_SNP | 3775819 | G | T |
| S_9429847 \|\| scaffold14851_3776575_SNP | 3776575 | G | A |
| S_9429862 \|\| scaffold14851_3776859_SNP | 3776859 | A | G |
| S_9429961 \|\| scaffold14851_3777897_SNP | 3777897 | C | A |
| S_9429992 \|\| scaffold14851_3778211_SNP | 3778211 | C | A |
| S_9430065 \|\| scaffold14851_3779232_SNP | 3779232 | T | C |
| S_9430076 \|\| scaffold14851_3779370_SNP | 3779370 | T | C |
| S_9430105 \|\| scaffold14851_3779753_SNP | 3779753 | C | T |
| S_9430188 \|\| scaffold14851_3780507_SNP | 3780507 | T | A |
| S_9430192 \|\| scaffold14851_3780589_SNP | 3780589 | G | A |
| S_9430217 \|\| scaffold14851_3780864_SNP | 3780864 | C | A |
| S_9430340 \|\| scaffold14851_3782949_SNP | 3782949 | A | G |
| S_9430345 \|\| scaffold14851_3783004_SNP | 3783004 | C | T |
| S_9430350 \|\| scaffold14851_3783044_SNP | 3783044 | C | T |
| S_9430439 \|\| scaffold14851_3784334_SNP | 3784334 | T | C |
| S_9430440 \|\| scaffold14851_3784409_SNP | 3784409 | T | A |
| S_9430488 \|\| scaffold14851_3785090_SNP | 3785090 | C | G |
| S_9430499 \|\| scaffold14851_3785349_SNP | 3785349 | A | G |
| S_9430511 \|\| scaffold14851_3785719_SNP | 3785719 | A | G |
| S_9430513 \|\| scaffold14851_3785763_SNP | 3785763 | A | G |
| S_9430514 \|\| scaffold14851_3785786_SNP | 3785786 | T | C |
| S_9430574 \|\| scaffold14851_3786391_SNP | 3786391 | T | G |
| S_9430585 \|\| scaffold14851_3786620_SNP | 3786620 | C | G |
| S_9430594 \|\| scaffold14851_3786692_SNP | 3786692 | A | T |
| S_9430671 \|\| scaffold14851_3787532_SNP | 3787532 | G | A |
| S_9430672 \|\| scaffold14851_3787534_SNP | 3787534 | A | G |
| S_9430687 \|\| scaffold14851_3787744_SNP | 3787744 | T | G |
| S_9430697 \|\| scaffold14851_3787814_SNP | 3787814 | A | C |
| S_9430731 \|\| scaffold14851_3788224_SNP | 3788224 | T | A |
| S_9430741 \|\| scaffold14851_3788385_SNP | 3788385 | T | C |
| S_9430754 \|\| scaffold14851_3788652_SNP | 3788652 | T | C |
| S_9430874 \|\| scaffold14851_3789899_SNP | 3789899 | A | G |
| S_9430876 \|\| scaffold14851_3790020_SNP | 3790020 | T | A |
| S_9430878 \|\| scaffold14851_3790133_SNP | 3790133 | C | T |
| S_9430880 \|\| scaffold14851_3790153_SNP | 3790153 | G | T |
| S_9430883 \|\| scaffold14851_3790210_SNP | 3790210 | C | T |
| S_9430884 \|\| scaffold14851_3790242_SNP | 3790242 | C | G |
| S_9430893 \|\| scaffold14851_3790305_SNP | 3790305 | C | T |
| S_9430896 \|\| scaffold14851_3790363_SNP | 3790363 | T | C |
| S_9430900 \|\| scaffold14851_3790379_SNP | 3790379 | C | A |
| S_9430901 \|\| scaffold14851_3790384_SNP | 3790384 | C | A |
| S_9430956 \|\| scaffold14851_3791216_SNP | 3791216 | C | A |
| S_9431215 \|\| scaffold14851_3794761_SNP | 3794761 | T | A |
| S_9431285 \|\| scaffold14851_3795492_SNP | 3795492 | T | A |
| S_9431313 \|\| scaffold14851_3795946_SNP | 3795946 | T | C |
| S_9431324 \|\| scaffold14851_3796252_SNP | 3796252 | G | A |
| S_9431376 \|\| scaffold14851_3797262_SNP | 3797262 | T | A |
| S_9431504 \|\| scaffold14851_3798940_SNP | 3798940 | T | A |
| S_9431574 \|\| scaffold14851_3799942_SNP | 3799942 | G | A |
| S_9431575 \|\| scaffold14851_3799959_SNP | 3799959 | G | T |
| S_9431618 \|\| scaffold14851_3800571_SNP | 3800571 | A | T |
| S_9431655 \|\| scaffold14851_3801208_SNP | 3801208 | C | G |
| S_9431657 \|\| scaffold14851_3801288_SNP | 3801288 | C | T |
| S_9431660 \|\| scaffold14851_3801360_SNP | 3801360 | G | T |
| S_9431665 \|\| scaffold14851_3801550_SNP | 3801550 | G | T |
| S_9431763 \|\| scaffold14851_3802534_SNP | 3802534 | T | A |
| S_9431866 \|\| scaffold14851_3803201_SNP | 3803201 | A | G |
| S_9431938 \|\| scaffold14851_3803669_SNP | 3803669 | C | T |
| S_9431948 \|\| scaffold14851_3803832_SNP | 3803832 | C | A |
| S_9432027 \|\| scaffold14851_3804295_SNP | 3804295 | G | A |
| S_9432174 \|\| scaffold14851_3805541_SNP | 3805541 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9432175 \| \| scaffold14851_3805558_SNP | 3805558 | A | T |
| S_9432179 \| \| scaffold14851_3805697_SNP | 3805697 | A | G |
| scaffold14851_3805858_SNP | 3805858 | G | A |
| S_9432197 \| \| scaffold14851_3805886_SNP | 3805886 | T | A |
| S_9432215 \| \| scaffold14851_3806079_SNP | 3806079 | C | T |
| S_9432216 \| \| scaffold14851_3806084_SNP | 3806084 | A | G |
| S_9432219 \| \| scaffold14851_3806137_SNP | 3806137 | G | T |
| S_9432229 \| \| scaffold14851_3806288_SNP | 3806288 | G | A |
| S_9432236 \| \| scaffold14851_3806344_SNP | 3806344 | T | A |
| S_9432238 \| \| scaffold14851_3806383_SNP | 3806383 | G | C |
| S_9432254 \| \| scaffold14851_3806655_SNP | 3806655 | A | G |
| S_9432257 \| \| scaffold14851_3806701_SNP | 3806701 | A | T |
| S_9432263 \| \| scaffold14851_3806802_SNP | 3806802 | C | T |
| S_9432313 \| \| scaffold14851_3807373_SNP | 3807373 | C | A |
| S_9432319 \| \| scaffold14851_3807389_SNP | 3807389 | A | T |
| S_9432341 \| \| scaffold14851_3807784_SNP | 3807784 | C | T |
| S_9432353 \| \| scaffold14851_3807924_SNP | 3807924 | A | T |
| S_9432358 \| \| scaffold14851_3808028_SNP | 3808028 | G | A |
| S_9432364 \| \| scaffold14851_3808181_SNP | 3808181 | A | C |
| S_9432365 \| \| scaffold14851_3808193_SNP | 3808193 | A | C |
| S_9432367 \| \| scaffold14851_3808201_SNP | 3808201 | T | A |
| S_9432368 \| \| scaffold14851_3808202_SNP | 3808202 | G | T |
| S_9432425 \| \| scaffold14851_3808902_SNP | 3808902 | G | T |
| S_9432438 \| \| scaffold14851_3809072_SNP | 3809072 | A | C |
| S_9432439 \| \| scaffold14851_3809073_SNP | 3809073 | C | T |
| S_9432446 \| \| scaffold14851_3809230_SNP | 3809230 | C | G |
| S_9432457 \| \| scaffold14851_3809448_SNP | 3809448 | A | T |
| S_9432459 \| \| scaffold14851_3809454_SNP | 3809454 | G | C |
| S_9432460 \| \| scaffold14851_3809456_SNP | 3809456 | G | A |
| S_9432466 \| \| scaffold14851_3809579_SNP | 3809579 | C | A |
| S_9432468 \| \| scaffold14851_3809601_SNP | 3809601 | T | C |
| S_9432477 \| \| scaffold14851_3809745_SNP | 3809745 | G | T |
| S_9432598 \| \| scaffold14851_3811146_SNP | 3811146 | G | A |
| S_9432652 \| \| scaffold14851_3811803_SNP | 3811803 | C | T |
| S_9432664 \| \| scaffold14851_3811913_SNP | 3811913 | G | T |
| S_9432701 \| \| scaffold14851_3812330_SNP | 3812330 | G | A |
| S_9432902 \| \| scaffold14851_3815064_SNP | 3815064 | T | A |
| S_9432936 \| \| scaffold14851_3815478_SNP | 3815478 | C | A |
| S_9432963 \| \| scaffold14851_3816139_SNP | 3816139 | T | C |
| S_9433151 \| \| scaffold14851_3817802_SNP | 3817802 | G | A |
| S_9433155 \| \| scaffold14851_3817863_SNP | 3817863 | C | A |
| S_9433161 \| \| scaffold14851_3818039_SNP | 3818039 | G | C |
| S_9433162 \| \| scaffold14851_3818059_SNP | 3818059 | C | G |
| S_9433167 \| \| scaffold14851_3818220_SNP | 3818220 | A | G |
| S_9433181 \| \| scaffold14851_3818432_SNP | 3818432 | G | A |
| S_9433183 \| \| scaffold14851_3818496_SNP | 3818496 | C | T |
| S_9433193 \| \| scaffold14851_3818619_SNP | 3818619 | G | A |
| S_9433197 \| \| scaffold14851_3818871_SNP | 3818871 | T | A |
| S_9433216 \| \| scaffold14851_3819166_SNP | 3819166 | G | C |
| S_9433227 \| \| scaffold14851_3819246_SNP | 3819246 | G | A |
| S_9433280 \| \| scaffold14851_3819788_SNP | 3819788 | A | G |
| S_9433323 \| \| scaffold14851_3820282_SNP | 3820282 | T | C |
| S_9433354 \| \| scaffold14851_3821086_SNP | 3821086 | G | T |
| S_9433398 \| \| scaffold14851_3821701_SNP | 3821701 | C | T |
| S_9433432 \| \| scaffold14851_3822331_SNP | 3822331 | G | T |
| S_9433477 \| \| scaffold14851_3822983_SNP | 3822983 | A | G |
| S_9433503 \| \| scaffold14851_3823329_SNP | 3823329 | A | G |
| S_9433511 \| \| scaffold14851_3823410_SNP | 3823410 | G | A |
| S_9433525 \| \| scaffold14851_3823500_SNP | 3823500 | C | T |
| S_9433610 \| \| scaffold14851_3824731_SNP | 3824731 | A | C |
| S_9433612 \| \| scaffold14851_3824781_SNP | 3824781 | G | C |
| S_9433620 \| \| scaffold14851_3824924_SNP | 3824924 | G | T |
| S_9433624 \| \| scaffold14851_3824993_SNP | 3824993 | T | G |
| S_9433633 \| \| scaffold14851_3825122_SNP | 3825122 | C | T |
| S_9433636 \| \| scaffold14851_3825153_SNP | 3825153 | T | C |
| S_9433664 \| \| scaffold14851_3825673_SNP | 3825673 | T | C |
| S_9433665 \| \| scaffold14851_3825693_SNP | 3825693 | T | C |
| S_9433759 \| \| scaffold14851_3827157_SNP | 3827157 | A | G |
| S_9434156 \| \| scaffold14851_3830437_SNP | 3830437 | C | G |
| S_9434260 \| \| scaffold14851_3831435_SNP | 3831435 | G | T |
| S_9434327 \| \| scaffold14851_3832561_SNP | 3832561 | T | A |
| S_9434358 \| \| scaffold14851_3832672_SNP | 3832672 | T | A |
| S_9434371 \| \| scaffold14851_3832714_SNP | 3832714 | C | A |
| S_9434395 \| \| scaffold14851_3833044_SNP | 3833044 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9434535 \| \| scaffold14851_3834801_SNP | 3834801 | A | T |
| scaffold14851_3834908_SNP | 3834908 | T | C |
| S_9434595 \| \| scaffold14851_3834945_SNP | 3834945 | A | T |
| S_9434828 \| \| scaffold14851_3837973_SNP | 3837973 | G | C |
| S_9434849 \| \| scaffold14851_3838052_SNP | 3838052 | A | G |
| S_9435340 \| \| scaffold14851_3842866_SNP | 3842866 | A | G |
| S_9435363 \| \| scaffold14851_3843093_SNP | 3843093 | C | T |
| S_9435492 \| \| scaffold14851_3844880_SNP | 3844880 | T | C |
| S_9435607 \| \| scaffold14851_3846458_SNP | 3846458 | C | A |
| S_9435608 \| \| scaffold14851_3846459_SNP | 3846459 | G | A |
| S_9435609 \| \| scaffold14851_3846460_SNP | 3846460 | A | G |
| S_9435610 \| \| scaffold14851_3846467_SNP | 3846467 | A | G |
| S_9435611 \| \| scaffold14851_3846469_SNP | 3846469 | A | G |
| S_9435627 \| \| scaffold14851_3846650_SNP | 3846650 | A | G |
| S_9435643 \| \| scaffold14851_3847162_SNP | 3847162 | A | G |
| S_9435685 \| \| scaffold14851_3847621_SNP | 3847621 | C | A |
| S_9435700 \| \| scaffold14851_3847823_SNP | 3847823 | C | G |
| S_9435708 \| \| scaffold14851_3847888_SNP | 3847888 | A | C |
| S_9435795 \| \| scaffold14851_3848925_SNP | 3848925 | G | A |
| S_9435796 \| \| scaffold14851_3848934_SNP | 3848934 | A | G |
| S_9435848 \| \| scaffold14851_3849684_SNP | 3849684 | A | G |
| S_9436190 \| \| scaffold14851_3854349_SNP | 3854349 | G | T |
| S_9436289 \| \| scaffold14851_3855095_SNP | 3855095 | G | A |
| S_9436406 \| \| scaffold14851_3856654_SNP | 3856654 | C | T |
| S_9436414 \| \| scaffold14851_3856730_SNP | 3856730 | A | G |
| S_9436417 \| \| scaffold14851_3856747_SNP | 3856747 | T | A |
| S_9436421 \| \| scaffold14851_3856786_SNP | 3856786 | G | T |
| S_9436428 \| \| scaffold14851_3856857_SNP | 3856857 | A | G |
| $_9436429 \| \| scaffold14851_3856862_SNP | 3856862 | C | T |
| S_9436519 \| \| scaffold14851_3858269_SNP | 3858269 | G | A |
| S_9436541 \| \| scaffold14851_3858565_SNP | 3858565 | G | T |
| S_9436558 \| \| scaffold14851_3858906_SNP | 3858906 | C | T |
| S_9436688 \| \| scaffold14851_3860162_SNP | 3860162 | T | A |
| S_9436811 \| \| scaffold14851_3861439_SNP | 3861439 | C | G |
| scaffold14851_3862050_SNP | 3862050 | G | A |
| S_9436909 \| \| scaffold14851_3863053_SNP | 3863053 | A | G |
| S_9436911 \| \| scaffold14851_3863100_SNP | 3863100 | G | C |
| S_9437081 \| \| scaffold14851_3865367_SNP | 3865367 | A | T |
| S_9437127 \| \| scaffold14851_3866044_SNP | 3866044 | A | G |
| S_9437154 \| \| scaffold14851_3866373_SNP | 3866373 | T | G |
| S_9437159 \| \| scaffold14851_3866423_SNP | 3866423 | T | C |
| S_9437161 \| \| scaffold14851_3866492_SNP | 3866492 | C | T |
| S_9437208 \| \| scaffold14851_3867187_SNP | 3867187 | T | G |
| S_9437209 \| \| scaffold14851_3867207_SNP | 3867207 | A | G |
| S_9437211 \| \| scaffold14851_3867259_SNP | 3867259 | T | C |
| S_9437282 \| \| scaffold14851_3868005_SNP | 3868005 | C | A |
| S_9437382 \| \| scaffold14851_3869103_SNP | 3869103 | T | C |
| S_9437393 \| \| scaffold14851_3869350_SNP | 3869350 | A | T |
| S_9437484 \| \| scaffold14851_3870594_SNP | 3870594 | C | T |
| S_9437552 \| \| scaffold14851_3871290_SNP | 3871290 | T | A |
| S_9437557 \| \| scaffold14851_3871365_SNP | 3871365 | T | C |
| S_9437567 \| \| scaffold14851_3871682_SNP | 3871682 | C | T |
| S_9437667 \| \| scaffold14851_3872695_SNP | 3872695 | C | T |
| S_9437671 \| \| scaffold14851_3872731_SNP | 3872731 | C | T |
| S_9437701 \| \| scaffold14851_3873156_SNP | 3873156 | A | T |
| S_9437702 \| \| scaffold14851_3873172_SNP | 3873172 | A | G |
| S_9437818 \| \| scaffold14851_3874593_SNP | 3874593 | A | G |
| S_9437819 \| \| scaffold14851_3874594_SNP | 3874594 | T | C |
| S_9437842 \| \| scaffold14851_3874979_SNP | 3874979 | G | T |
| S_9437852 \| \| scaffold14851_3875066_SNP | 3875066 | A | T |
| S_9437885 \| \| scaffold14851_3875700_SNP | 3875700 | G | T |
| S_9437888 \| \| scaffold14851_3875750_SNP | 3875750 | C | T |
| S_9437892 \| \| scaffold14851_3875766_SNP | 3875766 | T | C |
| S_9437894 \| \| scaffold14851_3875767_SNP | 3875767 | T | C |
| S_9437923 \| \| scaffold14851_3875943_SNP | 3875943 | A | C |
| S_9437927 \| \| scaffold14851_3875946_SNP | 3875946 | G | A |
| S_9437971 \| \| scaffold14851_3876206_SNP | 3876206 | C | T |
| S_9437974 \| \| scaffold14851_3876362_SNP | 3876362 | G | T |
| S_9437980 \| \| scaffold14851_3876410_SNP | 3876410 | T | C |
| S_9438052 \| \| scaffold14851_3877793_SNP | 3877793 | C | A |
| S_9438053 \| \| scaffold14851_3877794_SNP | 3877794 | C | T |
| S_9438065 \| \| scaffold14851_3878019_SNP | 3878019 | G | C |
| S_9438304 \| \| scaffold14851_3879971_SNP | 3879971 | G | C |
| S_9438334 \| \| scaffold14851_3880246_SNP | 3880246 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9438384 \| \| scaffold14851_3880898_SNP | 3880898 | C | G |
| S_9438493 \| \| scaffold14851_3882471_SNP | 3882471 | T | C |
| S_9438494 \| \| scaffold14851_3882474_SNP | 3882474 | A | T |
| S_9438531 \| \| scaffold14851_3883064_SNP | 3883064 | C | T |
| S_9438555 \| \| scaffold14851_3883714_SNP | 3883714 | G | A |
| S_9438612 \| \| scaffold14851_3884020_SNP | 3884020 | A | G |
| S_9438666 \| \| scaffold14851_3885251_SNP | 3885251 | C | G |
| S_9438667 \| \| scaffold14851_3885291_SNP | 3885291 | A | C |
| S_9438685 \| \| scaffold14851_3885588_SNP | 3885588 | A | G |
| S_9438690 \| \| scaffold14851_3885662_SNP | 3885662 | G | A |
| S_9438745 \| \| scaffold14851_3886338_SNP | 3886338 | C | T |
| S_9438747 \| \| scaffold14851_3886405_SNP | 3886405 | G | A |
| S_9438777 \| \| scaffold14851_3886704_SNP | 3886704 | C | T |
| S_9438804 \| \| scaffold14851_3887355_SNP | 3887355 | G | A |
| S_9438815 \| \| scaffold14851_3887551_SNP | 3887551 | T | C |
| S_9438818 \| \| scaffold14851_3887574_SNP | 3887574 | C | G |
| S_9438851 \| \| scaffold14851_3887881_SNP | 3887881 | A | G |
| S_9438899 \| \| scaffold14851_3888317_SNP | 3888317 | T | C |
| S_9438973 \| \| scaffold14851_3889389_SNP | 3889389 | A | C |
| S_9439073 \| \| scaffold14851_3889634_SNP | 3889634 | G | T |
| S_9439076 \| \| scaffold14851_3889698_SNP | 3889698 | A | T |
| S_9439080 \| \| scaffold14851_3889729_SNP | 3889729 | C | T |
| S_9439082 \| \| scaffold14851_3889750_SNP | 3889750 | A | C |
| S_9439120 \| \| scaffold14851_3890282_SNP | 3890282 | A | T |
| S_9439160 \| \| scaffold14851_3890613_SNP | 3890613 | T | A |
| S_9439165 \| \| scaffold14851_3890660_SNP | 3890660 | A | G |
| S_9439235 \| \| scaffold14851_3891946_SNP | 3891946 | G | A |
| S_9439242 \| \| scaffold14851_3892003_SNP | 3892003 | G | A |
| S_9439267 \| \| scaffold14851_3892249_SNP | 3892249 | G | T |
| S_9439271 \| \| scaffold14851_3892309_SNP | 3892309 | G | T |
| S_9439274 \| \| scaffold14851_3892363_SNP | 3892363 | G | T |
| S_9439369 \| \| scaffold14851_3893415_SNP | 3893415 | C | A |
| S_9439377 \| \| scaffold14851_3893517_SNP | 3893517 | G | T |
| S_9439386 \| \| scaffold14851_3893669_SNP | 3893669 | A | G |
| S_9439396 \| \| scaffold14851_3893771_SNP | 3893771 | A | G |
| S_9439410 \| \| scaffold14851_3893891_SNP | 3893891 | A | C |
| S_9439490 \| \| scaffold14851_3894979_SNP | 3894979 | A | C |
| S_9439498 \| \| scaffold14851_3895180_SNP | 3895180 | G | T |
| S_9439534 \| \| scaffold14851_3895530_SNP | 3895530 | C | T |
| S_9439561 \| \| scaffold14851_3895950_SNP | 3895950 | T | A |
| S_9439582 \| \| scaffold14851_3896275_SNP | 3896275 | T | A |
| S_9439585 \| \| scaffold14851_3896318_SNP | 3896318 | A | G |
| S_9439685 \| \| scaffold14851_3897461_SNP | 3897461 | A | G |
| S_9439716 \| \| scaffold14851_3898003_SNP | 3898003 | C | A |
| S_9439718 \| \| scaffold14851_3898195_SNP | 3898195 | C | A |
| S_9439733 \| \| scaffold14851_3898363_SNP | 3898363 | T | A |
| S_9439740 \| \| scaffold14851_3898396_SNP | 3898396 | G | T |
| S_9439756 \| \| scaffold14851_3898639_SNP | 3898639 | C | A |
| S_9439768 \| \| scaffold14851_3898932_SNP | 3898932 | A | G |
| S_9439894 \| \| scaffold14851_3900128_SNP | 3900128 | T | C |
| S_9439929 \| \| scaffold14851_3900655_SNP | 3900655 | T | C |
| S_9439945 \| \| scaffold14851_3900890_SNP | 3900890 | C | G |
| S_9439961 \| \| scaffold14851_3901052_SNP | 3901052 | A | G |
| S_9439965 \| \| scaffold14851_3901134_SNP | 3901134 | A | G |
| S_9439969 \| \| scaffold14851_3901198_SNP | 3901198 | G | A |
| S_9440020 \| \| scaffold14851_3901690_SNP | 3901690 | T | G |
| S_9440060 \| \| scaffold14851_3902190_SNP | 3902190 | T | G |
| S_9440215 \| \| scaffold14851_3903781_SNP | 3903781 | C | G |
| S_9440292 \| \| scaffold14851_3904689_SNP | 3904689 | A | C |
| S_9440445 \| \| scaffold14851_3906317_SNP | 3906317 | A | T |
| S_9440447 \| \| scaffold14851_3906355_SNP | 3906355 | A | G |
| S_9440453 \| \| scaffold14851_3906421_SNP | 3906421 | T | C |
| S_9440494 \| \| scaffold14851_3907354_SNP | 3907354 | T | C |
| S_9440665 \| \| scaffold14851_3909216_SNP | 3909216 | T | C |
| S_9440672 \| \| scaffold14851_3909337_SNP | 3909337 | G | C |
| S_9440734 \| \| scaffold14851_3910144_SNP | 3910144 | A | G |
| S_9440735 \| \| scaffold14851_3910156_SNP | 3910156 | A | G |
| S_9440774 \| \| scaffold14851_3910450_SNP | 3910450 | A | T |
| S_9440805 \| \| scaffold14851_3910955_SNP | 3910955 | G | A |
| S_9440838 \| \| scaffold14851_3911360_SNP | 3911360 | A | G |
| S_9440842 \| \| scaffold14851_3911592_SNP | 3911592 | C | T |
| S_9440969 \| \| scaffold14851_3912581_SNP | 3912581 | T | A |
| S_9441033 \| \| scaffold14851_3913696_SNP | 3913696 | T | C |
| S_9441034 \| \| scaffold14851_3913790_SNP | 3913790 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|------|------|------|------|
| S_9441035 \| \| scaffold14851_3913791_SNP | 3913791 | C | A |
| S_9441058 \| \| scaffold14851_3914071_SNP | 3914071 | C | T |
| S_9441062 \| \| scaffold14851_3914168_SNP | 3914168 | T | C |
| S_9441063 \| \| scaffold14851_3914171_SNP | 3914171 | T | A |
| S_9441064 \| \| scaffold14851_3914230_SNP | 3914230 | C | T |
| S_9441067 \| \| scaffold14851_3914266_SNP | 3914266 | T | A |
| S_9441069 \| \| scaffold14851_3914366_SNP | 3914366 | C | T |
| S_9441070 \| \| scaffold14851_3914367_SNP | 3914367 | A | G |
| S_9441080 \| \| scaffold14851_3914622_SNP | 3914622 | G | T |
| S_9441116 \| \| scaffold14851_3914947_SNP | 3914947 | A | G |
| S_9441124 \| \| scaffold14851_3915036_SNP | 3915036 | A | G |
| S_9441126 \| \| scaffold14851_3915042_SNP | 3915042 | C | T |
| S_9441155 \| \| scaffold14851_3915516_SNP | 3915516 | T | A |
| S_9441159 \| \| scaffold14851_3915525_SNP | 3915525 | G | A |
| S_9441161 \| \| scaffold14851_3915548_SNP | 3915548 | G | A |
| scaffold14851_3915599_SNP | 3915599 | C | T |
| scaffold14851_3915601_SNP | 3915601 | G | A |
| S_9441166 \| \| scaffold14851_3915620_SNP | 3915620 | G | A |
| S_9441167 \| \| scaffold14851_3915621_SNP | 3915621 | T | C |
| S_9441168 \| \| scaffold14851_3915643_SNP | 3915643 | A | C |
| S_9441180 \| \| scaffold14851_3915867_SNP | 3915867 | G | T |
| S_9441228 \| \| scaffold14851_3916483_SNP | 3916483 | A | G |
| S_9441282 \| \| scaffold14851_3917460_SNP | 3917460 | C | G |
| S_9441299 \| \| scaffold14851_3917648_SNP | 3917648 | T | C |
| S_9441305 \| \| scaffold14851_3917773_SNP | 3917773 | G | T |
| S_9441321 \| \| scaffold14851_3918076_SNP | 3918076 | A | C |
| S_9441361 \| \| scaffold14851_3918594_SNP | 3918594 | T | G |
| S_9441373 \| \| scaffold14851_3918711_SNP | 3918711 | C | A |
| S_9441378 \| \| scaffold14851_3918776_SNP | 3918776 | A | C |
| S_9441412 \| \| scaffold14851_3919049_SNP | 3919049 | T | C |
| S_9441417 \| \| scaffold14851_3919146_SNP | 3919146 | A | T |
| S_9441421 \| \| scaffold14851_3919215_SNP | 3919215 | G | T |
| S_9441423 \| \| scaffold14851_3919307_SNP | 3919307 | G | A |
| S_9441456 \| \| scaffold14851_3919650_SNP | 3919650 | A | C |
| S_9441457 \| \| scaffold14851_3919677_SNP | 3919677 | A | C |
| S_9441544 \| \| scaffold14851_3920328_SNP | 3920328 | G | A |
| scaffold14851_3920544_SNP | 3920544 | T | C |
| S_9441586 \| \| scaffold14851_3920709_SNP | 3920709 | A | G |
| S_9441587 \| \| scaffold14851_3920743_SNP | 3920743 | A | G |
| S_9441588 \| \| scaffold14851_3920753_SNP | 3920753 | G | A |
| S_9441590 \| \| scaffold14851_3920782_SNP | 3920782 | A | G |
| S_9441592 \| \| scaffold14851_3920807_SNP | 3920807 | T | C |
| scaffold14851_3921136_SNP | 3921136 | G | A |
| S_9441625 \| \| scaffold14851_3921251_SNP | 3921251 | C | T |
| S_9441627 \| \| scaffold14851_3921287_SNP | 3921287 | A | G |
| S_9441718 \| \| scaffold14851_3921636_SNP | 3921636 | C | G |
| S_9441782 \| \| scaffold14851_3922454_SNP | 3922454 | G | T |
| S_9441789 \| \| scaffold14851_3922582_SNP | 3922582 | T | G |
| S_9441829 \| \| scaffold14851_3923141_SNP | 3923141 | T | G |
| S_9441847 \| \| scaffold14851_3923416_SNP | 3923416 | G | A |
| S_9441858 \| \| scaffold14851_3923575_SNP | 3923575 | G | A |
| S_9441865 \| \| scaffold14851_3923650_SNP | 3923650 | G | A |
| S_9441886 \| \| scaffold14851_3923905_SNP | 3923905 | C | T |
| S_9441890 \| \| scaffold14851_3924036_SNP | 3924036 | C | G |
| S_9441929 \| \| scaffold14851_3924616_SNP | 3924616 | G | A |
| S_9441936 \| \| scaffold14851_3924697_SNP | 3924697 | A | G |
| S_9441952 \| \| scaffold14851_3924985_SNP | 3924985 | T | C |
| S_9441975 \| \| scaffold14851_3925352_SNP | 3925352 | C | T |
| S_9441994 \| \| scaffold14851_3925709_SNP | 3925709 | G | C |
| S_9441995 \| \| scaffold14851_3925720_SNP | 3925720 | T | C |
| scaffold14851_3927356_SNP | 3927356 | G | C |
| scaffold14851_3927357_SNP | 3927357 | T | G |
| S_9442090 \| \| scaffold14851_3927469_SNP | 3927469 | C | T |
| S_9442091 \| \| scaffold14851_3927480_SNP | 3927480 | T | C |
| S_9442096 \| \| scaffold14851_3927566_SNP | 3927566 | A | T |
| S_9442097 \| \| scaffold14851_3927587_SNP | 3927587 | C | T |
| S_9442100 \| \| scaffold14851_3927670_SNP | 3927670 | G | A |
| S_9442104 \| \| scaffold14851_3927815_SNP | 3927815 | A | T |
| S_9442106 \| \| scaffold14851_3927888_SNP | 3927888 | C | A |
| S_9442137 \| \| scaffold14851_3928430_SNP | 3928430 | G | A |
| S_9442138 \| \| scaffold14851_3928481_SNP | 3928481 | G | A |
| S_9442190 \| \| scaffold14851_3929132_SNP | 3929132 | A | C |
| S_9442227 \| \| scaffold14851_3930223_SNP | 3930223 | A | T |
| S_9442240 \| \| scaffold14851_3930449_SNP | 3930449 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9442244 \| \| scaffold14851_3930508_SNP | 3930508 | A | G |
| S_9442245 \| \| scaffold14851_3930520_SNP | 3930520 | C | A |
| S_9442250 \| \| scaffold14851_3930572_SNP | 3930572 | A | T |
| S_9442286 \| \| scaffold14851_3931099_SNP | 3931099 | G | A |
| S_9442287 \| \| scaffold14851_3931101_SNP | 3931101 | T | C |
| S_9442289 \| \| scaffold14851_3931149_SNP | 3931149 | A | G |
| S_9442291 \| \| scaffold14851_3931160_SNP | 3931160 | T | G |
| S_9442306 \| \| scaffold14851_3931357_SNP | 3931357 | C | A |
| S_9442315 \| \| scaffold14851_3931492_SNP | 3931492 | A | T |
| S_9442322 \| \| scaffold14851_3931572_SNP | 3931572 | C | T |
| S_9442323 \| \| scaffold14851_3931583_SNP | 3931583 | A | G |
| S_9442371 \| \| scaffold14851_3931956_SNP | 3931956 | G | T |
| S_9442445 \| \| scaffold14851_3932621_SNP | 3932621 | A | C |
| S_9442448 \| \| scaffold14851_3932703_SNP | 3932703 | T | G |
| S_9442449 \| \| scaffold14851_3932708_SNP | 3932708 | C | A |
| S_9442495 \| \| scaffold14851_3933234_SNP | 3933234 | A | G |
| S_9442505 \| \| scaffold14851_3933346_SNP | 3933346 | C | T |
| S_9442515 \| \| scaffold14851_3933514_SNP | 3933514 | G | A |
| S_9442542 \| \| scaffold14851_3934211_SNP | 3934211 | G | C |
| S_9442547 \| \| scaffold14851_3934302_SNP | 3934302 | G | C |
| S_9442552 \| \| scaffold14851_3934388_SNP | 3934388 | G | T |
| S_9442562 \| \| scaffold14851_3934481_SNP | 3934481 | T | A |
| S_9442591 \| \| scaffold14851_3934845_SNP | 3934845 | C | G |
| S_9442635 \| \| scaffold14851_3935417_SNP | 3935417 | C | T |
| S_9442639 \| \| scaffold14851_3935465_SNP | 3935465 | C | T |
| S_9442648 \| \| scaffold14851_3935570_SNP | 3935570 | T | C |
| S_9442688 \| \| scaffold14851_3935864_SNP | 3935864 | C | A |
| S_9442689 \| \| scaffold14851_3935867_SNP | 3935867 | G | A |
| S_9442718 \| \| scaffold14851_3936490_SNP | 3936490 | A | G |
| S_9442739 \| \| scaffold14851_3937075_SNP | 3937075 | A | G |
| S_9442745 \| \| scaffold14851_3937209_SNP | 3937209 | A | C |
| S_9442749 \| \| scaffold14851_3937313_SNP | 3937313 | C | T |
| S_9442763 \| \| scaffold14851_3937495_SNP | 3937495 | C | G |
| S_9442765 \| \| scaffold14851_3937502_SNP | 3937502 | A | G |
| S_9442830 \| \| scaffold14851_3938447_SNP | 3938447 | T | A |
| S_9442845 \| \| scaffold14851_3938586_SNP | 3938586 | G | C |
| S_9442849 \| \| scaffold14851_3938624_SNP | 3938624 | A | T |
| S_9442893 \| \| scaffold14851_3939404_SNP | 3939404 | T | A |
| S_9442906 \| \| scaffold14851_3939562_SNP | 3939562 | G | C |
| S_9443019 \| \| scaffold14851_3940470_SNP | 3940470 | G | A |
| S_9443043 \| \| scaffold14851_3940629_SNP | 3940629 | T | A |
| S_9443070 \| \| scaffold14851_3940910_SNP | 3940910 | G | A |
| S_9443073 \| \| scaffold14851_3940927_SNP | 3940927 | T | G |
| S_9443078 \| \| scaffold14851_3941000_SNP | 3941000 | T | C |
| S_9443079 \| \| scaffold14851_3941022_SNP | 3941022 | T | C |
| S_9443091 \| \| scaffold14851_3941195_SNP | 3941195 | T | C |
| S_9443092 \| \| scaffold14851_3941197_SNP | 3941197 | T | C |
| S_9443220 \| \| scaffold14851_3943645_SNP | 3943645 | A | G |
| S_9443226 \| \| scaffold14851_3943680_SNP | 3943680 | C | G |
| S_9443258 \| \| scaffold14851_3944232_SNP | 3944232 | T | A |
| S_9443269 \| \| scaffold14851_3944368_SNP | 3944368 | T | A |
| S_9443275 \| \| scaffold14851_3944423_SNP | 3944423 | C | T |
| S_9443282 \| \| scaffold14851_3944493_SNP | 3944493 | A | T |
| S_9443319 \| \| scaffold14851_3944979_SNP | 3944979 | A | G |
| S_9443341 \| \| scaffold14851_3945464_SNP | 3945464 | A | G |
| S_9443348 \| \| scaffold14851_3945643_SNP | 3945643 | A | G |
| S_9443383 \| \| scaffold14851_3946168_SNP | 3946168 | G | A |
| S_9443385 \| \| scaffold14851_3946173_SNP | 3946173 | G | A |
| S_9443386 \| \| scaffold14851_3946174_SNP | 3946174 | G | A |
| S_9443409 \| \| scaffold14851_3946590_SNP | 3946590 | A | G |
| S_9443566 \| \| scaffold14851_3947892_SNP | 3947892 | A | C |
| S_9443581 \| \| scaffold14851_3948027_SNP | 3948027 | C | T |
| S_9443608 \| \| scaffold14851_3948366_SNP | 3948366 | T | C |
| S_9443772 \| \| scaffold14851_3950622_SNP | 3950622 | C | T |
| S_9443978 \| \| scaffold14851_3952609_SNP | 3952609 | T | C |
| S_9444217 \| \| scaffold14851_3955988_SNP | 3955988 | G | T |
| S_9444285 \| \| scaffold14851_3956892_SNP | 3956892 | C | T |
| S_9444286 \| \| scaffold14851_3956893_SNP | 3956893 | T | G |
| S_9444329 \| \| scaffold14851_3957391_SNP | 3957391 | A | T |
| S_9444540 \| \| scaffold14851_3960500_SNP | 3960500 | T | C |
| S_9444583 \| \| scaffold14851_3961096_SNP | 3961096 | T | C |
| S_9444702 \| \| scaffold14851_3962731_SNP | 3962731 | A | C |
| S_9444749 \| \| scaffold14851_3963295_SNP | 3963295 | A | G |
| S_9444869 \| \| scaffold14851_3964584_SNP | 3964584 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9444874 \| \| scaffold14851_3964781_SNP | 3964781 | T | A |
| S_9444878 \| \| scaffold14851_3964865_SNP | 3964865 | A | C |
| S_9444884 \| \| scaffold14851_3965021_SNP | 3965021 | C | T |
| S_9444887 \| \| scaffold14851_3965098_SNP | 3965098 | C | A |
| S_9444889 \| \| scaffold14851_3965108_SNP | 3965108 | A | T |
| S_9444891 \| \| scaffold14851_3965182_SNP | 3965182 | T | G |
| S_9444893 \| \| scaffold14851_3965215_SNP | 3965215 | G | A |
| S_9444894 \| \| scaffold14851_3965231_SNP | 3965231 | T | C |
| S_9444895 \| \| scaffold14851_3965238_SNP | 3965238 | G | A |
| S_9444903 \| \| scaffold14851_3965361_SNP | 3965361 | G | C |
| S_9444915 \| \| scaffold14851_3965482_SNP | 3965482 | A | T |
| S_9444937 \| \| scaffold14851_3965774_SNP | 3965774 | C | G |
| S_9444962 \| \| scaffold14851_3966452_SNP | 3966452 | G | C |
| S_9445026 \| \| scaffold14851_3967129_SNP | 3967129 | C | T |
| S_9445134 \| \| scaffold14851_3968512_SNP | 3968512 | A | C |
| S_9445144 \| \| scaffold14851_3968749_SNP | 3968749 | G | A |
| S_9445203 \| \| scaffold14851_3969466_SNP | 3969466 | G | A |
| S_9445216 \| \| scaffold14851_3969693_SNP | 3969693 | G | A |
| S_9445224 \| \| scaffold14851_3969834_SNP | 3969834 | A | C |
| S_9445236 \| \| scaffold14851_3969918_SNP | 3969918 | G | C |
| S_9445418 \| \| scaffold14851_3972549_SNP | 3972549 | C | T |
| S_9445481 \| \| scaffold14851_3973389_SNP | 3973389 | C | T |
| S_9445503 \| \| scaffold14851_3973710_SNP | 3973710 | T | C |
| S_9445541 \| \| scaffold14851_3974232_SNP | 3974232 | T | C |
| S_9445542 \| \| scaffold14851_3974250_SNP | 3974250 | G | A |
| S_9445543 \| \| scaffold14851_3974313_SNP | 3974313 | A | G |
| S_9445557 \| \| scaffold14851_3974531_SNP | 3974531 | T | G |
| S_9445566 \| \| scaffold14851_3974750_SNP | 3974750 | T | A |
| S_9445615 \| \| scaffold14851_3975538_SNP | 3975538 | A | G |
| S_9445775 \| \| scaffold14851_3978035_SNP | 3978035 | G | T |
| S_9445858 \| \| scaffold14851_3978912_SNP | 3978912 | A | C |
| S_9445864 \| \| scaffold14851_3978961_SNP | 3978961 | C | G |
| S_9445957 \| \| scaffold14851_3980102_SNP | 3980102 | G | A |
| S_9446000 \| \| scaffold14851_3980612_SNP | 3980612 | C | T |
| S_9446001 \| \| scaffold14851_3980647_SNP | 3980647 | G | A |
| S_9446013 \| \| scaffold14851_3980872_SNP | 3980872 | C | G |
| S_9446014 \| \| scaffold14851_3980887_SNP | 3980887 | C | G |
| S_9446103 \| \| scaffold14851_3981904_SNP | 3981904 | C | G |
| S_9446104 \| \| scaffold14851_3981943_SNP | 3981943 | G | C |
| S_9446142 \| \| scaffold14851_3982800_SNP | 3982800 | A | G |
| S_9446154 \| \| scaffold14851_3982873_SNP | 3982873 | C | G |
| S_9446156 \| \| scaffold14851_3982949_SNP | 3982949 | A | G |
| S_9446163 \| \| scaffold14851_3983023_SNP | 3983023 | C | G |
| S_9446175 \| \| scaffold14851_3983216_SNP | 3983216 | T | G |
| S_9446205 \| \| scaffold14851_3983858_SNP | 3983858 | A | T |
| S_9446207 \| \| scaffold14851_3983924_SNP | 3983924 | C | T |
| S_9446213 \| \| scaffold14851_3984121_SNP | 3984121 | C | T |
| S_9446217 \| \| scaffold14851_3984287_SNP | 3984287 | A | T |
| S_9446218 \| \| scaffold14851_3984289_SNP | 3984289 | A | C |
| S_9446220 \| \| scaffold14851_3984294_SNP | 3984294 | T | C |
| S_9446230 \| \| scaffold14851_3984447_SNP | 3984447 | G | A |
| S_9446246 \| \| scaffold14851_3984775_SNP | 3984775 | C | G |
| S_9446270 \| \| scaffold14851_3985135_SNP | 3985135 | A | C |
| S_9446287 \| \| scaffold14851_3985156_SNP | 3985156 | A | T |
| S_9446298 \| \| scaffold14851_3985173_SNP | 3985173 | C | T |
| S_9446313 \| \| scaffold14851_3985261_SNP | 3985261 | G | A |
| S_9446315 \| \| scaffold14851_3985267_SNP | 3985267 | A | G |
| S_9446332 \| \| scaffold14851_3985488_SNP | 3985488 | G | A |
| S_9446398 \| \| scaffold14851_3985938_SNP | 3985938 | C | T |
| S_9446438 \| \| scaffold14851_3986124_SNP | 3986124 | C | G |
| S_9446557 \| \| scaffold14851_3987841_SNP | 3987841 | C | G |
| S_9446560 \| \| scaffold14851_3987886_SNP | 3987886 | A | T |
| S_9446576 \| \| scaffold14851_3988078_SNP | 3988078 | T | C |
| S_9446595 \| \| scaffold14851_3988369_SNP | 3988369 | T | A |
| S_9446605 \| \| scaffold14851_3988522_SNP | 3988522 | C | A |
| S_9446666 \| \| scaffold14851_3988690_SNP | 3988690 | T | A |
| S_9446671 \| \| scaffold14851_3988738_SNP | 3988738 | C | T |
| S_9446673 \| \| scaffold14851_3988782_SNP | 3988782 | G | A |
| S_9446683 \| \| scaffold14851_3988928_SNP | 3988928 | T | A |
| S_9446690 \| \| scaffold14851_3988999_SNP | 3988999 | A | G |
| S_9446711 \| \| scaffold14851_3989427_SNP | 3989427 | C | T |
| S_9446716 \| \| scaffold14851_3989574_SNP | 3989574 | A | T |
| S_9446727 \| \| scaffold14851_3989801_SNP | 3989801 | A | C |
| S_9446757 \| \| scaffold14851_3990348_SNP | 3990348 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9446758 \| \| scaffold14851_3990357_SNP | 3990357 | T | A |
| S_9446761 \| \| scaffold14851_3990444_SNP | 3990444 | A | G |
| S_9446762 \| \| scaffold14851_3990449_SNP | 3990449 | A | G |
| S_9446763 \| \| scaffold14851_3990450_SNP | 3990450 | T | A |
| S_9446818 \| \| scaffold14851_3991162_SNP | 3991162 | C | T |
| S_9446828 \| \| scaffold14851_3991420_SNP | 3991420 | C | A |
| S_9446830 \| \| scaffold14851_3991423_SNP | 3991423 | C | A |
| S_9446848 \| \| scaffold14851_3991601_SNP | 3991601 | T | A |
| S_9446874 \| \| scaffold14851_3992101_SNP | 3992101 | C | T |
| S_9446895 \| \| scaffold14851_3992375_SNP | 3992375 | A | G |
| S_9446899 \| \| scaffold14851_3992386_SNP | 3992386 | T | C |
| S_9446901 \| \| scaffold14851_3992393_SNP | 3992393 | T | C |
| S_9446911 \| \| scaffold14851_3992508_SNP | 3992508 | A | G |
| S_9446917 \| \| scaffold14851_3992547_SNP | 3992547 | G | A |
| S_9446940 \| \| scaffold14851_3992696_SNP | 3992696 | A | G |
| S_9446947 \| \| scaffold14851_3992792_SNP | 3992792 | A | C |
| S_9446952 \| \| scaffold14851_3992866_SNP | 3992866 | T | C |
| S_9446954 \| \| scaffold14851_3992877_SNP | 3992877 | G | A |
| S_9447057 \| \| scaffold14851_3993420_SNP | 3993420 | C | T |
| S_9447070 \| \| scaffold14851_3993627_SNP | 3993627 | T | C |
| S_9447111 \| \| scaffold14851_3994360_SNP | 3994360 | G | A |
| S_9447116 \| \| scaffold14851_3994421_SNP | 3994421 | A | G |
| S_9447120 \| \| scaffold14851_3994439_SNP | 3994439 | G | A |
| S_9447127 \| \| scaffold14851_3994623_SNP | 3994623 | T | A |
| S_9447129 \| \| scaffold14851_3994652_SNP | 3994652 | G | A |
| S_9447206 \| \| scaffold14851_3994948_SNP | 3994948 | G | A |
| S_9447209 \| \| scaffold14851_3995010_SNP | 3995010 | C | G |
| S_9447214 \| \| scaffold14851_3995107_SNP | 3995107 | G | A |
| S_9447232 \| \| scaffold14851_3995273_SNP | 3995273 | C | A |
| S_9447235 \| \| scaffold14851_3995287_SNP | 3995287 | A | T |
| S_9447272 \| \| scaffold14851_3995759_SNP | 3995759 | G | C |
| S_9447277 \| \| scaffold14851_3995815_SNP | 3995815 | G | T |
| S_9447302 \| \| scaffold14851_3996121_SNP | 3996121 | T | A |
| S_9447309 \| \| scaffold14851_3996248_SNP | 3996248 | G | A |
| S_9447310 \| \| scaffold14851_3996255_SNP | 3996255 | T | A |
| S_9447313 \| \| scaffold14851_3996271_SNP | 3996271 | C | T |
| S_9447331 \| \| scaffold14851_3996348_SNP | 3996348 | A | G |
| S_9447396 \| \| scaffold14851_3996697_SNP | 3996697 | A | G |
| S_9447398 \| \| scaffold14851_3996704_SNP | 3996704 | A | C |
| S_9447461 \| \| scaffold14851_3997299_SNP | 3997299 | A | T |
| S_9447462 \| \| scaffold14851_3997309_SNP | 3997309 | T | C |
| S_9447463 \| \| scaffold14851_3997311_SNP | 3997311 | A | C |
| S_9447464 \| \| scaffold14851_3997325_SNP | 3997325 | A | G |
| S_9447465 \| \| scaffold14851_3997333_SNP | 3997333 | T | A |
| S_9447466 \| \| scaffold14851_3997336_SNP | 3997336 | T | C |
| S_9447467 \| \| scaffold14851_3997395_SNP | 3997395 | G | T |
| S_9447468 \| \| scaffold14851_3997403_SNP | 3997403 | A | G |
| S_9447477 \| \| scaffold14851_3997620_SNP | 3997620 | A | G |
| S_9447478 \| \| scaffold14851_3997628_SNP | 3997628 | G | A |
| S_9447479 \| \| scaffold14851_3997649_SNP | 3997649 | T | C |
| S_9447530 \| \| scaffold14851_3998090_SNP | 3998090 | C | A |
| S_9447542 \| \| scaffold14851_3998202_SNP | 3998202 | C | T |
| S_9447546 \| \| scaffold14851_3998269_SNP | 3998269 | A | G |
| S_9447584 \| \| scaffold14851_3998569_SNP | 3998569 | T | C |
| S_9447586 \| \| scaffold14851_3998590_SNP | 3998590 | T | A |
| S_9447692 \| \| scaffold14851_3999874_SNP | 3999874 | T | C |
| S_9447706 \| \| scaffold14851_3999896_SNP | 3999896 | A | G |
| S_9447712 \| \| scaffold14851_3999901_SNP | 3999901 | T | A |
| S_9447752 \| \| scaffold14851_4000184_SNP | 4000184 | A | T |
| S_9447753 \| \| scaffold14851_4000188_SNP | 4000188 | G | T |
| S_9447754 \| \| scaffold14851_4000198_SNP | 4000198 | A | G |
| S_9447762 \| \| scaffold14851_4000271_SNP | 4000271 | C | T |
| S_9447818 \| \| scaffold14851_4000887_SNP | 4000887 | G | T |
| S_9447844 \| \| scaffold14851_4001095_SNP | 4001095 | A | G |
| S_9447882 \| \| scaffold14851_4001331_SNP | 4001331 | C | G |
| S_9447884 \| \| scaffold14851_4001362_SNP | 4001362 | C | G |
| S_9447957 \| \| scaffold14851_4002700_SNP | 4002700 | A | G |
| S_9447989 \| \| scaffold14851_4003147_SNP | 4003147 | G | C |
| S_9447991 \| \| scaffold14851_4003173_SNP | 4003173 | A | T |
| S_9448008 \| \| scaffold14851_4003426_SNP | 4003426 | G | A |
| S_9448009 \| \| scaffold14851_4003433_SNP | 4003433 | C | A |
| S_9448035 \| \| scaffold14851_4003662_SNP | 4003662 | G | A |
| S_9448044 \| \| scaffold14851_4003743_SNP | 4003743 | A | G |
| S_9448045 \| \| scaffold14851_4003771_SNP | 4003771 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9448047 \| \| scaffold14851_4003796_SNP | 4003796 | G | T |
| S_9448048 \| \| scaffold14851_4003802_SNP | 4003802 | C | A |
| S_9448063 \| \| scaffold14851_4004012_SNP | 4004012 | G | C |
| S_9448067 \| \| scaffold14851_4004028_SNP | 4004028 | T | A |
| S_9448075 \| \| scaffold14851_4004095_SNP | 4004095 | C | G |
| S_9448087 \| \| scaffold14851_4004288_SNP | 4004288 | T | C |
| S_9448089 \| \| scaffold14851_4004293_SNP | 4004293 | T | C |
| S_9448098 \| \| scaffold14851_4004419_SNP | 4004419 | T | C |
| S_9448125 \| \| scaffold14851_4004827_SNP | 4004827 | A | G |
| S_9448149 \| \| scaffold14851_4005027_SNP | 4005027 | G | T |
| S_9448162 \| \| scaffold14851_4005129_SNP | 4005129 | T | A |
| S_9448163 \| \| scaffold14851_4005135_SNP | 4005135 | G | T |
| S_9448164 \| \| scaffold14851_4005140_SNP | 4005140 | A | T |
| S_9448165 \| \| scaffold14851_4005149_SNP | 4005149 | A | C |
| S_9448174 \| \| scaffold14851_4005269_SNP | 4005269 | A | G |
| S_9448195 \| \| scaffold14851_4005484_SNP | 4005484 | A | T |
| S_9448206 \| \| scaffold14851_4005636_SNP | 4005636 | A | G |
| S_9448293 \| \| scaffold14851_4006840_SNP | 4006840 | G | A |
| S_9448307 \| \| scaffold14851_4007057_SNP | 4007057 | C | A |
| S_9448382 \| \| scaffold14851_4007853_SNP | 4007853 | A | G |
| S_9448405 \| \| scaffold14851_4007997_SNP | 4007997 | C | T |
| S_9448409 \| \| scaffold14851_4008052_SNP | 4008052 | T | C |
| S_9448436 \| \| scaffold14851_4008369_SNP | 4008369 | T | A |
| S_9448455 \| \| scaffold14851_4008762_SNP | 4008762 | A | C |
| S_9448458 \| \| scaffold14851_4008786_SNP | 4008786 | T | G |
| S_9448460 \| \| scaffold14851_4008795_SNP | 4008795 | C | T |
| S_9448462 \| \| scaffold14851_4008822_SNP | 4008822 | G | A |
| S_9448464 \| \| scaffold14851_4008844_SNP | 4008844 | C | A |
| S_9448471 \| \| scaffold14851_4009011_SNP | 4009011 | G | C |
| S_9448588 \| \| scaffold14851_4010021_SNP | 4010021 | C | A |
| S_9448603 \| \| scaffold14851_4010512_SNP | 4010512 | A | G |
| S_9448604 \| \| scaffold14851_4010514_SNP | 4010514 | G | A |
| S_9448607 \| \| scaffold14851_4010536_SNP | 4010536 | A | G |
| S_9448621 \| \| scaffold14851_4010704_SNP | 4010704 | A | T |
| S_9448648 \| \| scaffold14851_4011351_SNP | 4011351 | A | T |
| S_9448692 \| \| scaffold14851_4011922_SNP | 4011922 | A | C |
| S_9448743 \| \| scaffold14851_4012651_SNP | 4012651 | G | C |
| S_9448770 \| \| scaffold14851_4012965_SNP | 4012965 | A | C |
| S_9448780 \| \| scaffold14851_4013090_SNP | 4013090 | G | A |
| S_9448803 \| \| scaffold14851_4013506_SNP | 4013506 | A | T |
| S_9448821 \| \| scaffold14851_4013766_SNP | 4013766 | T | G |
| S_9448822 \| \| scaffold14851_4013773_SNP | 4013773 | G | C |
| S_9448868 \| \| scaffold14851_4014261_SNP | 4014261 | A | C |
| S_9448871 \| \| scaffold14851_4014281_SNP | 4014281 | G | T |
| S_9448902 \| \| scaffold14851_4014602_SNP | 4014602 | T | A |
| S_9449475 \| \| scaffold14851_4019761_SNP | 4019761 | T | A |
| S_9449494 \| \| scaffold14851_4019964_SNP | 4019964 | G | C |
| S_9449526 \| \| scaffold14851_4020360_SNP | 4020360 | G | A |
| S_9449544 \| \| scaffold14851_4020591_SNP | 4020591 | C | T |
| S_9449589 \| \| scaffold14851_4021278_SNP | 4021278 | G | C |
| S_9449647 \| \| scaffold14851_4022323_SNP | 4022323 | C | T |
| S_9449651 \| \| scaffold14851_4022494_SNP | 4022494 | C | T |
| S_9449667 \| \| scaffold14851_4022814_SNP | 4022814 | A | T |
| S_9449722 \| \| scaffold14851_4023608_SNP | 4023608 | T | A |
| S_9449764 \| \| scaffold14851_4024622_SNP | 4024622 | T | G |
| S_9449778 \| \| scaffold14851_4024913_SNP | 4024913 | G | T |
| S_9449787 \| \| scaffold14851_4025090_SNP | 4025090 | G | A |
| S_9449816 \| \| scaffold14851_4025476_SNP | 4025476 | G | T |
| S_9449817 \| \| scaffold14851_4025478_SNP | 4025478 | T | G |
| S_9449831 \| \| scaffold14851_4025730_SNP | 4025730 | T | C |
| S_9449834 \| \| scaffold14851_4025800_SNP | 4025800 | A | G |
| S_9449835 \| \| scaffold14851_4025832_SNP | 4025832 | A | C |
| S_9449836 \| \| scaffold14851_4025839_SNP | 4025839 | T | G |
| S_9449842 \| \| scaffold14851_4025903_SNP | 4025903 | T | C |
| S_9449843 \| \| scaffold14851_4025919_SNP | 4025919 | A | G |
| S_9449847 \| \| scaffold14851_4025998_SNP | 4025998 | A | T |
| S_9449939 \| \| scaffold14851_4027080_SNP | 4027080 | C | T |
| S_9449949 \| \| scaffold14851_4027152_SNP | 4027152 | A | G |
| S_9449972 \| \| scaffold14851_4027482_SNP | 4027482 | T | C |
| S_9450017 \| \| scaffold14851_4027855_SNP | 4027855 | C | G |
| S_9450024 \| \| scaffold14851_4027907_SNP | 4027907 | A | G |
| S_9450027 \| \| scaffold14851_4027971_SNP | 4027971 | G | A |
| S_9450075 \| \| scaffold14851_4028401_SNP | 4028401 | A | G |
| S_9450200 \| \| scaffold14851_4029280_SNP | 4029280 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9450229 \| \| scaffold14851_4029418_SNP | 4029418 | G | A |
| S_9450268 \| \| scaffold14851_4030182_SNP | 4030182 | C | A |
| scaffold14851_4031047_SNP | 4031047 | T | G |
| scaffold14851_4031733_SNP | 4031733 | A | G |
| S_9450706 \| \| scaffold14851_4032000_SNP | 4032000 | A | G |
| S_9450711 \| \| scaffold14851_4032033_SNP | 4032033 | G | A |
| S_9450716 \| \| scaffold14851_4032091_SNP | 4032091 | G | A |
| S_9450717 \| \| scaffold14851_4032097_SNP | 4032097 | G | A |
| S_9450730 \| \| scaffold14851_4032278_SNP | 4032278 | A | G |
| S_9450734 \| \| scaffold14851_4032340_SNP | 4032340 | T | C |
| S_9450738 \| \| scaffold14851_4032398_SNP | 4032398 | A | G |
| S_9450744 \| \| scaffold14851_4032442_SNP | 4032442 | C | T |
| S_9450760 \| \| scaffold14851_4032647_SNP | 4032647 | G | T |
| S_9450762 \| \| scaffold14851_4032696_SNP | 4032696 | T | C |
| S_9450777 \| \| scaffold14851_4032954_SNP | 4032954 | T | C |
| S_9450779 \| \| scaffold14851_4032997_SNP | 4032997 | T | C |
| S_9450794 \| \| scaffold14851_4033196_SNP | 4033196 | G | C |
| S_9450818 \| \| scaffold14851_4033651_SNP | 4033651 | G | C |
| S_9450838 \| \| scaffold14851_4033818_SNP | 4033818 | C | T |
| S_9450897 \| \| scaffold14851_4034601_SNP | 4034601 | G | A |
| S_9450905 \| \| scaffold14851_4034753_SNP | 4034753 | A | G |
| S_9450907 \| \| scaffold14851_4034782_SNP | 4034782 | T | A |
| S_9450923 \| \| scaffold14851_4035111_SNP | 4035111 | G | T |
| S_9450926 \| \| scaffold14851_4035162_SNP | 4035162 | G | C |
| S_9450934 \| \| scaffold14851_4035246_SNP | 4035246 | G | A |
| S_9451014 \| \| scaffold14851_4036593_SNP | 4036593 | A | C |
| S_9451047 \| \| scaffold14851_4037190_SNP | 4037190 | T | G |
| S_9451051 \| \| scaffold14851_4037269_SNP | 4037269 | G | T |
| S_9451053 \| \| scaffold14851_4037318_SNP | 4037318 | A | G |
| S_9451055 \| \| scaffold14851_4037387_SNP | 4037387 | G | T |
| S_9451106 \| \| scaffold14851_4038097_SNP | 4038097 | T | C |
| S_9451127 \| \| scaffold14851_4038316_SNP | 4038316 | C | T |
| S_9451160 \| \| scaffold14851_4038748_SNP | 4038748 | G | A |
| S_9451161 \| \| scaffold14851_4038780_SNP | 4038780 | A | T |
| S_9451164 \| \| scaffold14851_4038828_SNP | 4038828 | T | C |
| S_9451190 \| \| scaffold14851_4039067_SNP | 4039067 | C | T |
| S_9451201 \| \| scaffold14851_4039257_SNP | 4039257 | A | T |
| S_9451202 \| \| scaffold14851_4039258_SNP | 4039258 | T | C |
| S_9451236 \| \| scaffold14851_4039568_SNP | 4039568 | T | A |
| S_9451255 \| \| scaffold14851_4039927_SNP | 4039927 | G | A |
| S_9451295 \| \| scaffold14851_4040364_SNP | 4040364 | G | A |
| S_9451296 \| \| scaffold14851_4040370_SNP | 4040370 | T | G |
| S_9451320 \| \| scaffold14851_4040688_SNP | 4040688 | T | C |
| S_9451402 \| \| scaffold14851_4041578_SNP | 4041578 | C | A |
| S_9451479 \| \| scaffold14851_4042581_SNP | 4042581 | C | A |
| S_9451480 \| \| scaffold14851_4042584_SNP | 4042584 | C | G |
| S_9451481 \| \| scaffold14851_4042616_SNP | 4042616 | A | G |
| S_9451484 \| \| scaffold14851_4042654_SNP | 4042654 | T | G |
| S_9451809 \| \| scaffold14851_4045294_SNP | 4045294 | G | T |
| S_9451825 \| \| scaffold14851_4045641_SNP | 4045641 | A | G |
| S_9451829 \| \| scaffold14851_4045798_SNP | 4045798 | A | T |
| S_9451833 \| \| scaffold14851_4045937_SNP | 4045937 | C | T |
| S_9451839 \| \| scaffold14851_4046072_SNP | 4046072 | A | G |
| S_9451852 \| \| scaffold14851_4046313_SNP | 4046313 | G | C |
| S_9451869 \| \| scaffold14851_4046668_SNP | 4046668 | A | G |
| S_9451871 \| \| scaffold14851_4046680_SNP | 4046680 | G | C |
| S_9451906 \| \| scaffold14851_4047162_SNP | 4047162 | T | C |
| S_9451913 \| \| scaffold14851_4047332_SNP | 4047332 | T | C |
| S_9451930 \| \| scaffold14851_4047669_SNP | 4047669 | T | A |
| S_9451932 \| \| scaffold14851_4047712_SNP | 4047712 | G | A |
| S_9452017 \| \| scaffold14851_4048616_SNP | 4048616 | G | T |
| S_9452098 \| \| scaffold14851_4049819_SNP | 4049819 | T | A |
| S_9452099 \| \| scaffold14851_4049821_SNP | 4049821 | A | C |
| S_9452306 \| \| scaffold14851_4052352_SNP | 4052352 | C | T |
| S_9452328 \| \| scaffold14851_4052742_SNP | 4052742 | T | G |
| S_9452336 \| \| scaffold14851_4052923_SNP | 4052923 | C | T |
| S_9452337 \| \| scaffold14851_4052932_SNP | 4052932 | A | G |
| S_9452348 \| \| scaffold14851_4053167_SNP | 4053167 | A | C |
| S_9452416 \| \| scaffold14851_4054238_SNP | 4054238 | A | T |
| S_9452538 \| \| scaffold14851_4056084_SNP | 4056084 | C | A |
| S_9452698 \| \| scaffold14851_4057757_SNP | 4057757 | T | A |
| S_9452717 \| \| scaffold14851_4057941_SNP | 4057941 | T | C |
| S_9452723 \| \| scaffold14851_4058143_SNP | 4058143 | C | A |
| S_9452725 \| \| scaffold14851_4058193_SNP | 4058193 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9452746 \| \| scaffold14851_4058327_SNP | 4058327 | A | T |
| S_9452808 \| \| scaffold14851_4059261_SNP | 4059261 | G | A |
| S_9452817 \| \| scaffold14851_4059364_SNP | 4059364 | G | C |
| S_9452821 \| \| scaffold14851_4059386_SNP | 4059386 | G | T |
| S_9452893 \| \| scaffold14851_4060650_SNP | 4060650 | A | G |
| S_9452922 \| \| scaffold14851_4061177_SNP | 4061177 | C | T |
| S_9452932 \| \| scaffold14851_4061459_SNP | 4061459 | A | G |
| S_9453065 \| \| scaffold14851_4063229_SNP | 4063229 | T | A |
| S_9453159 \| \| scaffold14851_4064278_SNP | 4064278 | C | A |
| scaffold14851_4064884_SNP | 4064884 | A | T |
| S_9453251 \| \| scaffold14851_4065209_SNP | 4065209 | C | G |
| S_9453303 \| \| scaffold14851_4066143_SNP | 4066143 | A | G |
| S_9453310 \| \| scaffold14851_4066298_SNP | 4066298 | A | G |
| scaffold14851_4066622_SNP | 4066622 | T | A |
| S_9453401 \| \| scaffold14851_4067955_SNP | 4067955 | G | T |
| S_9453517 \| \| scaffold14851_4069352_SNP | 4069352 | C | A |
| S_9453537 \| \| scaffold14851_4069621_SNP | 4069621 | A | C |
| S_9453628 \| \| scaffold14851_4071230_SNP | 4071230 | T | C |
| S_9453659 \| \| scaffold14851_4071721_SNP | 4071721 | G | C |
| S_9453661 \| \| scaffold14851_4071724_SNP | 4071724 | G | T |
| S_9453789 \| \| scaffold14851_4073281_SNP | 4073281 | C | T |
| S_9453803 \| \| scaffold14851_4073448_SNP | 4073448 | A | T |
| S_9453808 \| \| scaffold14851_4073482_SNP | 4073482 | C | T |
| S_9453829 \| \| scaffold14851_4073688_SNP | 4073688 | C | T |
| S_9453842 \| \| scaffold14851_4073849_SNP | 4073849 | G | A |
| S_9453849 \| \| scaffold14851_4073999_SNP | 4073999 | G | C |
| S_9453869 \| \| scaffold14851_4074418_SNP | 4074418 | G | A |
| S_9453872 \| \| scaffold14851_4074477_SNP | 4074477 | G | A |
| S_9453885 \| \| scaffold14851_4074827_SNP | 4074827 | T | C |
| S_9453932 \| \| scaffold14851_4075601_SNP | 4075601 | C | T |
| S_9453954 \| \| scaffold14851_4075943_SNP | 4075943 | T | A |
| S_9453966 \| \| scaffold14851_4076178_SNP | 4076178 | T | G |
| S_9453990 \| \| scaffold14851_4076641_SNP | 4076641 | T | C |
| S_9453997 \| \| scaffold14851_4076759_SNP | 4076759 | A | T |
| S_9454008 \| \| scaffold14851_4076861_SNP | 4076861 | C | T |
| S_9454088 \| \| scaffold14851_4077811_SNP | 4077811 | C | A |
| S_9454098 \| \| scaffold14851_4078036_SNP | 4078036 | C | T |
| S_9454174 \| \| scaffold14851_4078367_SNP | 4078367 | G | C |
| S_9454250 \| \| scaffold14851_4078512_SNP | 4078512 | G | A |
| S_9454257 \| \| scaffold14851_4078580_SNP | 4078580 | C | G |
| S_9454264 \| \| scaffold14851_4078849_SNP | 4078849 | G | C |
| S_9454301 \| \| scaffold14851_4079552_SNP | 4079552 | C | T |
| S_9454331 \| \| scaffold14851_4079968_SNP | 4079968 | G | A |
| S_9454351 \| \| scaffold14851_4080281_SNP | 4080281 | A | G |
| S_9454408 \| \| scaffold14851_4081032_SNP | 4081032 | C | A |
| S_9454426 \| \| scaffold14851_4081233_SNP | 4081233 | A | T |
| S_9454508 \| \| scaffold14851_4082113_SNP | 4082113 | C | G |
| S_9454516 \| \| scaffold14851_4082212_SNP | 4082212 | A | G |
| S_9455400 \| \| scaffold14851_4088408_SNP | 4088408 | A | G |
| S_9455500 \| \| scaffold14851_4089154_SNP | 4089154 | A | G |
| S_9455510 \| \| scaffold14851_4089240_SNP | 4089240 | T | A |
| S_9455522 \| \| scaffold14851_4089310_SNP | 4089310 | A | G |
| S_9455528 \| \| scaffold14851_4089449_SNP | 4089449 | T | A |
| S_9455533 \| \| scaffold14851_4089550_SNP | 4089550 | T | G |
| S_9455550 \| \| scaffold14851_4089875_SNP | 4089875 | G | T |
| S_9455606 \| \| scaffold14851_4090388_SNP | 4090388 | T | G |
| S_9455608 \| \| scaffold14851_4090412_SNP | 4090412 | C | T |
| S_9455615 \| \| scaffold14851_4090554_SNP | 4090554 | T | G |
| S_9455637 \| \| scaffold14851_4090934_SNP | 4090934 | T | C |
| S_9455640 \| \| scaffold14851_4090963_SNP | 4090963 | T | A |
| S_9455655 \| \| scaffold14851_4091196_SNP | 4091196 | T | A |
| S_9455659 \| \| scaffold14851_4091224_SNP | 4091224 | C | T |
| S_9455687 \| \| scaffold14851_4091438_SNP | 4091438 | T | C |
| S_9455688 \| \| scaffold14851_4091439_SNP | 4091439 | G | A |
| S_9455694 \| \| scaffold14851_4091533_SNP | 4091533 | C | T |
| S_9455760 \| \| scaffold14851_4092636_SNP | 4092636 | T | G |
| S_9455775 \| \| scaffold14851_4092919_SNP | 4092919 | T | A |
| S_9455780 \| \| scaffold14851_4093055_SNP | 4093055 | G | A |
| S_9455885 \| \| scaffold14851_4094749_SNP | 4094749 | A | T |
| S_9456184 \| \| scaffold14851_4099006_SNP | 4099006 | C | T |
| S_9456191 \| \| scaffold14851_4099174_SNP | 4099174 | A | T |
| S_9456194 \| \| scaffold14851_4099274_SNP | 4099274 | C | T |
| S_9456224 \| \| scaffold14851_4099952_SNP | 4099952 | C | G |
| S_9456253 \| \| scaffold14851_4100475_SNP | 4100475 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9456254 \| \| scaffold14851_4100482_SNP | 4100482 | A | C |
| S_9456258 \| \| scaffold14851_4100595_SNP | 4100595 | C | T |
| S_9456304 \| \| scaffold14851_4101344_SNP | 4101344 | A | T |
| S_9456340 \| \| scaffold14851_4101777_SNP | 4101777 | T | G |
| S_9456341 \| \| scaffold14851_4101806_SNP | 4101806 | G | A |
| S_9456397 \| \| scaffold14851_4102436_SNP | 4102436 | G | T |
| S_9456448 \| \| scaffold14851_4104112_SNP | 4104112 | A | G |
| S_9456462 \| \| scaffold14851_4104293_SNP | 4104293 | T | C |
| S_9456487 \| \| scaffold14851_4104673_SNP | 4104673 | A | C |
| S_9456569 \| \| scaffold14851_4105268_SNP | 4105268 | T | A |
| S_9456572 \| \| scaffold14851_4105332_SNP | 4105332 | A | C |
| S_9456574 \| \| scaffold14851_4105378_SNP | 4105378 | G | A |
| S_9456599 \| \| scaffold14851_4105739_SNP | 4105739 | C | T |
| S_9456608 \| \| scaffold14851_4105953_SNP | 4105953 | T | C |
| S_9456629 \| \| scaffold14851_4106094_SNP | 4106094 | C | T |
| S_9456638 \| \| scaffold14851_4106202_SNP | 4106202 | C | A |
| S_9456676 \| \| scaffold14851_4106853_SNP | 4106853 | A | G |
| S_9456679 \| \| scaffold14851_4106883_SNP | 4106883 | T | A |
| S_9456711 \| \| scaffold14851_4107462_SNP | 4107462 | G | C |
| S_9456721 \| \| scaffold14851_4107540_SNP | 4107540 | T | C |
| S_9456723 \| \| scaffold14851_4107553_SNP | 4107553 | C | T |
| S_9456726 \| \| scaffold14851_4107571_SNP | 4107571 | C | A |
| S_9456727 \| \| scaffold14851_4107579_SNP | 4107579 | G | A |
| S_9456730 \| \| scaffold14851_4107649_SNP | 4107649 | T | G |
| S_9456733 \| \| scaffold14851_4107664_SNP | 4107664 | G | A |
| S_9456781 \| \| scaffold14851_4108311_SNP | 4108311 | T | G |
| S_9456796 \| \| scaffold14851_4108727_SNP | 4108727 | T | A |
| S_9456810 \| \| scaffold14851_4108925_SNP | 4108925 | G | T |
| S_9456816 \| \| scaffold14851_4109044_SNP | 4109044 | A | G |
| S_9456845 \| \| scaffold14851_4109492_SNP | 4109492 | G | T |
| S_9456884 \| \| scaffold14851_4110077_SNP | 4110077 | C | A |
| S_9456885 \| \| scaffold14851_4110081_SNP | 4110081 | G | T |
| S_9457012 \| \| scaffold14851_4111877_SNP | 4111877 | C | G |
| S_9457080 \| \| scaffold14851_4112825_SNP | 4112825 | G | T |
| S_9457125 \| \| scaffold14851_4113833_SNP | 4113833 | A | G |
| S_9457135 \| \| scaffold14851_4114069_SNP | 4114069 | A | T |
| S_9457181 \| \| scaffold14851_4115004_SNP | 4115004 | A | C |
| S_9457204 \| \| scaffold14851_4115214_SNP | 4115214 | C | A |
| S_9457240 \| \| scaffold14851_4115499_SNP | 4115499 | A | G |
| S_9457245 \| \| scaffold14851_4115540_SNP | 4115540 | C | G |
| S_9457284 \| \| scaffold14851_4116200_SNP | 4116200 | G | T |
| S_9457376 \| \| scaffold14851_4117092_SNP | 4117092 | C | T |
| S_9457378 \| \| scaffold14851_4117096_SNP | 4117096 | C | T |
| S_9457379 \| \| scaffold14851_4117121_SNP | 4117121 | C | T |
| S_9457392 \| \| scaffold14851_4117262_SNP | 4117262 | A | G |
| S_9457483 \| \| scaffold14851_4118226_SNP | 4118226 | C | G |
| S_9457496 \| \| scaffold14851_4118361_SNP | 4118361 | A | G |
| S_9457499 \| \| scaffold14851_4118394_SNP | 4118394 | T | A |
| S_9457527 \| \| scaffold14851_4118864_SNP | 4118864 | G | A |
| S_9457615 \| \| scaffold14851_4119863_SNP | 4119863 | G | T |
| S_9457628 \| \| scaffold14851_4120147_SNP | 4120147 | A | G |
| S_9457643 \| \| scaffold14851_4120377_SNP | 4120377 | T | G |
| S_9457653 \| \| scaffold14851_4120507_SNP | 4120507 | T | G |
| S_9457657 \| \| scaffold14851_4120573_SNP | 4120573 | A | T |
| S_9457693 \| \| scaffold14851_4121133_SNP | 4121133 | T | G |
| S_9458036 \| \| scaffold14851_4125885_SNP | 4125885 | A | G |
| S_9458093 \| \| scaffold14851_4126358_SNP | 4126358 | C | T |
| S_9458135 \| \| scaffold14851_4127135_SNP | 4127135 | G | A |
| S_9458160 \| \| scaffold14851_4127501_SNP | 4127501 | A | C |
| S_9458179 \| \| scaffold14851_4127808_SNP | 4127808 | A | T |
| S_9458189 \| \| scaffold14851_4127878_SNP | 4127878 | G | A |
| S_9458339 \| \| scaffold14851_4129710_SNP | 4129710 | G | C |
| S_9458346 \| \| scaffold14851_4129878_SNP | 4129878 | T | G |
| S_9458357 \| \| scaffold14851_4130219_SNP | 4130219 | A | T |
| scaffold14851_4130452_SNP | 4130452 | G | T |
| S_9458505 \| \| scaffold14851_4131040_SNP | 4131040 | G | T |
| S_9458514 \| \| scaffold14851_4131229_SNP | 4131229 | G | A |
| S_9458640 \| \| scaffold14851_4132666_SNP | 4132666 | A | C |
| S_9458868 \| \| scaffold14851_4136188_SNP | 4136188 | C | T |
| S_9458918 \| \| scaffold14851_4136750_SNP | 4136750 | G | A |
| S_9458943 \| \| scaffold14851_4137044_SNP | 4137044 | A | G |
| S_9458958 \| \| scaffold14851_4137298_SNP | 4137298 | G | A |
| S_9458968 \| \| scaffold14851_4137423_SNP | 4137423 | T | C |
| S_9458977 \| \| scaffold14851_4137509_SNP | 4137509 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9459091 \| \| scaffold14851_4138463_SNP | 4138463 | C | T |
| S_9459092 \| \| scaffold14851_4138478_SNP | 4138478 | G | C |
| S_9459093 \| \| scaffold14851_4138490_SNP | 4138490 | C | T |
| S_9459094 \| \| scaffold14851_4138493_SNP | 4138493 | G | A |
| S_9459095 \| \| scaffold14851_4138496_SNP | 4138496 | G | A |
| S_9459109 \| \| scaffold14851_4138702_SNP | 4138702 | T | C |
| S_9459200 \| \| scaffold14851_4139656_SNP | 4139656 | T | G |
| S_9459214 \| \| scaffold14851_4139881_SNP | 4139881 | A | G |
| S_9459223 \| \| scaffold14851_4140031_SNP | 4140031 | A | T |
| S_9459225 \| \| scaffold14851_4140068_SNP | 4140068 | G | A |
| S_9459230 \| \| scaffold14851_4140182_SNP | 4140182 | A | G |
| S_9460031 \| \| scaffold14851_4153224_SNP | 4153224 | A | C |
| S_9460215 \| \| scaffold14851_4157651_SNP | 4157651 | G | A |
| S_9460216 \| \| scaffold14851_4157674_SNP | 4157674 | A | G |
| S_9460230 \| \| scaffold14851_4157886_SNP | 4157886 | G | C |
| S_9460290 \| \| scaffold14851_4158385_SNP | 4158385 | A | G |
| S_9460297 \| \| scaffold14851_4158472_SNP | 4158472 | C | T |
| S_9460303 \| \| scaffold14851_4158679_SNP | 4158679 | T | G |
| S_9460441 \| \| scaffold14851_4160426_SNP | 4160426 | A | G |
| S_9460491 \| \| scaffold14851_4161014_SNP | 4161014 | C | T |
| S_9460519 \| \| scaffold14851_4161377_SNP | 4161377 | T | A |
| S_9460548 \| \| scaffold14851_4161568_SNP | 4161568 | G | A |
| S_9460746 \| \| scaffold14851_4164153_SNP | 4164153 | T | C |
| S_9460754 \| \| scaffold14851_4164224_SNP | 4164224 | G | A |
| S_9460756 \| \| scaffold14851_4164232_SNP | 4164232 | T | C |
| scaffold14851_4164271_SNP | 4164271 | C | T |
| S_9460778 \| \| scaffold14851_4164309_SNP | 4164309 | G | A |
| scaffold14851_4164334_SNP | 4164334 | C | T |
| S_9460790 \| \| scaffold14851_4164357_SNP | 4164357 | T | C |
| S_9460792 \| \| scaffold14851_4164376_SNP | 4164376 | T | C |
| S_9460805 \| \| scaffold14851_4164477_SNP | 4164477 | T | G |
| S_9460832 \| \| scaffold14851_4164923_SNP | 4164923 | C | A |
| S_9460839 \| \| scaffold14851_4165012_SNP | 4165012 | A | G |
| S_9460854 \| \| scaffold14851_4165170_SNP | 4165170 | G | A |
| S_9460860 \| \| scaffold14851_4165257_SNP | 4165257 | C | T |
| S_9460867 \| \| scaffold14851_4165332_SNP | 4165332 | A | G |
| S_9460868 \| \| scaffold14851_4165339_SNP | 4165339 | G | A |
| S_9460870 \| \| scaffold14851_4165375_SNP | 4165375 | C | T |
| S_9460874 \| \| scaffold14851_4165395_SNP | 4165395 | A | G |
| S_9460887 \| \| scaffold14851_4165499_SNP | 4165499 | G | T |
| S_9460888 \| \| scaffold14851_4165502_SNP | 4165502 | T | C |
| S_9460890 \| \| scaffold14851_4165523_SNP | 4165523 | C | A |
| S_9460916 \| \| scaffold14851_4165810_SNP | 4165810 | G | A |
| S_9460946 \| \| scaffold14851_4166081_SNP | 4166081 | G | A |
| S_9461012 \| \| scaffold14851_4166367_SNP | 4166367 | C | T |
| S_9461027 \| \| scaffold14851_4166556_SNP | 4166556 | T | A |
| S_9461050 \| \| scaffold14851_4166969_SNP | 4166969 | C | T |
| S_9461059 \| \| scaffold14851_4167047_SNP | 4167047 | T | C |
| S_9461064 \| \| scaffold14851_4167160_SNP | 4167160 | A | T |
| S_9461068 \| \| scaffold14851_4167206_SNP | 4167206 | T | G |
| S_9461070 \| \| scaffold14851_4167259_SNP | 4167259 | T | C |
| S_9461155 \| \| scaffold14851_4168455_SNP | 4168455 | C | A |
| S_9461156 \| \| scaffold14851_4168470_SNP | 4168470 | A | T |
| S_9461163 \| \| scaffold14851_4168616_SNP | 4168616 | A | T |
| S_9461165 \| \| scaffold14851_4168660_SNP | 4168660 | T | A |
| S_9461183 \| \| scaffold14851_4169040_SNP | 4169040 | A | T |
| S_9461330 \| \| scaffold14851_4169886_SNP | 4169886 | T | G |
| S_9461333 \| \| scaffold14851_4169906_SNP | 4169906 | C | G |
| S_9461363 \| \| scaffold14851_4170494_SNP | 4170494 | G | A |
| S_9461364 \| \| scaffold14851_4170510_SNP | 4170510 | G | A |
| S_9461371 \| \| scaffold14851_4170612_SNP | 4170612 | A | G |
| S_9461391 \| \| scaffold14851_4170949_SNP | 4170949 | C | A |
| S_9461410 \| \| scaffold14851_4171234_SNP | 4171234 | A | C |
| S_9461435 \| \| scaffold14851_4171658_SNP | 4171658 | T | G |
| S_9461457 \| \| scaffold14851_4172109_SNP | 4172109 | C | T |
| S_9461461 \| \| scaffold14851_4172221_SNP | 4172221 | T | C |
| S_9461464 \| \| scaffold14851_4172247_SNP | 4172247 | G | A |
| S_9461466 \| \| scaffold14851_4172325_SNP | 4172325 | T | C |
| S_9461489 \| \| scaffold14851_4172775_SNP | 4172775 | T | G |
| S_9461492 \| \| scaffold14851_4172819_SNP | 4172819 | A | G |
| S_9461496 \| \| scaffold14851_4172880_SNP | 4172880 | T | A |
| S_9461502 \| \| scaffold14851_4172943_SNP | 4172943 | A | G |
| S_9461506 \| \| scaffold14851_4172994_SNP | 4172994 | A | G |
| S_9461515 \| \| scaffold14851_4173088_SNP | 4173088 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9461519 \| \| scaffold14851_4173143_SNP | 4173143 | T | C |
| S_9461520 \| \| scaffold14851_4173144_SNP | 4173144 | G | C |
| S_9461591 \| \| scaffold14851_4173664_SNP | 4173664 | T | C |
| S_9461598 \| \| scaffold14851_4173769_SNP | 4173769 | A | C |
| S_9461601 \| \| scaffold14851_4173814_SNP | 4173814 | C | T |
| S_9461625 \| \| scaffold14851_4174070_SNP | 4174070 | G | C |
| S_9461773 \| \| scaffold14851_4176123_SNP | 4176123 | G | A |
| S_9461774 \| \| scaffold14851_4176137_SNP | 4176137 | T | A |
| S_9461775 \| \| scaffold14851_4176166_SNP | 4176166 | A | T |
| S_9461778 \| \| scaffold14851_4176222_SNP | 4176222 | T | G |
| S_9461801 \| \| scaffold14851_4176423_SNP | 4176423 | G | C |
| S_9461841 \| \| scaffold14851_4176684_SNP | 4176684 | G | A |
| S_9461844 \| \| scaffold14851_4176731_SNP | 4176731 | A | G |
| S_9461852 \| \| scaffold14851_4176781_SNP | 4176781 | C | G |
| S_9461853 \| \| scaffold14851_4176788_SNP | 4176788 | T | A |
| S_9461872 \| \| scaffold14851_4176831_SNP | 4176831 | T | A |
| S_9461875 \| \| scaffold14851_4176832_SNP | 4176832 | T | C |
| S_9461894 \| \| scaffold14851_4177023_SNP | 4177023 | T | G |
| S_9461905 \| \| scaffold14851_4177140_SNP | 4177140 | G | T |
| S_9461919 \| \| scaffold14851_4177257_SNP | 4177257 | A | T |
| S_9461991 \| \| scaffold14851_4178175_SNP | 4178175 | G | A |
| S_9462038 \| \| scaffold14851_4178751_SNP | 4178751 | G | A |
| S_9462039 \| \| scaffold14851_4178798_SNP | 4178798 | G | A |
| S_9462060 \| \| scaffold14851_4179067_SNP | 4179067 | A | G |
| S_9462063 \| \| scaffold14851_4179237_SNP | 4179237 | T | C |
| S_9462075 \| \| scaffold14851_4179456_SNP | 4179456 | C | T |
| S_9462077 \| \| scaffold14851_4179481_SNP | 4179481 | C | T |
| S_9462094 \| \| scaffold14851_4179750_SNP | 4179750 | G | A |
| S_9462095 \| \| scaffold14851_4179760_SNP | 4179760 | T | A |
| S_9462101 \| \| scaffold14851_4179850_SNP | 4179850 | G | C |
| S_9462106 \| \| scaffold14851_4179923_SNP | 4179923 | G | C |
| S_9462116 \| \| scaffold14851_4180098_SNP | 4180098 | T | C |
| S_9462117 \| \| scaffold14851_4180100_SNP | 4180100 | C | A |
| S_9462126 \| \| scaffold14851_4180178_SNP | 4180178 | G | C |
| S_9462131 \| \| scaffold14851_4180254_SNP | 4180254 | T | A |
| S_9462134 \| \| scaffold14851_4180305_SNP | 4180305 | G | C |
| S_9462154 \| \| scaffold14851_4180534_SNP | 4180534 | C | T |
| S_9462232 \| \| scaffold14851_4181468_SNP | 4181468 | G | C |
| S_9462247 \| \| scaffold14851_4181602_SNP | 4181602 | A | T |
| S_9462295 \| \| scaffold14851_4182296_SNP | 4182296 | A | T |
| S_9462296 \| \| scaffold14851_4182297_SNP | 4182297 | A | T |
| S_9462299 \| \| scaffold14851_4182424_SNP | 4182424 | A | C |
| S_9462318 \| \| scaffold14851_4182626_SNP | 4182626 | G | A |
| S_9462319 \| \| scaffold14851_4182640_SNP | 4182640 | T | A |
| S_9462321 \| \| scaffold14851_4182665_SNP | 4182665 | G | A |
| S_9462364 \| \| scaffold14851_4183196_SNP | 4183196 | A | T |
| S_9462367 \| \| scaffold14851_4183238_SNP | 4183238 | C | A |
| S_9462368 \| \| scaffold14851_4183267_SNP | 4183267 | T | C |
| S_9462380 \| \| scaffold14851_4183390_SNP | 4183390 | C | A |
| S_9462388 \| \| scaffold14851_4183523_SNP | 4183523 | A | G |
| S_9462411 \| \| scaffold14851_4183773_SNP | 4183773 | T | A |
| S_9462430 \| \| scaffold14851_4184035_SNP | 4184035 | A | G |
| S_9462431 \| \| scaffold14851_4184040_SNP | 4184040 | G | C |
| S_9462433 \| \| scaffold14851_4184093_SNP | 4184093 | A | G |
| S_9462435 \| \| scaffold14851_4184112_SNP | 4184112 | T | G |
| S_9462489 \| \| scaffold14851_4184846_SNP | 4184846 | T | C |
| S_9462496 \| \| scaffold14851_4184927_SNP | 4184927 | C | A |
| S_9462509 \| \| scaffold14851_4185004_SNP | 4185004 | C | T |
| S_9462546 \| \| scaffold14851_4185581_SNP | 4185581 | A | T |
| S_9462548 \| \| scaffold14851_4185641_SNP | 4185641 | T | C |
| S_9462553 \| \| scaffold14851_4185694_SNP | 4185694 | T | G |
| S_9462555 \| \| scaffold14851_4185703_SNP | 4185703 | T | A |
| S_9462564 \| \| scaffold14851_4185778_SNP | 4185778 | T | C |
| S_9462571 \| \| scaffold14851_4186030_SNP | 4186030 | A | G |
| S_9462572 \| \| scaffold14851_4186035_SNP | 4186035 | A | G |
| S_9462585 \| \| scaffold14851_4186183_SNP | 4186183 | C | T |
| S_9462586 \| \| scaffold14851_4186186_SNP | 4186186 | G | A |
| S_9462592 \| \| scaffold14851_4186258_SNP | 4186258 | T | C |
| S_9462599 \| \| scaffold14851_4186362_SNP | 4186362 | G | T |
| S_9462652 \| \| scaffold14851_4187173_SNP | 4187173 | T | C |
| S_9462682 \| \| scaffold14851_4187237_SNP | 4187237 | A | T |
| S_9462689 \| \| scaffold14851_4187246_SNP | 4187246 | C | T |
| S_9462694 \| \| scaffold14851_4187250_SNP | 4187250 | C | T |
| S_9462717 \| \| scaffold14851_4187318_SNP | 4187318 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9462739 \| \| scaffold14851_4187616_SNP | 4187616 | G | A |
| S_9462743 \| \| scaffold14851_4187722_SNP | 4187722 | A | T |
| S_9462755 \| \| scaffold14851_4187997_SNP | 4187997 | T | C |
| S_9462762 \| \| scaffold14851_4188078_SNP | 4188078 | A | G |
| S_9462770 \| \| scaffold14851_4188164_SNP | 4188164 | G | A |
| S_9462771 \| \| scaffold14851_4188167_SNP | 4188167 | T | A |
| S_9462773 \| \| scaffold14851_4188175_SNP | 4188175 | A | T |
| S_9462777 \| \| scaffold14851_4188232_SNP | 4188232 | T | G |
| S_9462779 \| \| scaffold14851_4188254_SNP | 4188254 | A | G |
| S_9462784 \| \| scaffold14851_4188291_SNP | 4188291 | A | G |
| S_9462852 \| \| scaffold14851_4189361_SNP | 4189361 | T | A |
| S_9462853 \| \| scaffold14851_4189376_SNP | 4189376 | G | C |
| S_9462868 \| \| scaffold14851_4189668_SNP | 4189668 | G | A |
| S_9462877 \| \| scaffold14851_4189797_SNP | 4189797 | T | C |
| S_9462878 \| \| scaffold14851_4189799_SNP | 4189799 | C | T |
| S_9462882 \| \| scaffold14851_4189885_SNP | 4189885 | C | T |
| S_9462893 \| \| scaffold14851_4189996_SNP | 4189996 | T | G |
| S_9462895 \| \| scaffold14851_4190029_SNP | 4190029 | A | G |
| S_9462905 \| \| scaffold14851_4190171_SNP | 4190171 | A | G |
| S_9462908 \| \| scaffold14851_4190190_SNP | 4190190 | A | G |
| S_9462909 \| \| scaffold14851_4190198_SNP | 4190198 | C | T |
| S_9462911 \| \| scaffold14851_4190266_SNP | 4190266 | G | A |
| S_9463000 \| \| scaffold14851_4191304_SNP | 4191304 | A | T |
| S_9463016 \| \| scaffold14851_4191469_SNP | 4191469 | C | T |
| scaffold14851_4191562_SNP | 4191562 | C | T |
| S_9463032 \| \| scaffold14851_4191569_SNP | 4191569 | T | A |
| S_9463057 \| \| scaffold14851_4191696_SNP | 4191696 | G | A |
| S_9463066 \| \| scaffold14851_4191781_SNP | 4191781 | A | T |
| S_9463146 \| \| scaffold14851_4192303_SNP | 4192303 | C | A |
| S_9463157 \| \| scaffold14851_4192399_SNP | 4192399 | G | C |
| S_9463168 \| \| scaffold14851_4192480_SNP | 4192480 | A | T |
| S_9463180 \| \| scaffold14851_4192634_SNP | 4192634 | A | G |
| S_9463187 \| \| scaffold14851_4192698_SNP | 4192698 | C | T |
| S_9463192 \| \| scaffold14851_4192754_SNP | 4192754 | A | T |
| S_9463197 \| \| scaffold14851_4192862_SNP | 4192862 | G | A |
| S_9463199 \| \| scaffold14851_4192871_SNP | 4192871 | A | T |
| S_9463298 \| \| scaffold14851_4194073_SNP | 4194073 | G | A |
| S_9463307 \| \| scaffold14851_4194196_SNP | 4194196 | G | A |
| S_9463308 \| \| scaffold14851_4194202_SNP | 4194202 | T | A |
| S_9463310 \| \| scaffold14851_4194237_SNP | 4194237 | G | A |
| S_9463320 \| \| scaffold14851_4194443_SNP | 4194443 | A | T |
| S_9463321 \| \| scaffold14851_4194444_SNP | 4194444 | A | G |
| S_9463327 \| \| scaffold14851_4194520_SNP | 4194520 | A | G |
| S_9463352 \| \| scaffold14851_4194746_SNP | 4194746 | T | C |
| S_9463493 \| \| scaffold14851_4196274_SNP | 4196274 | G | A |
| S_9463645 \| \| scaffold14851_4198479_SNP | 4198479 | A | T |
| S_9463670 \| \| scaffold14851_4199134_SNP | 4199134 | C | T |
| S_9463671 \| \| scaffold14851_4199141_SNP | 4199141 | T | C |
| S_9463722 \| \| scaffold14851_4199619_SNP | 4199619 | T | G |
| S_9463903 \| \| scaffold14851_4201020_SNP | 4201020 | T | A |
| S_9463932 \| \| scaffold14851_4201426_SNP | 4201426 | A | C |
| S_9463933 \| \| scaffold14851_4201435_SNP | 4201435 | T | C |
| S_9464032 \| \| scaffold14851_4202871_SNP | 4202871 | A | G |
| S_9464118 \| \| scaffold14851_4204017_SNP | 4204017 | C | T |
| S_9464135 \| \| scaffold14851_4204403_SNP | 4204403 | C | T |
| S_9464138 \| \| scaffold14851_4204459_SNP | 4204459 | A | C |
| S_9464140 \| \| scaffold14851_4204486_SNP | 4204486 | C | T |
| S_9464143 \| \| scaffold14851_4204512_SNP | 4204512 | C | T |
| S_9464154 \| \| scaffold14851_4204730_SNP | 4204730 | A | G |
| S_9464275 \| \| scaffold14851_4206374_SNP | 4206374 | G | T |
| S_9464350 \| \| scaffold14851_4207363_SNP | 4207363 | A | T |
| S_9464356 \| \| scaffold14851_4207523_SNP | 4207523 | A | G |
| S_9464396 \| \| scaffold14851_4208094_SNP | 4208094 | G | A |
| S_9464486 \| \| scaffold14851_4208353_SNP | 4208353 | G | T |
| S_9464495 \| \| scaffold14851_4208427_SNP | 4208427 | A | C |
| S_9464532 \| \| scaffold14851_4209171_SNP | 4209171 | G | C |
| S_9464623 \| \| scaffold14851_4210272_SNP | 4210272 | A | G |
| S_9464628 \| \| scaffold14851_4210341_SNP | 4210341 | G | T |
| S_9464661 \| \| scaffold14851_4210714_SNP | 4210714 | A | T |
| S_9464665 \| \| scaffold14851_4210819_SNP | 4210819 | A | G |
| S_9464677 \| \| scaffold14851_4210945_SNP | 4210945 | C | A |
| S_9464771 \| \| scaffold14851_4212542_SNP | 4212542 | C | T |
| S_9464780 \| \| scaffold14851_4212742_SNP | 4212742 | A | G |
| S_9464782 \| \| scaffold14851_4212777_SNP | 4212777 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9464787 \| \| scaffold14851_4212879_SNP | 4212879 | T | A |
| S_9464792 \| \| scaffold14851_4212953_SNP | 4212953 | G | T |
| S_9464876 \| \| scaffold14851_4214442_SNP | 4214442 | A | T |
| S_9464879 \| \| scaffold14851_4214520_SNP | 4214520 | A | G |
| S_9464887 \| \| scaffold14851_4214694_SNP | 4214694 | C | A |
| S_9464890 \| \| scaffold14851_4214744_SNP | 4214744 | T | C |
| S_9464891 \| \| scaffold14851_4214753_SNP | 4214753 | G | A |
| S_9464987 \| \| scaffold14851_4216281_SNP | 4216281 | C | G |
| S_9464997 \| \| scaffold14851_4216389_SNP | 4216389 | A | G |
| S_9465001 \| \| scaffold14851_4216429_SNP | 4216429 | G | A |
| S_9465015 \| \| scaffold14851_4216550_SNP | 4216550 | T | G |
| S_9465042 \| \| scaffold14851_4216848_SNP | 4216848 | A | T |
| S_9465044 \| \| scaffold14851_4216860_SNP | 4216860 | G | T |
| S_9465047 \| \| scaffold14851_4216936_SNP | 4216936 | G | A |
| S_9465060 \| \| scaffold14851_4217124_SNP | 4217124 | C | G |
| S_9465069 \| \| scaffold14851_4217285_SNP | 4217285 | C | T |
| S_9465078 \| \| scaffold14851_4217433_SNP | 4217433 | A | C |
| S_9465175 \| \| scaffold14851_4219066_SNP | 4219066 | G | A |
| S_9465180 \| \| scaffold14851_4219196_SNP | 4219196 | C | T |
| S_9465226 \| \| scaffold14851_4219662_SNP | 4219662 | A | C |
| S_9465245 \| \| scaffold14851_4220317_SNP | 4220317 | T | C |
| S_9465262 \| \| scaffold14851_4220569_SNP | 4220569 | G | A |
| S_9465389 \| \| scaffold14851_4221793_SNP | 4221793 | G | A |
| S_9465398 \| \| scaffold14851_4221869_SNP | 4221869 | G | T |
| S_9465425 \| \| scaffold14851_4222087_SNP | 4222087 | C | A |
| S_9465430 \| \| scaffold14851_4222170_SNP | 4222170 | A | T |
| S_9465434 \| \| scaffold14851_4222354_SNP | 4222354 | G | C |
| S_9465435 \| \| scaffold14851_4222370_SNP | 4222370 | A | T |
| scaffold14851_4222707_SNP | 4222707 | T | C |
| S_9465491 \| \| scaffold14851_4222809_SNP | 4222809 | T | C |
| S_9465497 \| \| scaffold14851_4222888_SNP | 4222888 | C | T |
| S_9465499 \| \| scaffold14851_4222906_SNP | 4222906 | A | G |
| S_9465504 \| \| scaffold14851_4222992_SNP | 4222992 | G | A |
| S_9465509 \| \| scaffold14851_4223049_SNP | 4223049 | C | A |
| S_9465567 \| \| scaffold14851_4223716_SNP | 4223716 | C | T |
| S_9465677 \| \| scaffold14851_4224818_SNP | 4224818 | A | C |
| S_9465682 \| \| scaffold14851_4224874_SNP | 4224874 | C | T |
| S_9465686 \| \| scaffold14851_4224960_SNP | 4224960 | C | T |
| S_9465695 \| \| scaffold14851_4225226_SNP | 4225226 | T | G |
| S_9465699 \| \| scaffold14851_4225457_SNP | 4225457 | T | C |
| S_9465759 \| \| scaffold14851_4226498_SNP | 4226498 | G | T |
| S_9465911 \| \| scaffold14851_4229078_SNP | 4229078 | G | A |
| S_9465954 \| \| scaffold14851_4229558_SNP | 4229558 | C | T |
| S_9465973 \| \| scaffold14851_4229853_SNP | 4229853 | T | C |
| S_9465977 \| \| scaffold14851_4229871_SNP | 4229871 | A | G |
| S_9465978 \| \| scaffold14851_4229876_SNP | 4229876 | T | C |
| S_9466036 \| \| scaffold14851_4230424_SNP | 4230424 | T | C |
| S_9466067 \| \| scaffold14851_4230827_SNP | 4230827 | G | A |
| S_9466074 \| \| scaffold14851_4230988_SNP | 4230988 | G | C |
| S_9466134 \| \| scaffold14851_4231607_SNP | 4231607 | T | G |
| S_9466186 \| \| scaffold14851_4232294_SNP | 4232294 | G | A |
| S_9466210 \| \| scaffold14851_4232540_SNP | 4232540 | C | A |
| S_9466299 \| \| scaffold14851_4233848_SNP | 4233848 | A | G |
| S_9466302 \| \| scaffold14851_4233859_SNP | 4233859 | T | C |
| S_9466351 \| \| scaffold14851_4234555_SNP | 4234555 | A | T |
| S_9466526 \| \| scaffold14851_4236760_SNP | 4236760 | A | G |
| S_9466537 \| \| scaffold14851_4236883_SNP | 4236883 | A | G |
| S_9467543 \| \| scaffold14851_4239271_SNP | 4239271 | C | T |
| scaffold14851_4241011_SNP | 4241011 | C | T |
| scaffold14851_4241479_SNP | 4241479 | T | C |
| S_9468194 \| \| scaffold14851_4241481_SNP | 4241481 | T | C |
| S_9468195 \| \| scaffold14851_4241482_SNP | 4241482 | A | G |
| scaffold14851_4241540_SNP | 4241540 | A | G |
| S_9470339 \| \| scaffold14851_4247827_SNP | 4247827 | A | G |
| S_9471342 \| \| scaffold14851_4252540_SNP | 4252540 | A | C |
| S_9471352 \| \| scaffold14851_4252607_SNP | 4252607 | G | A |
| S_9471353 \| \| scaffold14851_4252642_SNP | 4252642 | A | C |
| S_9471366 \| \| scaffold14851_4252787_SNP | 4252787 | A | G |
| S_9471415 \| \| scaffold14851_4253024_SNP | 4253024 | C | T |
| S_9471482 \| \| scaffold14851_4253185_SNP | 4253185 | C | T |
| S_9471484 \| \| scaffold14851_4253191_SNP | 4253191 | T | C |
| S_9471499 \| \| scaffold14851_4253261_SNP | 4253261 | C | T |
| S_9471502 \| \| scaffold14851_4253280_SNP | 4253280 | T | C |
| S_9471515 \| \| scaffold14851_4253336_SNP | 4253336 | C | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9471586 \| \| scaffold14851_4254438_SNP | 4254438 | T | A |
| S_9471589 \| \| scaffold14851_4254560_SNP | 4254560 | T | A |
| S_9471590 \| \| scaffold14851_4254574_SNP | 4254574 | T | C |
| S_9471630 \| \| scaffold14851_4255179_SNP | 4255179 | A | G |
| S_9471640 \| \| scaffold14851_4255233_SNP | 4255233 | G | A |
| S_9471657 \| \| scaffold14851_4255427_SNP | 4255427 | G | A |
| S_9471670 \| \| scaffold14851_4255626_SNP | 4255626 | A | T |
| S_9471761 \| \| scaffold14851_4256804_SNP | 4256804 | T | C |
| S_9471999 \| \| scaffold14851_4259159_SNP | 4259159 | G | A |
| S_9472000 \| \| scaffold14851_4259168_SNP | 4259168 | C | A |
| S_9472006 \| \| scaffold14851_4259233_SNP | 4259233 | C | A |
| S_9472007 \| \| scaffold14851_4259267_SNP | 4259267 | A | G |
| S_9472011 \| \| scaffold14851_4259300_SNP | 4259300 | G | T |
| S_9472018 \| \| scaffold14851_4259402_SNP | 4259402 | G | A |
| S_9472020 \| \| scaffold14851_4259419_SNP | 4259419 | T | C |
| S_9472035 \| \| scaffold14851_4259532_SNP | 4259532 | C | G |
| S_9472052 \| \| scaffold14851_4259631_SNP | 4259631 | G | A |
| S_9472057 \| \| scaffold14851_4259664_SNP | 4259664 | T | C |
| S_9472058 \| \| scaffold14851_4259693_SNP | 4259693 | A | C |
| S_9472091 \| \| scaffold14851_4259907_SNP | 4259907 | A | G |
| S_9472099 \| \| scaffold14851_4259943_SNP | 4259943 | T | G |
| S_9472187 \| \| scaffold14851_4260644_SNP | 4260644 | G | T |
| S_9472194 \| \| scaffold14851_4260792_SNP | 4260792 | T | A |
| S_9472214 \| \| scaffold14851_4261032_SNP | 4261032 | T | C |
| S_9472234 \| \| scaffold14851_4261452_SNP | 4261452 | A | C |
| S_9472235 \| \| scaffold14851_4261465_SNP | 4261465 | A | G |
| S_9472289 \| \| scaffold14851_4262228_SNP | 4262228 | C | T |
| S_9472308 \| \| scaffold14851_4262495_SNP | 4262495 | G | A |
| S_9472314 \| \| scaffold14851_4262570_SNP | 4262570 | T | A |
| S_9472336 \| \| scaffold14851_4262927_SNP | 4262927 | A | T |
| S_9472398 \| \| scaffold14851_4263231_SNP | 4263231 | C | A |
| S_9472430 \| \| scaffold14851_4263982_SNP | 4263982 | T | C |
| S_9472432 \| \| scaffold14851_4264066_SNP | 4264066 | G | T |
| S_9472474 \| \| scaffold14851_4264667_SNP | 4264667 | A | C |
| S_9472491 \| \| scaffold14851_4264912_SNP | 4264912 | C | T |
| S_9472502 \| \| scaffold14851_4265075_SNP | 4265075 | C | T |
| S_9472504 \| \| scaffold14851_4265090_SNP | 4265090 | T | A |
| S_9472517 \| \| scaffold14851_4265269_SNP | 4265269 | T | C |
| S_9472518 \| \| scaffold14851_4265275_SNP | 4265275 | A | T |
| S_9472519 \| \| scaffold14851_4265281_SNP | 4265281 | A | T |
| S_9472630 \| \| scaffold14851_4266816_SNP | 4266816 | C | T |
| S_9472632 \| \| scaffold14851_4266881_SNP | 4266881 | C | A |
| S_9472634 \| \| scaffold14851_4266931_SNP | 4266931 | A | T |
| S_9472646 \| \| scaffold14851_4267151_SNP | 4267151 | G | T |
| S_9472889 \| \| scaffold14851_4270419_SNP | 4270419 | C | T |
| S_9472933 \| \| scaffold14851_4271429_SNP | 4271429 | C | T |
| S_9472934 \| \| scaffold14851_4271441_SNP | 4271441 | G | A |
| S_9472938 \| \| scaffold14851_4271502_SNP | 4271502 | A | C |
| S_9472972 \| \| scaffold14851_4271852_SNP | 4271852 | T | C |
| S_9472974 \| \| scaffold14851_4271889_SNP | 4271889 | A | T |
| S_9473011 \| \| scaffold14851_4272611_SNP | 4272611 | A | T |
| S_9473023 \| \| scaffold14851_4272806_SNP | 4272806 | C | T |
| S_9473039 \| \| scaffold14851_4273047_SNP | 4273047 | C | T |
| S_9473046 \| \| scaffold14851_4273129_SNP | 4273129 | C | T |
| S_9473049 \| \| scaffold14851_4273136_SNP | 4273136 | A | C |
| S_9473064 \| \| scaffold14851_4273336_SNP | 4273336 | A | G |
| S_9473066 \| \| scaffold14851_4273365_SNP | 4273365 | G | A |
| S_9473075 \| \| scaffold14851_4273455_SNP | 4273455 | T | C |
| S_9473078 \| \| scaffold14851_4273509_SNP | 4273509 | G | A |
| S_9473206 \| \| scaffold14851_4274464_SNP | 4274464 | G | A |
| S_9473243 \| \| scaffold14851_4274924_SNP | 4274924 | A | T |
| S_9473353 \| \| scaffold14851_4276142_SNP | 4276142 | C | G |
| S_9473369 \| \| scaffold14851_4276379_SNP | 4276379 | A | G |
| S_9473380 \| \| scaffold14851_4276549_SNP | 4276549 | T | G |
| S_9473397 \| \| scaffold14851_4276696_SNP | 4276696 | G | C |
| S_9473457 \| \| scaffold14851_4277383_SNP | 4277383 | A | G |
| S_9473474 \| \| scaffold14851_4277694_SNP | 4277694 | A | G |
| S_9473589 \| \| scaffold14851_4279137_SNP | 4279137 | A | G |
| S_9473592 \| \| scaffold14851_4279232_SNP | 4279232 | C | T |
| S_9473627 \| \| scaffold14851_4279692_SNP | 4279692 | A | G |
| S_9473629 \| \| scaffold14851_4279711_SNP | 4279711 | T | C |
| S_9473649 \| \| scaffold14851_4280102_SNP | 4280102 | T | A |
| S_9473660 \| \| scaffold14851_4280214_SNP | 4280214 | T | A |
| S_9473662 \| \| scaffold14851_4280235_SNP | 4280235 | A | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9473666 \|\| scaffold14851_4280328_SNP | 4280328 | G | A |
| S_9473669 \|\| scaffold14851_4280365_SNP | 4280365 | T | A |
| S_9473671 \|\| scaffold14851_4280394_SNP | 4280394 | G | C |
| S_9473697 \|\| scaffold14851_4280634_SNP | 4280634 | T | C |
| S_9473698 \|\| scaffold14851_4280635_SNP | 4280635 | A | G |
| S_9473700 \|\| scaffold14851_4280665_SNP | 4280665 | G | A |
| S_9473705 \|\| scaffold14851_4280771_SNP | 4280771 | C | T |
| S_9473707 \|\| scaffold14851_4280802_SNP | 4280802 | C | T |
| S_9473708 \|\| scaffold14851_4280821_SNP | 4280821 | A | G |
| S_9473774 \|\| scaffold14851_4281295_SNP | 4281295 | T | C |
| S_9473779 \|\| scaffold14851_4281392_SNP | 4281392 | T | C |
| S_9473782 \|\| scaffold14851_4281413_SNP | 4281413 | G | A |
| S_9473784 \|\| scaffold14851_4281468_SNP | 4281468 | A | G |
| S_9473785 \|\| scaffold14851_4281495_SNP | 4281495 | A | G |
| S_9473799 \|\| scaffold14851_4281859_SNP | 4281859 | A | C |
| S_9473800 \|\| scaffold14851_4281874_SNP | 4281874 | T | G |
| S_9473972 \|\| scaffold14851_4284577_SNP | 4284577 | G | A |
| S_9473981 \|\| scaffold14851_4284737_SNP | 4284737 | G | A |
| S_9474053 \|\| scaffold14851_4284950_SNP | 4284950 | A | G |
| S_9474073 \|\| scaffold14851_4285007_SNP | 4285007 | C | T |
| S_9474100 \|\| scaffold14851_4285401_SNP | 4285401 | T | C |
| S_9474172 \|\| scaffold14851_4286340_SNP | 4286340 | T | C |
| S_9474181 \|\| scaffold14851_4286465_SNP | 4286465 | A | G |
| S_9474184 \|\| scaffold14851_4286474_SNP | 4286474 | A | C |
| S_9474187 \|\| scaffold14851_4286489_SNP | 4286489 | C | G |
| S_9474188 \|\| scaffold14851_4286544_SNP | 4286544 | A | T |
| S_9474245 \|\| scaffold14851_4287034_SNP | 4287034 | A | C |
| S_9474249 \|\| scaffold14851_4287086_SNP | 4287086 | A | G |
| S_9474281 \|\| scaffold14851_4287532_SNP | 4287532 | A | G |
| S_9474288 \|\| scaffold14851_4287599_SNP | 4287599 | A | C |
| S_9474296 \|\| scaffold14851_4287682_SNP | 4287682 | G | T |
| S_9474326 \|\| scaffold14851_4288135_SNP | 4288135 | T | G |
| S_9474344 \|\| scaffold14851_4288224_SNP | 4288224 | T | C |
| S_9474375 \|\| scaffold14851_4288772_SNP | 4288772 | A | G |
| S_9474376 \|\| scaffold14851_4288788_SNP | 4288788 | A | G |
| scaffold14851_4288958_SNP | 4288958 | T | A |
| S_9474393 \|\| scaffold14851_4288966_SNP | 4288966 | G | T |
| S_9474394 \|\| scaffold14851_4288967_SNP | 4288967 | G | T |
| S_9474415 \|\| scaffold14851_4289278_SNP | 4289278 | C | A |
| S_9474427 \|\| scaffold14851_4289458_SNP | 4289458 | C | T |
| S_9474430 \|\| scaffold14851_4289585_SNP | 4289585 | T | G |
| S_9474489 \|\| scaffold14851_4290307_SNP | 4290307 | A | T |
| S_9474494 \|\| scaffold14851_4290357_SNP | 4290357 | G | T |
| S_9474495 \|\| scaffold14851_4290358_SNP | 4290358 | G | T |
| S_9474500 \|\| scaffold14851_4290495_SNP | 4290495 | T | A |
| S_9474512 \|\| scaffold14851_4290610_SNP | 4290610 | G | T |
| S_9474531 \|\| scaffold14851_4290893_SNP | 4290893 | C | T |
| S_9474532 \|\| scaffold14851_4290896_SNP | 4290896 | A | G |
| S_9474533 \|\| scaffold14851_4290948_SNP | 4290948 | C | T |
| S_9474545 \|\| scaffold14851_4291117_SNP | 4291117 | A | C |
| S_9474554 \|\| scaffold14851_4291276_SNP | 4291276 | T | C |
| S_9474555 \|\| scaffold14851_4291277_SNP | 4291277 | A | C |
| S_9474567 \|\| scaffold14851_4291520_SNP | 4291520 | A | G |
| S_9474581 \|\| scaffold14851_4291715_SNP | 4291715 | G | A |
| S_9474582 \|\| scaffold14851_4291733_SNP | 4291733 | C | T |
| S_9474584 \|\| scaffold14851_4291809_SNP | 4291809 | A | T |
| S_9474590 \|\| scaffold14851_4291886_SNP | 4291886 | C | A |
| S_9474612 \|\| scaffold14851_4292179_SNP | 4292179 | C | A |
| S_9474629 \|\| scaffold14851_4292316_SNP | 4292316 | T | C |
| S_9474631 \|\| scaffold14851_4292333_SNP | 4292333 | C | T |
| S_9474761 \|\| scaffold14851_4293390_SNP | 4293390 | T | A |
| S_9474780 \|\| scaffold14851_4293635_SNP | 4293635 | A | G |
| S_9474789 \|\| scaffold14851_4293733_SNP | 4293733 | A | T |
| S_9474797 \|\| scaffold14851_4293865_SNP | 4293865 | G | T |
| S_9474799 \|\| scaffold14851_4293926_SNP | 4293926 | C | T |
| S_9474806 \|\| scaffold14851_4294008_SNP | 4294008 | A | G |
| S_9474810 \|\| scaffold14851_4294098_SNP | 4294098 | G | T |
| S_9474815 \|\| scaffold14851_4294163_SNP | 4294163 | C | G |
| S_9474822 \|\| scaffold14851_4294229_SNP | 4294229 | A | G |
| S_9474974 \|\| scaffold14851_4295265_SNP | 4295265 | C | A |
| S_9474997 \|\| scaffold14851_4295756_SNP | 4295756 | C | A |
| S_9475005 \|\| scaffold14851_4295891_SNP | 4295891 | C | T |
| S_9475007 \|\| scaffold14851_4295895_SNP | 4295895 | T | A |
| S_9475010 \|\| scaffold14851_4295949_SNP | 4295949 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9475065 \| \| scaffold14851_4296676_SNP | 4296676 | T | C |
| S_9475086 \| \| scaffold14851_4296872_SNP | 4296872 | A | C |
| S_9475089 \| \| scaffold14851_4296893_SNP | 4296893 | A | C |
| S_9475097 \| \| scaffold14851_4296978_SNP | 4296978 | C | A |
| S_9475107 \| \| scaffold14851_4297109_SNP | 4297109 | A | T |
| S_9475108 \| \| scaffold14851_4297112_SNP | 4297112 | A | C |
| S_9475126 \| \| scaffold14851_4297386_SNP | 4297386 | T | G |
| S_9475166 \| \| scaffold14851_4297758_SNP | 4297758 | C | T |
| S_9475334 \| \| scaffold14851_4299141_SNP | 4299141 | T | C |
| S_9475335 \| \| scaffold14851_4299167_SNP | 4299167 | A | T |
| S_9475337 \| \| scaffold14851_4299178_SNP | 4299178 | T | A |
| S_9475339 \| \| scaffold14851_4299280_SNP | 4299280 | G | A |
| S_9475341 \| \| scaffold14851_4299312_SNP | 4299312 | C | T |
| S_9475347 \| \| scaffold14851_4299379_SNP | 4299379 | G | A |
| S_9475350 \| \| scaffold14851_4299413_SNP | 4299413 | T | A |
| S_9475356 \| \| scaffold14851_4299495_SNP | 4299495 | T | A |
| S_9475499 \| \| scaffold14851_4300685_SNP | 4300685 | G | A |
| S_9475501 \| \| scaffold14851_4300699_SNP | 4300699 | C | T |
| S_9475661 \| \| scaffold14851_4302230_SNP | 4302230 | A | G |
| S_9475662 \| \| scaffold14851_4302234_SNP | 4302234 | G | A |
| S_9475669 \| \| scaffold14851_4302340_SNP | 4302340 | T | A |
| S_9475676 \| \| scaffold14851_4302516_SNP | 4302516 | G | C |
| S_9475677 \| \| scaffold14851_4302550_SNP | 4302550 | G | A |
| S_9475691 \| \| scaffold14851_4302795_SNP | 4302795 | A | T |
| S_9475692 \| \| scaffold14851_4302796_SNP | 4302796 | C | T |
| S_9475844 \| \| scaffold14851_4304063_SNP | 4304063 | A | T |
| S_9475849 \| \| scaffold14851_4304183_SNP | 4304183 | C | T |
| S_9475933 \| \| scaffold14851_4305486_SNP | 4305486 | T | G |
| S_9475985 \| \| scaffold14851_4306437_SNP | 4306437 | G | C |
| S_9476021 \| \| scaffold14851_4307396_SNP | 4307396 | T | G |
| S_9476159 \| \| scaffold14851_4309540_SNP | 4309540 | G | T |
| S_9476232 \| \| scaffold14851_4310678_SNP | 4310678 | A | G |
| S_9476367 \| \| scaffold14851_4312128_SNP | 4312128 | G | A |
| S_9476429 \| \| scaffold14851_4312719_SNP | 4312719 | G | A |
| S_9476495 \| \| scaffold14851_4313813_SNP | 4313813 | T | C |
| S_9476798 \| \| scaffold14851_4317135_SNP | 4317135 | G | A |
| S_9476843 \| \| scaffold14851_4317786_SNP | 4317786 | A | G |
| S_9476844 \| \| scaffold14851_4317791_SNP | 4317791 | G | T |
| S_9476845 \| \| scaffold14851_4317792_SNP | 4317792 | A | C |
| S_9476904 \| \| scaffold14851_4318304_SNP | 4318304 | C | G |
| S_9476953 \| \| scaffold14851_4319141_SNP | 4319141 | T | C |
| S_9477012 \| \| scaffold14851_4319691_SNP | 4319691 | T | C |
| S_9477014 \| \| scaffold14851_4319718_SNP | 4319718 | C | T |
| S_9477032 \| \| scaffold14851_4319829_SNP | 4319829 | G | T |
| S_9477059 \| \| scaffold14851_4320131_SNP | 4320131 | C | A |
| S_9477060 \| \| scaffold14851_4320151_SNP | 4320151 | G | A |
| S_9477064 \| \| scaffold14851_4320233_SNP | 4320233 | C | A |
| S_9477079 \| \| scaffold14851_4320419_SNP | 4320419 | G | C |
| S_9477105 \| \| scaffold14851_4320788_SNP | 4320788 | C | T |
| S_9477183 \| \| scaffold14851_4321506_SNP | 4321506 | A | T |
| S_9477199 \| \| scaffold14851_4321751_SNP | 4321751 | C | T |
| S_9477211 \| \| scaffold14851_4321957_SNP | 4321957 | T | A |
| S_9477214 \| \| scaffold14851_4322005_SNP | 4322005 | T | G |
| S_9477229 \| \| scaffold14851_4322280_SNP | 4322280 | A | C |
| S_9477231 \| \| scaffold14851_4322317_SNP | 4322317 | T | C |
| S_9477232 \| \| scaffold14851_4322319_SNP | 4322319 | A | C |
| S_9477246 \| \| scaffold14851_4322449_SNP | 4322449 | A | C |
| S_9477248 \| \| scaffold14851_4322472_SNP | 4322472 | T | G |
| S_9477249 \| \| scaffold14851_4322495_SNP | 4322495 | A | G |
| S_9477285 \| \| scaffold14851_4322879_SNP | 4322879 | C | T |
| S_9477321 \| \| scaffold14851_4323504_SNP | 4323504 | T | A |
| S_9477348 \| \| scaffold14851_4324016_SNP | 4324016 | G | A |
| S_9477354 \| \| scaffold14851_4324111_SNP | 4324111 | T | G |
| S_9477370 \| \| scaffold14851_4324391_SNP | 4324391 | C | T |
| S_9477376 \| \| scaffold14851_4324555_SNP | 4324555 | C | A |
| S_9477378 \| \| scaffold14851_4324570_SNP | 4324570 | C | T |
| S_9477379 \| \| scaffold14851_4324587_SNP | 4324587 | A | T |
| S_9477418 \| \| scaffold14851_4325114_SNP | 4325114 | T | G |
| S_9477424 \| \| scaffold14851_4325177_SNP | 4325177 | G | T |
| S_9477441 \| \| scaffold14851_4325377_SNP | 4325377 | T | C |
| S_9477451 \| \| scaffold14851_4325624_SNP | 4325624 | G | A |
| S_9477468 \| \| scaffold14851_4325881_SNP | 4325881 | T | C |
| S_9477480 \| \| scaffold14851_4325932_SNP | 4325932 | T | C |
| S_9477547 \| \| scaffold14851_4326721_SNP | 4326721 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9477572 \| \| scaffold14851_4327068_SNP | 4327068 | G | A |
| S_9477584 \| \| scaffold14851_4327240_SNP | 4327240 | G | T |
| S_9477717 \| \| scaffold14851_4328309_SNP | 4328309 | C | A |
| S_9477758 \| \| scaffold14851_4328647_SNP | 4328647 | G | T |
| S_9477836 \| \| scaffold14851_4329539_SNP | 4329539 | A | C |
| S_9477864 \| \| scaffold14851_4330199_SNP | 4330199 | A | G |
| S_9477868 \| \| scaffold14851_4330283_SNP | 4330283 | A | T |
| S_9477920 \| \| scaffold14851_4330880_SNP | 4330880 | G | A |
| S_9477930 \| \| scaffold14851_4330994_SNP | 4330994 | T | G |
| S_9477936 \| \| scaffold14851_4331102_SNP | 4331102 | A | G |
| S_9477946 \| \| scaffold14851_4331204_SNP | 4331204 | G | T |
| S_9477958 \| \| scaffold14851_4331426_SNP | 4331426 | G | C |
| S_9478006 \| \| scaffold14851_4331931_SNP | 4331931 | G | T |
| S_9478007 \| \| scaffold14851_4331971_SNP | 4331971 | A | G |
| S_9478065 \| \| scaffold14851_4333462_SNP | 4333462 | G | T |
| S_9478068 \| \| scaffold14851_4333521_SNP | 4333521 | C | G |
| S_9478271 \| \| scaffold14851_4336437_SNP | 4336437 | A | T |
| S_9478272 \| \| scaffold14851_4336453_SNP | 4336453 | C | A |
| S_9478276 \| \| scaffold14851_4336507_SNP | 4336507 | G | C |
| S_9478291 \| \| scaffold14851_4336768_SNP | 4336768 | C | T |
| S_9478332 \| \| scaffold14851_4337199_SNP | 4337199 | T | C |
| S_9478570 \| \| scaffold14851_4340278_SNP | 4340278 | C | T |
| S_9478657 \| \| scaffold14851_4341490_SNP | 4341490 | G | A |
| S_9478676 \| \| scaffold14851_4341782_SNP | 4341782 | A | T |
| S_9478741 \| \| scaffold14851_4342332_SNP | 4342332 | G | A |
| S_9478743 \| \| scaffold14851_4342343_SNP | 4342343 | A | G |
| S_9478744 \| \| scaffold14851_4342345_SNP | 4342345 | T | C |
| S_9478750 \| \| scaffold14851_4342421_SNP | 4342421 | G | A |
| S_9478755 \| \| scaffold14851_4342487_SNP | 4342487 | G | A |
| S_9478756 \| \| scaffold14851_4342508_SNP | 4342508 | G | A |
| S_9478758 \| \| scaffold14851_4342529_SNP | 4342529 | T | C |
| S_9478765 \| \| scaffold14851_4342784_SNP | 4342784 | T | C |
| S_9478814 \| \| scaffold14851_4343468_SNP | 4343468 | G | T |
| S_9478817 \| \| scaffold14851_4343491_SNP | 4343491 | T | C |
| S_9478849 \| \| scaffold14851_4344126_SNP | 4344126 | C | T |
| S_9478877 \| \| scaffold14851_4344402_SNP | 4344402 | A | T |
| S_9478963 \| \| scaffold14851_4345420_SNP | 4345420 | T | C |
| S_9479026 \| \| scaffold14851_4345814_SNP | 4345814 | T | G |
| S_9479050 \| \| scaffold14851_4346122_SNP | 4346122 | T | C |
| S_9479094 \| \| scaffold14851_4346624_SNP | 4346624 | G | A |
| S_9479099 \| \| scaffold14851_4346818_SNP | 4346818 | A | C |
| S_9479104 \| \| scaffold14851_4346889_SNP | 4346889 | G | T |
| S_9479116 \| \| scaffold14851_4347086_SNP | 4347086 | T | A |
| S_9479122 \| \| scaffold14851_4347140_SNP | 4347140 | A | C |
| S_9479161 \| \| scaffold14851_4347879_SNP | 4347879 | T | G |
| S_9479245 \| \| scaffold14851_4349223_SNP | 4349223 | G | A |
| S_9479269 \| \| scaffold14851_4349511_SNP | 4349511 | G | A |
| S_9479271 \| \| scaffold14851_4349534_SNP | 4349534 | T | A |
| S_9479318 \| \| scaffold14851_4350145_SNP | 4350145 | C | A |
| S_9479357 \| \| scaffold14851_4351183_SNP | 4351183 | C | T |
| S_9479374 \| \| scaffold14851_4351490_SNP | 4351490 | T | A |
| S_9479379 \| \| scaffold14851_4351593_SNP | 4351593 | T | C |
| S_9479382 \| \| scaffold14851_4351688_SNP | 4351688 | G | T |
| S_9479404 \| \| scaffold14851_4352157_SNP | 4352157 | T | C |
| S_9479406 \| \| scaffold14851_4352164_SNP | 4352164 | C | T |
| S_9479407 \| \| scaffold14851_4352211_SNP | 4352211 | G | A |
| S_9479518 \| \| scaffold14851_4353287_SNP | 4353287 | A | T |
| S_9479529 \| \| scaffold14851_4353404_SNP | 4353404 | A | G |
| S_9479660 \| \| scaffold14851_4354804_SNP | 4354804 | T | C |
| S_9479678 \| \| scaffold14851_4355110_SNP | 4355110 | C | A |
| S_9479679 \| \| scaffold14851_4355124_SNP | 4355124 | G | C |
| S_9479689 \| \| scaffold14851_4355238_SNP | 4355238 | A | C |
| S_9479743 \| \| scaffold14851_4356137_SNP | 4356137 | T | G |
| S_9479795 \| \| scaffold14851_4356732_SNP | 4356732 | A | C |
| S_9479842 \| \| scaffold14851_4356803_SNP | 4356803 | T | A |
| S_9479858 \| \| scaffold14851_4357023_SNP | 4357023 | G | T |
| S_9479875 \| \| scaffold14851_4357273_SNP | 4357273 | G | T |
| S_9479877 \| \| scaffold14851_4357296_SNP | 4357296 | C | T |
| S_9479881 \| \| scaffold14851_4357322_SNP | 4357322 | G | A |
| S_9479886 \| \| scaffold14851_4357385_SNP | 4357385 | T | A |
| S_9480011 \| \| scaffold14851_4358702_SNP | 4358702 | G | T |
| S_9480101 \| \| scaffold14851_4359371_SNP | 4359371 | C | A |
| S_9480112 \| \| scaffold14851_4359534_SNP | 4359534 | T | C |
| S_9480176 \| \| scaffold14851_4361143_SNP | 4361143 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9480211 \| \| scaffold14851_4361414_SNP | 4361414 | A | G |
| S_9480251 \| \| scaffold14851_4361977_SNP | 4361977 | G | T |
| S_9480258 \| \| scaffold14851_4362064_SNP | 4362064 | T | G |
| S_9480260 \| \| scaffold14851_4362128_SNP | 4362128 | T | A |
| S_9480288 \| \| scaffold14851_4362518_SNP | 4362518 | T | C |
| S_9480294 \| \| scaffold14851_4362621_SNP | 4362621 | C | G |
| S_9480335 \| \| scaffold14851_4362863_SNP | 4362863 | T | C |
| S_9480352 \| \| scaffold14851_4362881_SNP | 4362881 | T | C |
| S_9480400 \| \| scaffold14851_4363085_SNP | 4363085 | T | G |
| S_9480407 \| \| scaffold14851_4363132_SNP | 4363132 | T | A |
| S_9480408 \| \| scaffold14851_4363159_SNP | 4363159 | C | A |
| S_9480424 \| \| scaffold14851_4363436_SNP | 4363436 | G | T |
| S_9480425 \| \| scaffold14851_4363526_SNP | 4363526 | G | A |
| S_9480493 \| \| scaffold14851_4364539_SNP | 4364539 | G | T |
| S_9480495 \| \| scaffold14851_4364603_SNP | 4364603 | T | A |
| S_9480497 \| \| scaffold14851_4364619_SNP | 4364619 | G | T |
| S_9480548 \| \| scaffold14851_4365560_SNP | 4365560 | C | A |
| S_9480647 \| \| scaffold14851_4366520_SNP | 4366520 | G | T |
| S_9480665 \| \| scaffold14851_4366895_SNP | 4366895 | T | C |
| S_9480691 \| \| scaffold14851_4367340_SNP | 4367340 | T | C |
| S_9480702 \| \| scaffold14851_4367485_SNP | 4367485 | T | A |
| S_9480725 \| \| scaffold14851_4367764_SNP | 4367764 | T | A |
| S_9480727 \| \| scaffold14851_4367882_SNP | 4367882 | C | A |
| S_9480744 \| \| scaffold14851_4368062_SNP | 4368062 | G | T |
| S_9480746 \| \| scaffold14851_4368068_SNP | 4368068 | T | C |
| S_9480770 \| \| scaffold14851_4368115_SNP | 4368115 | C | G |
| S_9480848 \| \| scaffold14851_4368784_SNP | 4368784 | C | T |
| S_9480912 \| \| scaffold14851_4369562_SNP | 4369562 | G | A |
| S_9480922 \| \| scaffold14851_4369666_SNP | 4369666 | G | A |
| S_9480940 \| \| scaffold14851_4370115_SNP | 4370115 | G | T |
| S_9480942 \| \| scaffold14851_4370132_SNP | 4370132 | C | G |
| S_9480943 \| \| scaffold14851_4370133_SNP | 4370133 | T | G |
| S_9480948 \| \| scaffold14851_4370248_SNP | 4370248 | C | T |
| S_9480955 \| \| scaffold14851_4370327_SNP | 4370327 | G | A |
| S_9480956 \| \| scaffold14851_4370342_SNP | 4370342 | T | G |
| S_9481052 \| \| scaffold14851_4370948_SNP | 4370948 | G | A |
| S_9481097 \| \| scaffold14851_4371488_SNP | 4371488 | C | A |
| S_9481180 \| \| scaffold14851_4372793_SNP | 4372793 | C | G |
| S_9481182 \| \| scaffold14851_4372839_SNP | 4372839 | G | T |
| S_9481228 \| \| scaffold14851_4373499_SNP | 4373499 | T | C |
| S_9481260 \| \| scaffold14851_4373730_SNP | 4373730 | C | G |
| S_9481471 \| \| scaffold14851_4377529_SNP | 4377529 | A | G |
| S_9481614 \| \| scaffold14851_4379735_SNP | 4379735 | C | T |
| S_9481628 \| \| scaffold14851_4379996_SNP | 4379996 | A | G |
| S_9481640 \| \| scaffold14851_4380123_SNP | 4380123 | C | A |
| S_9481646 \| \| scaffold14851_4380237_SNP | 4380237 | C | G |
| S_9481736 \| \| scaffold14851_4381597_SNP | 4381597 | C | A |
| S_9481737 \| \| scaffold14851_4381603_SNP | 4381603 | G | T |
| S_9481980 \| \| scaffold14851_4384483_SNP | 4384483 | C | T |
| S_9481988 \| \| scaffold14851_4384514_SNP | 4384514 | C | T |
| S_9482052 \| \| scaffold14851_4384626_SNP | 4384626 | C | G |
| S_9482055 \| \| scaffold14851_4384627_SNP | 4384627 | G | T |
| S_9482067 \| \| scaffold14851_4384867_SNP | 4384867 | A | T |
| S_9482074 \| \| scaffold14851_4384911_SNP | 4384911 | T | C |
| S_9482120 \| \| scaffold14851_4385664_SNP | 4385664 | G | A |
| S_9482141 \| \| scaffold14851_4385937_SNP | 4385937 | T | A |
| S_9482142 \| \| scaffold14851_4385938_SNP | 4385938 | T | C |
| S_9482168 \| \| scaffold14851_4386448_SNP | 4386448 | T | C |
| S_9482179 \| \| scaffold14851_4386515_SNP | 4386515 | G | C |
| S_9482233 \| \| scaffold14851_4386884_SNP | 4386884 | A | G |
| S_9482237 \| \| scaffold14851_4386942_SNP | 4386942 | A | T |
| S_9482314 \| \| scaffold14851_4387756_SNP | 4387756 | C | G |
| S_9482319 \| \| scaffold14851_4388053_SNP | 4388053 | C | A |
| S_9482361 \| \| scaffold14851_4388491_SNP | 4388491 | C | G |
| S_9482362 \| \| scaffold14851_4388509_SNP | 4388509 | A | G |
| S_9482382 \| \| scaffold14851_4388722_SNP | 4388722 | G | A |
| S_9482389 \| \| scaffold14851_4388830_SNP | 4388830 | C | T |
| S_9482390 \| \| scaffold14851_4388867_SNP | 4388867 | T | C |
| S_9482406 \| \| scaffold14851_4389160_SNP | 4389160 | G | A |
| S_9482579 \| \| scaffold14851_4391585_SNP | 4391585 | G | A |
| S_9482619 \| \| scaffold14851_4392257_SNP | 4392257 | G | T |
| S_9482629 \| \| scaffold14851_4392412_SNP | 4392412 | G | A |
| S_9482783 \| \| scaffold14851_4394566_SNP | 4394566 | A | G |
| S_9482818 \| \| scaffold14851_4394986_SNP | 4394986 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9482886 \| \| scaffold14851_4395692_SNP | 4395692 | A | G |
| S_9482927 \| \| scaffold14851_4396025_SNP | 4396025 | T | C |
| S_9483177 \| \| scaffold14851_4398838_SNP | 4398838 | G | C |
| S_9483253 \| \| scaffold14851_4399656_SNP | 4399656 | A | G |
| S_9483361 \| \| scaffold14851_4400924_SNP | 4400924 | A | C |
| S_9483414 \| \| scaffold14851_4401365_SNP | 4401365 | T | C |
| S_9483431 \| \| scaffold14851_4401583_SNP | 4401583 | T | G |
| S_9483457 \| \| scaffold14851_4402117_SNP | 4402117 | C | A |
| S_9483502 \| \| scaffold14851_4402678_SNP | 4402678 | T | G |
| S_9483599 \| \| scaffold14851_4403879_SNP | 4403879 | T | C |
| S_9483846 \| \| scaffold14851_4408336_SNP | 4408336 | T | A |
| S_9483896 \| \| scaffold14851_4409004_SNP | 4409004 | T | C |
| S_9483897 \| \| scaffold14851_4409046_SNP | 4409046 | C | G |
| S_9483903 \| \| scaffold14851_4409127_SNP | 4409127 | A | G |
| S_9483957 \| \| scaffold14851_4409528_SNP | 4409528 | A | G |
| S_9483965 \| \| scaffold14851_4409603_SNP | 4409603 | A | G |
| S_9484075 \| \| scaffold14851_4410867_SNP | 4410867 | G | A |
| S_9484096 \| \| scaffold14851_4411036_SNP | 4411036 | A | C |
| S_9484212 \| \| scaffold14851_4412522_SNP | 4412522 | T | C |
| S_9484214 \| \| scaffold14851_4412578_SNP | 4412578 | T | G |
| S_9484219 \| \| scaffold14851_4412624_SNP | 4412624 | T | A |
| S_9484220 \| \| scaffold14851_4412638_SNP | 4412638 | A | C |
| S_9484321 \| \| scaffold14851_4414127_SNP | 4414127 | T | G |
| S_9484351 \| \| scaffold14851_4414582_SNP | 4414582 | T | A |
| S_9484382 \| \| scaffold14851_4415018_SNP | 4415018 | G | A |
| S_9484389 \| \| scaffold14851_4415168_SNP | 4415168 | T | A |
| S_9484433 \| \| scaffold14851_4415568_SNP | 4415568 | T | G |
| S_9484564 \| \| scaffold14851_4417852_SNP | 4417852 | C | A |
| S_9484591 \| \| scaffold14851_4418165_SNP | 4418165 | C | G |
| S_9484650 \| \| scaffold14851_4418598_SNP | 4418598 | C | T |
| S_9484760 \| \| scaffold14851_4419614_SNP | 4419614 | G | A |
| S_9484797 \| \| scaffold14851_4420098_SNP | 4420098 | T | C |
| S_9484812 \| \| scaffold14851_4420492_SNP | 4420492 | T | G |
| S_9484852 \| \| scaffold14851_4421049_SNP | 4421049 | A | T |
| S_9484855 \| \| scaffold14851_4421058_SNP | 4421058 | T | C |
| S_9484959 \| \| scaffold14851_4422287_SNP | 4422287 | T | C |
| S_9484963 \| \| scaffold14851_4422370_SNP | 4422370 | A | G |
| S_9484967 \| \| scaffold14851_4422406_SNP | 4422406 | C | T |
| S_9484968 \| \| scaffold14851_4422409_SNP | 4422409 | T | C |
| S_9484973 \| \| scaffold14851_4422437_SNP | 4422437 | A | G |
| S_9484983 \| \| scaffold14851_4422568_SNP | 4422568 | C | G |
| S_9485198 \| \| scaffold14851_4425487_SNP | 4425487 | G | A |
| S_9485283 \| \| scaffold14851_4426425_SNP | 4426425 | A | C |
| S_9485296 \| \| scaffold14851_4426705_SNP | 4426705 | G | A |
| S_9485298 \| \| scaffold14851_4426717_SNP | 4426717 | G | T |
| S_9485340 \| \| scaffold14851_4427351_SNP | 4427351 | A | T |
| S_9485344 \| \| scaffold14851_4427420_SNP | 4427420 | G | A |
| S_9485346 \| \| scaffold14851_4427462_SNP | 4427462 | G | T |
| S_9485347 \| \| scaffold14851_4427486_SNP | 4427486 | T | A |
| S_9485381 \| \| scaffold14851_4428316_SNP | 4428316 | T | G |
| S_9485397 \| \| scaffold14851_4428522_SNP | 4428522 | C | A |
| S_9485506 \| \| scaffold14851_4430012_SNP | 4430012 | C | A |
| S_9485543 \| \| scaffold14851_4430399_SNP | 4430399 | T | G |
| S_9485563 \| \| scaffold14851_4430794_SNP | 4430794 | G | A |
| S_9485689 \| \| scaffold14851_4432937_SNP | 4432937 | A | C |
| S_9485717 \| \| scaffold14851_4433362_SNP | 4433362 | G | A |
| S_9485791 \| \| scaffold14851_4434194_SNP | 4434194 | T | C |
| S_9485799 \| \| scaffold14851_4434430_SNP | 4434430 | A | G |
| S_9485831 \| \| scaffold14851_4434652_SNP | 4434652 | G | T |
| S_9485886 \| \| scaffold14851_4435081_SNP | 4435081 | C | T |
| S_9485887 \| \| scaffold14851_4435123_SNP | 4435123 | C | A |
| S_9485937 \| \| scaffold14851_4435962_SNP | 4435962 | T | G |
| S_9485941 \| \| scaffold14851_4435993_SNP | 4435993 | T | A |
| S_9485942 \| \| scaffold14851_4436018_SNP | 4436018 | C | T |
| S_9485943 \| \| scaffold14851_4436026_SNP | 4436026 | C | T |
| S_9485945 \| \| scaffold14851_4436057_SNP | 4436057 | A | G |
| S_9485946 \| \| scaffold14851_4436067_SNP | 4436067 | G | A |
| S_9485986 \| \| scaffold14851_4436555_SNP | 4436555 | C | T |
| S_9486012 \| \| scaffold14851_4436736_SNP | 4436736 | A | T |
| S_9486068 \| \| scaffold14851_4437349_SNP | 4437349 | G | C |
| S_9486111 \| \| scaffold14851_4437810_SNP | 4437810 | T | C |
| S_9486155 \| \| scaffold14851_4438197_SNP | 4438197 | T | C |
| S_9486205 \| \| scaffold14851_4438732_SNP | 4438732 | G | C |
| S_9486232 \| \| scaffold14851_4438909_SNP | 4438909 | T | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9486285 \| \| scaffold14851_4439886_SNP | 4439886 | A | G |
| $_9486302 \| \| scaffold14851_4440148_SNP | 4440148 | G | A |
| S_9486401 \| \| scaffold14851_4441412_SNP | 4441412 | T | C |
| S_9486402 \| \| scaffold14851_4441416_SNP | 4441416 | A | C |
| S_9486495 \| \| scaffold14851_4442161_SNP | 4442161 | A | G |
| S_9486573 \| \| scaffold14851_4442642_SNP | 4442642 | A | T |
| S_9486588 \| \| scaffold14851_4442905_SNP | 4442905 | G | T |
| S_9486660 \| \| scaffold14851_4444410_SNP | 4444410 | T | A |
| S_9486680 \| \| scaffold14851_4444821_SNP | 4444821 | A | G |
| S_9486729 \| \| scaffold14851_4445528_SNP | 4445528 | G | A |
| S_9486810 \| \| scaffold14851_4446308_SNP | 4446308 | G | A |
| S_9486811 \| \| scaffold14851_4446313_SNP | 4446313 | G | A |
| S_9486814 \| \| scaffold14851_4446416_SNP | 4446416 | C | A |
| S_9486857 \| \| scaffold14851_4447109_SNP | 4447109 | G | A |
| S_9486870 \| \| scaffold14851_4447527_SNP | 4447527 | C | T |
| S_9486930 \| \| scaffold14851_4448283_SNP | 4448283 | A | T |
| S_9486932 \| \| scaffold14851_4448294_SNP | 4448294 | G | A |
| S_9487068 \| \| scaffold14851_4450234_SNP | 4450234 | G | C |
| S_9487089 \| \| scaffold14851_4450610_SNP | 4450610 | G | A |
| S_9487134 \| \| scaffold14851_4450804_SNP | 4450804 | A | T |
| S_9487207 \| \| scaffold14851_4451983_SNP | 4451983 | A | G |
| S_9487273 \| \| scaffold14851_4453219_SNP | 4453219 | T | C |
| S_9487276 \| \| scaffold14851_4453273_SNP | 4453273 | C | T |
| S_9487364 \| \| scaffold14851_4454488_SNP | 4454488 | C | T |
| S_9487510 \| \| scaffold14851_4456489_SNP | 4456489 | A | G |
| S_9487528 \| \| scaffold14851_4456918_SNP | 4456918 | T | G |
| S_9487536 \| \| scaffold14851_4457098_SNP | 4457098 | T | C |
| S_9487538 \| \| scaffold14851_4457119_SNP | 4457119 | C | T |
| S_9487539 \| \| scaffold14851_4457133_SNP | 4457133 | G | T |
| S_9487648 \| \| scaffold14851_4458787_SNP | 4458787 | T | C |
| S_9487650 \| \| scaffold14851_4458842_SNP | 4458842 | G | T |
| S_9487652 \| \| scaffold14851_4458879_SNP | 4458879 | G | A |
| S_9487657 \| \| scaffold14851_4458935_SNP | 4458935 | T | G |
| S_9487665 \| \| scaffold14851_4459022_SNP | 4459022 | A | G |
| S_9487678 \| \| scaffold14851_4459142_SNP | 4459142 | A | G |
| S_9487904 \| \| scaffold14851_4461052_SNP | 4461052 | A | T |
| S_9487906 \| \| scaffold14851_4461092_SNP | 4461092 | A | C |
| S_9487914 \| \| scaffold14851_4461192_SNP | 4461192 | G | A |
| S_9487915 \| \| scaffold14851_4461217_SNP | 4461217 | C | G |
| S_9487916 \| \| scaffold14851_4461223_SNP | 4461223 | A | G |
| S_9487967 \| \| scaffold14851_4461877_SNP | 4461877 | C | T |
| S_9487987 \| \| scaffold14851_4462282_SNP | 4462282 | G | T |
| S_9488023 \| \| scaffold14851_4462640_SNP | 4462640 | G | A |
| S_9488370 \| \| scaffold14851_4467850_SNP | 4467850 | A | C |
| S_9488394 \| \| scaffold14851_4467987_SNP | 4467987 | G | A |
| S_9488397 \| \| scaffold14851_4468027_SNP | 4468027 | A | T |
| S_9488485 \| \| scaffold14851_4469303_SNP | 4469303 | T | G |
| S_9488486 \| \| scaffold14851_4469304_SNP | 4469304 | C | T |
| S_9488541 \| \| scaffold14851_4469900_SNP | 4469900 | T | G |
| S_9488543 \| \| scaffold14851_4469927_SNP | 4469927 | C | A |
| S_9488548 \| \| scaffold14851_4469970_SNP | 4469970 | T | G |
| S_9488549 \| \| scaffold14851_4469974_SNP | 4469974 | C | T |
| S_9488573 \| \| scaffold14851_4470160_SNP | 4470160 | A | T |
| S_9488584 \| \| scaffold14851_4470325_SNP | 4470325 | C | T |
| S_9488636 \| \| scaffold14851_4471345_SNP | 4471345 | G | T |
| S_9488638 \| \| scaffold14851_4471350_SNP | 4471350 | T | G |
| S_9488640 \| \| scaffold14851_4471411_SNP | 4471411 | A | G |
| S_9488679 \| \| scaffold14851_4471807_SNP | 4471807 | G | A |
| S_9488918 \| \| scaffold14851_4473775_SNP | 4473775 | T | A |
| S_9488938 \| \| scaffold14851_4474008_SNP | 4474008 | G | A |
| S_9488983 \| \| scaffold14851_4474673_SNP | 4474673 | G | A |
| S_9488986 \| \| scaffold14851_4474737_SNP | 4474737 | G | A |
| S_9489018 \| \| scaffold14851_4475049_SNP | 4475049 | A | G |
| S_9489019 \| \| scaffold14851_4475051_SNP | 4475051 | A | G |
| S_9489033 \| \| scaffold14851_4475138_SNP | 4475138 | G | A |
| S_9489036 \| \| scaffold14851_4475156_SNP | 4475156 | G | A |
| S_9489037 \| \| scaffold14851_4475158_SNP | 4475158 | A | G |
| S_9489040 \| \| scaffold14851_4475200_SNP | 4475200 | A | G |
| S_9489041 \| \| scaffold14851_4475214_SNP | 4475214 | G | A |
| S_9489048 \| \| scaffold14851_4475468_SNP | 4475468 | T | C |
| S_9489308 \| \| scaffold14851_4479562_SNP | 4479562 | T | A |
| S_9489604 \| \| scaffold14851_4482173_SNP | 4482173 | G | A |
| S_9489607 \| \| scaffold14851_4482211_SNP | 4482211 | A | G |
| S_9489747 \| \| scaffold14851_4483989_SNP | 4483989 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9489777 \| \| scaffold14851_4484468_SNP | 4484468 | T | A |
| S_9489781 \| \| scaffold14851_4484516_SNP | 4484516 | C | T |
| S_9489782 \| \| scaffold14851_4484519_SNP | 4484519 | C | T |
| S_9489838 \| \| scaffold14851_4485717_SNP | 4485717 | C | G |
| S_9489996 \| \| scaffold14851_4488212_SNP | 4488212 | A | C |
| S_9490039 \| \| scaffold14851_4488849_SNP | 4488849 | T | A |
| S_9490096 \| \| scaffold14851_4489713_SNP | 4489713 | C | A |
| S_9490115 \| \| scaffold14851_4490060_SNP | 4490060 | C | G |
| S_9490117 \| \| scaffold14851_4490096_SNP | 4490096 | T | C |
| S_9490130 \| \| scaffold14851_4490171_SNP | 4490171 | A | G |
| S_9490253 \| \| scaffold14851_4491170_SNP | 4491170 | G | A |
| S_9490255 \| \| scaffold14851_4491183_SNP | 4491183 | A | G |
| S_9490285 \| \| scaffold14851_4491530_SNP | 4491530 | C | T |
| S_9490311 \| \| scaffold14851_4491805_SNP | 4491805 | C | T |
| S_9490350 \| \| scaffold14851_4492438_SNP | 4492438 | A | G |
| S_9490351 \| \| scaffold14851_4492487_SNP | 4492487 | G | A |
| S_9490371 \| \| scaffold14851_4492837_SNP | 4492837 | T | A |
| S_9490372 \| \| scaffold14851_4492867_SNP | 4492867 | A | G |
| S_9490377 \| \| scaffold14851_4492962_SNP | 4492962 | G | A |
| S_9490494 \| \| scaffold14851_4495027_SNP | 4495027 | T | A |
| S_9491051 \| \| scaffold14851_4501715_SNP | 4501715 | A | G |
| S_9491056 \| \| scaffold14851_4501787_SNP | 4501787 | A | C |
| S_9491098 \| \| scaffold14851_4502533_SNP | 4502533 | G | A |
| S_9491100 \| \| scaffold14851_4502603_SNP | 4502603 | A | G |
| S_9491387 \| \| scaffold14851_4506125_SNP | 4506125 | G | A |
| S_9491388 \| \| scaffold14851_4506126_SNP | 4506126 | A | C |
| S_9491469 \| \| scaffold14851_4506765_SNP | 4506765 | A | G |
| S_9491554 \| \| scaffold14851_4507898_SNP | 4507898 | C | T |
| S_9491772 \| \| scaffold14851_4511068_SNP | 4511068 | C | G |
| S_9491779 \| \| scaffold14851_4511219_SNP | 4511219 | T | A |
| S_9491840 \| \| scaffold14851_4512163_SNP | 4512163 | C | G |
| S_9491842 \| \| scaffold14851_4512192_SNP | 4512192 | T | C |
| S_9491843 \| \| scaffold14851_4512200_SNP | 4512200 | T | C |
| S_9491845 \| \| scaffold14851_4512218_SNP | 4512218 | T | C |
| S_9491907 \| \| scaffold14851_4512947_SNP | 4512947 | G | A |
| S_9491984 \| \| scaffold14851_4514645_SNP | 4514645 | G | A |
| S_9492028 \| \| scaffold14851_4515620_SNP | 4515620 | T | C |
| S_9492083 \| \| scaffold14851_4516202_SNP | 4516202 | C | T |
| S_9492100 \| \| scaffold14851_4516403_SNP | 4516403 | C | T |
| S_9492165 \| \| scaffold14851_4517470_SNP | 4517470 | G | T |
| S_9492172 \| \| scaffold14851_4517538_SNP | 4517538 | G | A |
| S_9492280 \| \| scaffold14851_4518757_SNP | 4518757 | A | G |
| S_9492281 \| \| scaffold14851_4518759_SNP | 4518759 | G | A |
| S_9492401 \| \| scaffold14851_4520272_SNP | 4520272 | T | A |
| S_9492509 \| \| scaffold14851_4522101_SNP | 4522101 | G | T |
| S_9492527 \| \| scaffold14851_4522288_SNP | 4522288 | G | A |
| S_9492553 \| \| scaffold14851_4522632_SNP | 4522632 | T | C |
| S_9492790 \| \| scaffold14851_4525368_SNP | 4525368 | A | C |
| S_9492791 \| \| scaffold14851_4525370_SNP | 4525370 | G | A |
| S_9492879 \| \| scaffold14851_4526026_SNP | 4526026 | G | C |
| S_9492906 \| \| scaffold14851_4526409_SNP | 4526409 | T | C |
| S_9492930 \| \| scaffold14851_4526707_SNP | 4526707 | A | G |
| scaffold14851_4526771_SNP | 4526771 | A | G |
| scaffold14851_4527151_SNP | 4527151 | C | A |
| S_9493037 \| \| scaffold14851_4527158_SNP | 4527158 | A | G |
| S_9493950 \| \| scaffold14851_4541150_SNP | 4541150 | G | A |
| S_9493965 \| \| scaffold14851_4541543_SNP | 4541543 | G | C |
| S_9494055 \| \| scaffold14851_4542558_SNP | 4542558 | A | C |
| S_9494102 \| \| scaffold14851_4543196_SNP | 4543196 | A | T |
| S_9494155 \| \| scaffold14851_4543982_SNP | 4543982 | G | A |
| S_9494270 \| \| scaffold14851_4545268_SNP | 4545268 | T | C |
| S_9494334 \| \| scaffold14851_4545777_SNP | 4545777 | T | C |
| S_9494385 \| \| scaffold14851_4546397_SNP | 4546397 | G | A |
| S_9494425 \| \| scaffold14851_4546911_SNP | 4546911 | T | C |
| S_9494476 \| \| scaffold14851_4547172_SNP | 4547172 | T | C |
| S_9494487 \| \| scaffold14851_4547245_SNP | 4547245 | G | A |
| S_9494643 \| \| scaffold14851_4549269_SNP | 4549269 | C | T |
| S_9494644 \| \| scaffold14851_4549274_SNP | 4549274 | T | C |
| S_9494661 \| \| scaffold14851_4549501_SNP | 4549501 | C | A |
| S_9494668 \| \| scaffold14851_4549671_SNP | 4549671 | A | C |
| S_9494693 \| \| scaffold14851_4549876_SNP | 4549876 | T | C |
| S_9494764 \| \| scaffold14851_4550548_SNP | 4550548 | T | C |
| S_9494774 \| \| scaffold14851_4550606_SNP | 4550606 | A | G |
| S_9494798 \| \| scaffold14851_4550855_SNP | 4550855 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9494800 \| \| scaffold14851_4550868_SNP | 4550868 | C | T |
| S_9494807 \| \| scaffold14851_4550944_SNP | 4550944 | G | T |
| S_9494812 \| \| scaffold14851_4550981_SNP | 4550981 | T | C |
| S_9494853 \| \| scaffold14851_4551649_SNP | 4551649 | C | A |
| S_9494854 \| \| scaffold14851_4551659_SNP | 4551659 | T | C |
| S_9494856 \| \| scaffold14851_4551678_SNP | 4551678 | A | G |
| S_9494872 \| \| scaffold14851_4551854_SNP | 4551854 | G | A |
| S_9494877 \| \| scaffold14851_4551909_SNP | 4551909 | C | T |
| S_9494913 \| \| scaffold14851_4552387_SNP | 4552387 | G | T |
| S_9494928 \| \| scaffold14851_4552558_SNP | 4552558 | G | T |
| S_9495017 \| \| scaffold14851_4553256_SNP | 4553256 | A | C |
| S_9495047 \| \| scaffold14851_4553634_SNP | 4553634 | C | A |
| S_9495061 \| \| scaffold14851_4553783_SNP | 4553783 | C | T |
| S_9495063 \| \| scaffold14851_4553824_SNP | 4553824 | C | T |
| S_9495065 \| \| scaffold14851_4553921_SNP | 4553921 | A | T |
| S_9495066 \| \| scaffold14851_4553922_SNP | 4553922 | T | A |
| S_9495106 \| \| scaffold14851_4555068_SNP | 4555068 | G | A |
| S_9495108 \| \| scaffold14851_4555089_SNP | 4555089 | A | C |
| S_9495110 \| \| scaffold14851_4555135_SNP | 4555135 | A | C |
| S_9495112 \| \| scaffold14851_4555183_SNP | 4555183 | C | T |
| S_9495116 \| \| scaffold14851_4555246_SNP | 4555246 | A | C |
| S_9495117 \| \| scaffold14851_4555253_SNP | 4555253 | T | A |
| S_9495161 \| \| scaffold14851_4555720_SNP | 4555720 | C | T |
| S_9495192 \| \| scaffold14851_4556056_SNP | 4556056 | G | A |
| S_9495193 \| \| scaffold14851_4556079_SNP | 4556079 | T | A |
| S_9495223 \| \| scaffold14851_4556418_SNP | 4556418 | C | T |
| S_9495224 \| \| scaffold14851_4556467_SNP | 4556467 | A | G |
| S_9495234 \| \| scaffold14851_4556698_SNP | 4556698 | T | G |
| S_9495551 \| \| scaffold14851_4560725_SNP | 4560725 | C | T |
| S_9495686 \| \| scaffold14851_4561438_SNP | 4561438 | C | T |
| S_9495702 \| \| scaffold14851_4561668_SNP | 4561668 | A | C |
| S_9495711 \| \| scaffold14851_4561774_SNP | 4561774 | C | T |
| S_9495765 \| \| scaffold14851_4562805_SNP | 4562805 | G | C |
| S_9495863 \| \| scaffold14851_4563908_SNP | 4563908 | A | C |
| S_9495943 \| \| scaffold14851_4565031_SNP | 4565031 | A | T |
| S_9495976 \| \| scaffold14851_4565570_SNP | 4565570 | T | G |
| S_9496001 \| \| scaffold14851_4566052_SNP | 4566052 | C | G |
| S_9496006 \| \| scaffold14851_4566152_SNP | 4566152 | T | G |
| S_9496009 \| \| scaffold14851_4566318_SNP | 4566318 | T | A |
| S_9496017 \| \| scaffold14851_4566468_SNP | 4566468 | G | A |
| S_9496034 \| \| scaffold14851_4566804_SNP | 4566804 | A | G |
| S_9496036 \| \| scaffold14851_4566822_SNP | 4566822 | T | A |
| S_9496110 \| \| scaffold14851_4568362_SNP | 4568362 | C | G |
| S_9496302 \| \| scaffold14851_4571912_SNP | 4571912 | A | T |
| S_9496614 \| \| scaffold14851_4583123_SNP | 4583123 | G | A |
| S_9496618 \| \| scaffold14851_4583191_SNP | 4583191 | C | T |
| S_9496627 \| \| scaffold14851_4583422_SNP | 4583422 | C | T |
| S_9496718 \| \| scaffold14851_4585210_SNP | 4585210 | G | C |
| S_9496892 \| \| scaffold14851_4588146_SNP | 4588146 | T | C |
| S_9496980 \| \| scaffold14851_4589623_SNP | 4589623 | A | G |
| S_9497066 \| \| scaffold14851_4590460_SNP | 4590460 | T | A |
| S_9497248 \| \| scaffold14851_4592808_SNP | 4592808 | T | A |
| S_9497259 \| \| scaffold14851_4593019_SNP | 4593019 | C | A |
| S_9497465 \| \| scaffold14851_4594695_SNP | 4594695 | T | A |
| S_9497500 \| \| scaffold14851_4595284_SNP | 4595284 | C | T |
| S_9497633 \| \| scaffold14851_4596936_SNP | 4596936 | T | A |
| S_9497850 \| \| scaffold14851_4600220_SNP | 4600220 | G | C |
| S_9497870 \| \| scaffold14851_4600456_SNP | 4600456 | T | A |
| S_9497959 \| \| scaffold14851_4601511_SNP | 4601511 | A | G |
| S_9497978 \| \| scaffold14851_4601778_SNP | 4601778 | C | T |
| S_9498002 \| \| scaffold14851_4602102_SNP | 4602102 | T | C |
| S_9498083 \| \| scaffold14851_4602620_SNP | 4602620 | T | C |
| scaffold14851_4602697_SNP | 4602697 | C | T |
| S_9498112 \| \| scaffold14851_4602795_SNP | 4602795 | G | T |
| S_9498283 \| \| scaffold14851_4603386_SNP | 4603386 | T | A |
| S_9498292 \| \| scaffold14851_4603432_SNP | 4603432 | T | C |
| S_9498329 \| \| scaffold14851_4604651_SNP | 4604651 | C | T |
| S_9498330 \| \| scaffold14851_4604658_SNP | 4604658 | A | G |
| S_9498334 \| \| scaffold14851_4604778_SNP | 4604778 | A | G |
| S_9498374 \| \| scaffold14851_4605476_SNP | 4605476 | C | A |
| S_9498432 \| \| scaffold14851_4606655_SNP | 4606655 | G | A |
| S_9498434 \| \| scaffold14851_4606691_SNP | 4606691 | A | G |
| S_9498606 \| \| scaffold14851_4609060_SNP | 4609060 | T | G |
| S_9498746 \| \| scaffold14851_4610689_SNP | 4610689 | G | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9499096 \| \| scaffold14851_4615817_SNP | 4615817 | T | G |
| S_9499099 \| \| scaffold14851_4615834_SNP | 4615834 | A | G |
| S_9499330 \| \| scaffold14851_4619189_SNP | 4619189 | A | G |
| S_9499440 \| \| scaffold14851_4620661_SNP | 4620661 | T | C |
| S_9499767 \| \| scaffold14851_4624476_SNP | 4624476 | A | C |
| S_9499820 \| \| scaffold14851_4624948_SNP | 4624948 | C | A |
| S_9499904 \| \| scaffold14851_4625585_SNP | 4625585 | G | A |
| S_9499907 \| \| scaffold14851_4625612_SNP | 4625612 | A | G |
| S_9500116 \| \| scaffold14851_4628566_SNP | 4628566 | T | C |
| S_9500278 \| \| scaffold14851_4630468_SNP | 4630468 | C | T |
| S_9500285 \| \| scaffold14851_4630508_SNP | 4630508 | C | T |
| S_9500291 \| \| scaffold14851_4630588_SNP | 4630588 | T | C |
| S_9500307 \| \| scaffold14851_4630784_SNP | 4630784 | A | G |
| S_9500309 \| \| scaffold14851_4630792_SNP | 4630792 | C | T |
| S_9500315 \| \| scaffold14851_4630840_SNP | 4630840 | A | G |
| S_9500317 \| \| scaffold14851_4630850_SNP | 4630850 | G | A |
| S_9500318 \| \| scaffold14851_4630852_SNP | 4630852 | A | G |
| S_9500398 \| \| scaffold14851_4631548_SNP | 4631548 | G | T |
| S_9500404 \| \| scaffold14851_4631680_SNP | 4631680 | G | A |
| S_9500472 \| \| scaffold14851_4632603_SNP | 4632603 | G | A |
| S_9500524 \| \| scaffold14851_4633397_SNP | 4633397 | A | G |
| S_9500642 \| \| scaffold14851_4635219_SNP | 4635219 | A | G |
| S_9500754 \| \| scaffold14851_4636638_SNP | 4636638 | G | A |
| S_9500772 \| \| scaffold14851_4636768_SNP | 4636768 | G | C |
| S_9500794 \| \| scaffold14851_4637112_SNP | 4637112 | C | T |
| S_9500798 \| \| scaffold14851_4637161_SNP | 4637161 | A | G |
| S_9500994 \| \| scaffold14851_4639575_SNP | 4639575 | A | C |
| S_9501299 \| \| scaffold14851_4644461_SNP | 4644461 | T | C |
| S_9501330 \| \| scaffold14851_4644827_SNP | 4644827 | C | A |
| S_9501396 \| \| scaffold14851_4645720_SNP | 4645720 | C | T |
| S_9501495 \| \| scaffold14851_4647361_SNP | 4647361 | T | G |
| S_9501533 \| \| scaffold14851_4647914_SNP | 4647914 | A | T |
| S_9501732 \| \| scaffold14851_4650042_SNP | 4650042 | A | T |
| S_9501746 \| \| scaffold14851_4650312_SNP | 4650312 | A | T |
| S_9501748 \| \| scaffold14851_4650342_SNP | 4650342 | C | A |
| S_9501879 \| \| scaffold14851_4652762_SNP | 4652762 | A | T |
| S_9502276 \| \| scaffold14851_4657636_SNP | 4657636 | C | A |
| S_9502474 \| \| scaffold14851_4659937_SNP | 4659937 | C | G |
| S_9502511 \| \| scaffold14851_4660477_SNP | 4660477 | A | T |
| S_9502558 \| \| scaffold14851_4661046_SNP | 4661046 | T | C |
| S_9502677 \| \| scaffold14851_4662271_SNP | 4662271 | C | T |
| S_9502855 \| \| scaffold14851_4666570_SNP | 4666570 | G | A |
| S_9502859 \| \| scaffold14851_4666594_SNP | 4666594 | A | G |
| S_9502863 \| \| scaffold14851_4666639_SNP | 4666639 | A | C |
| S_9502927 \| \| scaffold14851_4667746_SNP | 4667746 | T | G |
| S_9502956 \| \| scaffold14851_4668054_SNP | 4668054 | T | A |
| S_9502984 \| \| scaffold14851_4668366_SNP | 4668366 | A | T |
| S_9503265 \| \| scaffold14851_4672017_SNP | 4672017 | A | C |
| S_9503341 \| \| scaffold14851_4672876_SNP | 4672876 | G | A |
| S_9503389 \| \| scaffold14851_4673486_SNP | 4673486 | A | G |
| S_9503397 \| \| scaffold14851_4673702_SNP | 4673702 | A | C |
| S_9503408 \| \| scaffold14851_4673854_SNP | 4673854 | A | G |
| S_9503409 \| \| scaffold14851_4673876_SNP | 4673876 | A | G |
| S_9503410 \| \| scaffold14851_4673885_SNP | 4673885 | A | G |
| S_9503439 \| \| scaffold14851_4674069_SNP | 4674069 | A | G |
| S_9503639 \| \| scaffold14851_4676268_SNP | 4676268 | T | A |
| S_9503644 \| \| scaffold14851_4676391_SNP | 4676391 | G | A |
| S_9503694 \| \| scaffold14851_4677137_SNP | 4677137 | C | G |
| S_9503716 \| \| scaffold14851_4677484_SNP | 4677484 | A | C |
| S_9503783 \| \| scaffold14851_4678818_SNP | 4678818 | G | A |
| S_9503868 \| \| scaffold14851_4680027_SNP | 4680027 | A | G |
| S_9503982 \| \| scaffold14851_4681132_SNP | 4681132 | G | C |
| S_9503996 \| \| scaffold14851_4681204_SNP | 4681204 | C | T |
| S_9504029 \| \| scaffold14851_4681452_SNP | 4681452 | A | G |
| S_9504114 \| \| scaffold14851_4682566_SNP | 4682566 | A | G |
| S_9504128 \| \| scaffold14851_4682719_SNP | 4682719 | T | C |
| S_9504150 \| \| scaffold14851_4682930_SNP | 4682930 | G | A |
| S_9504170 \| \| scaffold14851_4683209_SNP | 4683209 | C | T |
| S_9504237 \| \| scaffold14851_4683971_SNP | 4683971 | C | T |
| S_9504254 \| \| scaffold14851_4684106_SNP | 4684106 | T | C |
| S_9504355 \| \| scaffold14851_4685027_SNP | 4685027 | A | G |
| S_9504461 \| \| scaffold14851_4686038_SNP | 4686038 | G | A |
| S_9504516 \| \| scaffold14851_4686801_SNP | 4686801 | C | G |
| S_9504539 \| \| scaffold14851_4687229_SNP | 4687229 | A | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9504693 \| \| scaffold14851_4688922_SNP | 4688922 | A | T |
| S_9504950 \| \| scaffold14851_4692680_SNP | 4692680 | C | G |
| S_9504959 \| \| scaffold14851_4692776_SNP | 4692776 | C | T |
| S_9505006 \| \| scaffold14851_4693331_SNP | 4693331 | T | G |
| S_9505029 \| \| scaffold14851_4693713_SNP | 4693713 | C | G |
| S_9505031 \| \| scaffold14851_4693735_SNP | 4693735 | A | T |
| S_9505039 \| \| scaffold14851_4693840_SNP | 4693840 | A | G |
| S_9505041 \| \| scaffold14851_4693842_SNP | 4693842 | G | T |
| S_9505042 \| \| scaffold14851_4693859_SNP | 4693859 | T | C |
| S_9505055 \| \| scaffold14851_4694116_SNP | 4694116 | C | T |
| S_9505057 \| \| scaffold14851_4694128_SNP | 4694128 | G | C |
| S_9505105 \| \| scaffold14851_4694524_SNP | 4694524 | C | T |
| S_9505174 \| \| scaffold14851_4695359_SNP | 4695359 | C | A |
| S_9505322 \| \| scaffold14851_4697788_SNP | 4697788 | A | C |
| S_9505353 \| \| scaffold14851_4698233_SNP | 4698233 | G | A |
| S_9505356 \| \| scaffold14851_4698252_SNP | 4698252 | G | T |
| S_9505372 \| \| scaffold14851_4698451_SNP | 4698451 | G | C |
| S_9505382 \| \| scaffold14851_4698608_SNP | 4698608 | A | C |
| S_9505386 \| \| scaffold14851_4698653_SNP | 4698653 | G | T |
| S_9505480 \| \| scaffold14851_4700040_SNP | 4700040 | C | A |
| S_9505481 \| \| scaffold14851_4700050_SNP | 4700050 | G | C |
| S_9505482 \| \| scaffold14851_4700078_SNP | 4700078 | G | A |
| S_9505490 \| \| scaffold14851_4700255_SNP | 4700255 | A | T |
| S_9505491 \| \| scaffold14851_4700258_SNP | 4700258 | A | T |
| S_9505494 \| \| scaffold14851_4700304_SNP | 4700304 | G | A |
| S_9505514 \| \| scaffold14851_4700555_SNP | 4700555 | G | A |
| S_9505518 \| \| scaffold14851_4700618_SNP | 4700618 | A | G |
| S_9505519 \| \| scaffold14851_4700635_SNP | 4700635 | A | T |
| S_9505520 \| \| scaffold14851_4700638_SNP | 4700638 | A | C |
| S_9505521 \| \| scaffold14851_4700683_SNP | 4700683 | C | A |
| S_9505522 \| \| scaffold14851_4700712_SNP | 4700712 | C | G |
| S_9505543 \| \| scaffold14851_4701012_SNP | 4701012 | T | G |
| $_9505568 \| \| scaffold14851_4701401_SNP | 4701401 | A | T |
| S_9505614 \| \| scaffold14851_4701763_SNP | 4701763 | C | T |
| S_9505617 \| \| scaffold14851_4701845_SNP | 4701845 | A | T |
| S_9505621 \| \| scaffold14851_4701887_SNP | 4701887 | G | T |
| scaffold14851_4702227_SNP | 4702227 | A | C |
| scaffold14851_4702378_SNP | 4702378 | A | T |
| S_9505691 \| \| scaffold14851_4702410_SNP | 4702410 | C | A |
| S_9505692 \| \| scaffold14851_4702415_SNP | 4702415 | C | G |
| S_9505736 \| \| scaffold14851_4703235_SNP | 4703235 | G | C |
| S_9505740 \| \| scaffold14851_4703302_SNP | 4703302 | T | G |
| S_9505742 \| \| scaffold14851_4703312_SNP | 4703312 | G | T |
| S_9505761 \| \| scaffold14851_4703553_SNP | 4703553 | G | C |
| S_9505763 \| \| scaffold14851_4703588_SNP | 4703588 | A | G |
| scaffold14851_4703783_SNP | 4703783 | C | T |
| S_9505798 \| \| scaffold14851_4703791_SNP | 4703791 | T | C |
| S_9505802 \| \| scaffold14851_4703836_SNP | 4703836 | A | G |
| S_9505842 \| \| scaffold14851_4704102_SNP | 4704102 | A | T |
| S_9505868 \| \| scaffold14851_4704303_SNP | 4704303 | C | T |
| S_9505891 \| \| scaffold14851_4704572_SNP | 4704572 | C | G |
| S_9505895 \| \| scaffold14851_4704624_SNP | 4704624 | C | A |
| S_9505896 \| \| scaffold14851_4704626_SNP | 4704626 | A | G |
| S_9505901 \| \| scaffold14851_4704731_SNP | 4704731 | G | T |
| S_9505904 \| \| scaffold14851_4704779_SNP | 4704779 | A | T |
| S_9505910 \| \| scaffold14851_4704884_SNP | 4704884 | C | T |
| S_9505940 \| \| scaffold14851_4705298_SNP | 4705298 | G | A |
| S_9505963 \| \| scaffold14851_4705623_SNP | 4705623 | G | A |
| S_9506146 \| \| scaffold14851_4707754_SNP | 4707754 | T | C |
| S_9506171 \| \| scaffold14851_4707967_SNP | 4707967 | T | A |
| S_9506212 \| \| scaffold14851_4708551_SNP | 4708551 | T | C |
| S_9506213 \| \| scaffold14851_4708567_SNP | 4708567 | C | A |
| S_9506249 \| \| scaffold14851_4709139_SNP | 4709139 | G | T |
| S_9506266 \| \| scaffold14851_4709381_SNP | 4709381 | G | C |
| S_9506307 \| \| scaffold14851_4709966_SNP | 4709966 | C | T |
| S_9506338 \| \| scaffold14851_4710478_SNP | 4710478 | A | T |
| S_9506341 \| \| scaffold14851_4710500_SNP | 4710500 | G | A |
| S_9506351 \| \| scaffold14851_4710719_SNP | 4710719 | C | G |
| S_9506353 \| \| scaffold14851_4710775_SNP | 4710775 | A | G |
| S_9506360 \| \| scaffold14851_4710924_SNP | 4710924 | T | C |
| S_9506366 \| \| scaffold14851_4711029_SNP | 4711029 | T | G |
| S_9506369 \| \| scaffold14851_4711056_SNP | 4711056 | G | A |
| S_9506370 \| \| scaffold14851_4711063_SNP | 4711063 | A | G |
| S_9506437 \| \| scaffold14851_4712026_SNP | 4712026 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9506451 \| \| scaffold14851_4712278_SNP | 4712278 | A | G |
| S_9506460 \| \| scaffold14851_4712357_SNP | 4712357 | G | A |
| S_9506462 \| \| scaffold14851_4712375_SNP | 4712375 | G | C |
| S_9506466 \| \| scaffold14851_4712429_SNP | 4712429 | A | G |
| S_9506486 \| \| scaffold14851_4712711_SNP | 4712711 | G | A |
| S_9506679 \| \| scaffold14851_4715033_SNP | 4715033 | T | G |
| S_9506707 \| \| scaffold14851_4715319_SNP | 4715319 | C | G |
| S_9506735 \| \| scaffold14851_4715620_SNP | 4715620 | A | G |
| S_9506739 \| \| scaffold14851_4715666_SNP | 4715666 | A | T |
| S_9506744 \| \| scaffold14851_4715774_SNP | 4715774 | A | T |
| S_9506809 \| \| scaffold14851_4716671_SNP | 4716671 | G | A |
| S_9506874 \| \| scaffold14851_4717633_SNP | 4717633 | G | A |
| S_9507079 \| \| scaffold14851_4720732_SNP | 4720732 | G | A |
| S_9507163 \| \| scaffold14851_4721245_SNP | 4721245 | T | C |
| S_9507222 \| \| scaffold14851_4721981_SNP | 4721981 | G | A |
| S_9507438 \| \| scaffold14851_4724588_SNP | 4724588 | C | G |
| S_9507444 \| \| scaffold14851_4724642_SNP | 4724642 | G | A |
| S_9507458 \| \| scaffold14851_4724775_SNP | 4724775 | G | T |
| S_9507574 \| \| scaffold14851_4726763_SNP | 4726763 | C | T |
| S_9507673 \| \| scaffold14851_4727866_SNP | 4727866 | G | T |
| S_9507680 \| \| scaffold14851_4727942_SNP | 4727942 | A | C |
| S_9507681 \| \| scaffold14851_4727945_SNP | 4727945 | C | T |
| S_9507744 \| \| scaffold14851_4728176_SNP | 4728176 | T | C |
| S_9507952 \| \| scaffold14851_4730017_SNP | 4730017 | T | C |
| S_9507953 \| \| scaffold14851_4730059_SNP | 4730059 | C | T |
| S_9507963 \| \| scaffold14851_4730246_SNP | 4730246 | A | G |
| S_9507967 \| \| scaffold14851_4730323_SNP | 4730323 | A | G |
| S_9507996 \| \| scaffold14851_4730838_SNP | 4730838 | C | A |
| S_9508022 \| \| scaffold14851_4731102_SNP | 4731102 | C | T |
| S_9508035 \| \| scaffold14851_4731248_SNP | 4731248 | C | T |
| S_9508143 \| \| scaffold14851_4732950_SNP | 4732950 | T | C |
| S_9508147 \| \| scaffold14851_4732980_SNP | 4732980 | A | G |
| S_9508239 \| \| scaffold14851_4734593_SNP | 4734593 | C | G |
| S_9508441 \| \| scaffold14851_4736190_SNP | 4736190 | T | A |
| S_9508724 \| \| scaffold14851_4739398_SNP | 4739398 | G | A |
| S_9508736 \| \| scaffold14851_4739629_SNP | 4739629 | C | G |
| S_9508765 \| \| scaffold14851_4740131_SNP | 4740131 | G | A |
| S_9508767 \| \| scaffold14851_4740164_SNP | 4740164 | C | A |
| S_9508811 \| \| scaffold14851_4740862_SNP | 4740862 | T | C |
| S_9508827 \| \| scaffold14851_4741093_SNP | 4741093 | C | A |
| scaffold14851_4742600_SNP | 4742600 | G | A |
| S_9509178 \| \| scaffold14851_4745135_SNP | 4745135 | G | A |
| S_9509251 \| \| scaffold14851_4746224_SNP | 4746224 | A | C |
| S_9509252 \| \| scaffold14851_4746234_SNP | 4746234 | T | G |
| S_9509260 \| \| scaffold14851_4746416_SNP | 4746416 | T | C |
| S_9509265 \| \| scaffold14851_4746459_SNP | 4746459 | A | G |
| S_9509342 \| \| scaffold14851_4747380_SNP | 4747380 | A | C |
| S_9509411 \| \| scaffold14851_4747929_SNP | 4747929 | G | T |
| S_9509555 \| \| scaffold14851_4749523_SNP | 4749523 | C | T |
| S_9509593 \| \| scaffold14851_4750174_SNP | 4750174 | G | A |
| S_9509597 \| \| scaffold14851_4750219_SNP | 4750219 | T | G |
| S_9509640 \| \| scaffold14851_4750706_SNP | 4750706 | T | G |
| S_9509644 \| \| scaffold14851_4750742_SNP | 4750742 | C | G |
| S_9509671 \| \| scaffold14851_4751078_SNP | 4751078 | A | G |
| S_9509677 \| \| scaffold14851_4751098_SNP | 4751098 | T | G |
| S_9509679 \| \| scaffold14851_4751158_SNP | 4751158 | A | G |
| S_9509829 \| \| scaffold14851_4752404_SNP | 4752404 | T | C |
| S_9509832 \| \| scaffold14851_4752476_SNP | 4752476 | A | G |
| S_9509833 \| \| scaffold14851_4752485_SNP | 4752485 | C | A |
| S_9509844 \| \| scaffold14851_4752707_SNP | 4752707 | T | A |
| S_9509877 \| \| scaffold14851_4753273_SNP | 4753273 | T | C |
| S_9509892 \| \| scaffold14851_4753484_SNP | 4753484 | G | A |
| S_9509900 \| \| scaffold14851_4753538_SNP | 4753538 | T | C |
| S_9509929 \| \| scaffold14851_4753952_SNP | 4753952 | T | C |
| S_9509938 \| \| scaffold14851_4754144_SNP | 4754144 | A | T |
| S_9509939 \| \| scaffold14851_4754155_SNP | 4754155 | G | A |
| S_9509941 \| \| scaffold14851_4754174_SNP | 4754174 | A | G |
| S_9509955 \| \| scaffold14851_4754316_SNP | 4754316 | A | G |
| S_9510029 \| \| scaffold14851_4755073_SNP | 4755073 | T | A |
| S_9510042 \| \| scaffold14851_4755356_SNP | 4755356 | T | G |
| S_9510043 \| \| scaffold14851_4755358_SNP | 4755358 | A | G |
| S_9510044 \| \| scaffold14851_4755362_SNP | 4755362 | C | A |
| S_9510178 \| \| scaffold14851_4757154_SNP | 4757154 | T | A |
| S_9510204 \| \| scaffold14851_4757864_SNP | 4757864 | G | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9510209 \| \| scaffold14851_4757984_SNP | 4757984 | T | A |
| S_9510210 \| \| scaffold14851_4757989_SNP | 4757989 | A | G |
| S_9510225 \| \| scaffold14851_4758112_SNP | 4758112 | A | T |
| S_9510244 \| \| scaffold14851_4758475_SNP | 4758475 | T | A |
| S_9510308 \| \| scaffold14851_4759660_SNP | 4759660 | T | C |
| S_9510619 \| \| scaffold14851_4762895_SNP | 4762895 | A | T |
| S_9510620 \| \| scaffold14851_4762897_SNP | 4762897 | A | T |
| S_9510879 \| \| scaffold14851_4765681_SNP | 4765681 | G | C |
| S_9510894 \| \| scaffold14851_4765956_SNP | 4765956 | C | A |
| S_9511365 \| \| scaffold14851_4768744_SNP | 4768744 | A | G |
| S_9511452 \| \| scaffold14851_4769774_SNP | 4769774 | T | A |
| S_9511492 \| \| scaffold14851_4770070_SNP | 4770070 | T | A |
| S_9511493 \| \| scaffold14851_4770071_SNP | 4770071 | T | A |
| S_9511494 \| \| scaffold14851_4770072_SNP | 4770072 | T | A |
| S_9511495 \| \| scaffold14851_4770073_SNP | 4770073 | T | A |
| S_9511511 \| \| scaffold14851_4770478_SNP | 4770478 | A | T |
| S_9511512 \| \| scaffold14851_4770505_SNP | 4770505 | G | A |
| S_9511518 \| \| scaffold14851_4770693_SNP | 4770693 | C | T |
| S_9511529 \| \| scaffold14851_4770804_SNP | 4770804 | G | A |
| S_9511570 \| \| scaffold14851_4771379_SNP | 4771379 | T | C |
| S_9511584 \| \| scaffold14851_4771807_SNP | 4771807 | A | G |
| S_9511585 \| \| scaffold14851_4771833_SNP | 4771833 | C | T |
| S_9511586 \| \| scaffold14851_4771888_SNP | 4771888 | T | C |
| S_9511587 \| \| scaffold14851_4771899_SNP | 4771899 | A | G |
| S_9511588 \| \| scaffold14851_4771930_SNP | 4771930 | A | G |
| S_9511590 \| \| scaffold14851_4772009_SNP | 4772009 | T | C |
| S_9511591 \| \| scaffold14851_4772010_SNP | 4772010 | A | C |
| S_9511592 \| \| scaffold14851_4772040_SNP | 4772040 | G | A |
| S_9511594 \| \| scaffold14851_4772072_SNP | 4772072 | T | C |
| S_9511595 \| \| scaffold14851_4772076_SNP | 4772076 | G | A |
| S_9511605 \| \| scaffold14851_4772351_SNP | 4772351 | A | G |
| S_9511747 \| \| scaffold14851_4774353_SNP | 4774353 | C | G |
| S_9511748 \| \| scaffold14851_4774356_SNP | 4774356 | A | T |
| S_9511761 \| \| scaffold14851_4774529_SNP | 4774529 | T | G |
| S_9511762 \| \| scaffold14851_4774537_SNP | 4774537 | T | C |
| S_9511778 \| \| scaffold14851_4774763_SNP | 4774763 | T | A |
| S_9511794 \| \| scaffold14851_4775086_SNP | 4775086 | C | G |
| S_9511800 \| \| scaffold14851_4775244_SNP | 4775244 | T | A |
| S_9511811 \| \| scaffold14851_4775373_SNP | 4775373 | G | T |
| S_9511815 \| \| scaffold14851_4775401_SNP | 4775401 | C | T |
| S_9511816 \| \| scaffold14851_4775423_SNP | 4775423 | C | T |
| S_9511818 \| \| scaffold14851_4775440_SNP | 4775440 | T | G |
| S_9511822 \| \| scaffold14851_4775557_SNP | 4775557 | C | T |
| S_9511823 \| \| scaffold14851_4775609_SNP | 4775609 | T | C |
| S_9511824 \| \| scaffold14851_4775624_SNP | 4775624 | A | G |
| S_9511825 \| \| scaffold14851_4775640_SNP | 4775640 | T | A |
| S_9511896 \| \| scaffold14851_4775888_SNP | 4775888 | T | A |
| S_9511905 \| \| scaffold14851_4776001_SNP | 4776001 | G | C |
| S_9511961 \| \| scaffold14851_4776444_SNP | 4776444 | C | A |
| S_9512063 \| \| scaffold14851_4777406_SNP | 4777406 | G | A |
| S_9512123 \| \| scaffold14851_4778145_SNP | 4778145 | G | A |
| S_9512127 \| \| scaffold14851_4778178_SNP | 4778178 | T | G |
| S_9512225 \| \| scaffold14851_4779649_SNP | 4779649 | C | T |
| S_9512227 \| \| scaffold14851_4779660_SNP | 4779660 | C | T |
| S_9512228 \| \| scaffold14851_4779696_SNP | 4779696 | T | A |
| S_9512229 \| \| scaffold14851_4779801_SNP | 4779801 | C | T |
| S_9512245 \| \| scaffold14851_4779997_SNP | 4779997 | T | G |
| scaffold14851_4783411_SNP | 4783411 | T | A |
| scaffold14851_4783412_SNP | 4783412 | T | A |
| scaffold14851_4783413_SNP | 4783413 | T | A |
| S_9512538 \| \| scaffold14851_4783415_SNP | 4783415 | T | A |
| S_9512642 \| \| scaffold14851_4784629_SNP | 4784629 | G | C |
| S_9512643 \| \| scaffold14851_4784651_SNP | 4784651 | A | G |
| S_9512646 \| \| scaffold14851_4784688_SNP | 4784688 | T | A |
| S_9512665 \| \| scaffold14851_4784876_SNP | 4784876 | A | T |
| S_9512704 \| \| scaffold14851_4785502_SNP | 4785502 | C | T |
| S_9512705 \| \| scaffold14851_4785505_SNP | 4785505 | C | T |
| S_9512740 \| \| scaffold14851_4786480_SNP | 4786480 | G | A |
| S_9512817 \| \| scaffold14851_4787719_SNP | 4787719 | A | G |
| S_9512958 \| \| scaffold14851_4789730_SNP | 4789730 | G | C |
| S_9513004 \| \| scaffold14851_4790443_SNP | 4790443 | A | C |
| S_9513005 \| \| scaffold14851_4790456_SNP | 4790456 | A | G |
| S_9513006 \| \| scaffold14851_4790467_SNP | 4790467 | G | A |
| S_9513021 \| \| scaffold14851_4790694_SNP | 4790694 | C | G |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9513023 \| \| scaffold14851_4790704_SNP | 4790704 | C | G |
| S_9513027 \| \| scaffold14851_4790745_SNP | 4790745 | A | T |
| S_9513042 \| \| scaffold14851_4790966_SNP | 4790966 | T | C |
| S_9513054 \| \| scaffold14851_4791108_SNP | 4791108 | A | T |
| S_9513065 \| \| scaffold14851_4791278_SNP | 4791278 | A | C |
| S_9513078 \| \| scaffold14851_4791636_SNP | 4791636 | T | A |
| S_9513085 \| \| scaffold14851_4791686_SNP | 4791686 | A | C |
| S_9513172 \| \| scaffold14851_4793061_SNP | 4793061 | T | G |
| S_9513200 \| \| scaffold14851_4793296_SNP | 4793296 | A | G |
| S_9513356 \| \| scaffold14851_4794651_SNP | 4794651 | G | A |
| S_9513375 \| \| scaffold14851_4795024_SNP | 4795024 | T | C |
| S_9513376 \| \| scaffold14851_4795027_SNP | 4795027 | G | A |
| S_9513436 \| \| scaffold14851_4795336_SNP | 4795336 | G | T |
| S_9513480 \| \| scaffold14851_4795922_SNP | 4795922 | C | G |
| S_9513493 \| \| scaffold14851_4796346_SNP | 4796346 | C | A |
| S_9513533 \| \| scaffold14851_4796902_SNP | 4796902 | G | T |
| S_9513557 \| \| scaffold14851_4797292_SNP | 4797292 | A | C |
| S_9513563 \| \| scaffold14851_4797356_SNP | 4797356 | G | A |
| S_9513564 \| \| scaffold14851_4797363_SNP | 4797363 | T | G |
| S_9513570 \| \| scaffold14851_4797511_SNP | 4797511 | G | A |
| S_9513637 \| \| scaffold14851_4798445_SNP | 4798445 | G | T |
| S_9513640 \| \| scaffold14851_4798460_SNP | 4798460 | A | T |
| S_9513698 \| \| scaffold14851_4799386_SNP | 4799386 | G | C |
| S_9513714 \| \| scaffold14851_4799667_SNP | 4799667 | G | A |
| S_9513715 \| \| scaffold14851_4799676_SNP | 4799676 | T | C |
| S_9513717 \| \| scaffold14851_4799696_SNP | 4799696 | T | A |
| S_9513723 \| \| scaffold14851_4799745_SNP | 4799745 | T | C |
| S_9514041 \| \| scaffold14851_4804078_SNP | 4804078 | A | T |
| S_9514046 \| \| scaffold14851_4804129_SNP | 4804129 | T | A |
| S_9514047 \| \| scaffold14851_4804132_SNP | 4804132 | A | C |
| S_9514089 \| \| scaffold14851_4804908_SNP | 4804908 | C | T |
| S_9514092 \| \| scaffold14851_4804954_SNP | 4804954 | C | A |
| S_9514263 \| \| scaffold14851_4807348_SNP | 4807348 | T | G |
| S_9514338 \| \| scaffold14851_4808505_SNP | 4808505 | C | T |
| S_9514359 \| \| scaffold14851_4808689_SNP | 4808689 | C | G |
| S_9514379 \| \| scaffold14851_4809016_SNP | 4809016 | A | T |
| S_9514449 \| \| scaffold14851_4810083_SNP | 4810083 | A | T |
| S_9514519 \| \| scaffold14851_4810555_SNP | 4810555 | C | A |
| S_9514573 \| \| scaffold14851_4811398_SNP | 4811398 | T | A |
| S_9514579 \| \| scaffold14851_4811492_SNP | 4811492 | T | G |
| S_9514610 \| \| scaffold14851_4812011_SNP | 4812011 | A | C |
| S_9514657 \| \| scaffold14851_4812208_SNP | 4812208 | G | T |
| S_9514658 \| \| scaffold14851_4812216_SNP | 4812216 | A | G |
| S_9514685 \| \| scaffold14851_4812526_SNP | 4812526 | T | A |
| S_9514688 \| \| scaffold14851_4812591_SNP | 4812591 | C | T |
| S_9514689 \| \| scaffold14851_4812637_SNP | 4812637 | T | G |
| S_9514716 \| \| scaffold14851_4813108_SNP | 4813108 | T | A |
| S_9514746 \| \| scaffold14851_4813563_SNP | 4813563 | A | C |
| S_9514808 \| \| scaffold14851_4813669_SNP | 4813669 | T | C |
| S_9514831 \| \| scaffold14851_4813723_SNP | 4813723 | C | T |
| S_9514835 \| \| scaffold14851_4813806_SNP | 4813806 | A | G |
| S_9514843 \| \| scaffold14851_4813964_SNP | 4813964 | T | G |
| S_9514853 \| \| scaffold14851_4814260_SNP | 4814260 | C | G |
| S_9514857 \| \| scaffold14851_4814292_SNP | 4814292 | G | T |
| S_9514901 \| \| scaffold14851_4814637_SNP | 4814637 | G | T |
| S_9514977 \| \| scaffold14851_4816351_SNP | 4816351 | A | C |
| S_9515108 \| \| scaffold14851_4818327_SNP | 4818327 | G | C |
| S_9515152 \| \| scaffold14851_4819084_SNP | 4819084 | A | T |
| S_9515157 \| \| scaffold14851_4819139_SNP | 4819139 | A | G |
| S_9515160 \| \| scaffold14851_4819189_SNP | 4819189 | C | G |
| S_9515198 \| \| scaffold14851_4820314_SNP | 4820314 | T | C |
| S_9515289 \| \| scaffold14851_4821486_SNP | 4821486 | T | C |
| S_9515626 \| \| scaffold14851_4824784_SNP | 4824784 | T | C |
| S_9515767 \| \| scaffold14851_4827081_SNP | 4827081 | A | C |
| S_9515792 \| \| scaffold14851_4827457_SNP | 4827457 | A | T |
| S_9516000 \| \| scaffold14851_4829823_SNP | 4829823 | A | G |
| S_9516012 \| \| scaffold14851_4830132_SNP | 4830132 | G | A |
| S_9516013 \| \| scaffold14851_4830166_SNP | 4830166 | C | T |
| S_9516015 \| \| scaffold14851_4830175_SNP | 4830175 | A | T |
| S_9516016 \| \| scaffold14851_4830179_SNP | 4830179 | A | T |
| S_9516020 \| \| scaffold14851_4830213_SNP | 4830213 | C | G |
| S_9516021 \| \| scaffold14851_4830233_SNP | 4830233 | A | G |
| S_9516076 \| \| scaffold14851_4830973_SNP | 4830973 | G | A |
| S_9516138 \| \| scaffold14851_4832252_SNP | 4832252 | C | A |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9516146 \| \| scaffold14851_4832486_SNP | 4832486 | A | T |
| S_9516154 \| \| scaffold14851_4832699_SNP | 4832699 | G | A |
| S_9516253 \| \| scaffold14851_4833926_SNP | 4833926 | A | T |
| S_9516355 \| \| scaffold14851_4835328_SNP | 4835328 | A | G |
| S_9516363 \| \| scaffold14851_4835539_SNP | 4835539 | C | G |
| S_9516412 \| \| scaffold14851_4836527_SNP | 4836527 | C | G |
| S_9516592 \| \| scaffold14851_4839191_SNP | 4839191 | T | A |
| S_9516627 \| \| scaffold14851_4839797_SNP | 4839797 | G | A |
| S_9516691 \| \| scaffold14851_4840590_SNP | 4840590 | A | G |
| S_9516725 \| \| scaffold14851_4841251_SNP | 4841251 | A | G |
| S_9516728 \| \| scaffold14851_4841276_SNP | 4841276 | A | G |
| S_9516731 \| \| scaffold14851_4841341_SNP | 4841341 | C | T |
| S_9516846 \| \| scaffold14851_4842604_SNP | 4842604 | T | C |
| S_9516968 \| \| scaffold14851_4843908_SNP | 4843908 | T | C |
| S_9517108 \| \| scaffold14851_4845999_SNP | 4845999 | C | G |
| S_9517162 \| \| scaffold14851_4846770_SNP | 4846770 | T | A |
| S_9517170 \| \| scaffold14851_4846911_SNP | 4846911 | T | C |
| S_9517250 \| \| scaffold14851_4847987_SNP | 4847987 | G | A |
| S_9517270 \| \| scaffold14851_4848218_SNP | 4848218 | A | C |
| S_9517314 \| \| scaffold14851_4848861_SNP | 4848861 | A | T |
| S_9517382 \| \| scaffold14851_4849642_SNP | 4849642 | T | C |
| S_9517416 \| \| scaffold14851_4849907_SNP | 4849907 | C | G |
| S_9517433 \| \| scaffold14851_4850068_SNP | 4850068 | T | C |
| S_9517434 \| \| scaffold14851_4850092_SNP | 4850092 | A | G |
| S_9517453 \| \| scaffold14851_4850540_SNP | 4850540 | C | T |
| S_9517494 \| \| scaffold14851_4851296_SNP | 4851296 | A | G |
| S_9517495 \| \| scaffold14851_4851299_SNP | 4851299 | T | A |
| S_9517523 \| \| scaffold14851_4851864_SNP | 4851864 | T | A |
| S_9517558 \| \| scaffold14851_4852533_SNP | 4852533 | T | A |
| S_9517560 \| \| scaffold14851_4852572_SNP | 4852572 | C | T |
| S_9517565 \| \| scaffold14851_4852659_SNP | 4852659 | A | C |
| S_9517574 \| \| scaffold14851_4852884_SNP | 4852884 | C | T |
| S_9517599 \| \| scaffold14851_4853364_SNP | 4853364 | T | C |
| S_9517760 \| \| scaffold14851_4855197_SNP | 4855197 | G | T |
| S_9517766 \| \| scaffold14851_4855354_SNP | 4855354 | C | A |
| S_9517802 \| \| scaffold14851_4855855_SNP | 4855855 | A | G |
| S_9517805 \| \| scaffold14851_4855918_SNP | 4855918 | T | C |
| S_9517844 \| \| scaffold14851_4856421_SNP | 4856421 | G | A |
| S_9518042 \| \| scaffold14851_4858944_SNP | 4858944 | C | A |
| scaffold14851_4863712_SNP | 4863712 | G | A |
| S_9518602 \| \| scaffold14851_4866480_SNP | 4866480 | A | G |
| S_9518848 \| \| scaffold14851_4868054_SNP | 4868054 | A | C |
| S_9518991 \| \| scaffold14851_4870098_SNP | 4870098 | T | C |
| S_9518998 \| \| scaffold14851_4870214_SNP | 4870214 | A | C |
| S_9519097 \| \| scaffold14851_4871095_SNP | 4871095 | G | A |
| S_9519118 \| \| scaffold14851_4871519_SNP | 4871519 | C | T |
| S_9519154 \| \| scaffold14851_4872041_SNP | 4872041 | A | G |
| S_9519155 \| \| scaffold14851_4872051_SNP | 4872051 | T | G |
| S_9519165 \| \| scaffold14851_4872287_SNP | 4872287 | G | A |
| S_9519166 \| \| scaffold14851_4872297_SNP | 4872297 | T | C |
| S_9519167 \| \| scaffold14851_4872301_SNP | 4872301 | A | G |
| S_9519343 \| \| scaffold14851_4874803_SNP | 4874803 | G | A |
| S_9519392 \| \| scaffold14851_4875468_SNP | 4875468 | A | G |
| S_9519403 \| \| scaffold14851_4875591_SNP | 4875591 | G | C |
| S_9519419 \| \| scaffold14851_4875833_SNP | 4875833 | A | C |
| S_9519420 \| \| scaffold14851_4875835_SNP | 4875835 | G | T |
| S_9519791 \| \| scaffold14851_4880574_SNP | 4880574 | A | G |
| S_9519827 \| \| scaffold14851_4881075_SNP | 4881075 | T | C |
| S_9519973 \| \| scaffold14851_4882672_SNP | 4882672 | A | T |
| S_9519979 \| \| scaffold14851_4882833_SNP | 4882833 | T | C |
| S_9520001 \| \| scaffold14851_4883115_SNP | 4883115 | G | A |
| S_9520006 \| \| scaffold14851_4883189_SNP | 4883189 | G | A |
| S_9520008 \| \| scaffold14851_4883198_SNP | 4883198 | C | T |
| S_9520009 \| \| scaffold14851_4883199_SNP | 4883199 | A | T |
| S_9520242 \| \| scaffold14851_4886665_SNP | 4886665 | C | G |
| S_9520255 \| \| scaffold14851_4886804_SNP | 4886804 | T | A |
| S_9520303 \| \| scaffold14851_4887433_SNP | 4887433 | C | G |
| S_9520313 \| \| scaffold14851_4887551_SNP | 4887551 | T | C |
| S_9520314 \| \| scaffold14851_4887554_SNP | 4887554 | C | T |
| S_9520317 \| \| scaffold14851_4887600_SNP | 4887600 | T | C |
| S_9520322 \| \| scaffold14851_4887676_SNP | 4887676 | C | A |
| S_9520418 \| \| scaffold14851_4888666_SNP | 4888666 | A | G |
| S_9520487 \| \| scaffold14851_4889160_SNP | 4889160 | T | C |
| S_9520488 \| \| scaffold14851_4889176_SNP | 4889176 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9520489 \|\| scaffold14851_4889177_SNP | 4889177 | A | G |
| S_9520490 \|\| scaffold14851_4889192_SNP | 4889192 | C | T |
| S_9520492 \|\| scaffold14851_4889209_SNP | 4889209 | T | C |
| S_9520507 \|\| scaffold14851_4889482_SNP | 4889482 | T | C |
| S_9520508 \|\| scaffold14851_4889483_SNP | 4889483 | C | T |
| S_9520511 \|\| scaffold14851_4889512_SNP | 4889512 | G | A |
| S_9520514 \|\| scaffold14851_4889541_SNP | 4889541 | T | C |
| S_9520737 \|\| scaffold14851_4892744_SNP | 4892744 | G | A |
| scaffold14851_4892782_SNP | 4892782 | A | G |
| scaffold14851_4892796_SNP | 4892796 | T | C |
| scaffold14851_4892803_SNP | 4892803 | C | T |
| S_9520756 \|\| scaffold14851_4892906_SNP | 4892906 | T | G |
| S_9520911 \|\| scaffold14851_4894896_SNP | 4894896 | G | A |
| S_9520912 \|\| scaffold14851_4894898_SNP | 4894898 | G | A |
| $_9520970 \|\| scaffold14851_4895394_SNP | 4895394 | C | G |
| S_9521068 \|\| scaffold14851_4896001_SNP | 4896001 | C | T |
| S_9521160 \|\| scaffold14851_4897319_SNP | 4897319 | G | C |
| S_9521166 \|\| scaffold14851_4897356_SNP | 4897356 | G | C |
| S_9521259 \|\| scaffold14851_4898615_SNP | 4898615 | G | A |
| S_9521298 \|\| scaffold14851_4899266_SNP | 4899266 | C | A |
| S_9521310 \|\| scaffold14851_4899345_SNP | 4899345 | C | T |
| S_9521341 \|\| scaffold14851_4899694_SNP | 4899694 | T | A |
| S_9521396 \|\| scaffold14851_4900598_SNP | 4900598 | C | G |
| S_9521483 \|\| scaffold14851_4901932_SNP | 4901932 | A | T |
| S_9521507 \|\| scaffold14851_4902114_SNP | 4902114 | A | T |
| S_9521518 \|\| scaffold14851_4902264_SNP | 4902264 | G | C |
| S_9521561 \|\| scaffold14851_4902827_SNP | 4902827 | A | C |
| S_9521562 \|\| scaffold14851_4902828_SNP | 4902828 | G | T |
| S_9521564 \|\| scaffold14851_4902853_SNP | 4902853 | C | G |
| S_9521629 \|\| scaffold14851_4903724_SNP | 4903724 | T | G |
| S_9521631 \|\| scaffold14851_4903729_SNP | 4903729 | G | A |
| S_9521690 \|\| scaffold14851_4904792_SNP | 4904792 | G | T |
| S_9521711 \|\| scaffold14851_4905191_SNP | 4905191 | T | A |
| S_9521713 \|\| scaffold14851_4905237_SNP | 4905237 | A | G |
| S_9521726 \|\| scaffold14851_4905516_SNP | 4905516 | G | A |
| S_9521775 \|\| scaffold14851_4906170_SNP | 4906170 | T | C |
| S_9521776 \|\| scaffold14851_4906172_SNP | 4906172 | C | T |
| S_9521799 \|\| scaffold14851_4906709_SNP | 4906709 | T | C |
| S_9521851 \|\| scaffold14851_4907335_SNP | 4907335 | A | T |
| S_9521894 \|\| scaffold14851_4907481_SNP | 4907481 | C | G |
| S_9521900 \|\| scaffold14851_4907555_SNP | 4907555 | T | C |
| S_9521906 \|\| scaffold14851_4907640_SNP | 4907640 | C | T |
| S_9522088 \|\| scaffold14851_4910641_SNP | 4910641 | A | T |
| S_9522204 \|\| scaffold14851_4913076_SNP | 4913076 | A | C |
| S_9522263 \|\| scaffold14851_4913997_SNP | 4913997 | C | T |
| S_9522297 \|\| scaffold14851_4914799_SNP | 4914799 | G | A |
| S_9522299 \|\| scaffold14851_4914817_SNP | 4914817 | A | G |
| S_9522447 \|\| scaffold14851_4916282_SNP | 4916282 | C | G |
| S_9522537 \|\| scaffold14851_4917152_SNP | 4917152 | T | C |
| S_9522538 \|\| scaffold14851_4917154_SNP | 4917154 | A | T |
| S_9522601 \|\| scaffold14851_4917946_SNP | 4917946 | C | T |
| S_9522610 \|\| scaffold14851_4918036_SNP | 4918036 | C | G |
| S_9522623 \|\| scaffold14851_4918227_SNP | 4918227 | G | A |
| S_9522814 \|\| scaffold14851_4921414_SNP | 4921414 | A | C |
| S_9523024 \|\| scaffold14851_4923475_SNP | 4923475 | T | A |
| S_9523033 \|\| scaffold14851_4923709_SNP | 4923709 | T | C |
| S_9523048 \|\| scaffold14851_4923942_SNP | 4923942 | T | A |
| S_9523059 \|\| scaffold14851_4924046_SNP | 4924046 | T | A |
| S_9523062 \|\| scaffold14851_4924155_SNP | 4924155 | C | T |
| S_9523064 \|\| scaffold14851_4924230_SNP | 4924230 | G | A |
| S_9523071 \|\| scaffold14851_4924417_SNP | 4924417 | T | C |
| S_9523073 \|\| scaffold14851_4924424_SNP | 4924424 | G | A |
| S_9523175 \|\| scaffold14851_4925737_SNP | 4925737 | A | T |
| S_9523190 \|\| scaffold14851_4926163_SNP | 4926163 | A | T |
| S_9523263 \|\| scaffold14851_4926927_SNP | 4926927 | T | G |
| S_9523274 \|\| scaffold14851_4927171_SNP | 4927171 | A | T |
| S_9523279 \|\| scaffold14851_4927262_SNP | 4927262 | C | T |
| S_9523291 \|\| scaffold14851_4927590_SNP | 4927590 | A | G |
| S_9523311 \|\| scaffold14851_4927703_SNP | 4927703 | C | T |
| S_9523417 \|\| scaffold14851_4929369_SNP | 4929369 | C | T |
| S_9523572 \|\| scaffold14851_4930786_SNP | 4930786 | A | T |
| S_9523574 \|\| scaffold14851_4930848_SNP | 4930848 | A | G |
| S_9523704 \|\| scaffold14851_4932395_SNP | 4932395 | C | A |
| S_9523761 \|\| scaffold14851_4933130_SNP | 4933130 | C | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9523881 \| \| scaffold14851_4934969_SNP | 4934969 | C | A |
| S_9523989 \| \| scaffold14851_4936533_SNP | 4936533 | A | G |
| S_9524024 \| \| scaffold14851_4936877_SNP | 4936877 | C | T |
| S_9524114 \| \| scaffold14851_4937941_SNP | 4937941 | G | C |
| S_9524279 \| \| scaffold14851_4940129_SNP | 4940129 | G | A |
| S_9524289 \| \| scaffold14851_4940244_SNP | 4940244 | G | C |
| S_9524545 \| \| scaffold14851_4942765_SNP | 4942765 | A | T |
| S_9524885 \| \| scaffold14851_4946974_SNP | 4946974 | T | C |
| S_9524886 \| \| scaffold14851_4946979_SNP | 4946979 | C | T |
| S_9524908 \| \| scaffold14851_4947352_SNP | 4947352 | G | A |
| S_9524918 \| \| scaffold14851_4947625_SNP | 4947625 | A | G |
| S_9524943 \| \| scaffold14851_4947957_SNP | 4947957 | C | G |
| S_9524950 \| \| scaffold14851_4948101_SNP | 4948101 | T | C |
| S_9524954 \| \| scaffold14851_4948225_SNP | 4948225 | A | T |
| S_9524968 \| \| scaffold14851_4948429_SNP | 4948429 | C | T |
| S_9524998 \| \| scaffold14851_4948691_SNP | 4948691 | G | A |
| S_9524999 \| \| scaffold14851_4948692_SNP | 4948692 | G | C |
| S_9525040 \| \| scaffold14851_4949051_SNP | 4949051 | G | A |
| S_9525151 \| \| scaffold14851_4950361_SNP | 4950361 | A | T |
| S_9525158 \| \| scaffold14851_4950504_SNP | 4950504 | T | C |
| S_9525160 \| \| scaffold14851_4950566_SNP | 4950566 | A | G |
| S_9525174 \| \| scaffold14851_4950760_SNP | 4950760 | T | C |
| S_9525179 \| \| scaffold14851_4950831_SNP | 4950831 | A | G |
| S_9525214 \| \| scaffold14851_4951241_SNP | 4951241 | C | T |
| S_9525232 \| \| scaffold14851_4951410_SNP | 4951410 | A | G |
| S_9525254 \| \| scaffold14851_4951861_SNP | 4951861 | A | C |
| S_9525382 \| \| scaffold14851_4954056_SNP | 4954056 | G | T |
| S_9525385 \| \| scaffold14851_4954111_SNP | 4954111 | C | G |
| S_9525386 \| \| scaffold14851_4954139_SNP | 4954139 | A | G |
| S_9525392 \| \| scaffold14851_4954179_SNP | 4954179 | T | C |
| S_9525395 \| \| scaffold14851_4954210_SNP | 4954210 | T | G |
| S_9525397 \| \| scaffold14851_4954218_SNP | 4954218 | A | G |
| S_9525399 \| \| scaffold14851_4954238_SNP | 4954238 | G | C |
| S_9525539 \| \| scaffold14851_4956626_SNP | 4956626 | A | T |
| S_9525621 \| \| scaffold14851_4957608_SNP | 4957608 | G | A |
| S_9525631 \| \| scaffold14851_4957776_SNP | 4957776 | T | A |
| S_9525650 \| \| scaffold14851_4957997_SNP | 4957997 | T | C |
| S_9525696 \| \| scaffold14851_4958712_SNP | 4958712 | T | A |
| S_9525697 \| \| scaffold14851_4958719_SNP | 4958719 | T | C |
| S_9525788 \| \| scaffold14851_4959878_SNP | 4959878 | A | G |
| S_9525885 \| \| scaffold14851_4961078_SNP | 4961078 | G | C |
| S_9525920 \| \| scaffold14851_4961724_SNP | 4961724 | G | A |
| S_9526019 \| \| scaffold14851_4965635_SNP | 4965635 | T | A |
| S_9526033 \| \| scaffold14851_4965823_SNP | 4965823 | A | G |
| S_9526107 \| \| scaffold14851_4967178_SNP | 4967178 | C | G |
| S_9526328 \| \| scaffold14851_4969020_SNP | 4969020 | T | A |
| S_9526389 \| \| scaffold14851_4969759_SNP | 4969759 | G | T |
| S_9526390 \| \| scaffold14851_4969769_SNP | 4969769 | C | T |
| S_9526442 \| \| scaffold14851_4970584_SNP | 4970584 | T | A |
| S_9526596 \| \| scaffold14851_4974375_SNP | 4974375 | T | A |
| S_9526598 \| \| scaffold14851_4974385_SNP | 4974385 | A | T |
| S_9526751 \| \| scaffold14851_4976486_SNP | 4976486 | A | T |
| S_9526795 \| \| scaffold14851_4977106_SNP | 4977106 | G | A |
| S_9526797 \| \| scaffold14851_4977131_SNP | 4977131 | T | C |
| S_9526801 \| \| scaffold14851_4977173_SNP | 4977173 | C | G |
| S_9526826 \| \| scaffold14851_4977375_SNP | 4977375 | A | T |
| S_9526830 \| \| scaffold14851_4977429_SNP | 4977429 | G | A |
| S_9526839 \| \| scaffold14851_4977547_SNP | 4977547 | T | C |
| S_9526889 \| \| scaffold14851_4978383_SNP | 4978383 | A | C |
| S_9526890 \| \| scaffold14851_4978386_SNP | 4978386 | T | G |
| S_9526951 \| \| scaffold14851_4979088_SNP | 4979088 | A | G |
| S_9526996 \| \| scaffold14851_4979825_SNP | 4979825 | T | C |
| S_9527020 \| \| scaffold14851_4979999_SNP | 4979999 | C | T |
| S_9527079 \| \| scaffold14851_4980269_SNP | 4980269 | A | T |
| S_9527131 \| \| scaffold14851_4980740_SNP | 4980740 | C | A |
| S_9527134 \| \| scaffold14851_4980857_SNP | 4980857 | C | T |
| S_9527145 \| \| scaffold14851_4981068_SNP | 4981068 | A | T |
| S_9527169 \| \| scaffold14851_4981352_SNP | 4981352 | C | T |
| S_9527474 \| \| scaffold14851_4984704_SNP | 4984704 | A | G |
| S_9527493 \| \| scaffold14851_4984820_SNP | 4984820 | T | A |
| S_9527646 \| \| scaffold14851_4987504_SNP | 4987504 | T | C |
| S_9527696 \| \| scaffold14851_4988046_SNP | 4988046 | A | G |
| S_9527887 \| \| scaffold14851_4990419_SNP | 4990419 | G | A |
| S_9527961 \| \| scaffold14851_4991690_SNP | 4991690 | T | C |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9528207 \| \| scaffold14851_4995023_SNP | 4995023 | A | G |
| S_9528236 \| \| scaffold14851_4995331_SNP | 4995331 | A | T |
| S_9528557 \| \| scaffold14851_5000071_SNP | 5000071 | C | A |
| S_9528565 \| \| scaffold14851_5000221_SNP | 5000221 | G | C |
| S_9528690 \| \| scaffold14851_5001590_SNP | 5001590 | T | A |
| S_9528704 \| \| scaffold14851_5001790_SNP | 5001790 | A | T |
| S_9528766 \| \| scaffold14851_5002264_SNP | 5002264 | T | A |
| S_9528831 \| \| scaffold14851_5002827_SNP | 5002827 | A | G |
| S_9528863 \| \| scaffold14851_5003215_SNP | 5003215 | C | A |
| S_9528936 \| \| scaffold14851_5003596_SNP | 5003596 | T | A |
| S_9528943 \| \| scaffold14851_5003624_SNP | 5003624 | C | T |
| S_9528944 \| \| scaffold14851_5003626_SNP | 5003626 | G | A |
| S_9529193 \| \| scaffold14851_5004304_SNP | 5004304 | A | G |
| scaffold14851_5004438_SNP | 5004438 | G | A |
| S_9529231 \| \| scaffold14851_5004487_SNP | 5004487 | C | T |
| S_9529271 \| \| scaffold14851_5004951_SNP | 5004951 | A | G |
| S_9529310 \| \| scaffold14851_5005409_SNP | 5005409 | G | A |
| S_9529385 \| \| scaffold14851_5006453_SNP | 5006453 | C | T |
| scaffold14851_5008356_SNP | 5008356 | G | T |
| S_9529834 \| \| scaffold14851_5009933_SNP | 5009933 | G | A |
| S_9529904 \| \| scaffold14851_5011338_SNP | 5011338 | A | C |
| S_9529940 \| \| scaffold14851_5011836_SNP | 5011836 | A | G |
| S_9530168 \| \| scaffold14851_5013529_SNP | 5013529 | T | G |
| S_9530199 \| \| scaffold14851_5013962_SNP | 5013962 | A | G |
| S_9530217 \| \| scaffold14851_5014122_SNP | 5014122 | T | C |
| S_9530251 \| \| scaffold14851_5014539_SNP | 5014539 | G | A |
| S_9530263 \| \| scaffold14851_5014625_SNP | 5014625 | C | T |
| S_9530512 \| \| scaffold14851_5022950_SNP | 5022950 | T | G |
| S_9530537 \| \| scaffold14851_5023114_SNP | 5023114 | C | T |
| S_9530542 \| \| scaffold14851_5023239_SNP | 5023239 | A | G |
| S_9530596 \| \| scaffold14851_5023498_SNP | 5023498 | C | T |
| S_9530600 \| \| scaffold14851_5023525_SNP | 5023525 | T | A |
| S_9530770 \| \| scaffold14851_5026066_SNP | 5026066 | T | G |
| S_9530801 \| \| scaffold14851_5026478_SNP | 5026478 | G | C |
| S_9530961 \| \| scaffold14851_5028130_SNP | 5028130 | G | A |
| S_9531062 \| \| scaffold14851_5029530_SNP | 5029530 | T | C |
| S_9531114 \| \| scaffold14851_5030097_SNP | 5030097 | A | T |
| S_9531381 \| \| scaffold14851_5034009_SNP | 5034009 | T | C |
| S_9531449 \| \| scaffold14851_5034422_SNP | 5034422 | T | C |
| S_9531587 \| \| scaffold14851_5035090_SNP | 5035090 | G | T |
| S_9531787 \| \| scaffold14851_5036372_SNP | 5036372 | C | T |
| S_9532133 \| \| scaffold14851_5038521_SNP | 5038521 | A | G |
| S_9532195 \| \| scaffold14851_5038679_SNP | 5038679 | A | T |
| scaffold14851_5038727_SNP | 5038727 | A | G |
| S_9532687 \| \| scaffold14851_5041344_SNP | 5041344 | A | G |
| S_9532858 \| \| scaffold14851_5044024_SNP | 5044024 | G | A |
| S_9532871 \| \| scaffold14851_5044337_SNP | 5044337 | A | G |
| S_9532877 \| \| scaffold14851_5044520_SNP | 5044520 | T | C |
| S_9532882 \| \| scaffold14851_5044630_SNP | 5044630 | G | A |
| S_9533477 \| \| scaffold14851_5050528_SNP | 5050528 | A | T |
| S_9533484 \| \| scaffold14851_5050735_SNP | 5050735 | C | T |
| S_9533507 \| \| scaffold14851_5051061_SNP | 5051061 | A | G |
| S_9533581 \| \| scaffold14851_5052115_SNP | 5052115 | A | C |
| S_9533607 \| \| scaffold14851_5052595_SNP | 5052595 | T | C |
| S_9533612 \| \| scaffold14851_5052703_SNP | 5052703 | C | A |
| S_9533782 \| \| scaffold14851_5057969_SNP | 5057969 | T | C |
| S_9533948 \| \| scaffold14851_5059250_SNP | 5059250 | G | A |
| S_9534126 \| \| scaffold14851_5061562_SNP | 5061562 | A | G |
| S_9534129 \| \| scaffold14851_5061648_SNP | 5061648 | C | T |
| S_9534198 \| \| scaffold14851_5062494_SNP | 5062494 | C | T |
| S_9534199 \| \| scaffold14851_5062497_SNP | 5062497 | T | C |
| S_9534235 \| \| scaffold14851_5063120_SNP | 5063120 | C | G |
| S_9534259 \| \| scaffold14851_5063410_SNP | 5063410 | T | C |
| S_9534262 \| \| scaffold14851_5063444_SNP | 5063444 | A | G |
| S_9534263 \| \| scaffold14851_5063446_SNP | 5063446 | A | C |
| S_9534294 \| \| scaffold14851_5063574_SNP | 5063574 | T | C |
| S_9534295 \| \| scaffold14851_5063576_SNP | 5063576 | A | G |
| S_9534326 \| \| scaffold14851_5063687_SNP | 5063687 | C | T |
| S_9534327 \| \| scaffold14851_5063690_SNP | 5063690 | C | T |
| S_9534328 \| \| scaffold14851_5063692_SNP | 5063692 | A | G |
| S_9534425 \| \| scaffold14851_5064936_SNP | 5064936 | A | G |
| S_9534524 \| \| scaffold14851_5065217_SNP | 5065217 | T | C |
| S_9534526 \| \| scaffold14851_5065248_SNP | 5065248 | A | G |
| S_9534748 \| \| scaffold14851_5069297_SNP | 5069297 | A | T |

TABLE 1-continued

SNP Positions within SEQ ID NO: 1 that are associated with increased resistance to ASR

| Name | Position SEQ ID NO: 1 | Favorabale Allele (Rust Resistant) | Unfavorable Allele (Rust Susceptible) |
|---|---|---|---|
| S_9534770 \| \| scaffold14851_5069467_SNP | 5069467 | A | G |
| S_9534864 \| \| scaffold14851_5070369_SNP | 5070369 | T | C |
| S_9534875 \| \| scaffold14851_5070537_SNP | 5070537 | A | G |
| S_9534913 \| \| scaffold14851_5071007_SNP | 5071007 | A | G |
| S_9534937 \| \| scaffold14851_5071215_SNP | 5071215 | C | T |
| S_9534938 \| \| scaffold14851_5071254_SNP | 5071254 | C | T |
| S_9535054 \| \| scaffold14851_5073143_SNP | 5073143 | C | T |
| S_9535076 \| \| scaffold14851_5073430_SNP | 5073430 | A | C |
| S_9535404 \| \| scaffold14851_5076755_SNP | 5076755 | T | C |
| S_9535405 \| \| scaffold14851_5076756_SNP | 5076756 | C | G |
| S_9535543 \| \| scaffold14851_5077635_SNP | 5077635 | T | G |
| S_9535674 \| \| scaffold14851_5078863_SNP | 5078863 | T | C |
| S_9535675 \| \| scaffold14851_5078883_SNP | 5078883 | T | C |
| S_9535950 \| \| scaffold14851_5082024_SNP | 5082024 | G | A |
| S_9535965 \| \| scaffold14851_5082263_SNP | 5082263 | T | G |
| S_9536781 \| \| scaffold14851_5092454_SNP | 5092454 | C | G |
| S_9536840 \| \| scaffold14851_5093421_SNP | 5093421 | A | T |
| S_9536956 \| \| scaffold14851_5095043_SNP | 5095043 | C | T |
| S_9537246 \| \| scaffold14851_5099641_SNP | 5099641 | T | G |
| S_9537407 \| \| scaffold14851_5102531_SNP | 5102531 | A | T |
| S_9538041 \| \| scaffold14851_5111660_SNP | 5111660 | A | T |
| S_9538469 \| \| scaffold14851_5118189_SNP | 5118189 | C | G |
| S_9538724 \| \| scaffold14851_5121082_SNP | 5121082 | T | C |
| S_9538976 \| \| scaffold14851_5124755_SNP | 5124755 | T | C |
| S_9539124 \| \| scaffold14851_5126954_SNP | 5126954 | A | G |
| S_9539301 \| \| scaffold14851_5129046_SNP | 5129046 | G | A |
| S_9539430 \| \| scaffold14851_5130678_SNP | 5130678 | G | C |
| S_9539441 \| \| scaffold14851_5130891_SNP | 5130891 | C | A |
| S_9539688 \| \| scaffold14851_5133044_SNP | 5133044 | G | A |
| S_9539837 \| \| scaffold14851_5135015_SNP | 5135015 | T | G |
| S_9539848 \| \| scaffold14851_5135167_SNP | 5135167 | G | A |
| S_9540002 \| \| scaffold14851_5137706_SNP | 5137706 | A | G |
| S_9540595 \| \| scaffold14851_5145034_SNP | 5145034 | T | C |
| S_9540718 \| \| scaffold14851_5146238_SNP | 5146238 | A | G |
| S_9540745 \| \| scaffold14851_5146506_SNP | 5146506 | A | C |
| S_9540977 \| \| scaffold14851_5147242_SNP | 5147242 | A | G |
| S_9541238 \| \| scaffold14851_5147742_SNP | 5147742 | T | C |
| S_9541397 \| \| scaffold14851_5148433_SNP | 5148433 | G | A |
| S_9541865 \| \| scaffold14851_5150716_SNP | 5150716 | A | G |
| S_9541866 \| \| scaffold14851_5150720_SNP | 5150720 | C | T |
| S_9541870 \| \| scaffold14851_5150782_SNP | 5150782 | T | C |
| S_9542272 \| \| scaffold14851_5154104_SNP | 5154104 | A | G |
| S_9542302 \| \| scaffold14851_5154462_SNP | 5154462 | A | G |
| S_9542315 \| \| scaffold14851_5154597_SNP | 5154597 | G | T |
| scaffold14851_5154944_SNP | 5154944 | C | T |
| S_9542575 \| \| scaffold14851_5156318_SNP | 5156318 | T | C |
| S_9542617 \| \| scaffold14851_5156977_SNP | 5156977 | T | C |
| S_9542875 \| \| scaffold14851_5159802_SNP | 5159802 | A | G |
| S_9542953 \| \| scaffold14851_5160657_SNP | 5160657 | T | C |
| S_9543329 \| \| scaffold14851_5163762_SNP | 5163762 | A | G |

It is well known in the art that given the sequence and the SNP allele associated with a given trait (e.g. ASR resistance), one having ordinary skill in the art could develop oligonucleotide primers and use said primers to identify plants carrying any one of the chromosomal intervals depicted in SEQ ID NO: 1. A TAQMAN® assay (e.g. generally a two-step allelic discrimination assay or similar), a KASP™ assay (generally a one-step allelic discrimination assay defined below or similar), or both can be employed to assay the SNPs as disclosed herein. In an exemplary two-step assay, a forward primer, a reverse primer, and two assay probes (or hybridization oligos) are employed. The forward and reverse primers are employed to amplify genetic loci that comprise SNPs that are associated with ASR resistance loci. The particular nucleotides that are present at the SNP positions are then assayed using the assay primers (which in some embodiments are differentially labeled with, for example, fluorophores to permit distinguishing between the two assay probes in a single reaction), which in each pair differ from each other with respect to the nucleotides that are present at the SNP position (although it is noted that in any given pair, the probes can differ in their 5' or 3' ends without impacting their abilities to differentiate between nucleotides present at the corresponding SNP positions). In some embodiments, the assay primers and the reaction conditions are designed such that an assay primer will only hybridize to the reverse complement of a 100% perfectly matched sequence, thereby permitting identification of which allele(s) is/are present based upon detection of hybridizations.

Compositions and methods for identifying, selecting and producing Glycine plants (including wild Glycines and Glycine max lines) with enhanced disease resistance are provided. Disease resistant soybean plants and germplasms are also provided.

In some embodiments, methods of identifying a disease resistant soybean plant or germplasm are provided. Such methods may comprise detecting, in the soybean plant or germplasm, a genetic loci or molecular marker (e.g. SNP or a Quantitative Trait Loci (QTL)) associated with enhanced disease resistance, in particular ASR resistance. In some embodiments the genetic loci or molecular marker associates with the presence of a chromosomal interval comprising the nucleotide sequence or a portion thereof of SEQ ID NO: 1.

In some embodiments, methods of producing a disease resistant soybean plant are provided. Such methods may comprise detecting, in a soybean germplasm, the presence of a genetic loci and/or a genetic marker associated with enhanced pathogen resistance (e.g. ASR) and producing a progeny plant from said soybean germplasm.

In some embodiments, methods of selecting a disease resistant soybean plant or germplasm are provided. Such methods may comprise crossing a first soybean plant or germplasm with a second soybean plant or germplasm, wherein the first soybean plant or germplasm comprises a genetic loci derived from soybean *Glycine clandestina* accession PI339656, or a progeny thereof comprising any one of SEQ ID NO: 1 or a portion thereof associated with enhanced disease resistance and/or tolerance, and selecting a progeny plant or germplasm that possesses the genetic loci. In further embodiments, the first soybean plant or germplasm comprises a genetic loci derived from soybean *Glycine clandestina* accession PI591576.

In some embodiments, methods of introgressing a genetic loci derived from soybean accession number PI339656, PI591576, or a progeny thereof associated with enhanced pathogen resistance into a soybean plant or germplasm are provided. Such methods may comprise crossing a first soybean plant or germplasm comprising a chromosomal interval derived from soybean accession number PI339656, PI591576 or a progeny thereof associated with enhanced pathogen resistance with a second soybean plant or germplasm that lacks said genetic loci and optionally repeatedly backcrossing progeny plants comprising said genetic allele with the second soybean plant or germplasm to produce an soybean plant (e.g. *Glycine max*) or germplasm with enhanced pathogen resistance comprising the chromosomal interval derived from soybean accession number PI339656, PI591576 or a progeny thereof associated with enhanced pathogen resistance. Progeny comprising the chromosomal interval associated with enhanced pathogen resistance may be identified by detecting, in their genomes, the presence of a marker associated with said chromosomal interval derived from soybean accession number PI339656, PI591576 or a progeny thereof wherein said chromosomal interval comprises SEQ ID NO: 1 or a portion thereof. R-Genes from PI339656, PI591576 or a progeny thereof can be introgressed into a *Glycine max* line through the use of embryo rescue methods known by those skilled in the art for example as is disclosed in U.S. Pat. No. 7,842,850 herein incorporated by reference and through methods as described in the working Examples herein.

In some embodiments, a plant, a progeny plant, or plant part of the species *Glycine max* is provided, wherein a portion of a genome of the plant is obtained from a wild glycine species through the use of chemically induced chromosome doubling, and wherein said portion confers the plant with increased resistance to ASR as compared to a control plant not comprising the portion.

In some embodiments, a plant, progeny plant, or plant part of the species *Glycine max* is provided, wherein a genome of the plant comprises a chromosomal interval that confers increased resistance to ASR as compared to a control plant not comprising the interval, wherein said chromosomal interval is introduced into the plant from a wild glycine species, and wherein said plant with said chromosomal interval is obtained through chemically induced chromosomal doubling.

Soybean plants and/or germplasms identified, produced or selected by the methods of this invention are also provided, as are any progeny and/or seeds derived from a soybean plant or germplasm identified, produced or selected by these methods. In one embodiment a molecular markers associating with the presence of a chromosomal intervals depicted in SEQ ID NO: 1 may be used to identify or select for plant lines resistant to ASR. Further said molecular markers may be located within 20 cM, 10 cM, 5 cM, 4 cM, 3 cM, 2 cM, 1 cM of said chromosomal interval. In another embodiment, said molecular marker may be located within 20 cM, 10 cM, 5 cM, 4 cM, 3 cM, 2 cM, 1 cM of any SNP markers associated with ASR as described in Table 1.

Non-naturally occurring soybean seeds, plants and/or germplasms comprising one or genetic loci derived from soybean plant accession number PI339656, PI591576 or a progeny thereof associated with enhanced pathogen resistance (e.g. ASR, Cyst Nematode, *Phytophtora*, brown stem rot etc.) are also provided.

A marker associated with enhanced pathogen resistance may comprise, consist essentially of or consist of a single allele or a combination of alleles at one or more genetic loci derived from PI339656, PI591576 or a progeny thereof that associate with enhanced pathogen resistance. In one embodiment the marker is within a chromosomal interval as described by SEQ ID NO: 1.

The foregoing and other objects and aspects of the present invention are explained in detail in the drawings and specification set forth below.

BRIEF DESCRIPTION OF THE DRAWINGS

FIG. 1 shows the screening of Wild Glycine lines for rust resistance against a panel of 16 rust isolates.

FIG. 2 illustrates the rust rating scale used to measure plant phenotype.

FIG. 3 shows a depiction of *Glycine clandestina* (PI339656) SNPs associated with ASR Resistance on scaffold 14851 and scaffold 9588.

FIG. 4 is mapping interval within scaffold 14851 of markers associated with ASR FIG. 5 is a marker association map for *Glycine clandestina* (PI339656) where bands indicate regions/intervals of respective chromosomes associated with ASR resistance.

DETAILED DESCRIPTION OF THE INVENTION

The presently disclosed subject matter relates at least in part to the identification of a genomic region (i.e. chromosomal interval) derived from *Glycine clandestina* accession line PI339656, PI591576 or a progeny thereof associated with enhanced pathogen resistance (e.g. Asian soy rust or Soybean cyst nematode). As such, said chromosomal interval from PI339656, PI591576 or a progeny thereof, may be introgressed into *Glycine max* lines via somatic embryo rescue (see for example U.S. Patent Publication 2007/0261139 and examples herein) or through the use of a *Glycine max* donor line having introgressed into its genome the genetic region from PI339656, PI591576 or a progeny thereof wherein the region comprises SEQ ID NO: 1 or a portion thereof where presence of said genetic region is associated with increased soybean disease resistance to, for example, ASR, SCN, Stem termination, Stem Canker, Bacterial pustule, root knot nematode, brown stem rot, frogeye leaf spot, or phytophthora. In another embodiment a chromosomal interval derived from PI339656, PI591576 or a progeny thereof is introduced into a *Glycine max* line not comprising said chromosomal interval wherein said introduction confers in the *Glycine max* line or it's progeny increased resistances to disease (e.g. ASR) wherein the said chromosome interval is derived from chromosome 1, 2 3, 4, 5, 6, 7, 8, 9, 10, 11, 12, 13, 14, 15, 16, 17, 18, 19, or chromosome 20 of *Glycine clandestina* and further wherein said chromosomal interval comprises at least one allele that associates with the trait of increased disease resistance wherein said allele is any one of the alleles respectively selected from any one as depicted in Table 1.

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Definitions

Unless defined otherwise, all technical and scientific terms used herein have the same meaning as commonly understood to one of ordinary skill in the art to which the presently disclosed subject matter belongs.

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker can mean one marker or a plurality of markers.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

The term "consists essentially of" (and grammatical variants thereof), as applied to a polynucleotide sequence of this invention, means a polynucleotide sequence that consists of both the recited sequence (e.g., SEQ ID NO: 1) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together. The term "materially altered," as applied to polynucleotides of the invention, refers to an increase or decrease in ability to express the polynucleotide sequence of at least about 50% or more as compared to the expression level of a polynucleotide sequence consisting of the recited sequence.

As used herein, the term "wild glycine" refers to a *Glycine clandestina* plant.

As used herein, the term "allele" refers to one of two or more different nucleotides or nucleotide sequences that occur at a specific locus.

A marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced pathogen resistance" refers to a marker whose presence or absence can be used to predict whether and/or to what extent a plant will display an pathogen resistant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval defined by and including," used in reference to particular loci and/or alleles, refers to a chromosomal interval delimited by and encompassing the stated loci/alleles.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele" and "allele of interest" are used interchangeably to refer to an allele associated with a desired trait. In some embodiments, a "desired allele" and/or "allele of interest" may be associated with either an increase or a decrease of or in a given trait, depending on the nature of the desired phenotype. In some embodiments, a "desired allele" and/or "allele of interest" may be associated with a change in morphology, color, etc.

As used herein, the terms "enhanced pathogen resistance" or "enhanced disease resistance" refers to an improvement, enhancement, or increase in a plant's ability to endure and/or thrive despite being infected with a disease (e.g. Asian soybean rust) as compared to one or more control plants (e.g., one or both of the parents, or a plant lacking a marker associated with enhanced pathogen resistance to respective pathogen/disease). Enhanced disease resistance includes any mechanism (other than whole-plant immunity or resistance) that reduces the expression of symptoms indicative of infection for a respective disease such as Asian soybean rust, soybean cyst nematode, *Phytophthora*, etc.

As used herein, the terms "elite" and "elite line" refer to any line that has resulted from breeding and selection for desirable agronomic performance. An elite line may be substantially homozygous. Numerous elite lines are available and known to those of skill in the art.

As used herein, the term "elite germplasm" refers to any germplasm that is derived from or is capable of giving rise to an elite plant.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm may refer to seeds, cells (including protoplasts and calli) or tissues from which new plants may be grown, as well as plant parts that can be cultured into a whole plant (e.g., stems, buds, roots, leaves, etc.).

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" refers to a seed and/or plant produced when at least two genetically dissimilar parents are crossed.

As used herein, the term "inbred" refers to a substantially homozygous plant or variety. The term may refer to a plant or variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced ASR tolerance may be introgressed from a donor into a recurrent parent that is not Disease resistant. The resulting offspring could then be repeatedly backcrossed and selected until the progeny possess the ASR tolerance allele(s) in the recurrent parent background.

As used herein, the term "linkage" refers to the degree with which one marker locus is associated with another marker locus or some other locus (for example, an ASR tolerance locus). The linkage relationship between a molecular marker and a phenotype may be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

In some aspects of the present invention, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) may also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome may be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., Asian Soybean Rust (herein 'ASR'). The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker or allele is located. In some embodiments, a locus may encompass one or more nucleotides.

As used herein, the terms "marker" and "genetic marker" are used interchangeably to refer to a nucleotide and/or a nucleotide sequence that has been associated with a phenotype, trait or trait form. In some embodiments, a marker may be associated with an allele or alleles of interest and may be indicative of the presence or absence of the allele or alleles of interest in a cell or organism. A marker may be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138: 255 (2004)), a single-stranded conformation polymorphism (SSCP) (Orita et al., *Proc. Natl. Acad. Sci. USA* 86:2766

(1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), a chromosome interval, or an RNA cleavage product (such as a Lynx tag). A marker may be present in genomic or expressed nucleic acids (e.g., ESTs). The term marker may also refer to nucleic acids used as probes or primers (e.g., primer pairs) for use in amplifying, hybridizing to and/or detecting nucleic acid molecules according to methods well known in the art. A large number of soybean molecular markers are known in the art, and are published or available from various sources, such as the SoyBase internet resource.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. In some embodiments, marker genotypes are used to identify plants that will be selected for a breeding program or for planting. In some embodiments, marker genotypes are used to identify plants that will not be selected for a breeding program or for planting (i.e., counter-selected plants), allowing them to be removed from the breeding/planting population.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the terms "molecular marker" or "genetic marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., SNP technology is used in the examples provided herein.

A "non-naturally occurring variety of soybean" is any variety of soybean that does not naturally exist in nature. A "non-naturally occurring variety of soybean" may be produced by any method known in the art, including, but not limited to, transforming a soybean plant or germplasm, transfecting a soybean plant or germplasm and crossing a naturally occurring variety of soybean with a non-naturally occurring variety of soybean. In some embodiments, a "non-naturally occurring variety of soybean" may comprise one of more heterologous nucleotide sequences. In some embodiments, a "non-naturally occurring variety of soybean" may comprise one or more non-naturally occurring copies of a naturally occurring nucleotide sequence (i.e., extraneous copies of a gene that naturally occurs in soybean). In some embodiments, a "non-naturally occurring variety of soybean" may comprise a non-natural combination of two or more naturally occurring nucleotide sequences (i.e., two or more naturally occurring genes that do not naturally occur in the same soybean, for instance genes not found in *Glycine max* lines).

As used herein, the terms "phenotype," "phenotypic trait" or "trait" refer to one or more traits and/or manifestations of an organism. The phenotype can be a manifestation that is observable to the naked eye, or by any other means of evaluation known in the art, e.g., microscopy, biochemical analysis, or an electromechanical assay. In some cases, a phenotype or trait is directly controlled by a single gene or genetic locus, i.e., a "single gene trait." In other cases, a phenotype or trait is the result of several genes. It is noted that, as used herein, the term "disease resistant phenotype" takes into account environmental conditions that might affect the respective disease such that the effect is real and reproducible.

As used herein, the term "plant" may refer to a whole plant, any part thereof, or a cell or tissue culture derived from a plant. Thus, the term "plant" can refer to any of: whole plants, plant components or organs (e.g., roots, stems, leaves, buds, flowers, pods, etc.), plant tissues, seeds and/or plant cells. A plant cell is a cell of a plant, taken from a plant, or derived through culture from a cell taken from a plant. Thus, the term "soybean plant" may refer to a whole soybean plant, one or more parts of a soybean plant (e.g., roots, root tips, stems, leaves, buds, flowers, pods, seeds, cotyledons, etc.), soybean plant cells, soybean plant protoplasts and/or soybean plant calli.

As used herein, the term "polymorphism" refers to a variation in the nucleotide sequence at a locus, where said variation is too common to be due merely to a spontaneous mutation. A polymorphism can be a single nucleotide polymorphism (SNP) or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "population" refers to a genetically heterogeneous collection of plants sharing a common genetic derivation.

As used herein, the terms "progeny" and "progeny plant" refer to a plant generated from a vegetative or sexual reproduction from one or more parent plants. A progeny plant may be obtained by cloning or selfing a single parent plant, or by crossing two parental plants.

As used herein, the term "reference sequence" refers to a defined nucleotide sequence used as a basis for nucleotide sequence comparison. The reference sequence for a marker, for example, is obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

As used herein, the terms "disease tolerance" and "Disease resistant" refer to a plant's ability to endure and/or thrive despite being infected with a respective disease. When used in reference to germplasm, the terms refer to the ability of a plant that arises from that germplasm to endure and/or thrive despite being infected with a respective disease. In some embodiments, infected Disease resistant soybean plants may yield as well (or nearly as well) as uninfected soybean plants. In general, a plant or germplasm is labeled as "Disease resistant" if it displays "enhanced pathogen resistance."

An "unfavorable allele" of a marker is a marker allele that segregates with the unfavorable plant phenotype, therefore providing the benefit of identifying plants that can be removed from a breeding program or planting.

"PI339656" refers to *Glycine clandestina* accession numbers PI339656, PI446934, PI483193, PI505154, PI595799, or PI591576.

Genetic Mapping

Genetic loci correlating with particular phenotypes, such as disease resistance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with enhanced disease resistance. Detection of these markers and/or other linked markers can be used to identify, select and/or produce Disease resistant plants and/or to eliminate plants that are not Disease resistant from breeding programs or planting.

*Glycine Clandestina* Genetic Loci Associated with Enhanced Disease Resistance Markers associated with enhanced disease resistance are identified herein (see Table 1). A marker of the present invention may comprise a single allele or a combination of alleles at one or more genetic loci (for example, any marker combination from Table 1. For example, the marker may comprise one or more marker alleles located within a first chromosomal interval (e.g. SEQ ID NO: 1).

Markers of the present invention are described herein with respect to the positions of marker loci within chromosomal intervals comprising sequenced genomic DNA of PI339656, or a progeny thereof as depicted by any one of SEQ ID NO: 1: and as represented in Table 1.

Marker-Assisted Selection

Markers can be used in a variety of plant breeding applications. See, e.g., Staub et al., *Hortscience* 31: 729 (1996); Tanksley, *Plant Molecular Biology Reporter* 1: 3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. The ideal situation is to have a marker within the causative gene itself, so that recombination cannot occur between the marker and the gene. Such a marker is called a "perfect marker."

When a gene is introgressed by MAS, it is not only the gene that is introduced but also the flanking regions. Gepts, *Crop Sci* 42:1780 (2002). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite soybean line. This is also sometimes referred to as "yield drag." The size of the flanking region can be decreased by additional backcrossing, although this is not always successful, as breeders do not have control over the size of the region or the recombination breakpoints. Young et al., *Genetics* 120:579 (1998). In classical breeding, it is usually only by chance that recombinations that contribute to a reduction in the size of the donor segment are selected. Tanksley et al., *Biotechnology* 7: 257 (1989). Even after 20 backcrosses, one might find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the soybean genome containing increasing densities of public soybean markers has facilitated soybean genetic mapping and MAS.

Of all the molecular marker types, SNPs are the most abundant and have the potential to provide the highest genetic map resolution. Bhattramakki et al., *Plant Molec. Biol.* 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, mini-sequencing and coded spheres. Such methods have been reviewed in various publications: Gut, *Hum. Mutat.* 17:475 (2001); Shi, Clin. Chem. 47:164 (2001); Kwok, *Pharmacogenomics* 1:95 (2000); Bhattramakki and Rafalski, *Discovery and application of single nucleotide polymorphism markers in plants*, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, MD), Invader® (Hologic, Madison, WI), SnapShot® (Applied Biosystems, Foster City, CA), Taqman® (Applied Biosystems, Foster City, CA) and Beadarrays™ (Illumina, San Diego, CA).

A number of SNP alleles together within a sequence, or across linked sequences, can be used to describe a haplotype for any particular genotype. Ching et al., *BMC Genet.* 3:19 (2002); Gupta et al., (2001), Rafalski, *Plant Sci.* 162:329 (2002b). Haplotypes can be more informative than single SNPs and can be more descriptive of any particular genotype. For example, a single SNP may be allele "T" for a specific Disease resistant line or variety, but the allele "T" might also occur in the soybean breeding population being utilized for recurrent parents. In this case, a combination of alleles at linked SNPs may be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the present invention can be used in marker-assisted selection protocols to identify and/or select progeny with enhanced Asian soybean rust tolerance. Such methods can comprise, consist essentially of or consist of crossing a first soybean plant or germplasm with a second soybean plant or germplasm, wherein the first soybean plant or germplasm comprises a chromosomal interval derived from PI339656, or a progeny thereof wherein said chromosomal interval corresponds with nucleotide base 1 to nucleotide base 5166731 of SEQ ID NO: 1 and selecting a progeny plant that possesses the marker. Either of the first and second soybean plants, or both, may be of a non-naturally occurring variety of soybean. In some embodiments, the second soybean plant or germplasm is of an elite variety of soybean. In some embodiments, the genome of the second soybean plant or germplasm is at least about 50%, 55%, 60%, 65%, 70%, 75%, 80%, 85%, 90%, 95%, 97%, 99% or 100% identical to that of an elite variety of soybean. In another embodiment, the first soybean plant comprises a chromosomal interval derived from PI339656, or a progeny thereof wherein said chromosomal interval corresponds with nucleotide base 1 to nucleotide base 5166731 of SEQ ID NO: 1 wherein the chromosome interval further comprises at least one allele as depicted in any one of respective Table 1.

Methods for identifying and/or selecting a disease resistant soybean plant or germplasm may comprise, consist essentially of or consist of detecting the presence of a marker associated with enhanced ASR tolerance. The marker may be detected in any sample taken from the plant or germplasm, including, but not limited to, the whole plant or germplasm, a portion of said plant or germplasm (e.g., a seed chip, a leaf punch disk or a cell from said plant or germplasm) or a nucleotide sequence from said plant or germplasm. Such a sample may be taken from the plant or germplasm using any present or future method known in the art, including, but not limited to, automated methods of removing a portion of endosperm with a sharp blade, drilling a small hole in the seed and collecting the resultant powder, cutting the seed with a laser and punching a leaf disk. The soybean plant may be of a non-naturally occurring variety of soybean. In some embodiments, the genome of the soybean plant or germplasm is at least about 50%, 55%, 60%, 65%, 70%, 75%, 80%, 85%, 90%, 95%, 97%, 99% or 100% identical to that of an elite variety of soybean.

In some embodiments, the marker detected in the sample may comprise, consist essentially of or consist of one or more marker alleles located within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or
2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or
3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

Methods for producing an disease resistant soybean plant may comprise, consist essentially of or consist of detecting, in a germplasm, a marker associated with enhanced disease resistance (e.g. ASR) wherein said marker is selected from any one of Table 1 or wherein marker is a closely linked loci of any marker described in any of Table 1 and producing a soybean plant from said germplasm. The marker may be detected in any sample taken from the germplasm, including, but not limited to, a portion of said germplasm (e.g., a seed chip or a cell from said germplasm) or a nucleotide sequence from said germplasm. Such a sample may be taken from the germplasm using any present or future method known in the art, including, but not limited to, automated methods of removing a portion of endosperm with a sharp blade, drilling a small hole in the seed and collecting the resultant powder, cutting the seed with a laser and punching a leaf disk. The germplasm may be of a non-naturally occurring variety of soybean. In some embodiments, the genome of the germplasm is at least about 50%, 55%, 60%, 65%, 70%, 75%, 80%, 85%, 90%, 95%, 97%, 99% or 100% identical to that of an elite variety of soybean. An Disease resistant soybean plant is then produced from the germplasm identified as having the marker associated with enhanced disease resistance (e.g. ASR) according to methods well known in the art for breeding and producing plants from germplasm.

In some embodiments, the marker detected in the germplasm may comprise, consist essentially of or consist of one or more marker alleles located within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or
2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or
3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

In some embodiments, the marker detected in the germplasm may comprise, consist essentially of or consist of one or more marker alleles selected from any one of Table 1.

Methods for producing and/or selecting an Asian soy rust resistant/tolerant soybean plant or germplasm may comprise crossing a first soybean plant or germplasm with a second soybean plant or germplasm, wherein said first soybean plant or germplasm comprises a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or
2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or
3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

Also provided herein is a method of introgressing an allele associated with enhanced Disease (e.g. ASR, SCN, SDS, RKN, *Phytophtora*, etc.) resistance/tolerance (e.g. ASR, SCN, SDS, RKN, *Phytophtora*, etc.) into a soybean plant. Such methods for introgressing an allele associated with enhanced Disease (e.g. ASR, SCN, SDS, RKN, *Phy-*

*tophtora*, etc.) resistance/tolerance into a soybean plant or germplasm may comprise, consist essentially of or consist of crossing a first soybean plant or germplasm comprising said allele (the donor) wherein said allele is selected from any allele listed in Table 1 or a maker in "close proximity" to a marker listed in Table 1 with a second soybean plant or germplasm that lacks said allele (the recurrent parent) and repeatedly backcrossing progeny comprising said allele with the recurrent parent. Progeny comprising said allele may be identified by detecting, in their genomes, the presence of a marker associated with enhanced Disease (e.g. ASR, SCN, SDS, RKN, *Phytophtora*, etc.) resistance/tolerance. The marker may be detected in any sample taken from the progeny, including, but not limited to, a portion of said progeny (e.g., a seed chip, a leaf punch disk or a cell from said plant or germplasm) or a nucleotide sequence from said progeny. Such a sample may be taken from the progeny using any present or future method known in the art, including, but not limited to, automated methods of removing a portion of endosperm with a sharp blade, drilling a small hole in the seed and collecting the resultant powder, cutting the seed with a laser and punching a leaf disk. Either the donor or the recurrent parent, or both, may be of a non-naturally occurring variety of soybean. In some embodiments, the recurrent parent is of an elite variety of soybean. In some embodiments, the genome of the recurrent parent is at least about 50%, 55%, 60%, 65%, 70%, 75%, 80%, 85%, 90%, 95%, 97%, 99% or 100% identical to that of an elite variety of soybean.

In some embodiments, the marker used to identify progeny comprising an allele associated with enhanced Disease (e.g. ASR, SCN, SDS, RKN, *Phytophtora*, brown stem rot etc.) resistance/tolerance may comprise, consist essentially of or consist of one or more marker alleles located within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or
2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or
3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

In some embodiments, the marker may comprise, consist essentially of or consist of marker alleles located in at least two different chromosomal intervals. For example, the marker may comprise one or more alleles located in the chromosomal interval defined by and including any two markers in Table 1.

Disease Resistant Soybean Plants and Germplasms

The present invention provides Disease resistant soybean plants and germplasms. As discussed above, the methods of the present invention may be utilized to identify, produce and/or select a Disease resistant soybean plant or germplasm (for example a soybean plant resistant or having increased tolerance to Asian Soybean Rust). In addition to the methods described above, an Disease resistant soybean plant or germplasm may be produced by any method whereby a marker associated with enhanced Disease tolerance is introduced into the soybean plant or germplasm, including, but not limited to, transformation, protoplast transformation or fusion, a double haploid technique, embryo rescue, gene editing and/or by any other nucleic acid transfer system.

In some embodiments, the soybean plant or germplasm comprises a non-naturally occurring variety of soybean. In some embodiments, the soybean plant or germplasm is at least about 50%, 55%, 60%, 65%, 70%, 75%, 80%, 85%, 90%, 95%, 97%, 99% or 100% identical to that of an elite variety of soybean.

The Disease resistant soybean plant or germplasm may be the progeny of a cross between an elite variety of soybean and a variety of soybean that comprises an allele associated with enhanced Disease tolerance (e.g. ASR) wherein the allele is within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or
2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or
3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

The Disease resistant soybean plant or germplasm may be the progeny of an introgression wherein the recurrent parent is an elite variety of soybean and the donor comprises an allele associated with enhanced Disease tolerance and/or resistance wherein the donor carries a chromosomal interval or a portion thereof comprising any one of SEQ ID NO: 1 and wherein the chromosome interval comprises at least one allele selected respectively from Table 1.

The Disease resistant soybean plant or germplasm may be the progeny of a cross between a first elite variety of soybean (e.g., a tester line) and the progeny of a cross between a second elite variety of soybean (e.g., a recurrent parent) and a variety of soybean that comprises an allele associated with enhanced ASR tolerance (e.g., a donor).

The Disease resistant soybean plant or germplasm may be the progeny of a cross between a first elite variety of soybean and the progeny of an introgression wherein the recurrent parent is a second elite variety of soybean and the donor comprises an allele associated with enhanced ASR tolerance.

A Disease resistant soybean plant and germplasm of the present invention may comprise one or more markers of the present invention (e.g. any marker described in Table 1; or any marker in close proximity to any marker as described in Table 1).

In some embodiments, the Disease resistant soybean plant or germplasm may comprise within its genome, a marker associated with enhanced ASR tolerance, wherein said marker is located within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or 2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or 3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

In some embodiments, the Disease resistant soybean plant or germplasm may comprise within its genome a marker that comprises, consists essentially of or consists of marker alleles located in at least two different chromosomal intervals. For example, the marker may comprise one or more alleles located in the chromosomal interval defined by and including any combination of two markers of Table 1.

Disease Resistant Soybean Seeds

The present invention provides Disease resistant soybean seeds. As discussed above, the methods of the present invention may be utilized to identify, produce and/or select an Disease resistant soybean seed. In addition to the methods described above, an Disease resistant soybean seed may be produced by any method whereby a marker associated with enhanced ASR tolerance is introduced into the soybean seed, including, but not limited to, transformation, protoplast transformation or fusion, a double haploid technique, embryo rescue, genetic editing (e.g. CRISPR or TALEN or MegaNucleases) and/or by any other nucleic acid transfer system.

In some embodiments, the Disease resistant soybean seed comprises a non-naturally occurring variety of soybean. In some embodiments, the soybean seed is at least about 50%, 55%, 60%, 65%, 70%, 75%, 80%, 85%, 90%, 95%, 97%, 99% or 100% identical to that of an elite variety of soybean.

The Disease resistant soybean seed may be produced by an Disease resistant soybean plant identified, produced or selected by the methods of the present invention. In some embodiments, the Disease resistant soybean seed is produced by an Disease resistant soybean plant of the present invention.

A Disease resistant soybean seed of the present invention may comprise one or more markers from Table 1 of the present invention.

In some embodiments, the Disease resistant soybean seed may comprise within its genome, a marker associated with enhanced ASR tolerance, wherein said marker is located within a chromosomal interval selected from the group consisting of:

1) A chromosomal interval derived from PI339656, or a progeny thereof wherein said chromosomal interval corresponds with nucleotide base 1 to nucleotide base 5166731 of SEQ ID NO: 1; or 2) chromosomal interval derived from PI339656, or a progeny thereof wherein said chromosomal interval comprises a portion of any one of the chromosome intervals described in 1) and wherein the chromosome interval comprises at least one SNP marker as demonstrated respectfully in any one of Table 1; or 3) A chromosomal interval spanning 20 cM, 15 cM, 10 cM, 5 cM, 1 cM, 0.5 cM from a SNP marker that associates with increased ASR resistance in soybean wherein the SNP marker is selected from the group consisting of any SNP marker displayed in any one of Table 1.

EXAMPLES

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

Example 1 Identification of ASR Resistant Wild Glycine Lines

Figure 1:
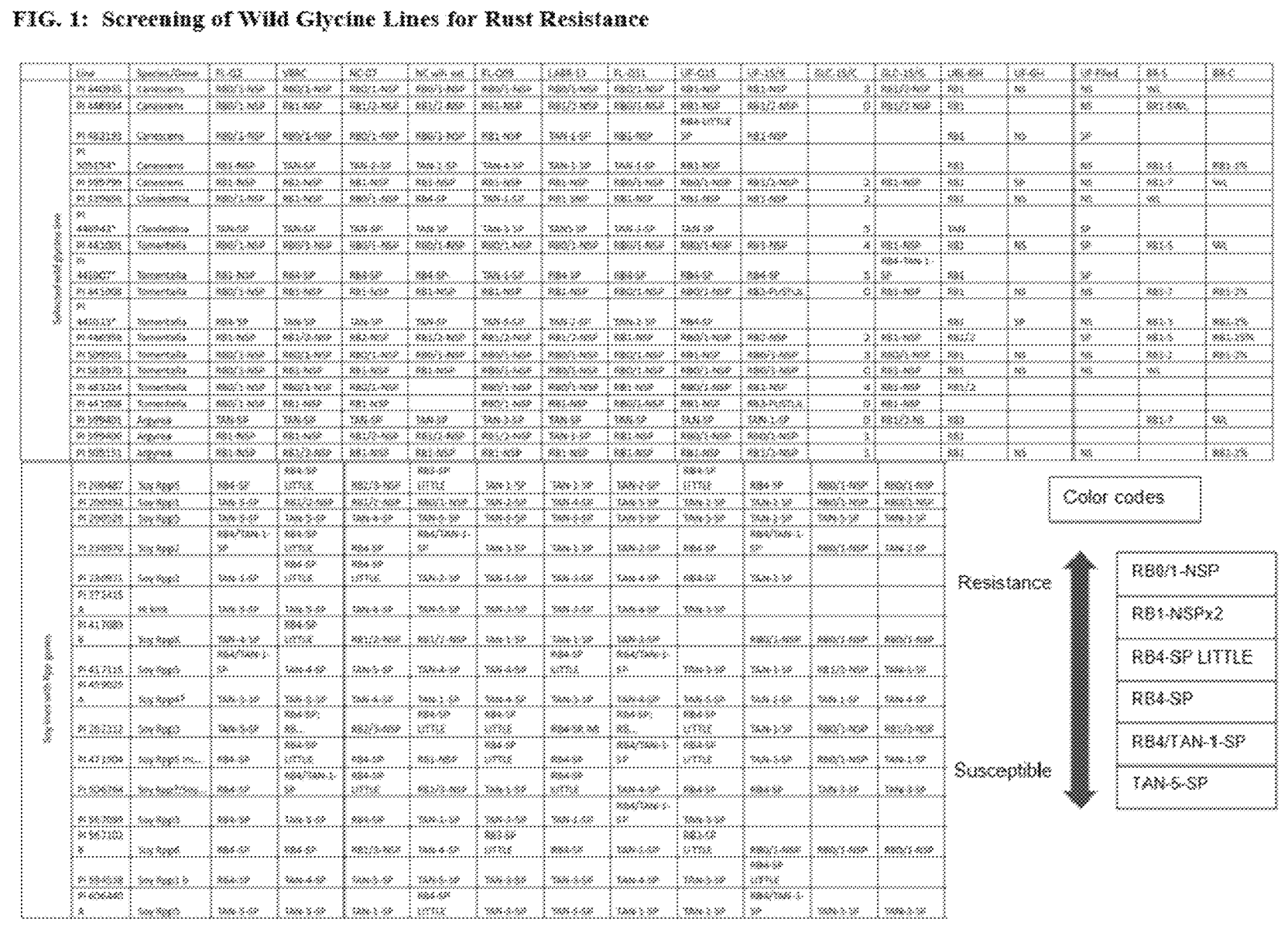

Wild glycine lines were evaluated for rust resistance against sixteen rust strains (See FIG. 1). The rust data were generated using single pustule derived isolates from USDA-ARS (FL Q09, FL Q12, LABR13, FLQ11) and field populations (FL Q15, NC06, Vero, GLC15, UBL, BR south and BR central), the screening was carried out in contained facilities.

The rust rating is categorized based on groupings modified from Burdon and Speer, T A G, 1984 (see FIG. 2). Each accession was screened >2 times with ~4 plants each time in North & South America.

Example 2 Allele Mining & Associations to PI339656 ASR Loci

The resistant parent was crossed to a susceptible G. clandestina line and an F1 plant was generated (See Table 2). The F1 plant was self-fertilized and F2 seed was harvested from the selfed F1 plant. Around 200 F2 seed were sown and leaf tissue from each plant was collected for DNA preps and then the plants were inoculated with Phakopsora pachyrhizi to determine the resistance/susceptible phenotype of each F2 individual. Tissue from 50 resistant F2s and 50 susceptible F2s were combined in separate pools and genomic DNA was prepared from each pool. Illumina sequencing libraries were prepared from DNA for each of the pools and each library was sequenced in two Illumina HiSeq2000 2×100 bp Paired-End (PE) lanes. The sequencing reads were trimmed to remove bases with PHRED quality scores of <15.

As one non-limiting example, an ASR resistance phenotype may include the formation of lesions without spores on leaves of a plant exposed to ASR, while an ASR susceptible phenotype includes the formation of spores on the leaves of a plant exposed to ASR. Still other phenotypes may be used to distinguish ASR resistant plants from susceptible plants.

Quality trimmed reads were aligned to the PI339656 reference genome sequence using GSNAP (WU and NACU 2010) as paired-end fragments. If a pair of reads could not be aligned together, they were treated as singletons for alignment. Reads were used in subsequent analyses if they mapped uniquely to the reference (≤2 mismatches every 36 bp and less than 5 bases for every 75 bp as tails).

SNPs were filtered prior to BSA analysis based on read depth, with SNPs having between 40 and 200× read depth being retained. A Chi-square test was used to select SNPs with significantly different read counts between the two alleles in the two pools. An empirical Bayesian approach (LIU et al. 2012) was used to estimate the conditional probability that there is no recombination between each SNP marker and the causal locus in both the resistant pool and in the susceptible pool. The probability of the linkage between the SNP and the causal gene is the geometric mean of these two conditional probabilities. Around 780 SNPs were found to have possible linkage to the target locus. A subset of these putatively linked SNPs was used to fine map the locus using phenotyped F2 individuals.

See references: LIU, S., C.-T. YEH, H. M. TANG, D. NETTLETON AND P. S. SCHNABLE, 2012 Gene Mapping via Bulked Segregant RNA-Seq (BSR-Seq). PLoS ONE 7: e36406 & Wu, T. D., and S. Nacu, 2010 Fast and SNP-tolerant detection of complex variants and splicing in short reads. Bioinformatics 26: 873-881.

TABLE 8

| | | | | |
|---|---|---|---|---|
| | | Plant Crossings & Study Type | | |
| Species | PI# (male) | PI # (female | Study Type | F2: Resistant to Susceptible Ratio |
| G. clandestina | PI 339656 | PI 446943 | BSA | 3 to 1 |

1. PI339656 Data2Bio LLC (Ames, Iowa) Lab Methodology for gBSA-Seq Analysis for Tetraploid Soybean.

Chromosome discovery for causal loci in the tetraploid soybean population,

PI339656 was carried out using Data2Bio's Genomic Bulked Segregant Analysis (gBSA) technology. It was theorized that resistance is controlled by a single dominant allele. Data2Bio generated several libraries from DNA samples extracted from two susceptible tissue pools and two resistant tissue pools and sequenced these in eight (8) Illumina HiSeq2000 2×100 bp Paired-End (PE) lanes. A summary of the reference genomes used for subsequent analyses, read processing from raw data to quality trimming, alignment, SNP discovery and SNP impact are demonstrated in FIGS. 3-5. After various filtering steps 4,610,234 informative SNPs were identified in the PI339656 genome. A Bayesian approach was then used to calculate trait-associated probabilities. Next, physical maps of trait-associated SNPs (probability cutoff 0.01) for the top contigs were created (FIGS. 3-5). One scaffold, scaffold 14851, was identified and mapped to chromosome 14 of PI339656 (SEQ ID NO: 1). SNPs from this enriched scaffold were mapped to the public G. max genome. The data suggest that the causative Rgene may map within or near the interval from 3.18 to 3.5 MB on chromosome 14.

Example 3 Embryo Rescue & Introgression of R Gene Intervals into Glycine max Lines Embryo rescue is performed and chemical treatment is applied in order to generate amphidiploid shoots. If the amphidiploid plants are fertile they will be used to backcross with G. max. Backcrossing with G. max and subsequent embryo rescue will need to be performed for several generations in order to gradually eliminate the perennial Glycine chromosomes.

Wide crosses: Elite Syngenta soybean lines (RM 3.7 to 4.8) are used as the females (pollen recipients) and multiple accessions of Glycine clandestina are used as the males or pollen donors. Selecting flowers from the glycine plant containing anthers at the proper developmental stage is important. New, fully-opened, brightly colored flowers hold anthers with mature pollen. The pollen should appear as loose, yellow dust. These flowers are removed from the glycine plant and taken to the soybean plant for pollination. Pollen from the Glycine plants should be used within 30 minutes of flower removal. It is also important to identify and select soybean flower buds that are ready for pollination. A soybean flower bud is generally ready when it is larger in size when compared to an immature bud. The sepals of the soybean blossoms are lighter in color and the petals are just beginning to appear. First, use a pair of fine-tipped tweezers to carefully detach the sepals from the flower bud to expose the outer set of petals. Then gently grasp and remove the petals (5 in total) from the flower exposing the ring of stamens surrounding the pistil. Since the stigma is receptive to pollen 1 day before the anthers begin shedding pollen it is important to recognize the stage development of "female ready, male not ready". When pollinating soybean flowers at this developmental stage it is not necessary to emasculate the female flower. Locate the stigma on the soybean flower. Then using 1 male flower, carefully peel off the petals to expose the anthers and gently dust the pollen grains onto the stigma of the soybean flower. Care should be taken not to damage the stigma at any time during this process. Starting the day after pollination a hormone mixture is sprayed onto the pollinated flower and eventual developing F1 pod 1× every day until harvest. The pollinated flower or pod is saturated with a light mist of the hormone mixture, taking care not to cause the flower/pod to prematurely detach from the plant. The mixture contains 100 mg GA3, 25 mg NAA and 5 mg kinetin/L distilled water. These hormones aid in the retention of the developing pod and in increased pod growth.

Harvest: Pods from wide crosses are harvested at approximately 14 to 16 days post pollination. Harvest dates in the literature suggest 19 to 21 days. Pod harvest at 14 to 16 days after pollination is ~5 days earlier than suggested in literature, reducing timeline. Before selecting an individual pod to harvest verify that the sepals were removed (this indicates a wide cross attempt) and that the seed size is as expected for a wide cross. Pods are collected and counted according to wide cross combination to determine crossing success. The average crossing success across multiple soybean females and 5 different accessions of Glycine clandestina is approximately 40%. The wide cross pods can contain 1 to 3 seeds but generally 2 seeds are found in each F1 pod.

Embryo rescue: Our embryo rescue protocol involves direct shoot regeneration from embryos, rather than regeneration through embryogenesis, thus making plant recovery quicker (shoot recovery in approximately 2-3 months, compared to reported up to 1 year timeline). Our protocol does not include culture in the dark following transfer to germination medium. Our protocol does not require a transfer to rooting medium.

Harvested pods are collected and brought back to the lab to be sterilized. The pods are first rinsed with 70% EtOH for 2 to 3 minutes and then placed in 10% Clorox bleach for an additional 30 minutes on a platform shaker at approximately 130 RPM. Finally, the pods are rinsed multiple times with sterile water to remove any residual bleach. Embryo isolation can begin immediately following pod sterilization or pods can be stored at 4° C. for up to 24 hours prior to embryo isolation. The sterilized pods are next taken to a laminar flow hood where the embryos can be rescued. Individual pods are placed in a sterile petri dish and opened using a scalpel and forceps. An incision is made along the length of the wide cross pod away from the seed. The pod can then be easily opened to expose the seed. Alternatively, two pair of forceps can be used to separate the pod shell. Carefully remove the seed from the pod and place in a sterile petri dish under the dissection microscope. Very fine forceps are needed to isolate the embryo from the seed. With forceps in one hand, gently hold the side of the seed away from the embryo, with hilum facing up. Use another pair of forceps in the other hand to remove the seed coat from the side of the seed containing the embryo. Peel off the membrane surrounding the embryo and push the embryo up from tis bottom side. Embryos should be past the globular developmental stage and preferably past the early heart developmental stage (middle to late heart stage, cotyledon stage and early maturation stage embryos are desired). Isolated embryos are transferred to embryo rescue medium such as Soy ER1-1. Embryos can be treated to induce chromosome doubling at this time. (See below for chromosome doubling details.) Isolated embryos remain on embryo rescue medium for 21 to 30 days at 24° C. Embryos may remain in the dark for the entire incubation on ER1-1, may begin the incubation in the dark and complete it in the light, or may spend the entire incubation in the light. There is not a callus induction stage in this protocol. Shoots are developed directly from the embryos.

Chromosome doubling treatments: Either colchicine of trifluralin can be used to induce chromosome doubling. Ideally, late heart stage wide cross embryos (or larger) are chemically treated to induce chromosome doubling at any time from immediately following isolation up to 1 week post isolation. The doubling agent can be mixed in either solid or liquid medium and applied for several hours or up to a few days. Trifluralin is used at a concentration of 10-40 uM in either solid or liquid media. Additionally, colchicine is used at a concentration of 0.4-1 mg/ml in either solid or liquid media. Following the chemical treatment the embryos are transferred to fresh embryo rescue medium. Colchicine or trifluralin treatment can be done immediately following embryo rescue.

Shoot regeneration: Developing embryos are transferred from rescue medium to germination medium such as Soy ER GSMv2 for approximately 3 to 5 weeks in the light at 24° C. Alternatively, developing embryos may be transferred from rescue medium to elongation medium such as Soy El 0 No TCV for approximately 3 to 5 weeks in the light at 24° C. Developing shoots may be transferred from media plates to Phytocons containing either germination or elongation medium for further shoot development. Established shoots are moved to soil. Initial plant care is critical for survival of these shoots.

Ploidy Analysis: Ploidy analysis is conducted using a flow cytometer. Leaf tissue for ploidy analysis is collected from small shoots either in culture or after establishment in soil. Tissue is collected on dry ice and stored at –80° C. until analysis, or collected on wet ice and analyzed the same day. A sample size of 0.5 cm$^2$ is sufficient. Samples are prepared according to the instructions in the Sysmex kit. Each sample set contains an untreated F1 plant (not treated to induce chromosome doubling) as a control. The following are method notes: Wide crosses—Our wide cross success rate is significantly higher than that reported in the literature. No emasculation of female flowers is performed, which saves time and reduces risk of damage to the stigma.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

SEQUENCE LISTING

The patent contains a lengthy sequence listing. A copy of the sequence listing is available in electronic form from the USPTO web site (https://seqdata.uspto.gov/docdetail?docId=US12599070B2). An electronic copy of the sequence listing will also be available from the USPTO upon request and payment of the fee set forth in 37 CFR 1.19(b)(3).

That which is claimed:

1. A method of selecting a soybean plant having an Asian Soy Rust (ASR) resistance allele, the method comprising the steps of:
   a. Isolating a nucleic acid from a soybean plant;
   b. Detecting in the nucleic acid the presence of a molecular marker that associates with an ASR resistance allele, wherein the molecular marker is a T at a position corresponding to position 3,275,655 of SEQ ID NO: 1, or a T at a position corresponding to position 3,274,672 of SEQ ID NO: 1, or a T at a position corresponding to position 3,291,351 of SEQ ID NO: 1;
   c. thereby identifying a soybean plant having an ASR resistance allele; and
   d. selecting the soybean plant identified at step c as having the ASR resistance allele.

2. The method of claim 1, wherein the ASR resistance allele is a T at position 3,274,672 of SEQ ID NO: 1.

3. The method of claim 1, wherein the ASR resistance allele is a T at position 3,291,351 of SEQ ID NO: 1.

* * * * *